United States Patent
Choi et al.

(10) Patent No.: US 11,177,443 B2
(45) Date of Patent: Nov. 16, 2021

(54) COMPOUND AND LIGHT EMITTING DIODE INCLUDING SAME

(71) Applicant: LMS Co., Ltd., Pyeongtaek-si (KR)

(72) Inventors: Jeong Og Choi, Seoul (KR); Joon Ho Jung, Hwaseong-si (KR)

(73) Assignee: LMS CO., LTD, Pyeongtaek-si (KR)

( * ) Notice: Subject to any disclaimer, the term of this patent is extended or adjusted under 35 U.S.C. 154(b) by 646 days.

(21) Appl. No.: 15/753,678

(22) PCT Filed: Aug. 20, 2016

(86) PCT No.: PCT/KR2016/009216
§ 371 (c)(1),
(2) Date: Feb. 20, 2018

(87) PCT Pub. No.: WO2017/030424
PCT Pub. Date: Feb. 23, 2017

(65) Prior Publication Data
US 2018/0240984 A1 Aug. 23, 2018

(30) Foreign Application Priority Data

Aug. 20, 2015 (KR) .................. 10-2015-0117368

(51) Int. Cl.
*H01L 51/00* (2006.01)
*C09K 11/06* (2006.01)
(Continued)

(52) U.S. Cl.
CPC ........ *H01L 51/0072* (2013.01); *C07D 209/08* (2013.01); *C07D 405/04* (2013.01);
(Continued)

(58) Field of Classification Search
CPC .. C07D 405/04; C07D 209/08; C07D 405/10; C07D 409/04; C07D 409/10;
(Continued)

(56) References Cited

U.S. PATENT DOCUMENTS 6,605,823 B1    8/2003  Pichler et al.
2007/0224448 A1*  9/2007  Ikeda ..................... C09K 11/06
                                                    428/690

(Continued)

FOREIGN PATENT DOCUMENTS

EP       0 686 662 B2      5/2006
JP       2005-093159 A  *  4/2005
(Continued)

OTHER PUBLICATIONS

Machine translation for JP 2005-093159 A (publication date: Apr. 2005). (Year: 2005).*
(Continued)

*Primary Examiner* — Dawn L Garrett
(74) *Attorney, Agent, or Firm* — Polsinelli PC

(57) ABSTRACT

A light emitting diode according to the present invention comprises: a first electrode; an organic layer provided on the first electrode; a light emitting layer provided on the organic layer; an electron transport layer provided on the light emitting layer; and a second electrode provided on the electron transport layer, wherein the organic layer includes a compound represented by Chemical Formula 1. In Chemical Formula 1, below, $Ar_1$, $Ar_2$, $Ar_3$, $L_1$, $L_2$, $L_3$ and Y are as defined in the present specification.

(Continued)

<Chemical Formula 1>

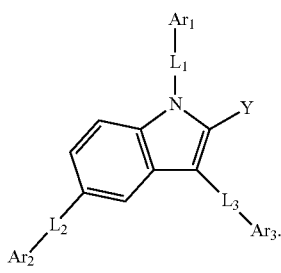

20 Claims, 1 Drawing Sheet

(51) Int. Cl.
*C07D 405/04* (2006.01)
*C07F 7/08* (2006.01)
*C07D 409/04* (2006.01)
*C07D 209/08* (2006.01)
*C07D 405/10* (2006.01)
*C07D 409/10* (2006.01)
*C07D 409/14* (2006.01)
*H01L 51/50* (2006.01)

(52) U.S. Cl.
CPC ......... *C07D 405/10* (2013.01); *C07D 409/04* (2013.01); *C07D 409/10* (2013.01); *C07D 409/14* (2013.01); *C07F 7/0812* (2013.01); *C07F 7/0816* (2013.01); *C09K 11/06* (2013.01); *H01L 51/0058* (2013.01); *H01L 51/0073* (2013.01); *H01L 51/0074* (2013.01); *H01L 51/0094* (2013.01); *C09K 2211/1018* (2013.01); *H01L 51/0071* (2013.01); *H01L 51/5072* (2013.01); *H01L 51/5096* (2013.01); *H01L 2251/308* (2013.01)

(58) Field of Classification Search
CPC .. C07D 409/14; C07D 209/04; C07D 307/91; C09K 11/06; C09K 2211/1018; C09K 2211/1029; C09K 2211/1088; C07F 7/0812; C07F 7/0816; H01L 2251/308; H01L 51/0058; H01L 51/0071; H01L 51/0072; H01L 51/0073; H01L 51/0074; H01L 51/0094; H01L 51/5072; H01L 51/5096; H01L 51/5016

See application file for complete search history.

(56) References Cited

U.S. PATENT DOCUMENTS

2015/0034915 A1* 2/2015 Kim .................. H01L 51/0054 257/40
2017/0179403 A1* 6/2017 Kim .................. H01L 51/0058

FOREIGN PATENT DOCUMENTS

KR 10-2012-0083241 A 7/2012
KR 2013-0119870 A 11/2013
KR 2014-0083898 A 7/2014
KR 2014-0087805 A 7/2014
KR 2015-0039131 A 4/2015

OTHER PUBLICATIONS

Machine translation for KR 10-2014-0087805 (publication date: Jul. 2014). (Year: 2014).*
International Search Report dated Dec. 8, 2016 issued in parent application PCT/KR2016/009216.
Ta-ya Chu et al., Enhanced performance of organic light-emitting diodes with an air-stable n-type hole-injection layer, Applied Physics Letters, 2008, vol. 92, Article No. 233307 (pp. 1-3).
Song et al., "Nickel-catalyzed alkyne annulation by anilines: versatile indole synthesis by C-H/N-H functionalization" Chem. Commun., 2013, 49, pp. 6638-6640.
Chinese Office Action dated Aug. 14, 2020 issued in Patent Application No. 201680048574.3 (7 pages).
Korean Office Action dated Sep. 30, 2019 issued in a related Korean Application No. KR 2015-0117368 (6 pages).
Chemical Abstract_2013:1015720; Nickel-catalyzed alkyne annulation by anilines: versatile indole synthesis by C-H/N-H functionalization; Song et al.; Chemical Communications (Cambridge, United Kingdom) (2013), 49(59), pp. 6638-6640; Royal Society of Chemistry, Cambridge, United Kingdom (GB).
CAS registry No. 1447064-38-1; 1H-Indole, 2,3,5-triphenyl-1-(2-pyrimidinyl)-.

* cited by examiner

COMPOUND AND LIGHT EMITTING DIODE INCLUDING SAME

CROSS-REFERENCE TO RELATED APPLICATIONS

This application is the United States national phase of International Application No. PCT/KR2016/009216 filed on Aug. 20, 2016, which claims priority to Korean patent application No. 10-2015-0117368 filed on Aug. 20, 2015, which are hereby incorporated by reference in their entirety.

BACKGROUND

Field of the Invention

The present invention relates to a novel compound and a light emitting diode including the same.

Discussion of Related Art

A light emitting diode (organic light emitting diode (OLED)) is a type of organic electronic device, which basically has a structure in which an organic thin film including an organic light emitting layer is sandwiched between two electrodes, in which at least one of the electrodes is transparent, and when a proper voltage, generally a direct current voltage of 5 to 10 V, is applied between the two electrodes, the light emitting diode utilizes the emission of light in a visible ray region from the organic light emitting layer.

Since the light emitting diode basically has an actual diode thickness of several micrometers or less, which is very thin, including an electrode, and is a self-light emitting diode that emits light directly from the diode itself, it has a fast response speed and a wide viewing angle. Further, since the manufacturing process is simple, a flexible diode using an organic thin film can be implemented, and a diode can be implemented through not only a vacuum process, but also a printing process in a solution state in some cases, the organic light emitting diode has attracted much attention in terms of a next-generation display device and illumination.

In the related art, the light emitting diode has been applied as a part which is applied to mobile products with low current/low output, but recently, the utilization range thereof has been extended to a high current/high output field, and accordingly, high luminance/high reliability is required. According to these trends, various methods for improving the light emitting efficiency of a light emitting diode have been studied.

Research results attained so far are as follows:

First, European Patent EP No. 0,686,662 relates to a light emitting diode including PEDOT/PSS as a hole transporting material, and a composition including the PEDOT/PSS provides an intermediate ionization potential (an intermediate value between an ionization potential of an anode and an ionization potential of a light emitting body), which is slightly higher than 4.8 eV. The intermediate ionization potential occurs as the composition induces holes injected from the anode to reach the HOMO level of an organic light emitting material or a hole transporting material.

Next, U.S. Pat. No. 6,605,823 relates to a composition including PEDOT/PSS, and there is an advantage in that a solution process such as inkjet printing can be performed on the composition, and thus, a device can be manufactured more easily. In addition, since an excessive amount of PSS (that is, an amount exceeding an amount required for stabilizing electric charges on PEDOT) is used in the composition, the composition may extend the service life of a light emitting diode and prevent PSS from being precipitated from a PEDOT solution.

However, since the light emitting diode according to European Patent No. 0,686,662 has a lower LUMO energy level of PEDOT/PSS than a LUMO energy level of an organic material used as a light emitting layer material, it is difficult to manufacture a light emitting diode with high efficiency and long service life. Further, in the case of U.S. Pat. No. 6,605,823, a composition used for a light emitting diode exhibits strong acidity by including an excessive amount of PSS, and the strong acidity may cause problems such as indium, tin, and oxygen components are released in PEDOT by etching indium tin oxide (ITO), or a light emitting polymer is degraded, and the like.

As described above, studies for improving the light emitting efficiency and light emitting lifetime of a light emitting diode in the related art have been continuously conducted. However, since there is a slight effect for light emitting diodes and compounds used for the light emitting diode, which have been developed so far, to be used in the high current/high output field, there is a desperate need for an alternative capable of solving the problems.

SUMMARY OF THE INVENTION

Technical Problem

An object of the present invention is to provide a compound capable of increasing the light emitting efficiency of a light emitting diode and improving a light emitting lifetime by lowering the driving voltage.

Another object of the present invention is to provide a light emitting diode in which the light emitting efficiency is increased and the light emitting lifetime is improved by including the compound.

Yet another object of the present invention is to provide an electronic device including the light emitting diode.

Technical Solution

In order to achieve the objects, the present invention, in an exemplary embodiment, provides a compound represented by Chemical Formula 1 below:

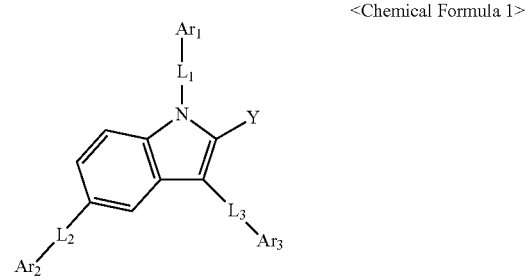

<Chemical Formula 1>

In the above Chemical Formula 1, $Ar_1$ is a fluorenyl group, a dibenzosilolyl group, or an aryl group having 6 to 30 carbon atoms or a heteroaryl group having 2 to 20 carbon atoms, which is unsubstituted or substituted with one or more substituents selected from the group consisting of an alkyl group having 1 to 4 carbon atoms, $Si(R_1)_3$, a cyano group, a halogen group, a haloalkyl group having 1 to 6 carbon atoms, an alkoxy group having 1 to 6 carbon atoms, an aryl group having 6 to 30 carbon atoms and a heteroaryl group having 2 to 20 carbon atoms;

the fluorenyl group or the dibenzosilolyl group is each independently unsubstituted or substituted with one or more substituents selected from the group consisting of an alkyl group having 1 to 4 carbon atoms and an aryl group having 6 to 10 carbon atoms;

$R_1$ is each independently hydrogen or an alkyl group having 1 to 4 carbon atoms;

$L_1$ is a single bond or an arylene group having 6 to 20 carbon atoms;

$L_2$ and $L_3$ are each independently a single bond or an arylene group having 6 to 20 carbon atoms, which is unsubstituted or substituted with an aryl group having 6 to 30 carbon atoms;

$Ar_2$ and $Ar_3$ are each independently an aryl group having 6 to 30 carbon atoms, which is unsubstituted or substituted with an aryl group having 6 to 30 carbon atoms, and an aryl group having 6 to 30 carbon atoms, which is a substituent of the aryl group having 6 to 30 carbon atoms, is unsubstituted or substituted with an aryl group having 6 to 20 carbon atoms; and Y is hydrogen, or an aryl group having 6 to 30 carbon atoms, which is unsubstituted or substituted with an aryl group having 6 to 30 carbon atoms.

Further, the present invention, in an exemplary embodiment, provides a light emitting diode comprising:

a first electrode;

an organic layer provided on the first electrode;

a light emitting layer provided on the organic layer;

an electron transport layer provided on the light emitting layer; and a second electrode provided on the electron transport layer, wherein the organic layer includes a compound represented by Chemical Formula 1 below:

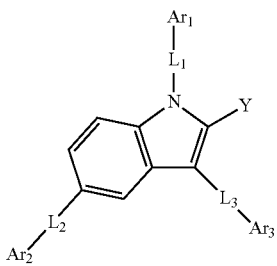

<Chemical Formula 1>

In the above Chemical Formula 1, $Ar_1$, $Ar_2$, $Ar_3$, $L_1$, $L_2$, $L_3$ and Y are defined as above.

Furthermore, the present invention, in an exemplary embodiment, provides an electronic device including the light emitting diode.

Effect of the Invention

Since a light emitting diode according to the present invention has excellent light emitting efficiency and an excellent light emitting lifetime by forming an organic layer including a compound represented by Chemical Formula 1 between a first electrode and a light emitting layer, it may be easily used in an electronic device such as a display device and an illumination device using the light emitting diode.

DETAILED DESCRIPTION OF THE INVENTION

Figure 1:
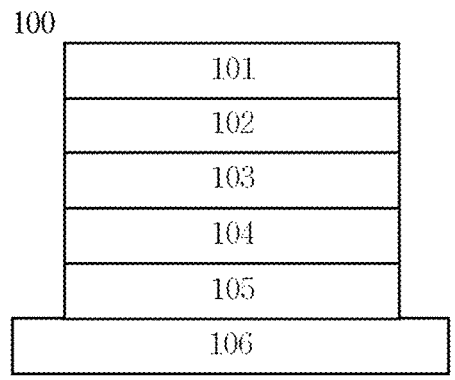
FIG. 1 is an image illustrating a structure of a light emitting diode manufactured in an exemplary embodiment according to the present invention.

Since the present invention may be modified in various forms and include various embodiments, specific embodiments will be illustrated in the drawings and described in detail in the Detailed Description.

However, the description is not intended to limit the present invention to the specific embodiments, and it is to be understood that all the changes, equivalents and substitutions included in the idea and technical scope of the present invention are included in the present invention.

In the present invention, the term "include" or "have" is intended to indicate the presence of a characteristic, number, step, operation, constituent element, part or any combination thereof described in the specification, but it should be understood that the possibility of the presence or addition of one or more other characteristics or numbers, steps, operations, constituent elements, parts or any combination thereof is not precluded.

Further, it should be understood that the accompanying drawings in the present invention are illustrated in an enlarged or reduced size for the convenience of explanation.

Hereinafter, the present invention will be described in detail with reference to drawings, and the same or corresponding constituent elements are assigned with the same reference numerals regardless of drawing numerals and the repetitive description thereof will be omitted.

In the present invention, "an alkyl group" means a functional group derived from a linear or branched, saturated hydrocarbon.

In this case, examples of the "alkyl group" include a methyl group, an ethyl group, an n-propyl group, an isopropyl group, an n-butyl group, a sec-butyl group, a tert-butyl group, an n-pentyl group, a 1,1-dimethylpropyl group, a 1,2-dimethylpropyl group, a 2,2-dimethylpropyl group, a 1-ethylpropyl group, a 2-ethylpropyl group, an n-hexyl group, a 1-methyl-2-ethylpropyl group, a 1-ethyl-2-methylpropyl group, a 1,1,2-trimethylpropyl group, a 1-propylpropyl group, a 1-methylbutyl group, a 2-methylbutyl group, a 1,1-dimethylbutyl group, a 1,2-dimethylbutyl group, a 2,2-dimethylbutyl group, a 1,3-dimethylbutyl group, a 2,3-dimethylbutyl group, a 2-ethylbutyl group, a 2-methylpentyl group, a 3-methylpentyl group, and the like.

Further, the "alkyl group" may have 1 to 20 carbon atoms, for example, 1 to 12 carbon atoms, 1 to 6 carbon atoms, or 1 to 4 carbon atoms.

In the present invention, "an aryl group" means a monovalent substituent derived from an aromatic hydrocarbon.

In this case, examples of the "aryl group" include a phenyl group, a naphthyl group, an anthracenyl group, a phenanthryl group, a naphthacenyl group, a pyrenyl group, a tolyl group, a biphenyl group, a terphenyl group, a chrycenyl group, a spirobifluorenyl group, a fluoranthenyl group, a fluorenyl group, a perylenyl group, an indenyl group, an azulenyl group, a heptalenyl group, a phenalenyl group, a phenanthrenyl group, and the like.

Further, the "aryl group" may have 6 to 30 carbon atoms, for example, 6 to 12 carbon atoms, 6 to 14 carbon atoms, 6 to 18 carbon atoms, or 6 to 12 carbon atoms.

In the present invention, "a heteroaryl group" means "an aromatic heterocyclic ring" or "a heterocyclic compound" derived from a monocyclic or condensed ring. The "heteroaryl group" may include at least one, for example, one, two, three or four of nitrogen (N), sulfur (S), oxygen (O), phosphorus (P), selenium (Se), and silicon (Si) as a heteroatom.

In this case, examples of the "heteroaryl group" include a nitrogen-containing heteroaryl group including a pyrrolyl group, a pyridyl group, a pyridazinyl group, a pyrimidinyl group, a pyrazinyl group, a triazolyl group, a tetrazolyl group, a benzotriazolyl group, a pyrazolyl group, an imidazolyl group, a benzimidazolyl group, an indolyl group, an isoindolyl group, an indolizinyl group, a purinyl group, an indazolyl group, a quinolyl group, an isoquinolinyl group, a quinolizinyl group, a phthalazinyl group, a naphthylidinyl group, a quinoxalinyl group, a quinazolinyl group, a cinnolinyl group, a pteridinyl group, an imidazotriazinyl group, an acridinyl group, a phenanthridinyl group, a carbazolyl group, a carbazolinyl group, a pyrimidinyl group, a phenanthrolinyl group, a phenazinyl group, an imidazopyridinyl group, an imidazopyrimidinyl group, a pyrazolopyridinyl group, and the like; a sulfur-containing heteroaryl group including a thienyl group, a benzothienyl group, a dibenzothienyl group, and the like; an oxygen-containing heteroaryl group including a furyl group, a pyranyl group, a cyclopentapyranyl group, a benzofuranyl group, an isobenzofuranyl group, a dibenzofuranyl group, and the like; and the like.

In addition, specific examples of the "heteroaryl group" include compounds including at least two heteroatoms, such as a thiazolyl group, an isothiazolyl group, a benzothiazolyl group, a benzothiadiazolyl group, a phenothiazinyl group, an isoxazolyl group, a furazanyl group, a phenoxazinyl group, an oxazolyl group, a benzoxazolyl group, an oxadiazolyl group, a pyrazoloxazolyl group, an imidazothiazolyl group, a thienofuranyl group, a furopyrrolyl group, and a pyridoxazinyl group.

Furthermore, the "heteroaryl group" may have 2 to 20 carbon atoms, for example, 3 to 19 carbon atoms, 4 to 15 carbon atoms, or 5 to 11 carbon atoms. For example, when a heteroaryl group includes a heteroatom, the heteroaryl group may have 5 to 21 ring members.

In the present invention, "an arylene group" may mean a divalent substituent derived from the aryl group described above.

Further, in the present invention, "a heteroarylene group" may mean a divalent substituent derived from the heteroaryl group described above.

Furthermore, in the present invention, in a heteroaryl group having fused two rings, the position of a carbon atom which may substitute or be substituted is represented as follows based on the heteroatom, and will be described below based on this.

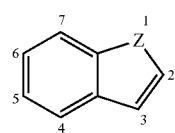

The present invention provides a compound capable of increasing the light emitting efficiency of a light emitting diode and improving the light emitting lifetime by lowering a driving voltage, and a light emitting diode including the same.

Light emitting diodes developed so far have problems in that the light emitting lifetime is short and the power efficiency is low. In order to solve these problems, various compounds have been developed as a material for the light emitting diode, but there is a limitation in manufacturing a light emitting diode which satisfies both the light emitting lifetime and the power efficiency.

In order to solve these problems, the present invention suggests a compound represented by Chemical Formula 1 according to the present invention and a light emitting diode in which an organic layer including the compound represented by Chemical Formula 1 according to the present invention is formed between a first electrode and a light emitting layer. Since the light emitting diode according to the present invention has improved light emitting efficiency and low driving voltage by forming an organic layer including a compound represented by Chemical Formula 1 between a first electrode and a light emitting layer, the light emitting lifetime may be improved. Therefore, the light emitting diode according to the present invention may be usefully used in an electronic device, such as a display device and an illumination device, in which the light emitting diode is used.

Hereinafter, the present invention will be described in more detail.

The present invention, in an exemplary embodiment, provides a compound represented by Chemical Formula 1 below:

[Chemical Formula 1]

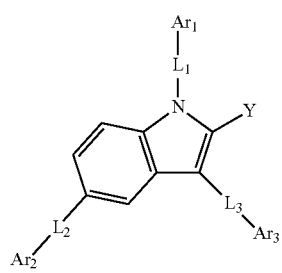

In the above Chemical Formula 1, $Ar_1$ is a fluorenyl group, a dibenzosilolyl group, or an aryl group having 6 to 30 carbon atoms or a heteroaryl group having 2 to 20 carbon atoms, which is unsubstituted or substituted with one or more substituents selected from the group consisting of an alkyl group having 1 to 4 carbon atoms, $Si(R_1)_3$, a cyano group, a halogen group, a haloalkyl group having 1 to 6 carbon atoms, an alkoxy group having 1 to 6 carbon atoms, an aryl group having 6 to 30 carbon atoms and a heteroaryl group having 2 to 20 carbon atoms;

the fluorenyl group or the dibenzosilolyl group is each independently unsubstituted or substituted with one or more substituents selected from the group consisting of an alkyl group having 1 to 4 carbon atoms and an aryl group having 6 to 10 carbon atoms;

$R_1$ is each independently hydrogen or an alkyl group having 1 to 4 carbon atoms;

$L_1$ is a single bond or an arylene group having 6 to 20 carbon atoms;

$L_2$ and $L_3$ are each independently a single bond, or an arylene group having 6 to 20 carbon atoms, which is unsubstituted or substituted with an aryl group having 6 to 30 carbon atoms;

$Ar_2$ and $Ar_3$ are each independently an aryl group having 6 to 30 carbon atoms, which is unsubstituted or substituted with an aryl group having 6 to 30 carbon atoms, and an aryl group having 6 to 30 carbon atoms, which is a substituent of the aryl group having 6 to 30 carbon atoms, is unsubstituted or substituted with an aryl group having 6 to 20 carbon atoms; and Y is hydrogen, or an aryl group having 6 to 30 carbon atoms, which is unsubstituted or substituted with an aryl group having 6 to 30 carbon atoms.

As an example, in Chemical Formula 1 according to the present invention, $L_1$ may be a phenylene group or a naphthylene group, $L_2$ and $L_3$ may be each independently a single bond, or a phenylene group which is unsubstituted or substituted with a phenyl group, $Ar_2$ and $Ar_3$ may be each independently a phenyl group, a naphthyl group, or a phenanthryl group, and here, the phenyl group may be unsubstituted or substituted with a phenyl group, a biphenyl group, a naphthyl group, or a phenanthryl group, and Y may be hydrogen, a phenyl group, or a biphenyl group.

In this case, in the above Chemical Formula 1, $Ar_1$ may be a phenyl group, a naphthyl group, or a phenanthryl group.

Specifically, the compound represented by Chemical Formula 1 may have a structure of any one of the chemical formula of a-1 to a-66 below.

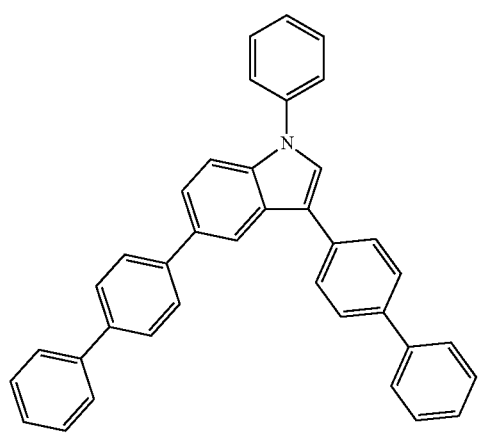

<a-1>

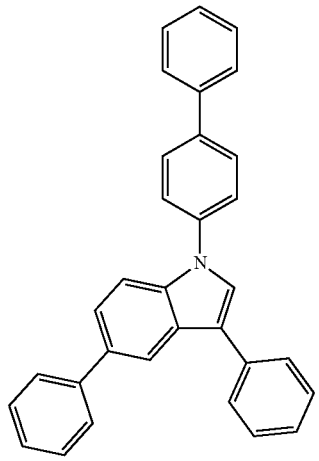

<a-2>

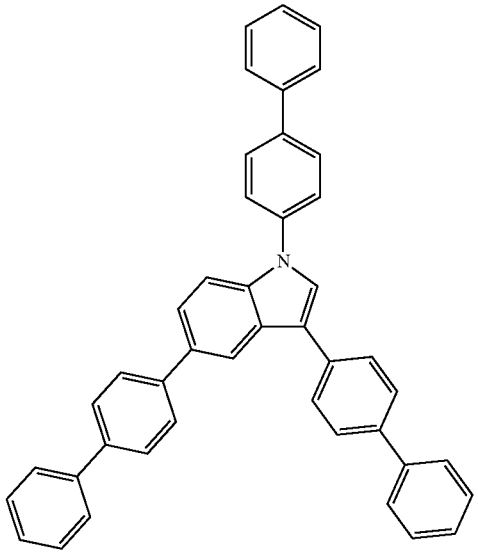

<a-3>

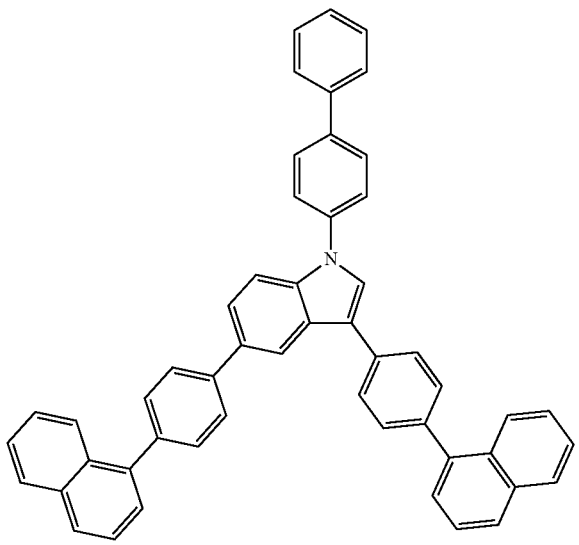

<a-4>

<a-5>
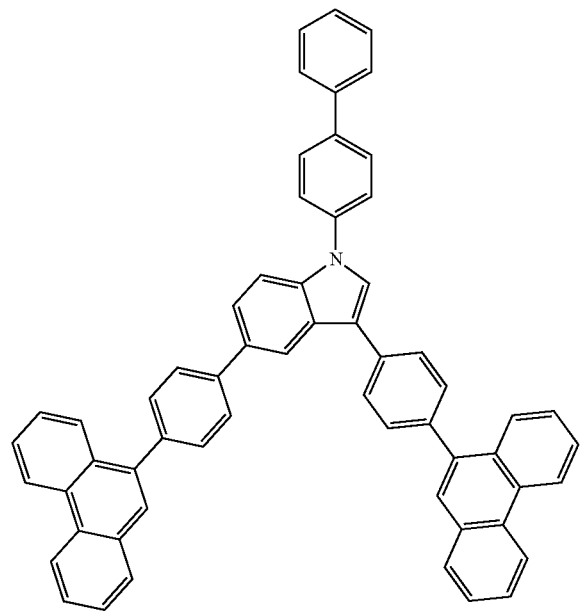
<a-6>
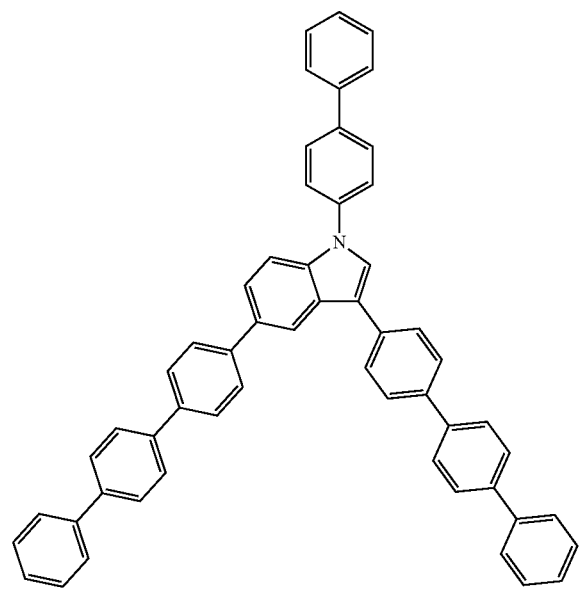
<a-7>
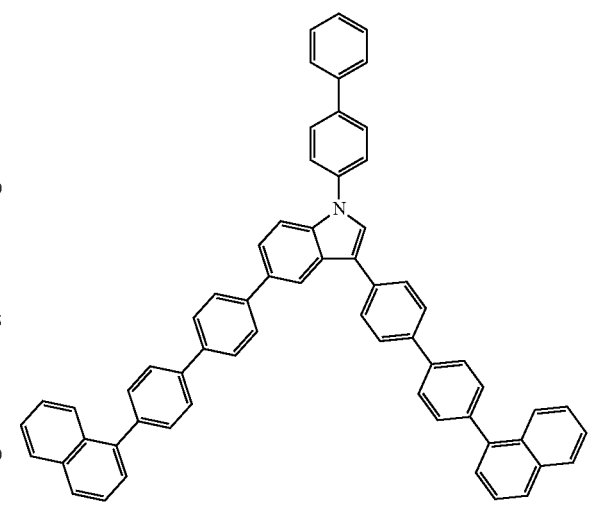
<a-8>
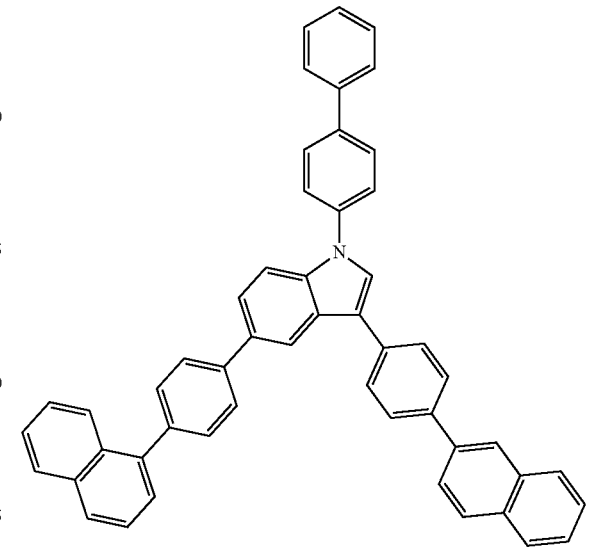
<a-9>

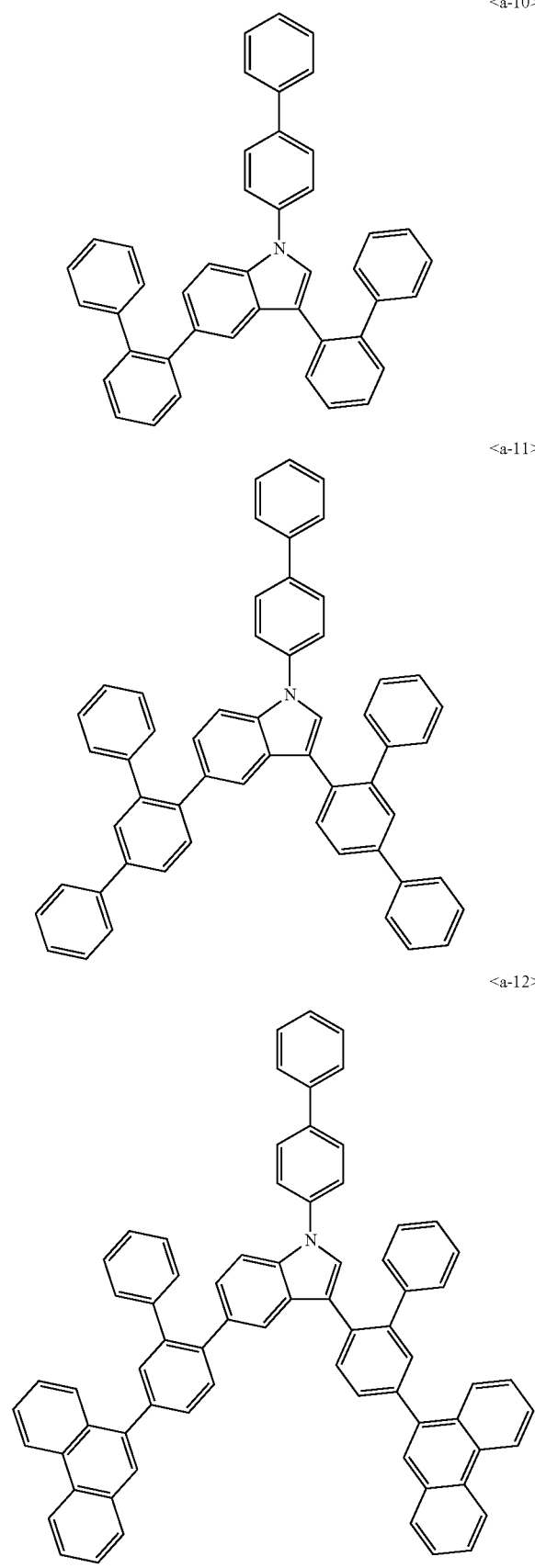 [SMILES: c1ccc(-c2ccc(-n3cc(-c4ccccc4-c4ccccc4)c4cc(-c5ccccc5-c5ccccc5)ccc43)cc2)cc1 ; c1ccc(-c2ccc(-n3cc(-c4ccc(-c5ccccc5)cc4-c4ccccc4)c4cc(-c5ccc(-c6ccccc6)cc5-c5ccccc5)ccc43)cc2)cc1 ; c1ccc(-c2ccc(-n3cc(-c4ccc(-c5cc6ccccc6c6ccccc56)cc4-c4ccccc4)c4cc(-c5ccc(-c6cc7ccccc7c7ccccc67)cc5-c5ccccc5)ccc43)cc2)cc1]
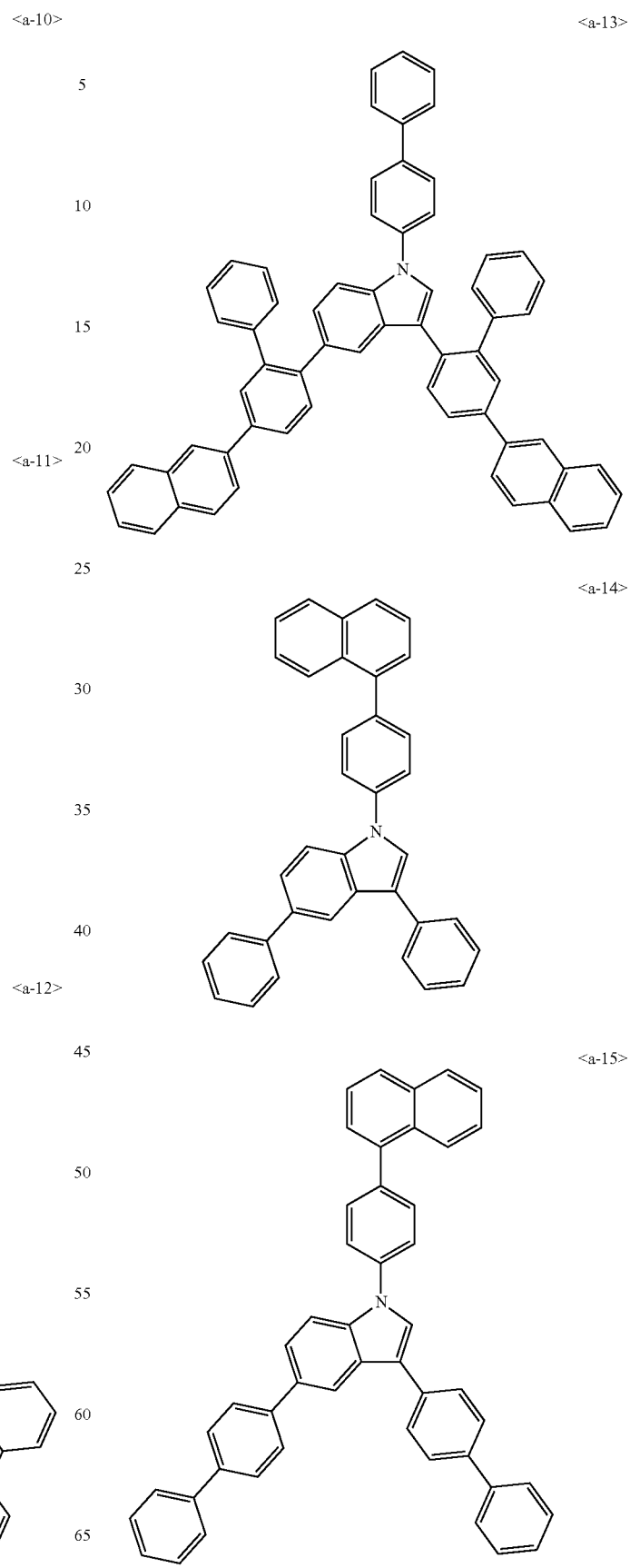

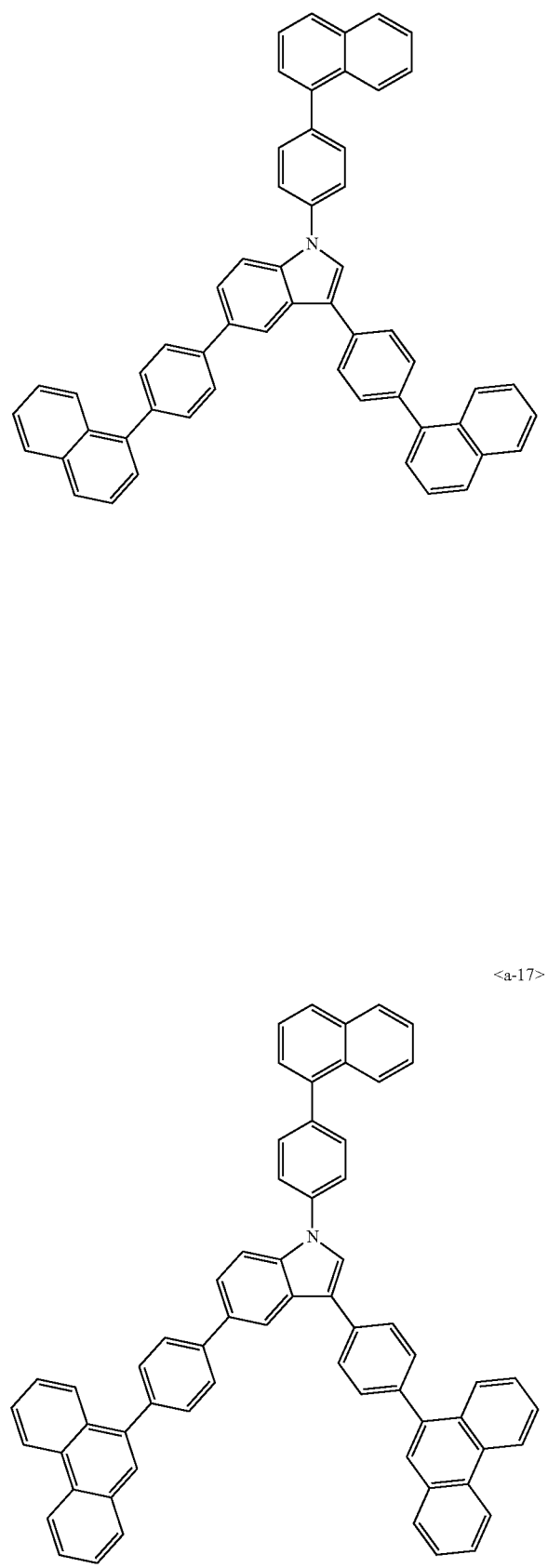
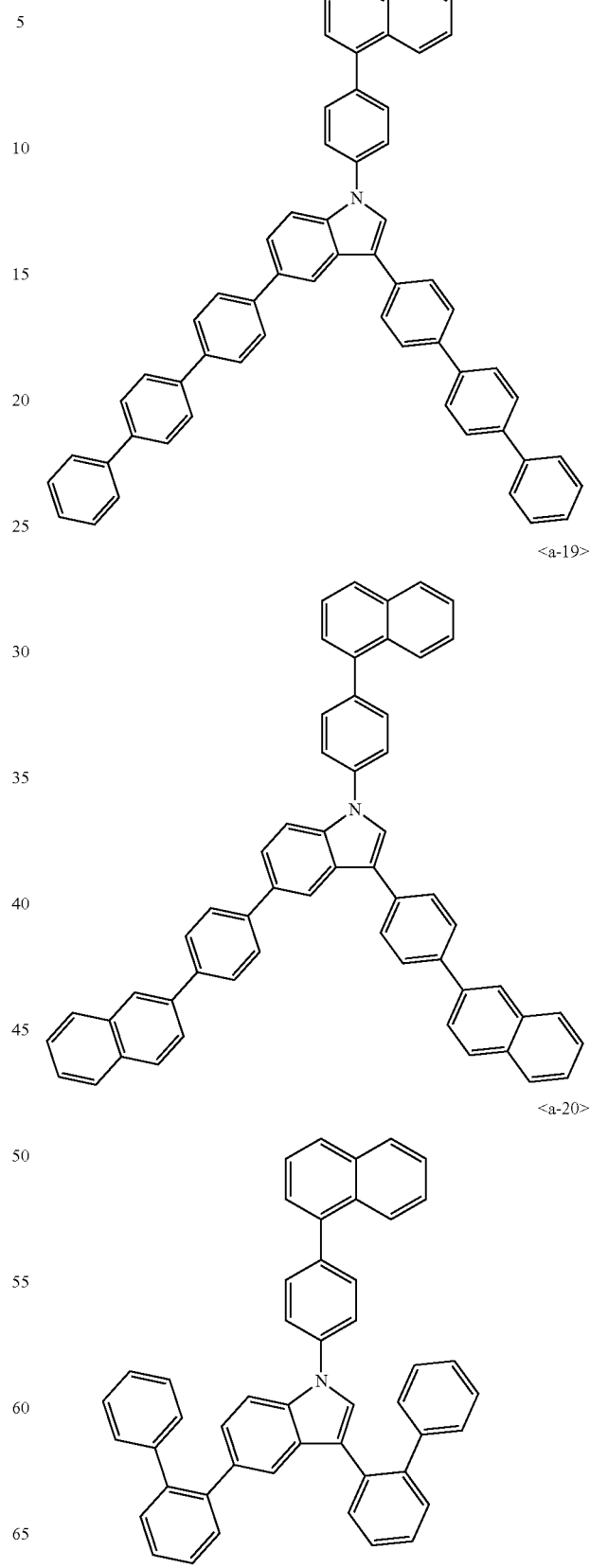

<a-21>
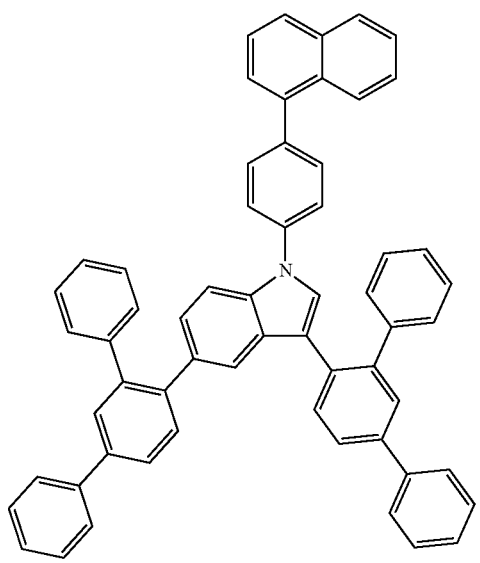
<a-22>
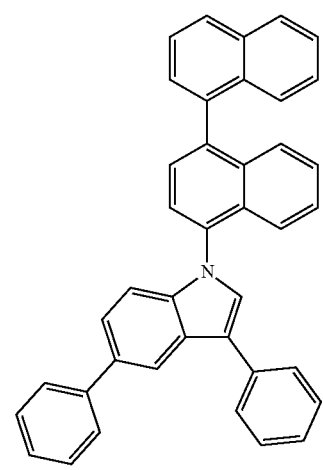
<a-23>
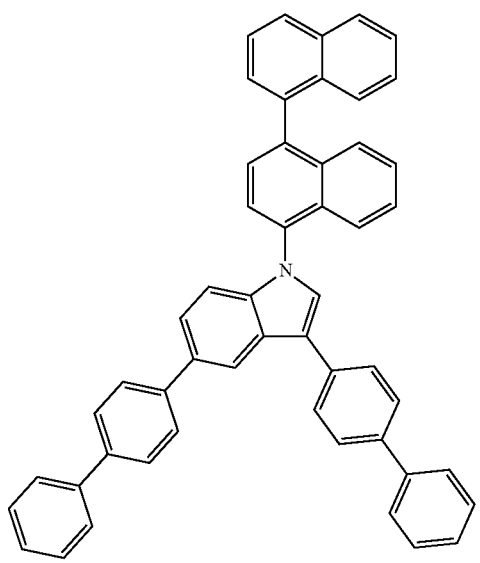
<a-24>
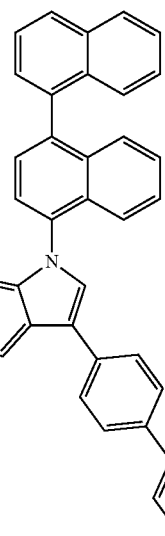
<a-25>
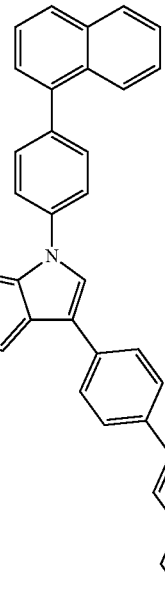

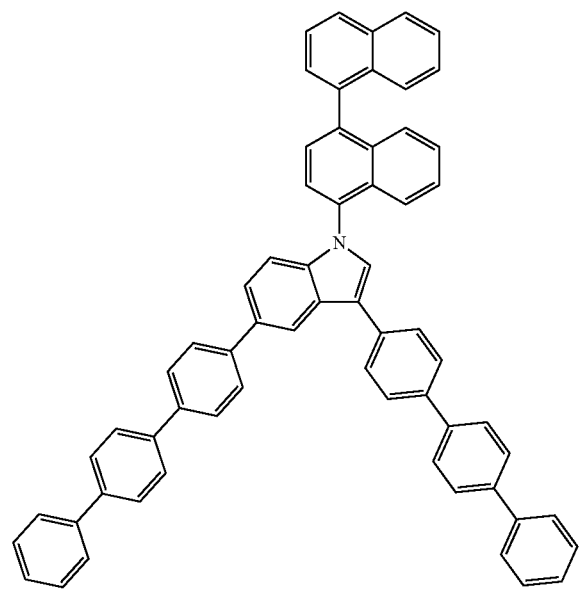
<a-26>
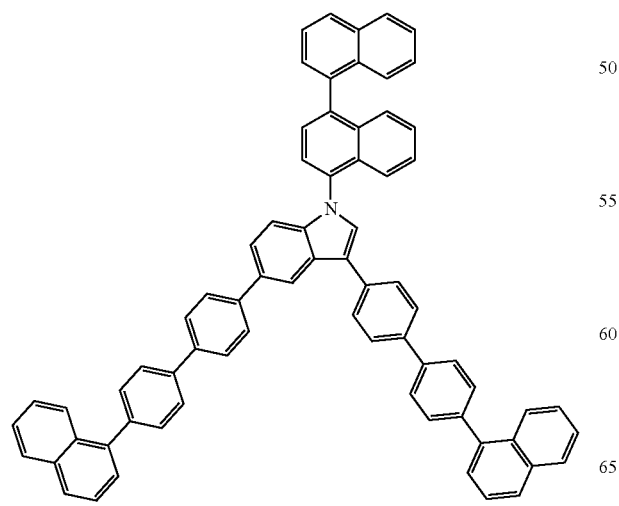
<a-27>
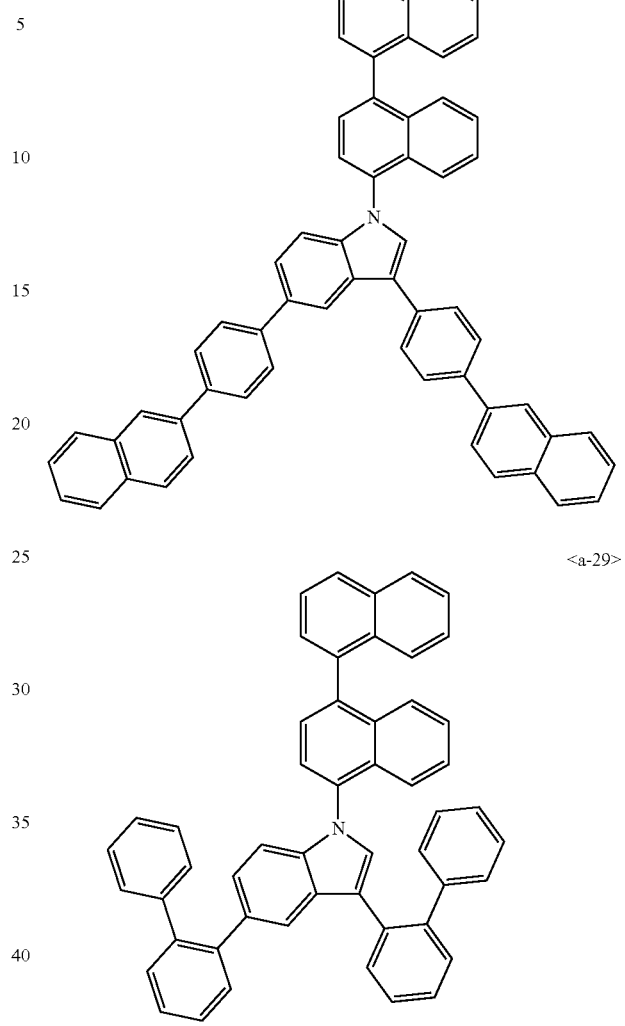
<a-28>
<a-29>
<a-30>
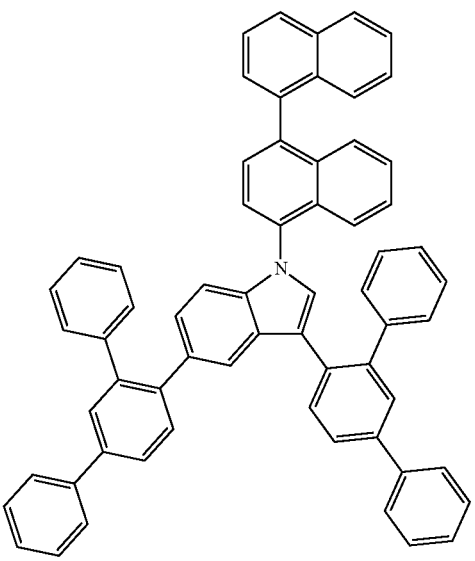

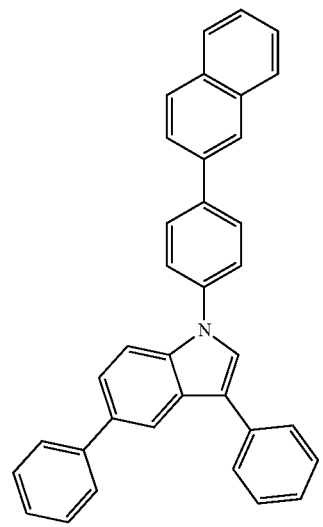 <a-31>
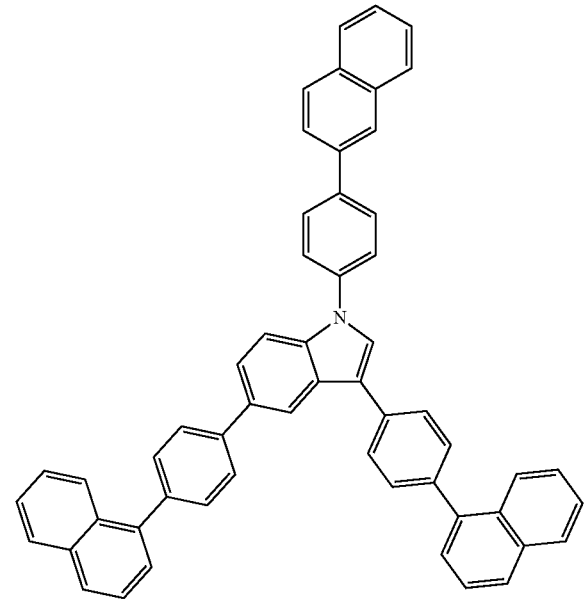 <a-33>
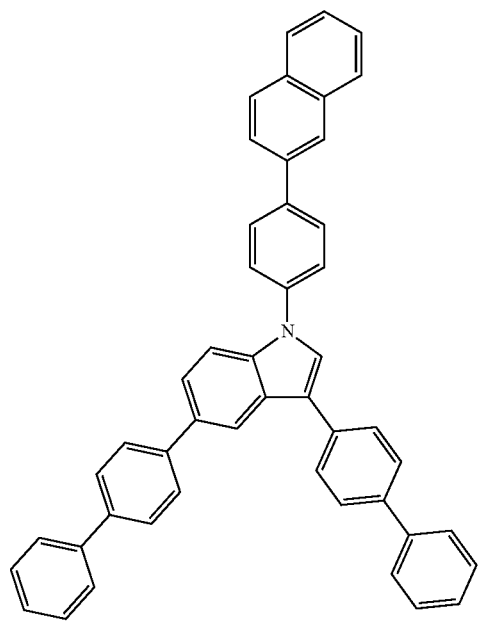 <a-32>
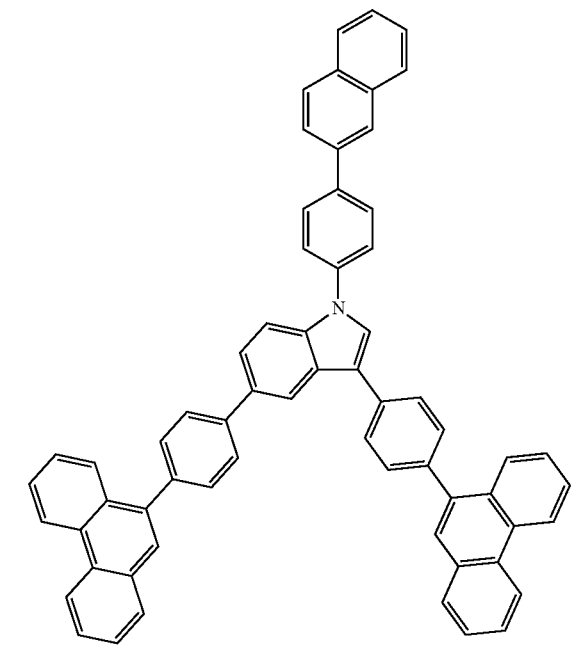 <a-34>

<a-35>
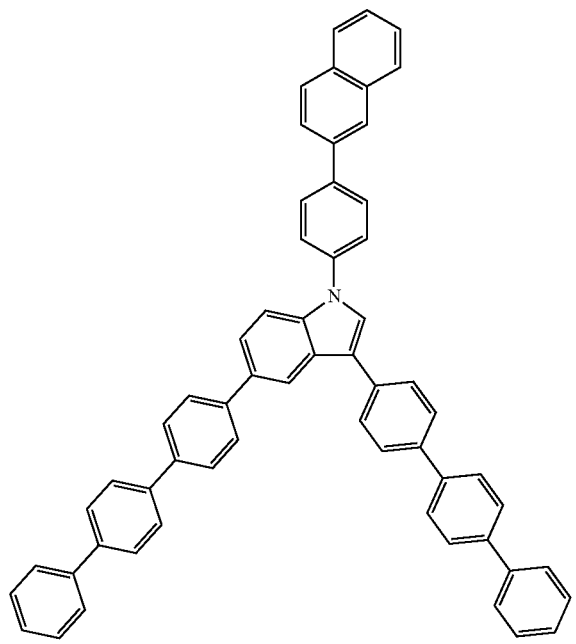
<a-37>
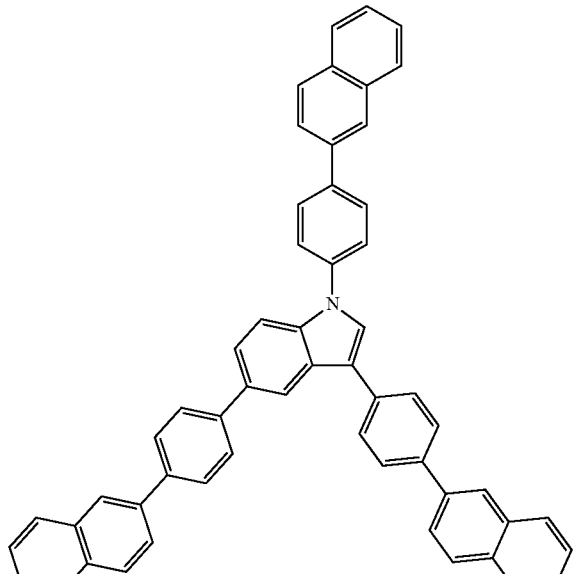
<a-36>
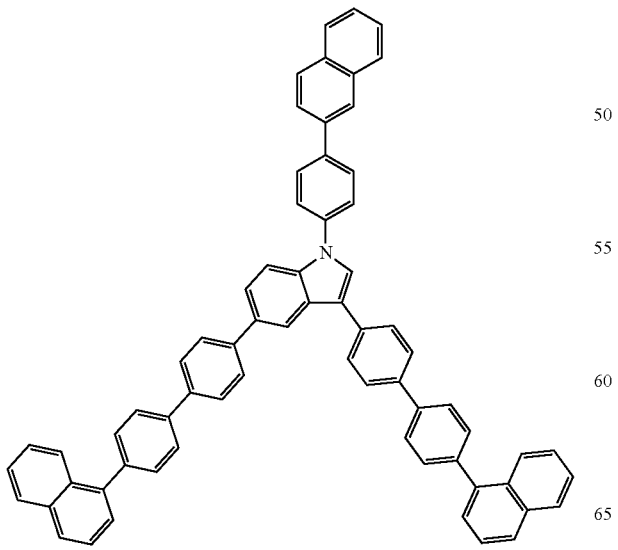
<a-38>
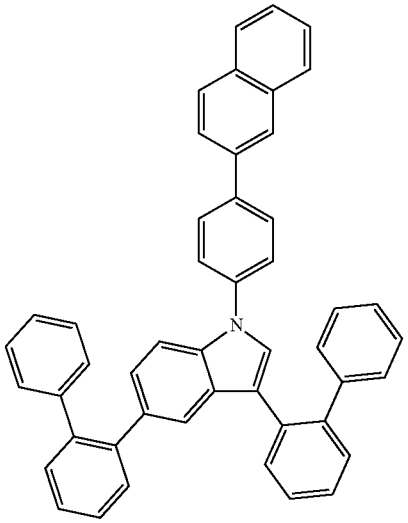

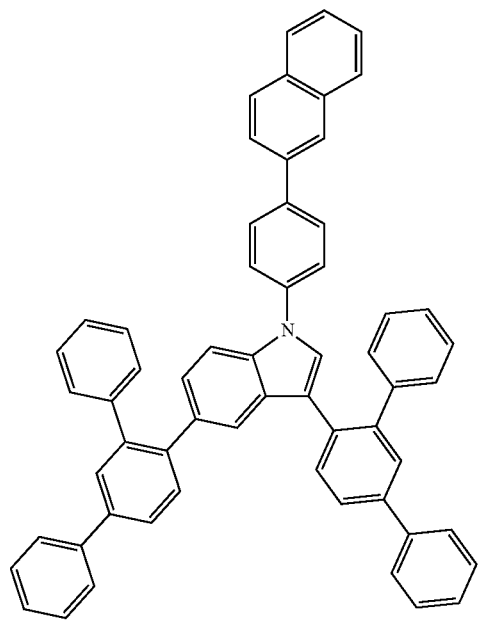
<a-39>
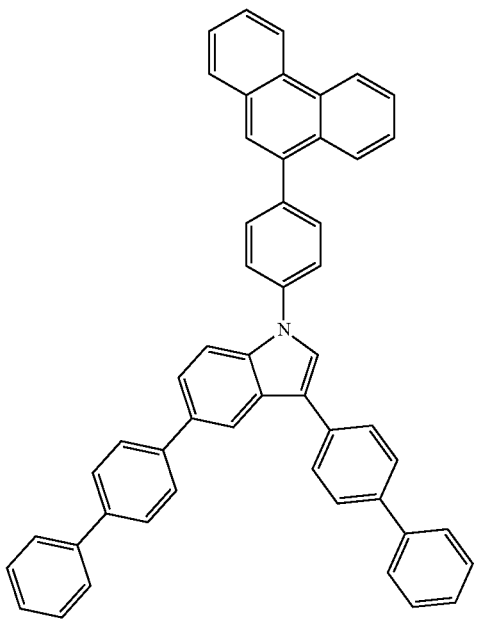
<a-41>
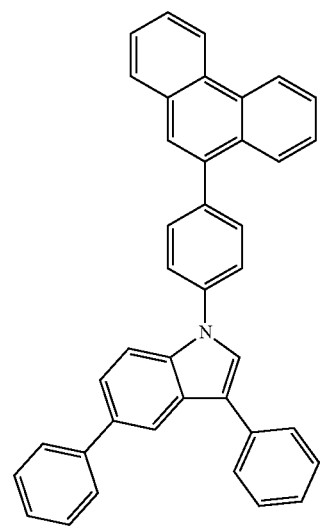
<a-40>
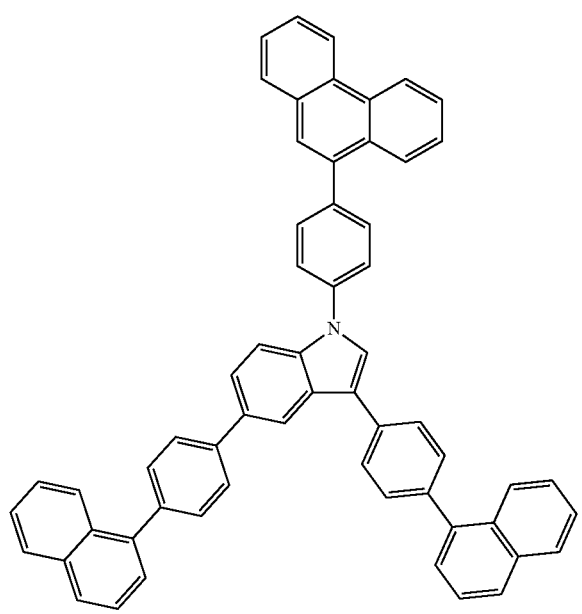
<a-42>

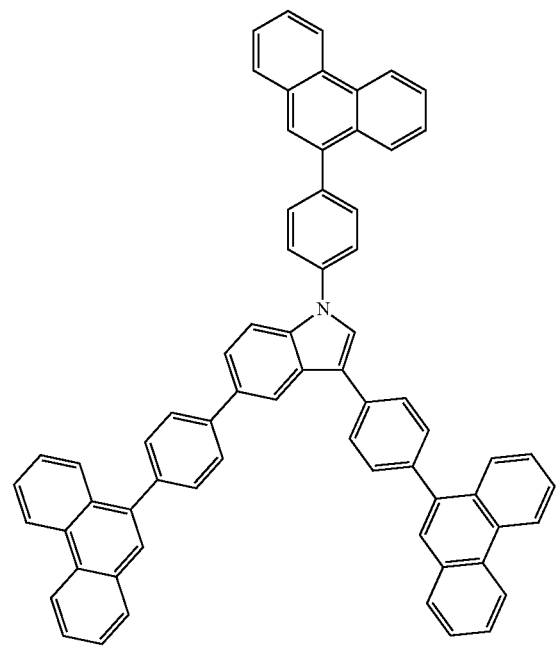
<a-43>
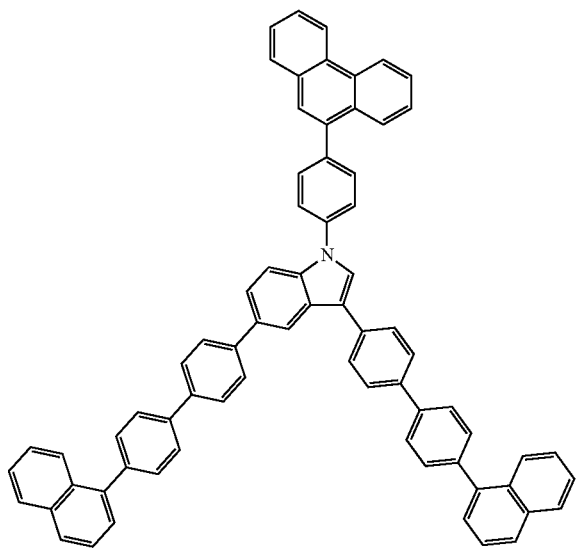
<a-45>
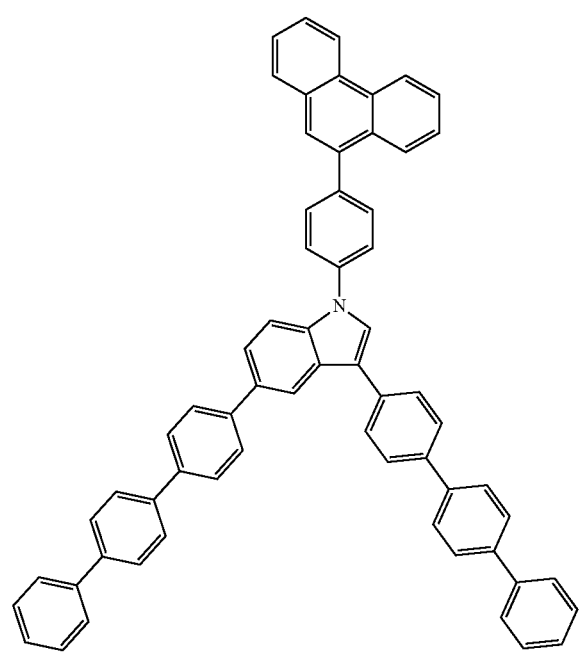
<a-44>
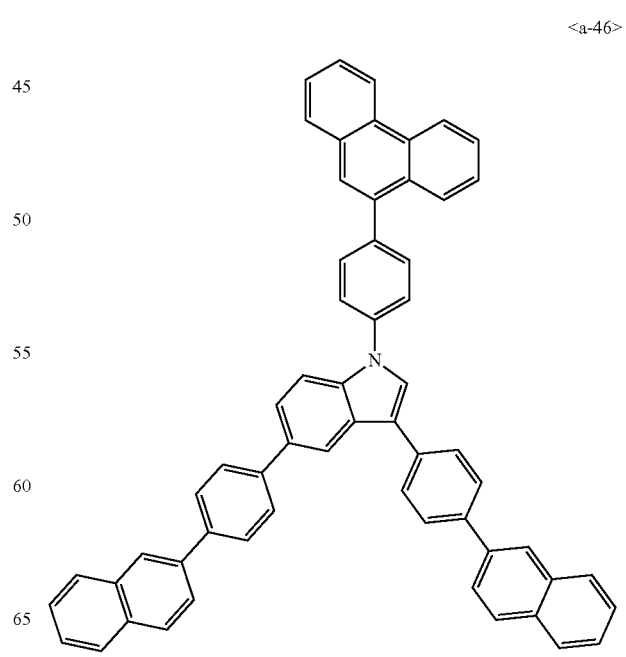
<a-46>

<a-47>
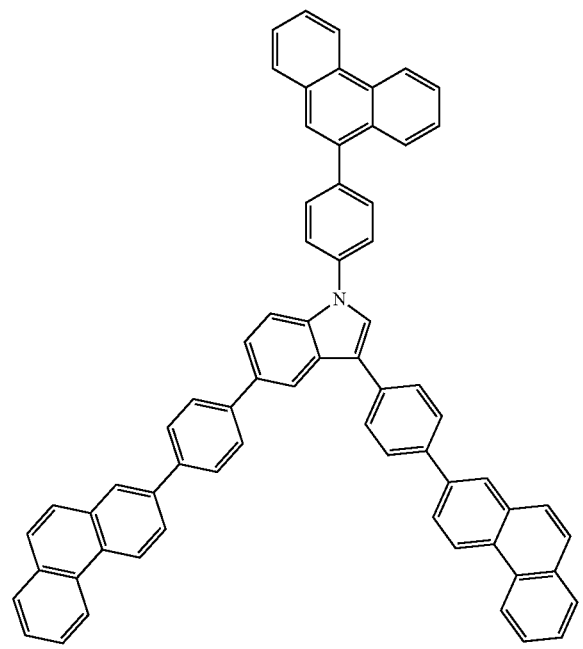
<a-48>
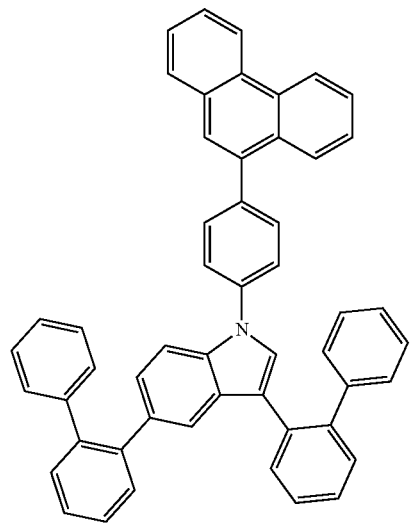
<a-49>
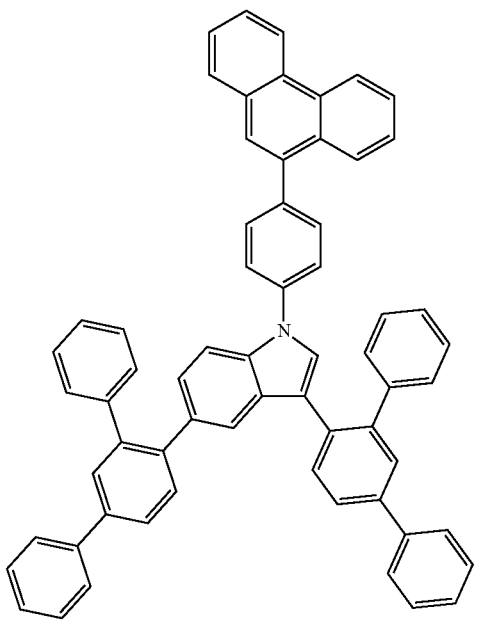
<a-50>
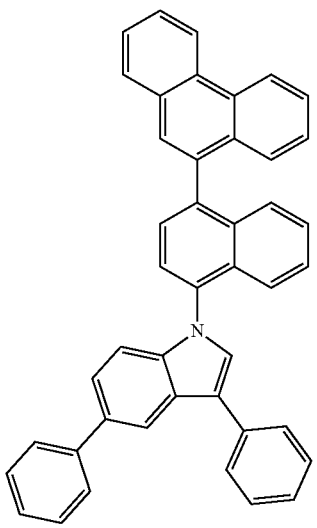

<a-51>
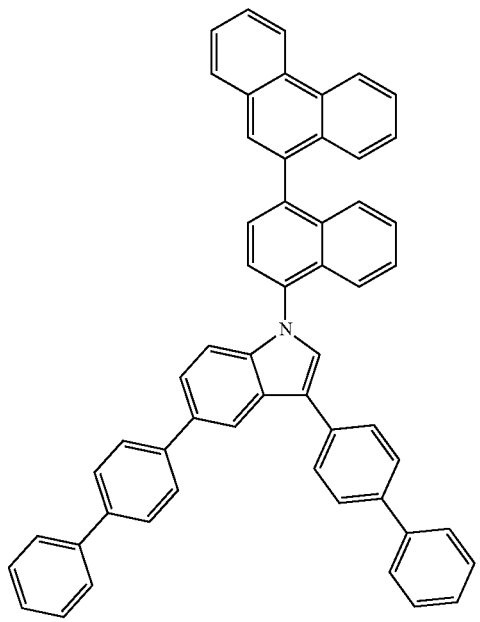
<a-53>
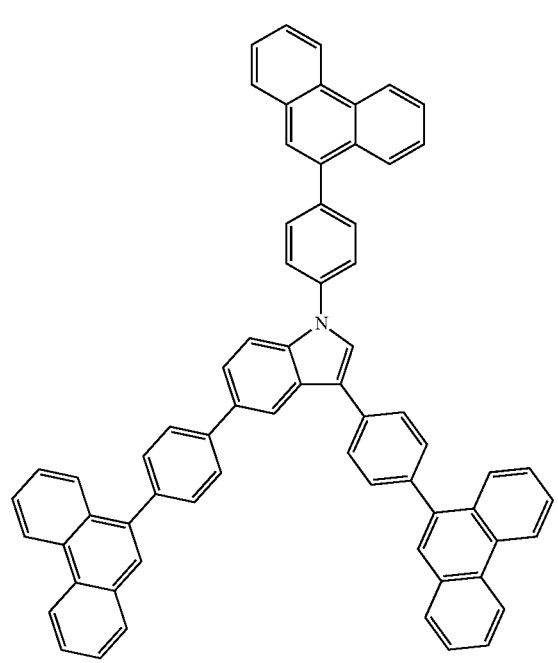
<a-52>
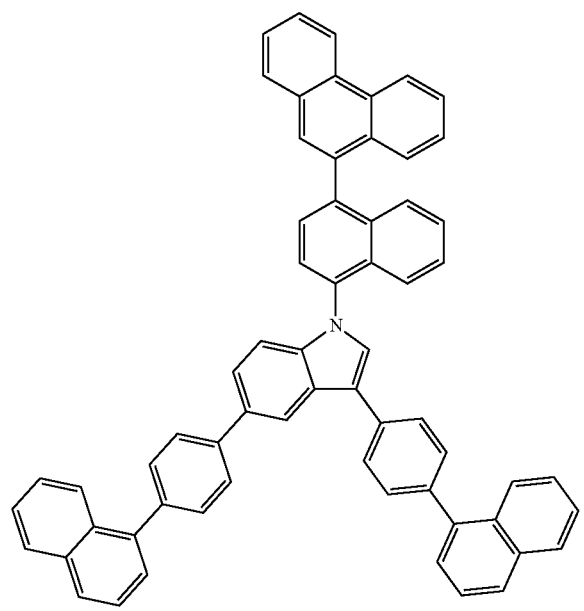
<a-54>
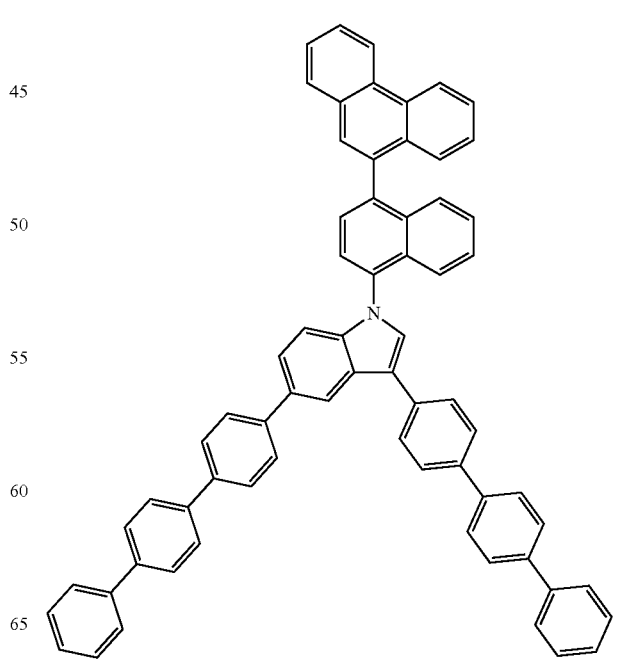

<a-55>
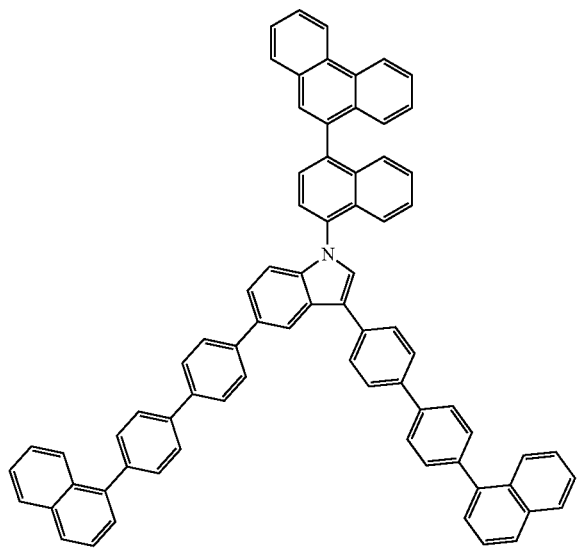
<a-56>
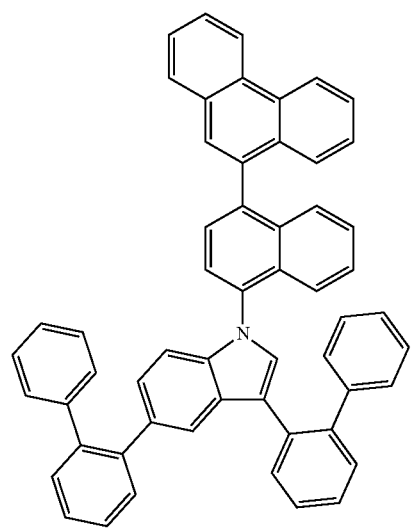
<a-57>
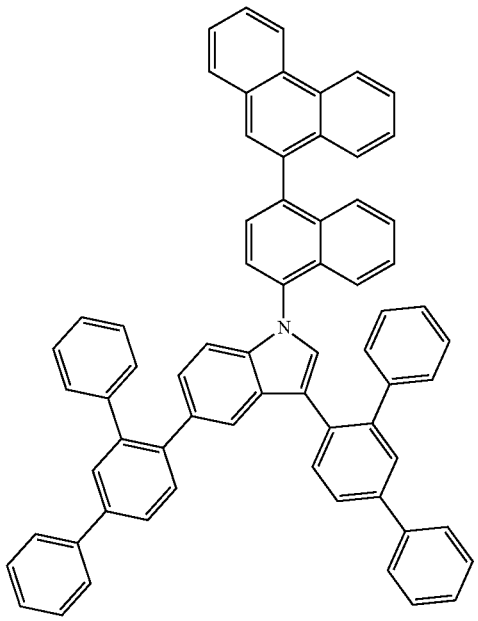
<a-58>
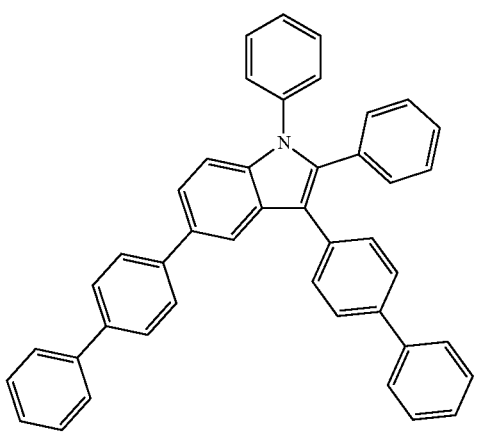
<a-59>
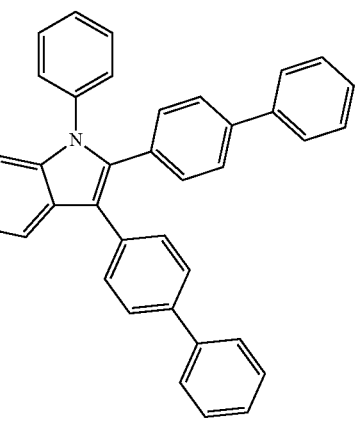

<a-60>
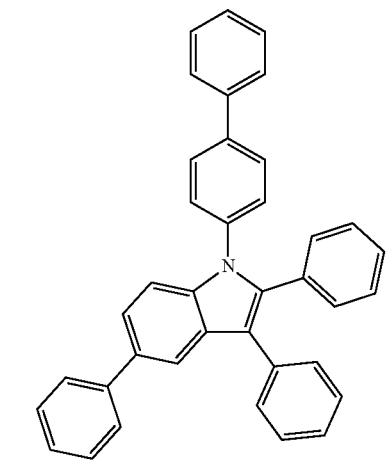
<a-61>
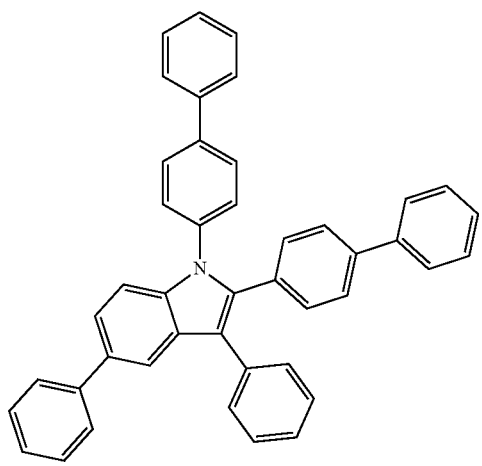
<a-62>
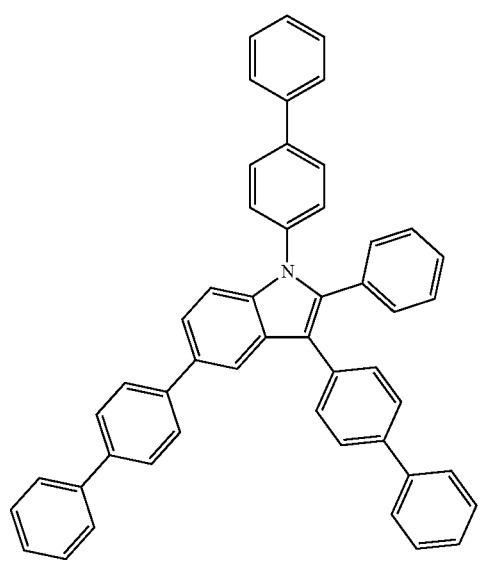
<a-63>
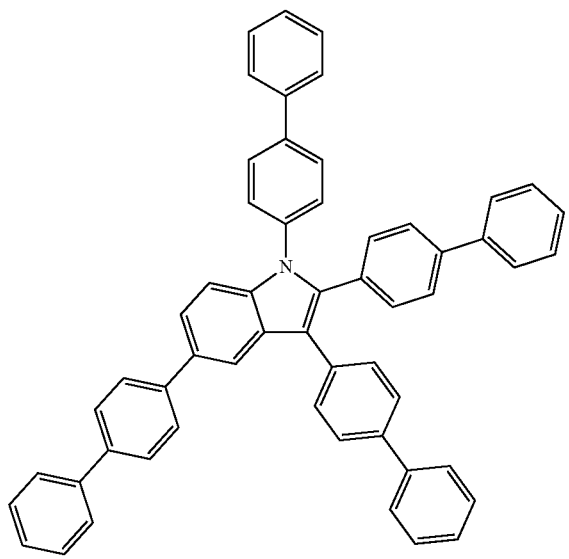
<a-64>
<a-65>
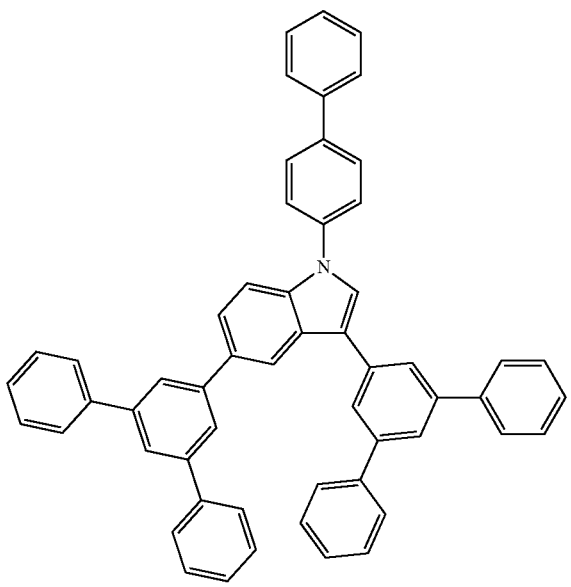

<a-66>
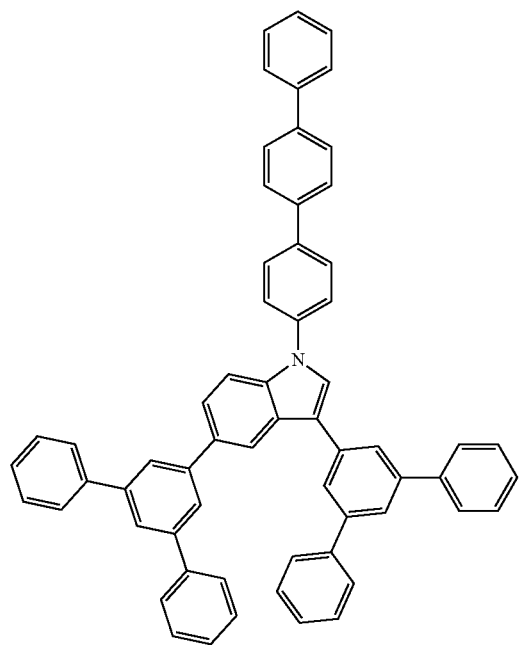
<b-2>
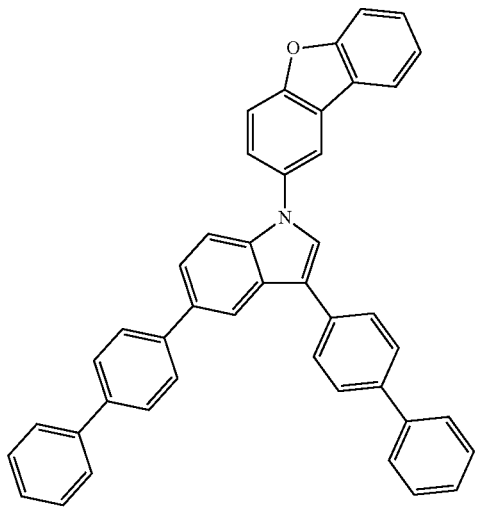
Further, in the above Chemical Formula 1 according to the present invention, Ar₁ may be a dibenzofuranyl group or a dibenzothiophenyl group.
Specifically, the compound represented by Chemical Formula 1 may have a structure of any one of the chemical formula of b-1 to b-48 below.
<b-3>
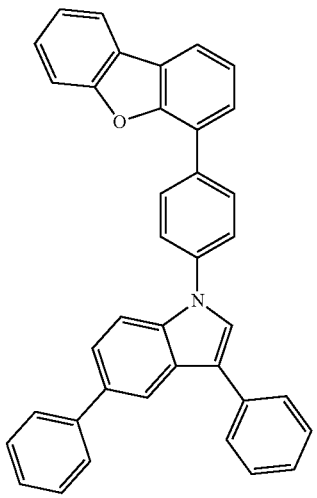
<b-1>
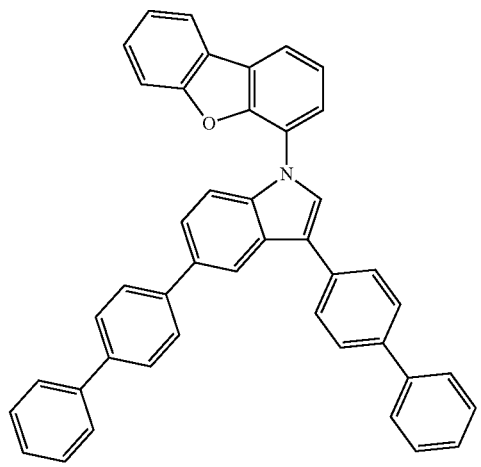
<b-4>
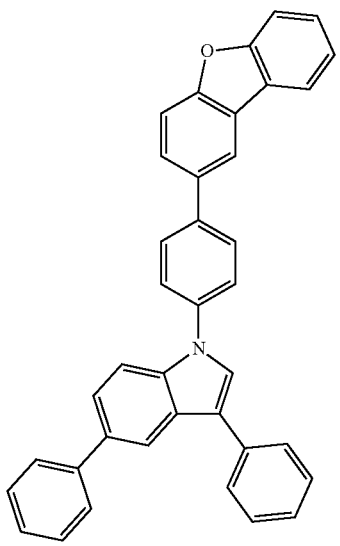

<b-5>
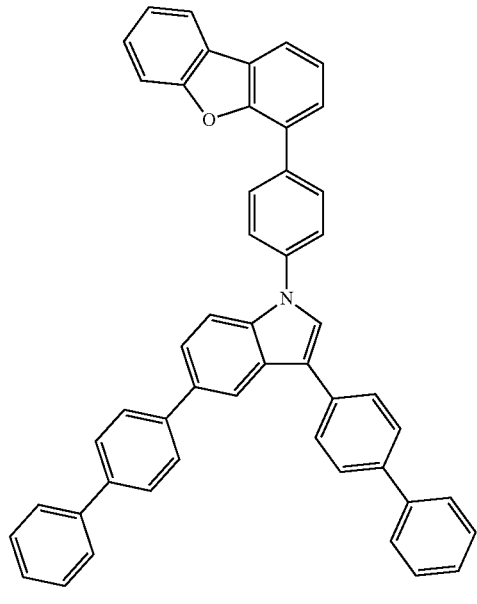
<b-6>
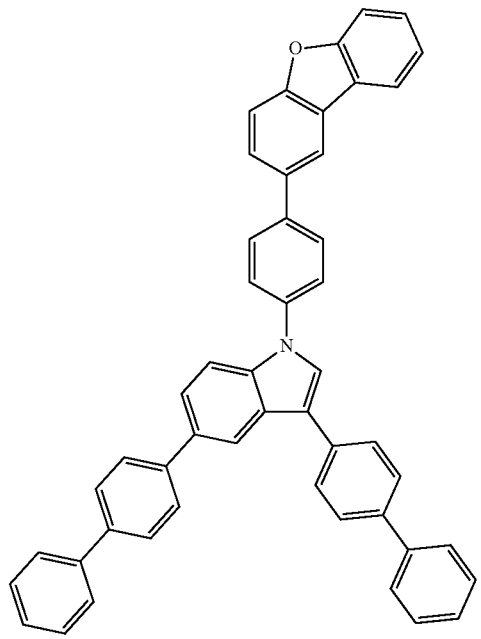
<b-7>
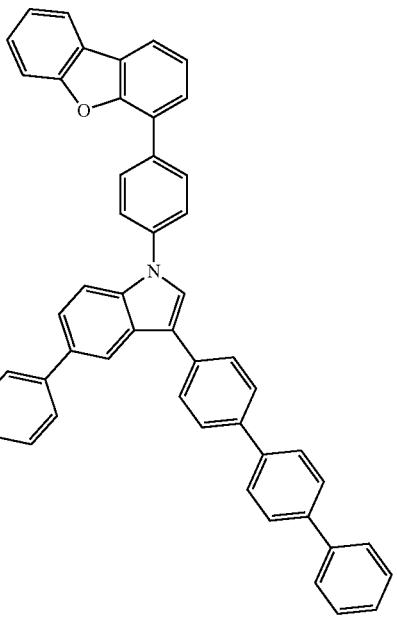
<b-8>
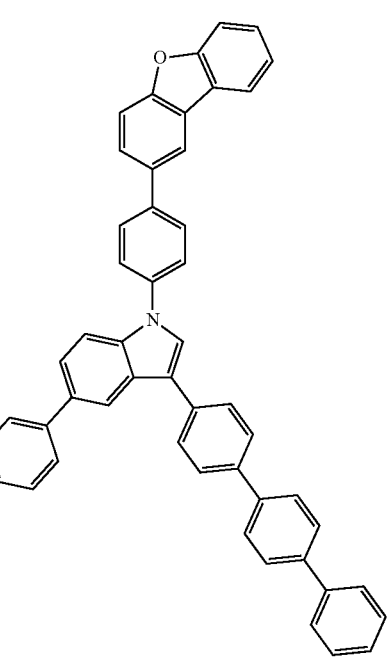

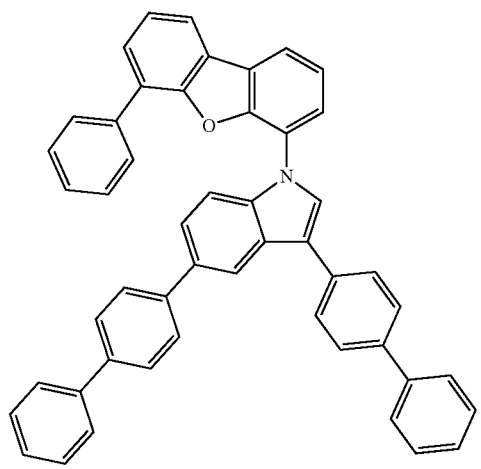
<b-9>
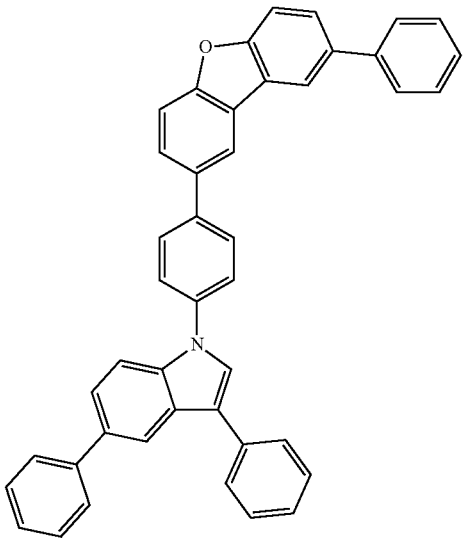
<b-12>
<b-10>
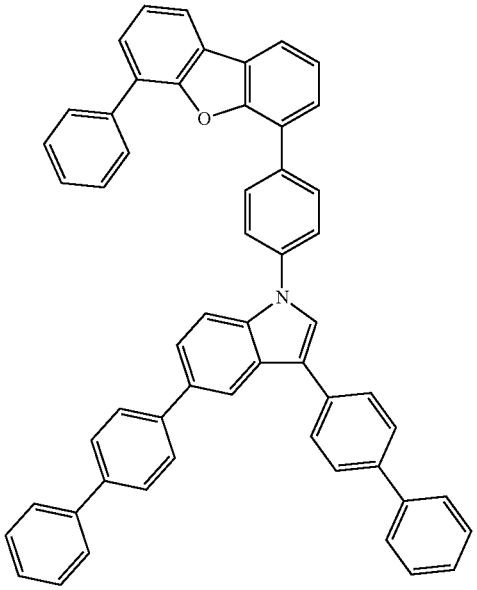
<b-11>
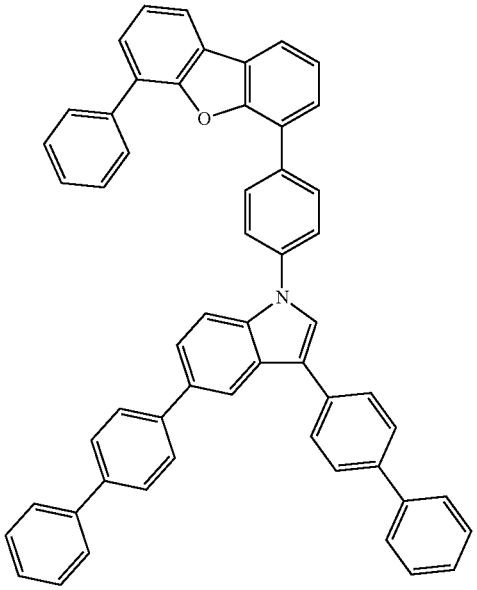
<b-13>

<b-14>
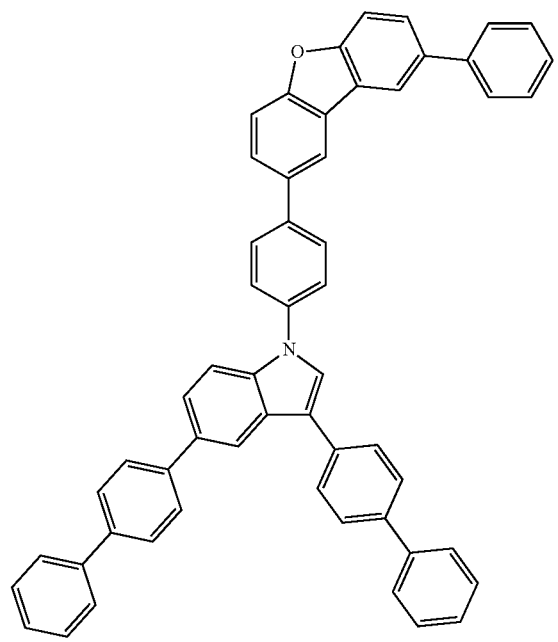
<b-16>
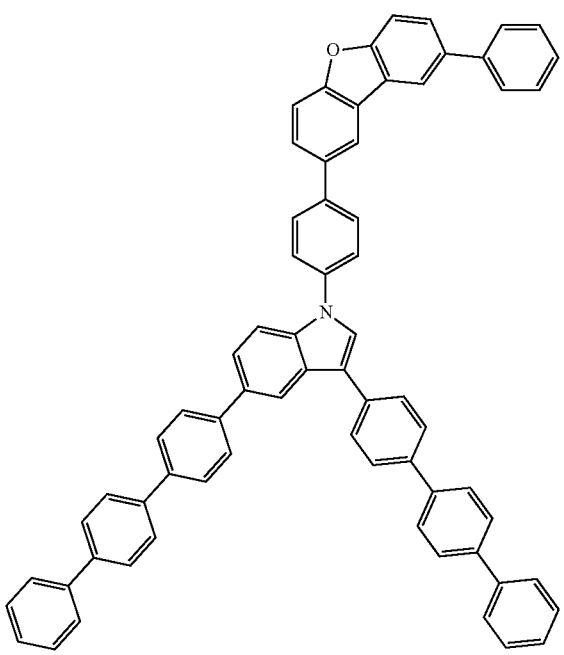
<b-17>
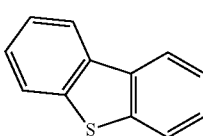
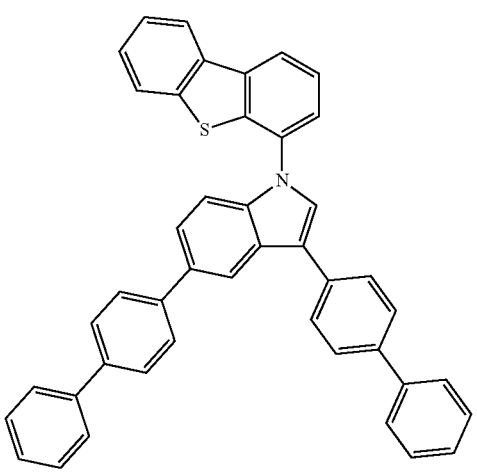
<b-15>
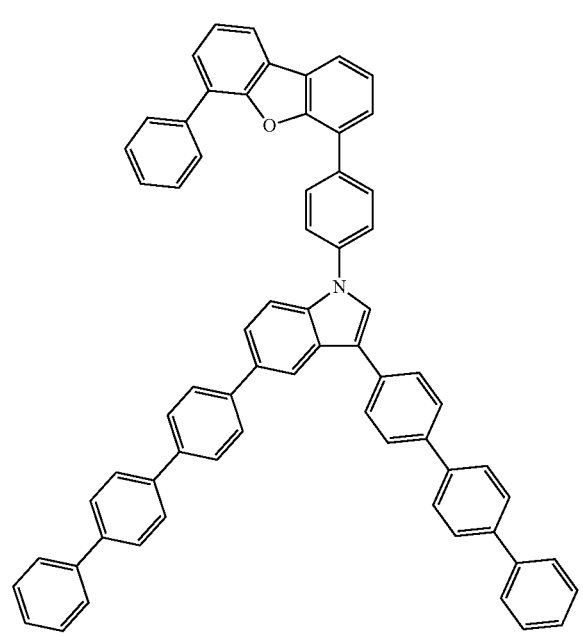
<b-18>
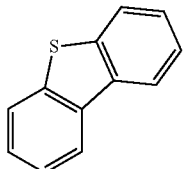

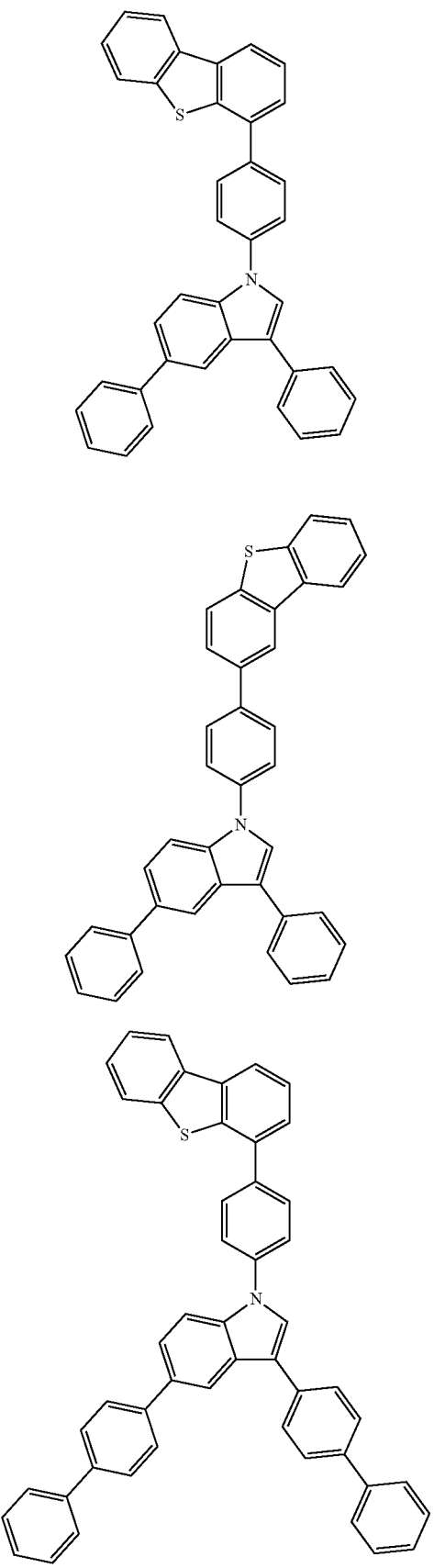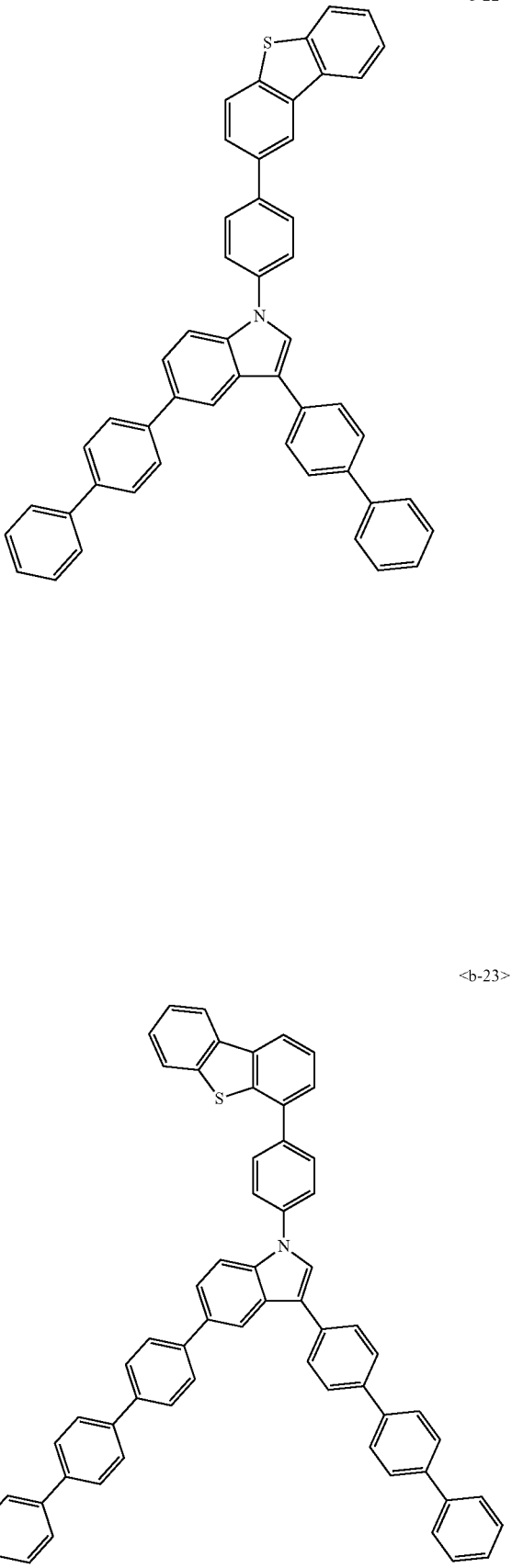

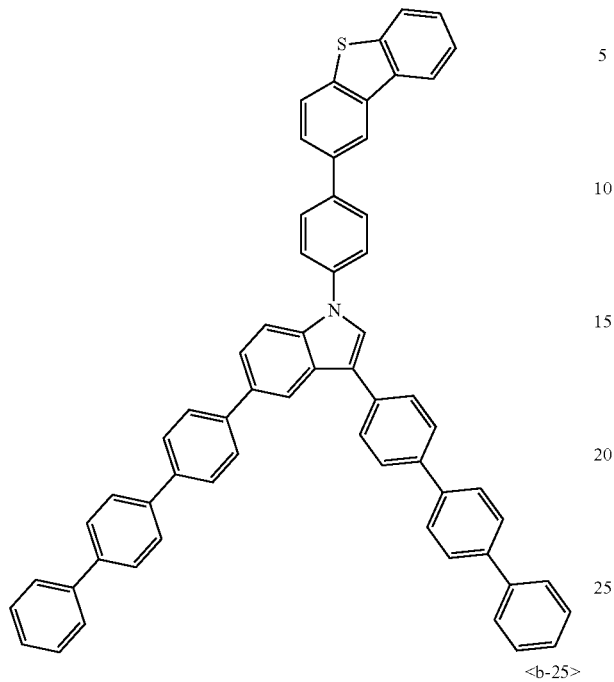

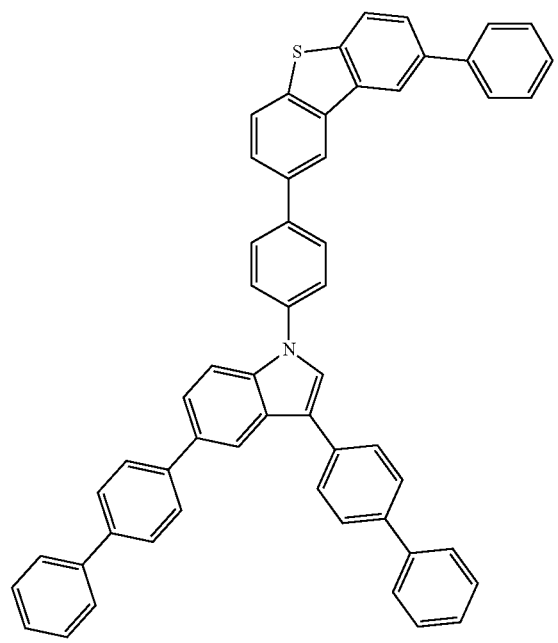
<b-30>
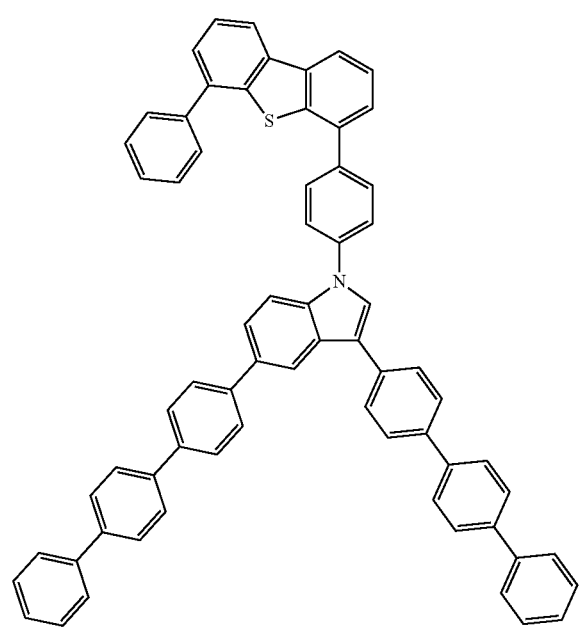
<b-31>
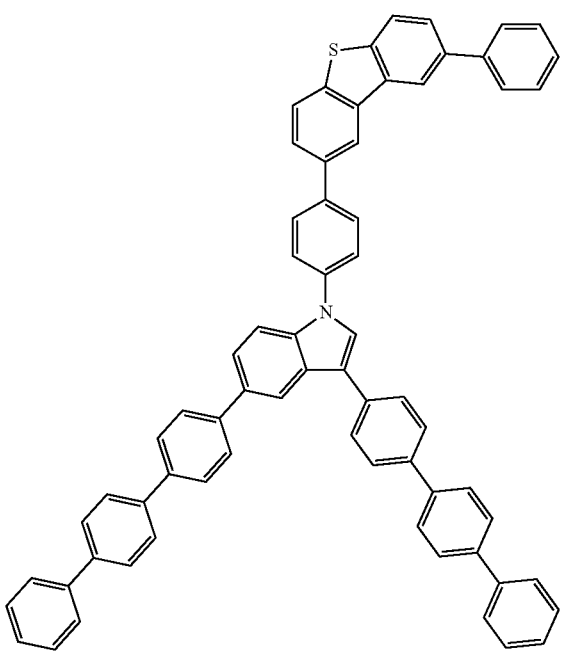
<b-32>
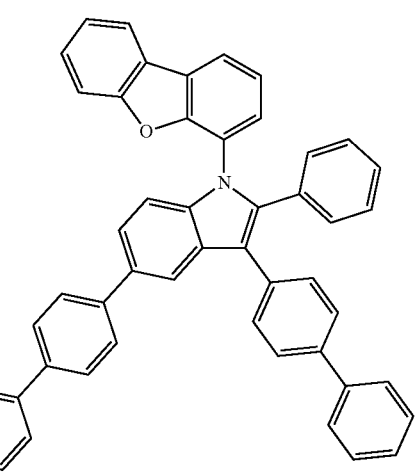
<b-33>
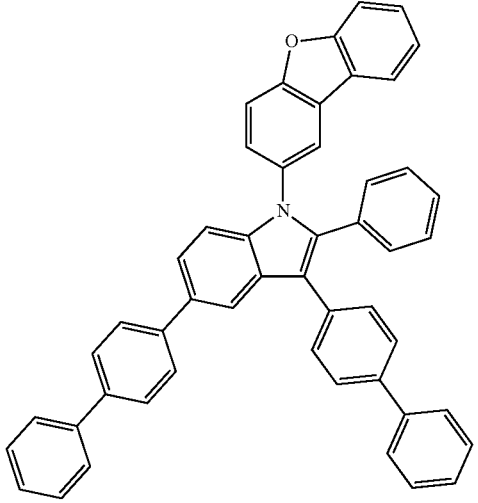
<b-34>

<b-35>
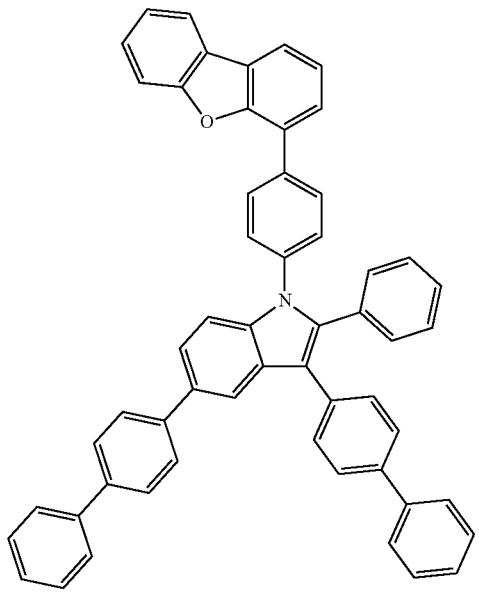
<b-36>
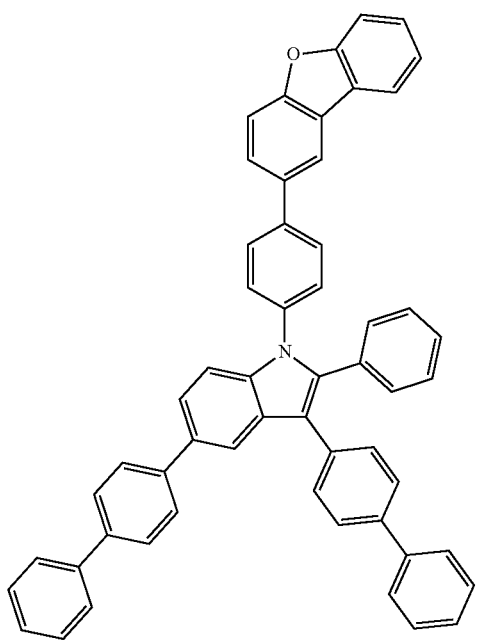
<b-37>
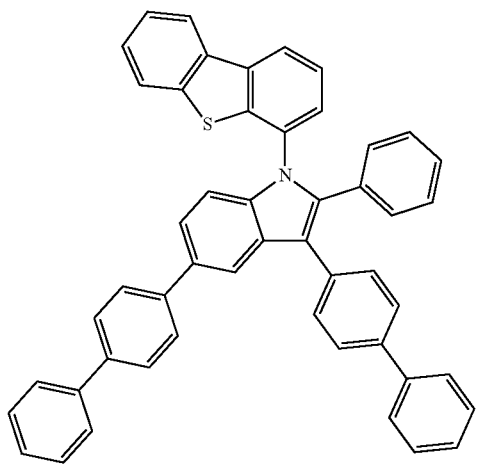
<b-38>
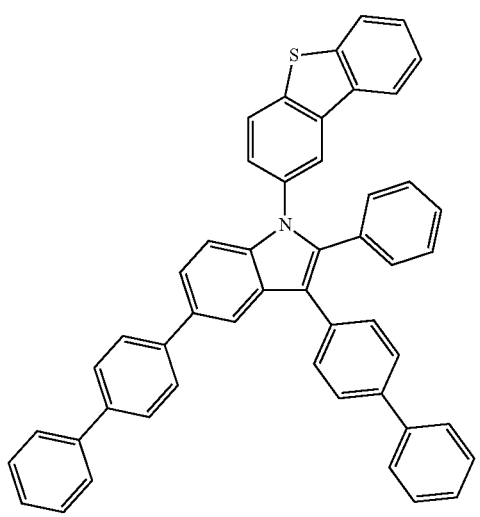
<b-39>
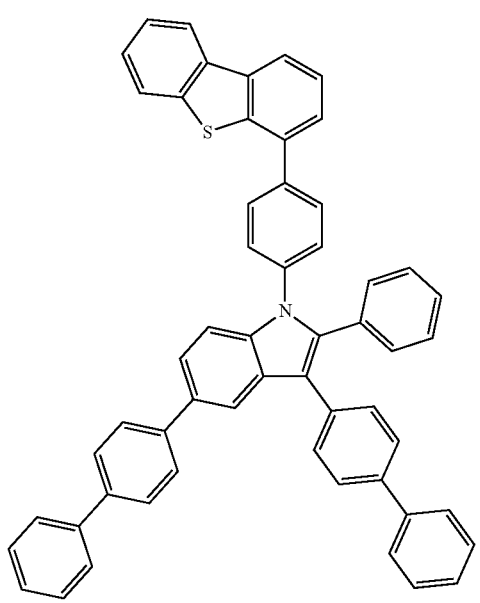

<b-40>
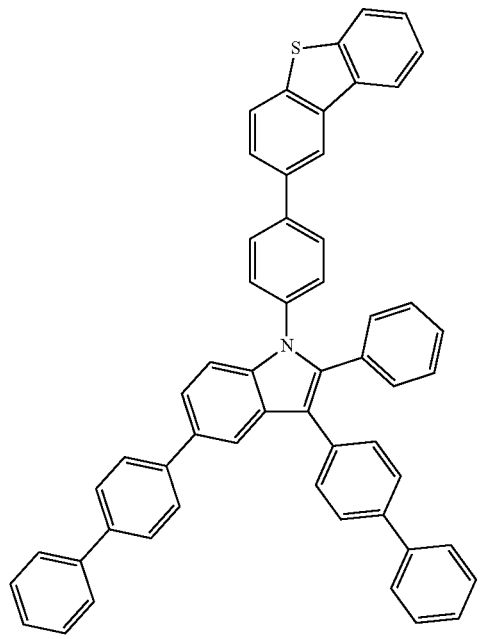
<b-41>
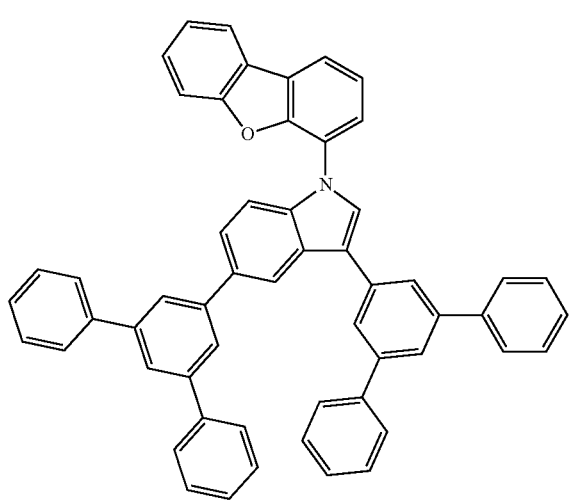
<b-42>
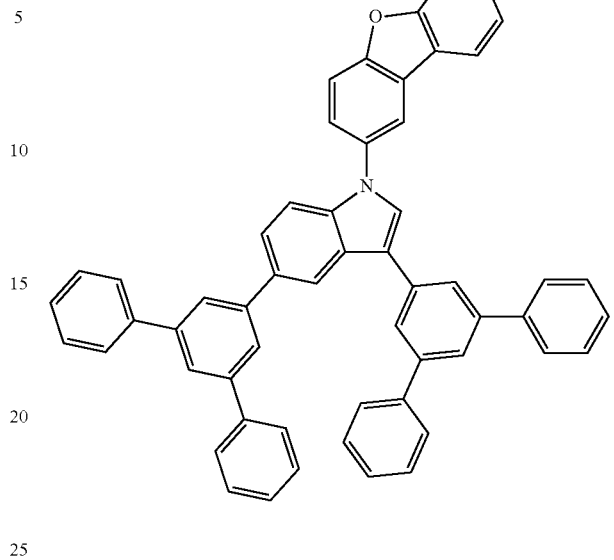
<b-43>
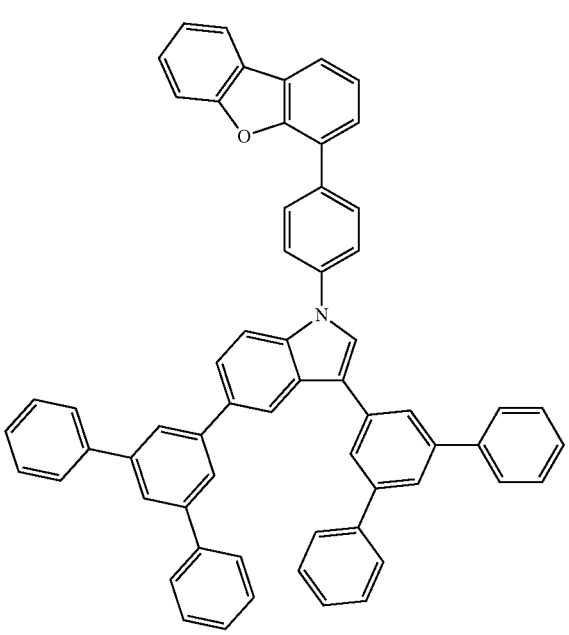

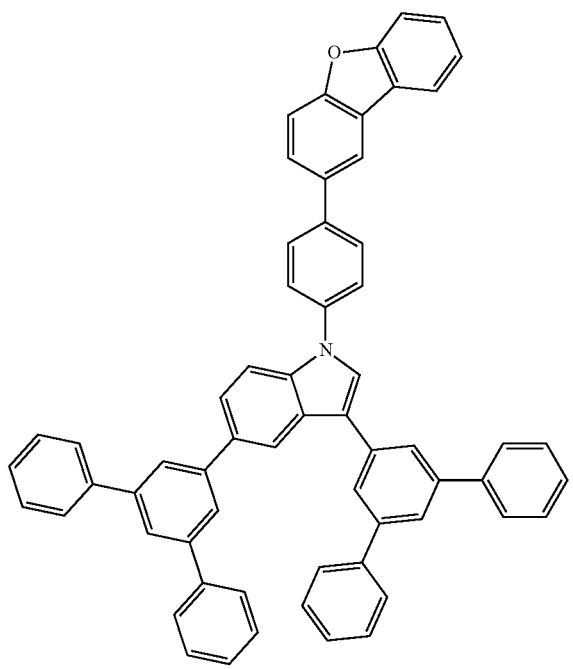
<b-44>
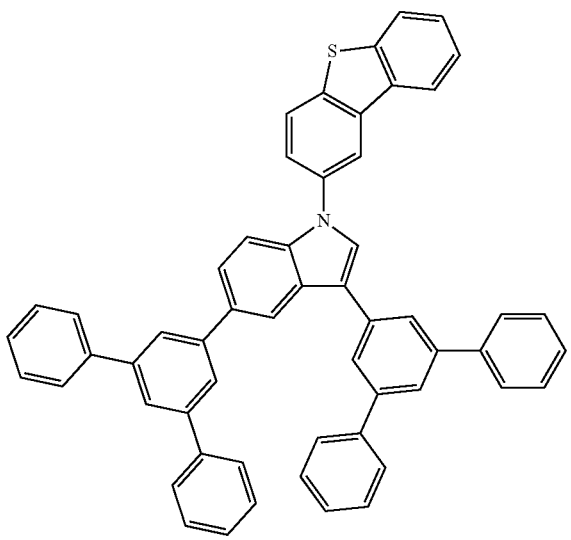
<b-46>
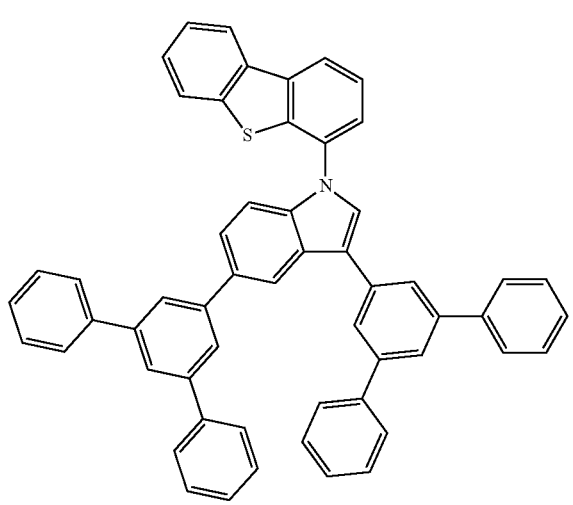
<b-45>
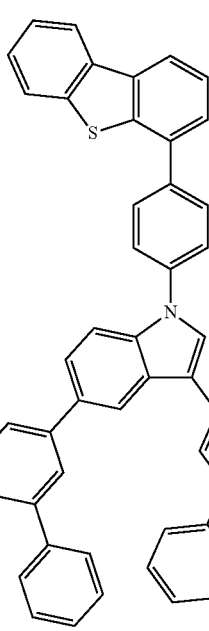
<b-47>

<b-48>
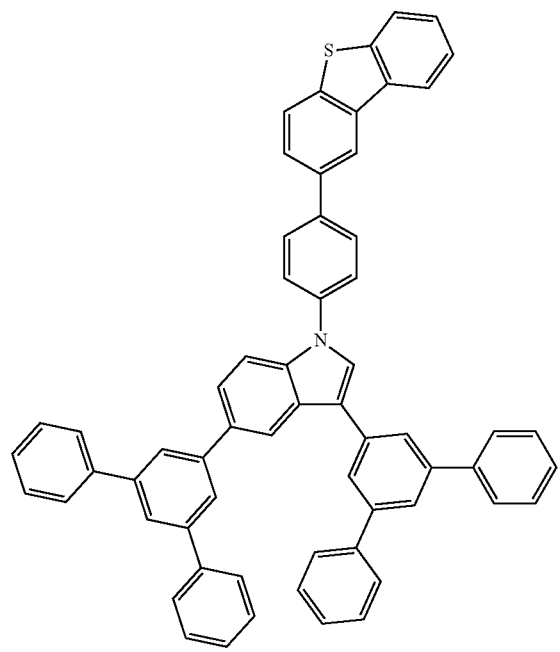
<c-2>
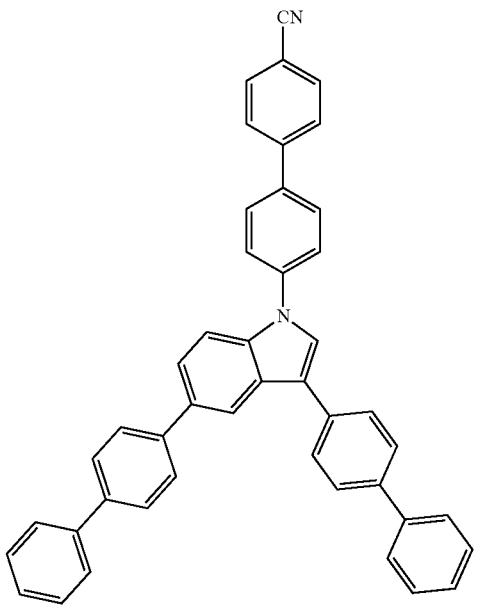
Furthermore, in the above Chemical Formula 1 according to the present invention, $Ar_1$ may be a trimethylsilyl group; a cyano group; a trifluoromethyl group; a fluoro group; or a phenyl group substituted with a methoxy group.
Specifically, the compound represented by Chemical Formula 1 may have a structure of any one of the chemical formula of c-1 to c-20 below.
<c-1>
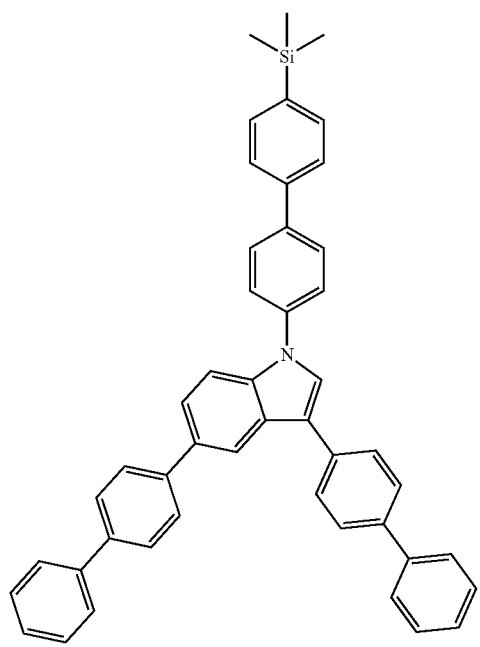
<c-3>
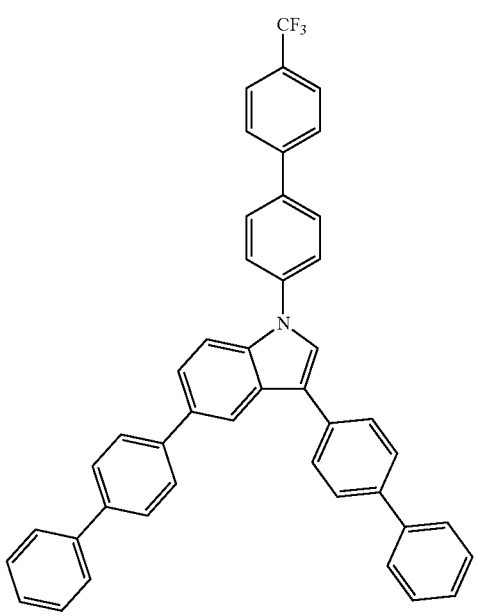

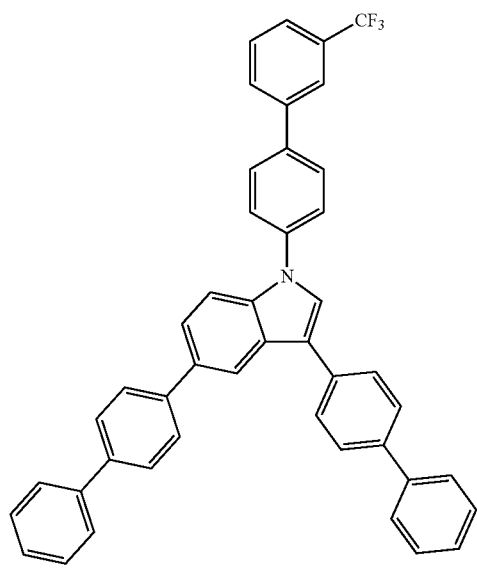
<c-4>
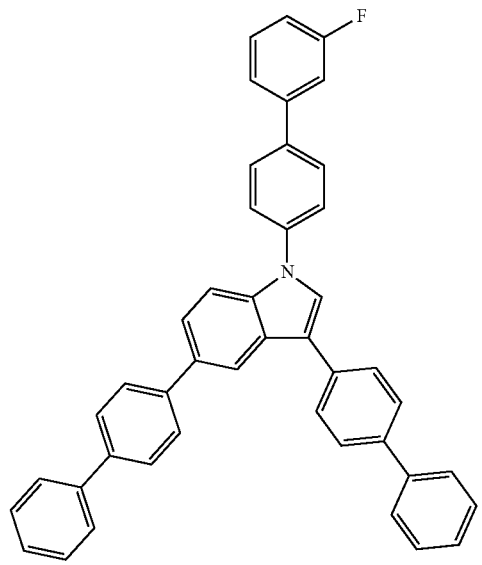
<c-6>
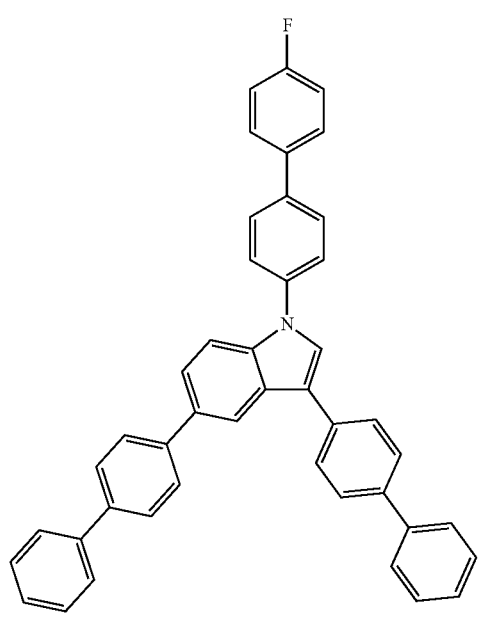
<c-5>
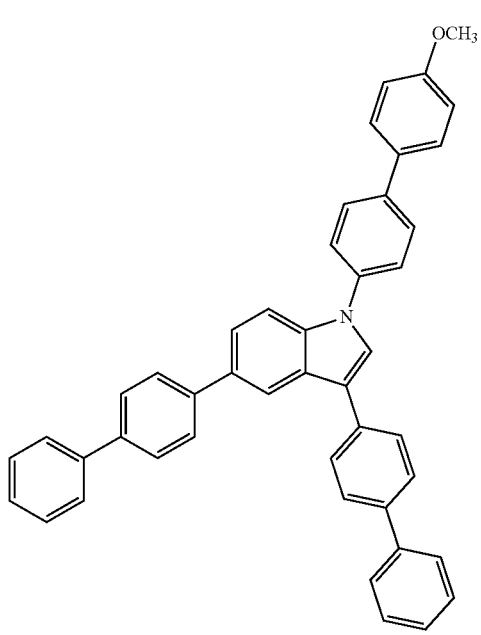
<c-7>

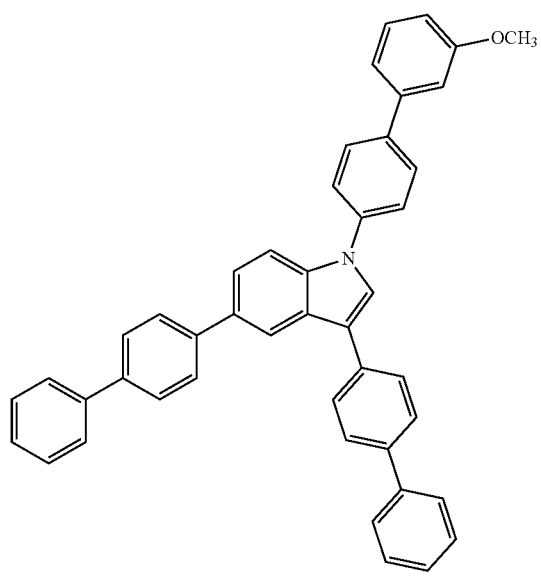
<c-8>
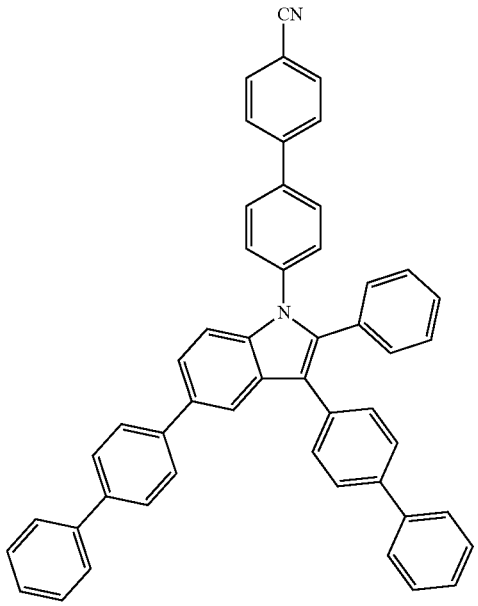
<c-10>
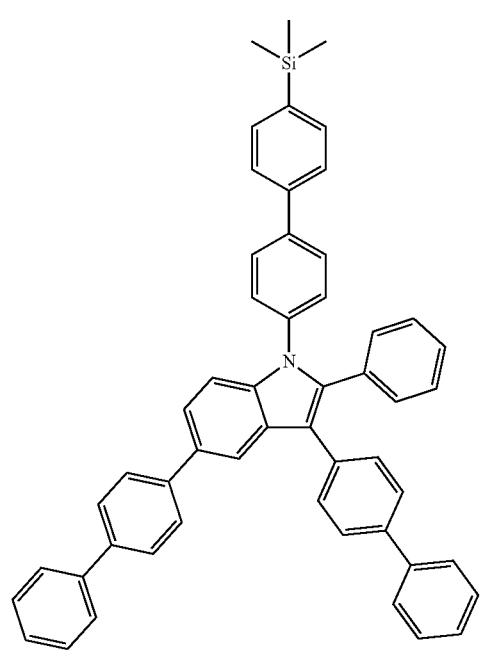
<c-9>
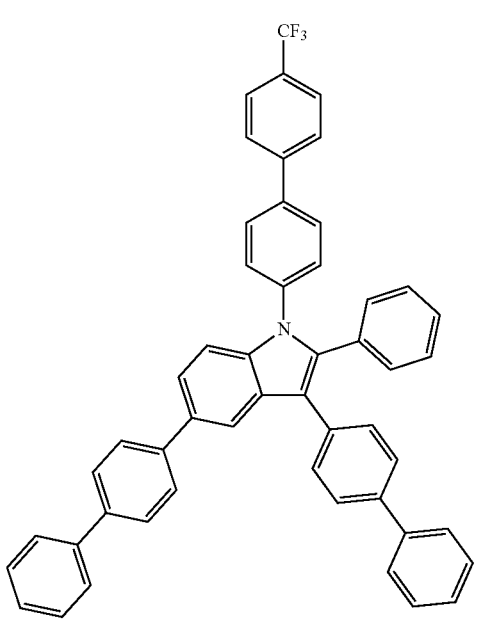
<c-11>

-continued
<c-12>
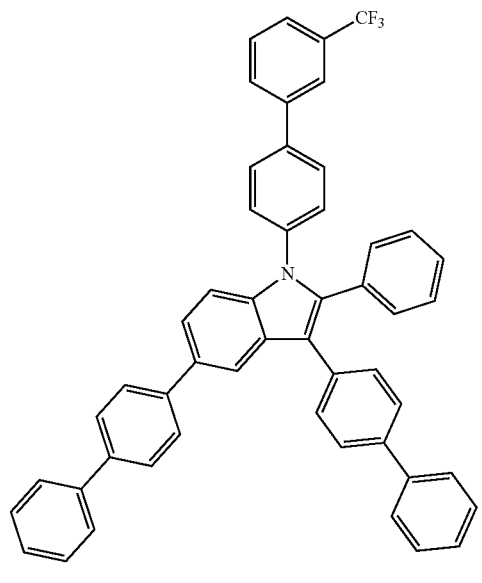
<c-14>
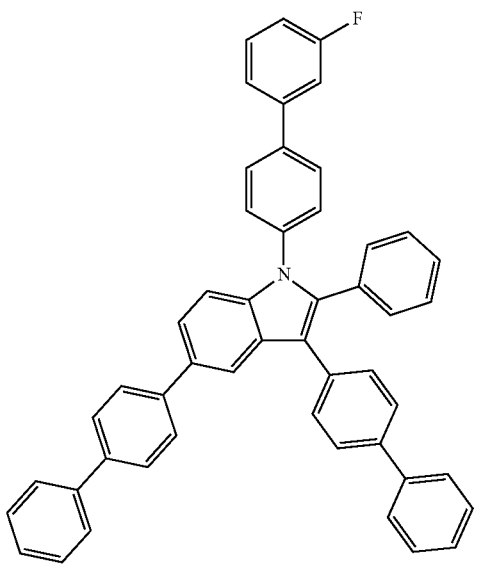
<c-13>
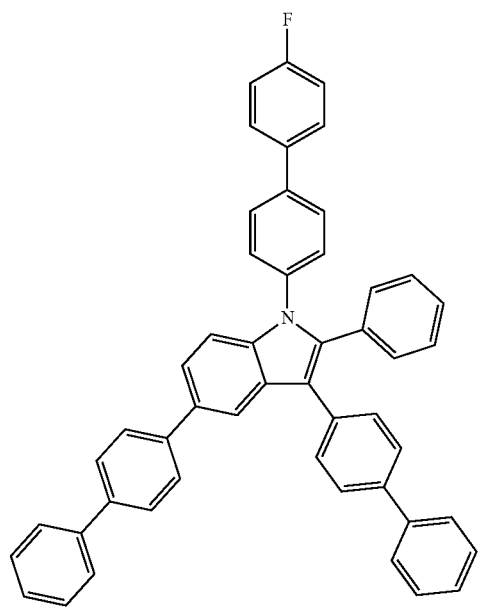
<c-15>
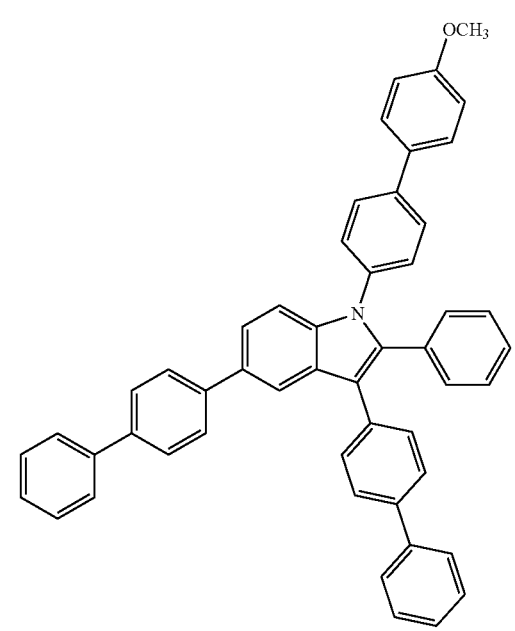

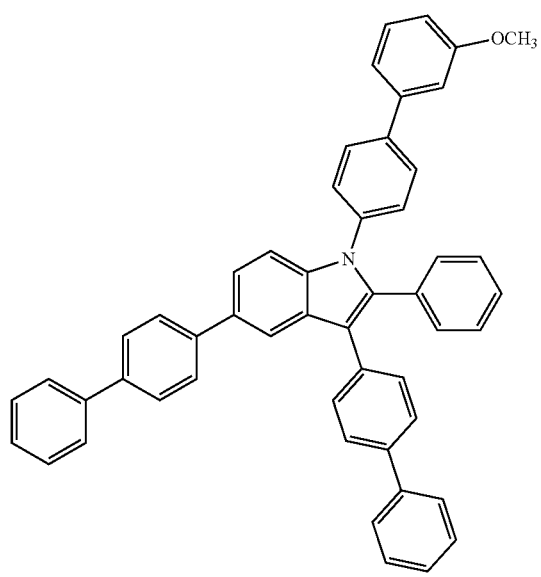
<c-16>
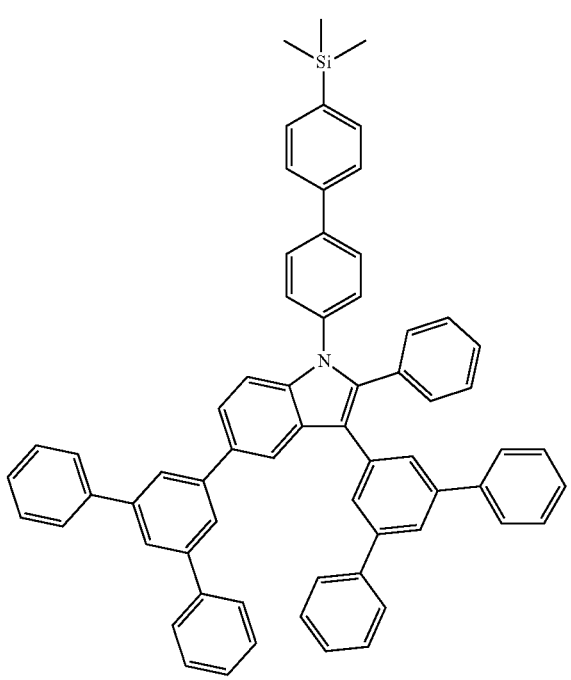
<c-18>
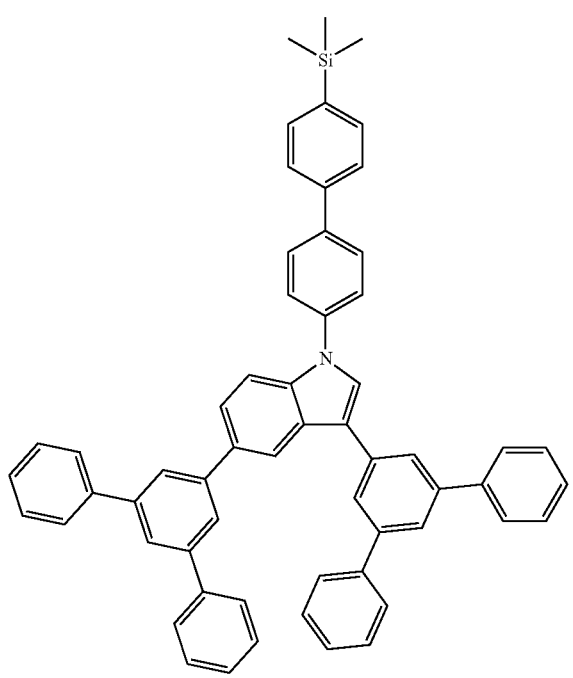
<c-17>
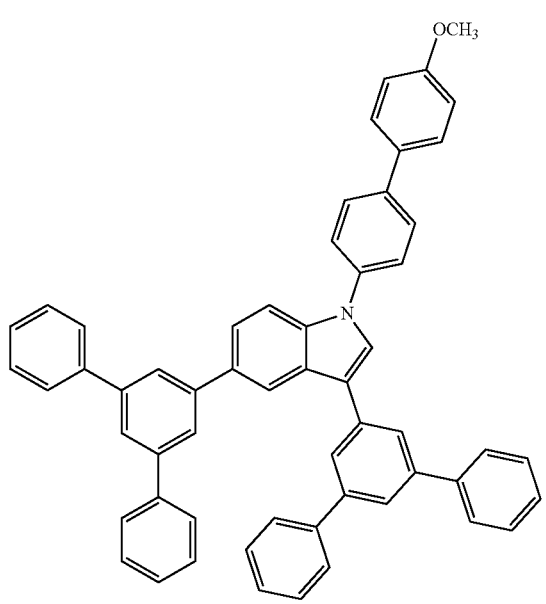
<c-19>

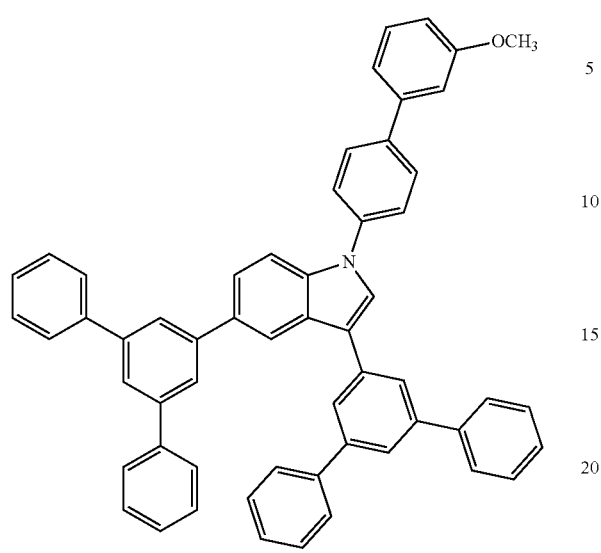
<c-20>

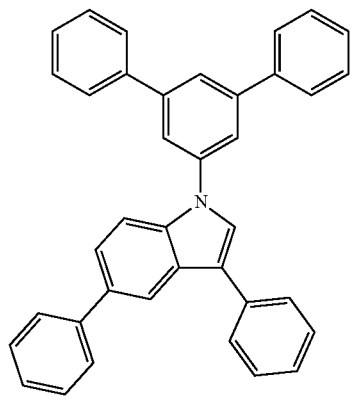
<d-1>

As another example, in the above Chemical Formula 1 according to the present invention,
Ar₁ may be a structure of Chemical Formula 2 below,
L₁ may be a single bond or a phenylene group,
L₂ and L₃ may be each independently a single bond; or a phenylene group which is unsubstituted or substituted with a phenyl group,
Ar₂ and Ar₃ may be each independently a phenyl group, a naphthyl group, or a phenanthryl group, and here, the phenyl group may be unsubstituted or substituted with a phenyl group, a biphenyl group, a naphthyl group, or a phenanthryl group, and
Y may be hydrogen, a phenyl group, or a biphenyl group.

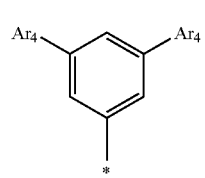

[Chemical Formula 2]

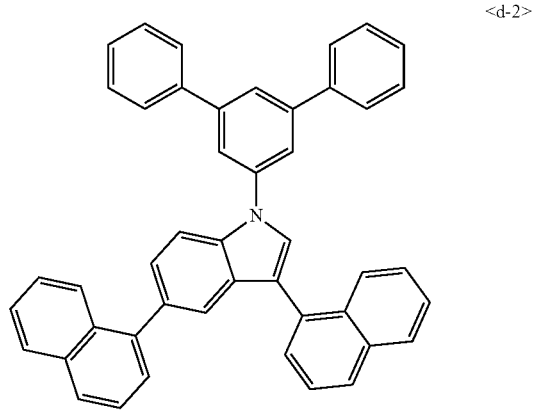
<d-2>

In the above Chemical Formula 2,
Ar₄ is an aryl group having 6 to 30 carbon atoms or a heteroaryl group having 2 to 20 carbon atoms, which is unsubstituted or substituted with one or more substituents selected from the group consisting of an alkyl group having 1 to 4 carbon atoms, Si(R₂)₃, a cyano group, a halogen group, a haloalkyl group having 1 to 6 carbon atoms, an alkoxy group having 1 to 6 carbon atoms, and an aryl group having 6 to 30 carbon atoms, and here, R₂ is an alkyl group having 1 to 4 carbon atoms.

In this case, in the above Chemical Formula 1 according to the present invention, Ar₄ may be a phenyl group, a biphenyl group, a naphthyl group or a phenanthryl group, which is unsubstituted or substituted with one or more substituents selected from the group consisting of a trimethylsilyl group, a cyano group, a trifluoromethyl group, a fluoro group, and a methoxy group.

Specifically, the compound represented by Chemical Formula 1 may have a structure of any one of the chemical formula of d-1 to d-37 below.

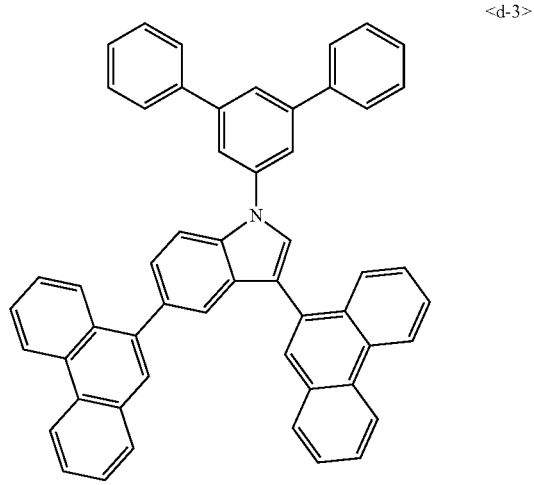
<d-3>

<d-4>
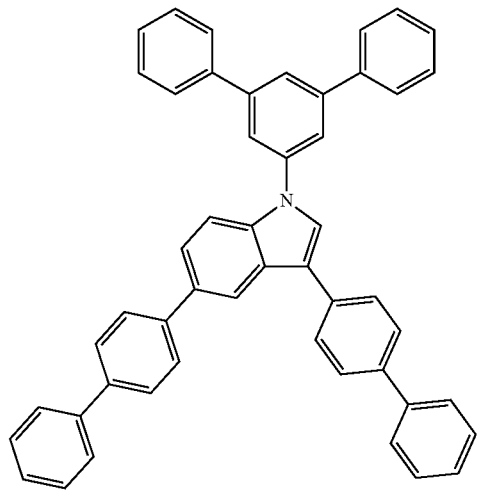
<d-5>
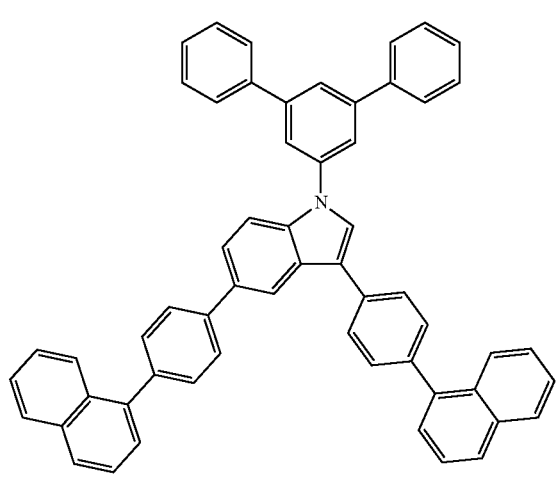
<d-6>
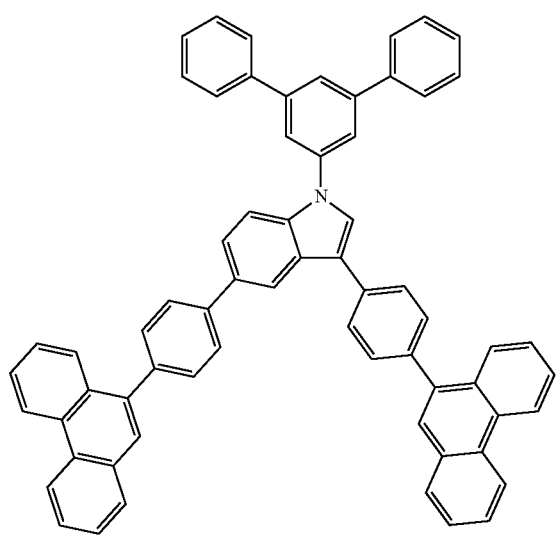
<d-7>
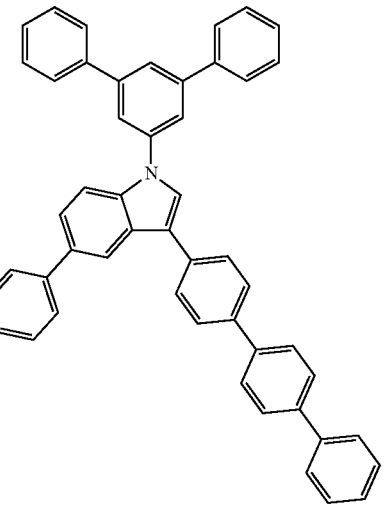
<d-8>
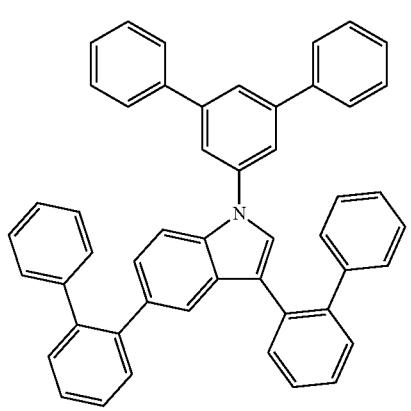
<d-9>
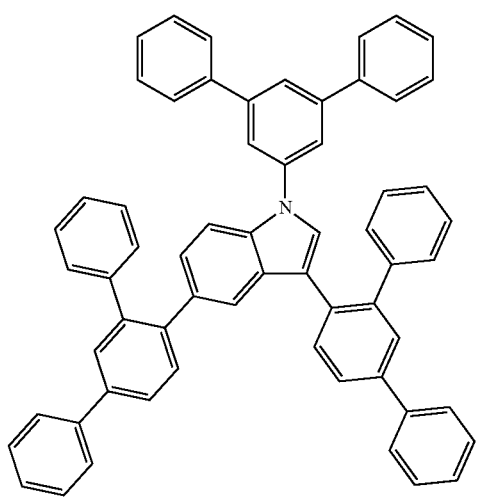

<d-10>
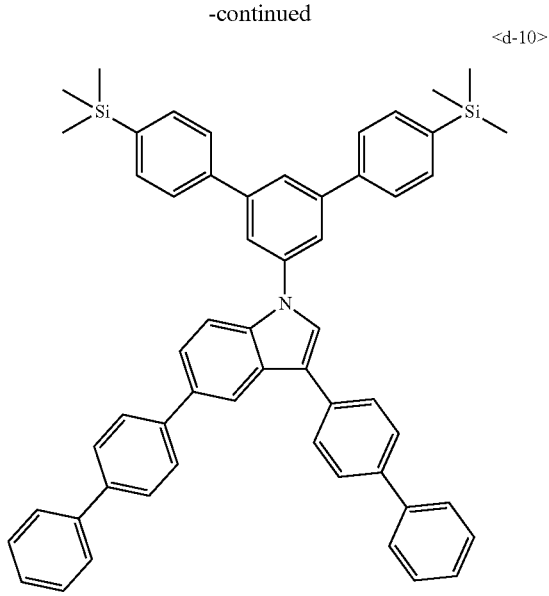
<d-11>
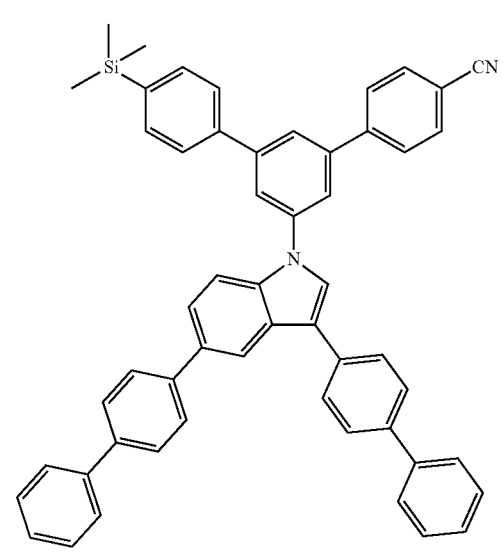
<d-12>
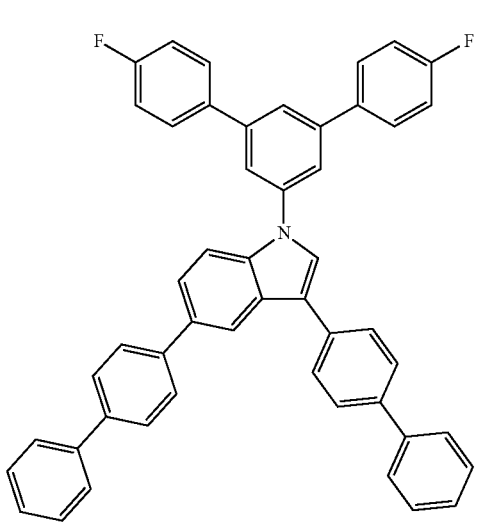
<d-13>
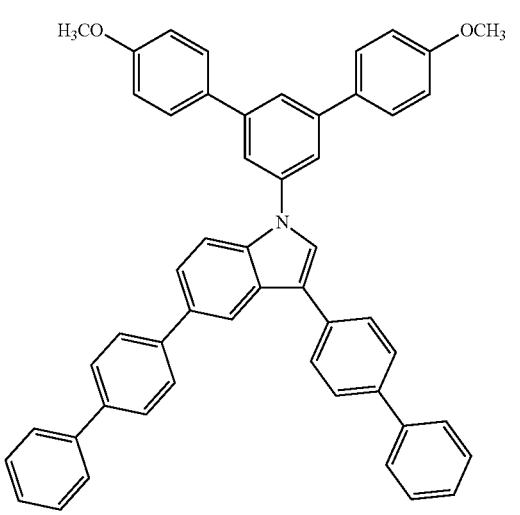
<d-14>
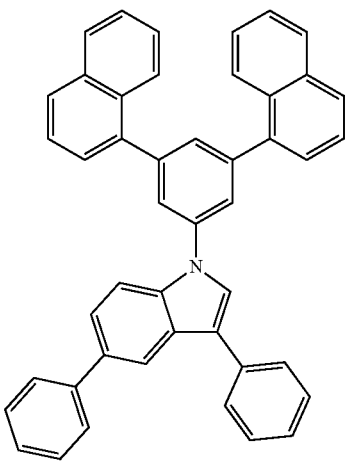
<d-15>
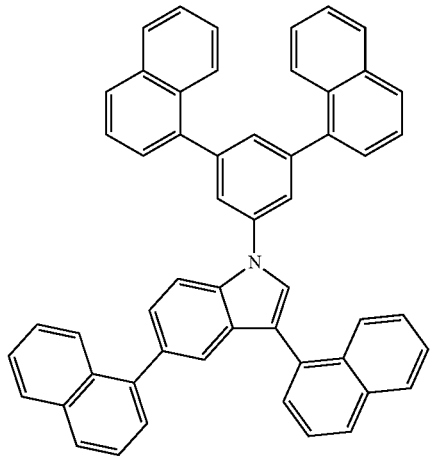

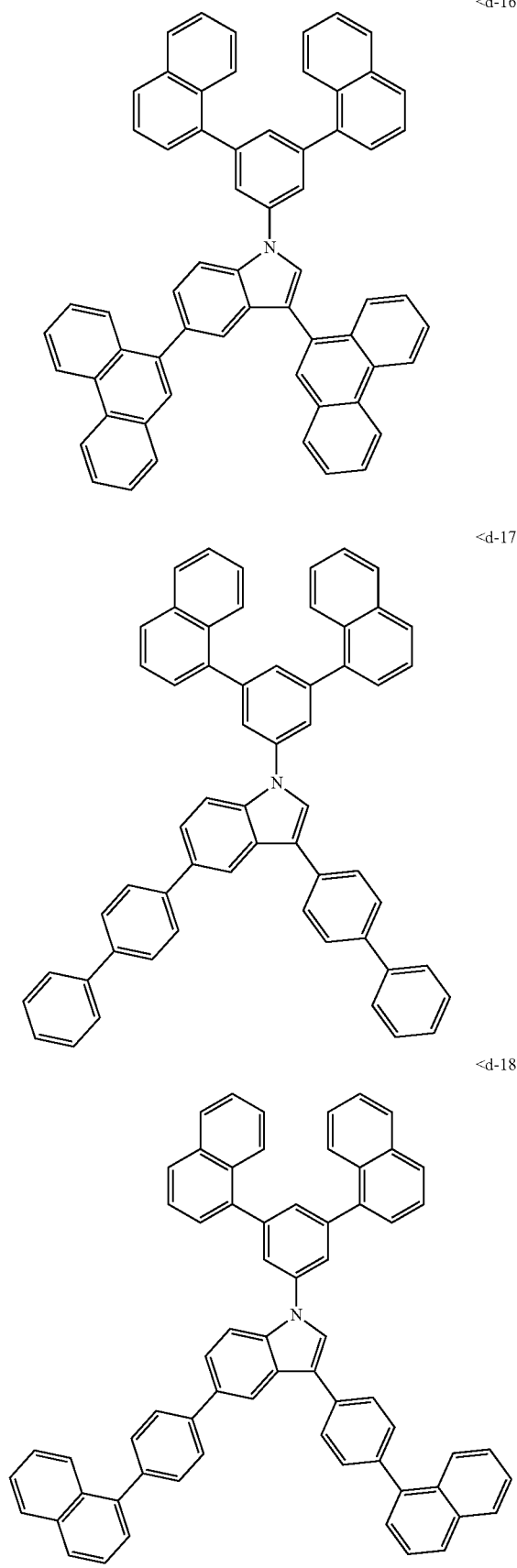
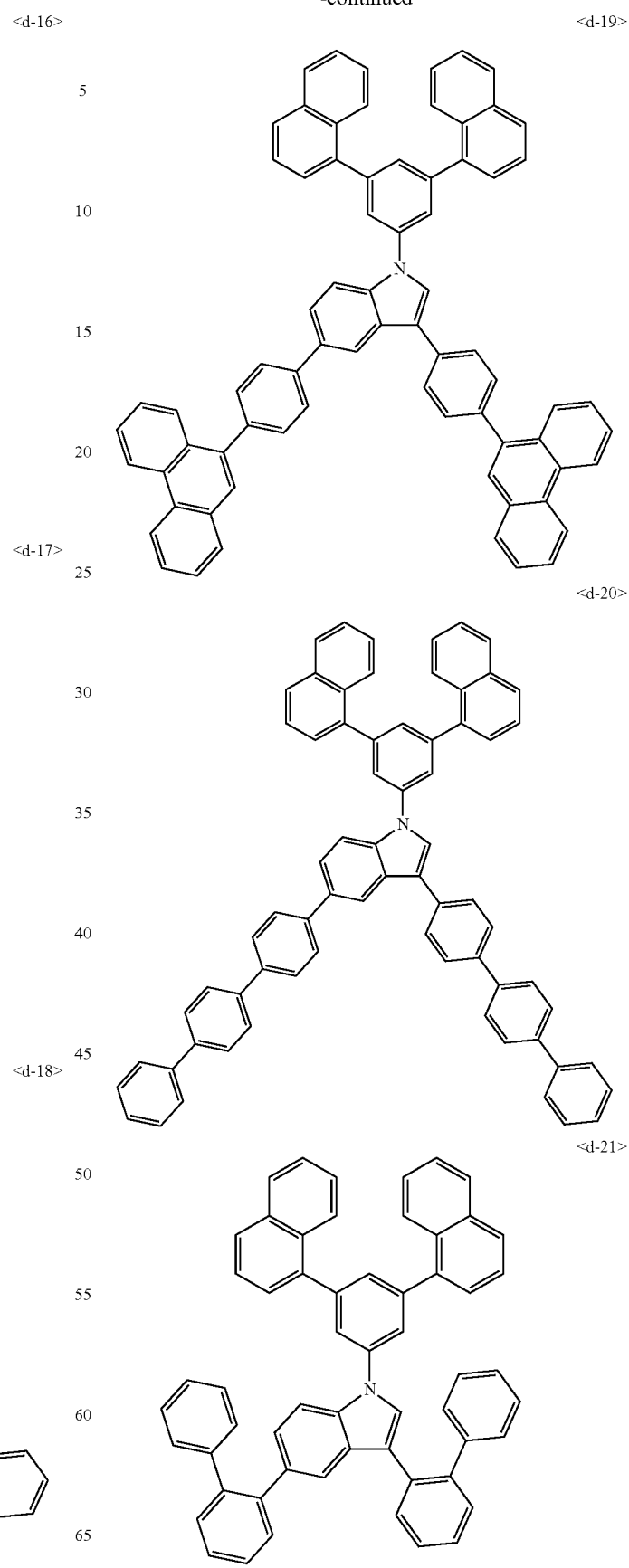

<d-22>
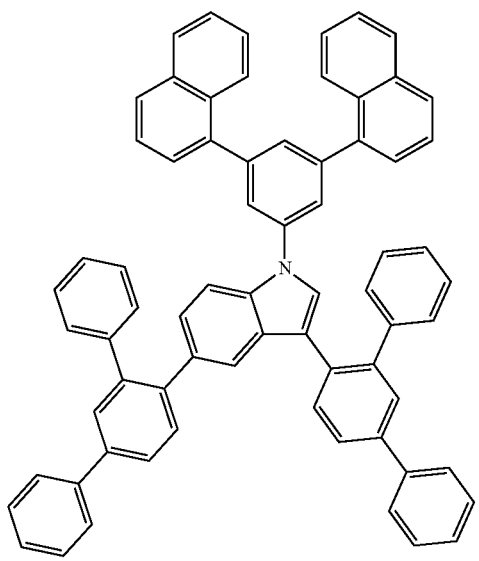
<d-23>
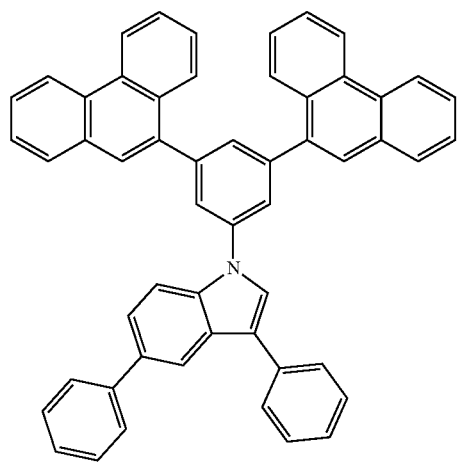
<d-24>
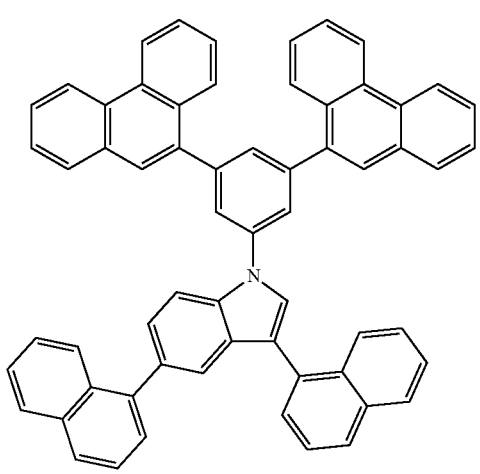
<d-25>
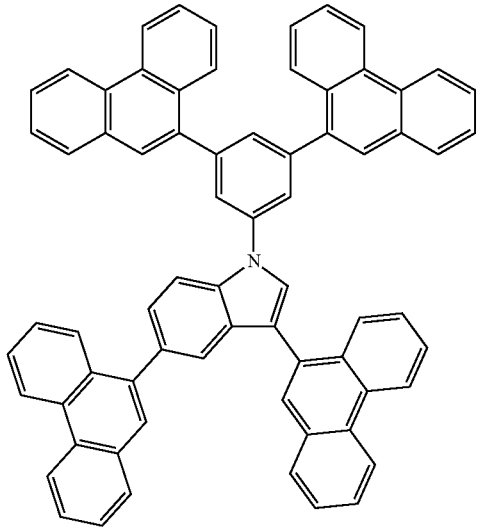
<d-26>
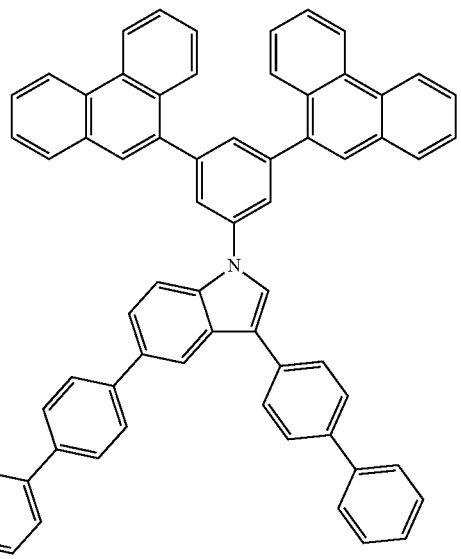
<d-27>
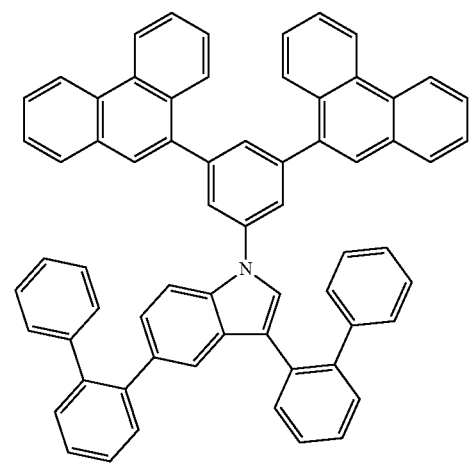

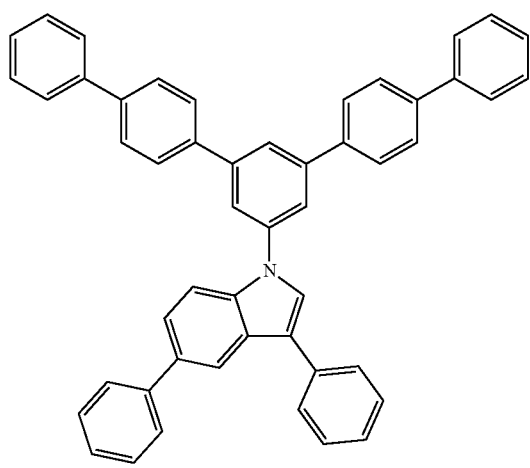
<d-28>
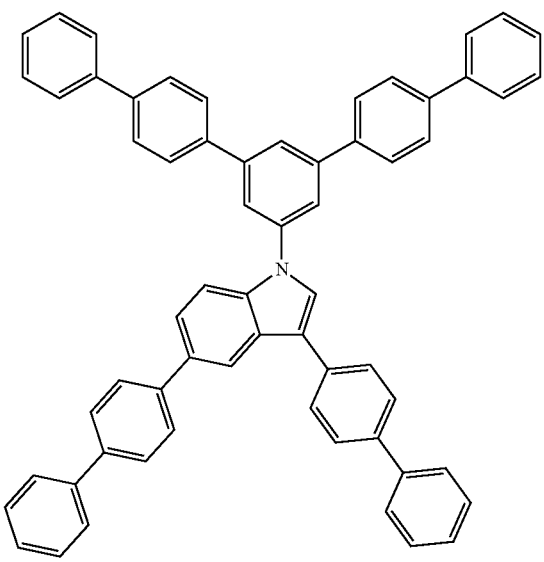
<d-31>
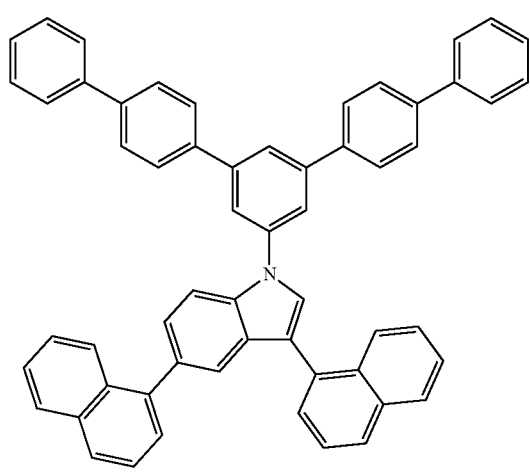
<d-29>
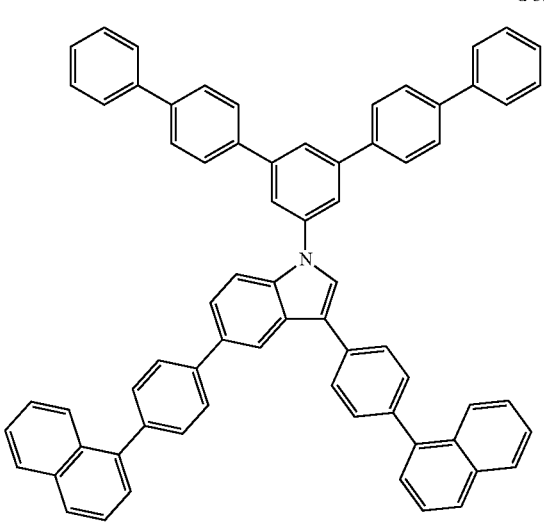
<d-32>
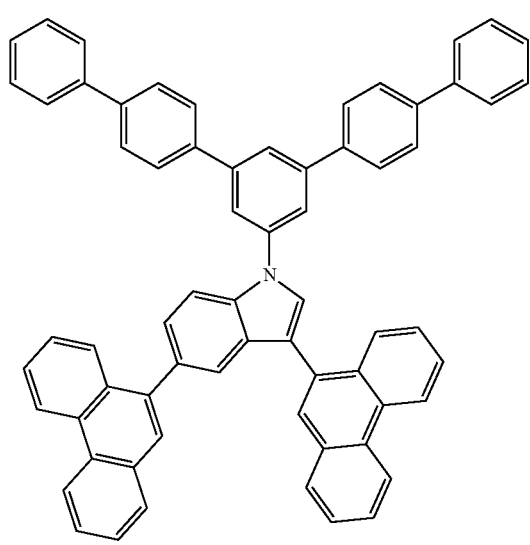
<d-30>
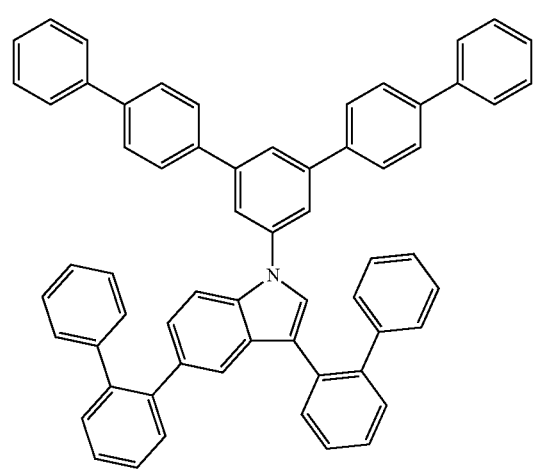
<d-33>

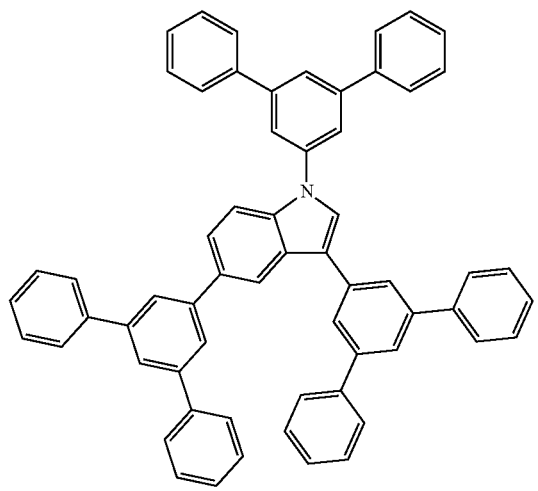
<d-34>
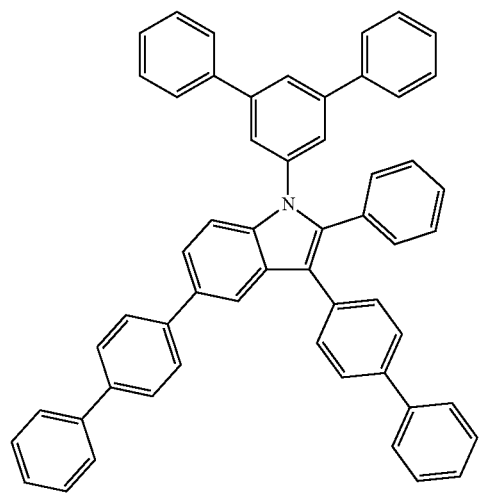
<d-37>
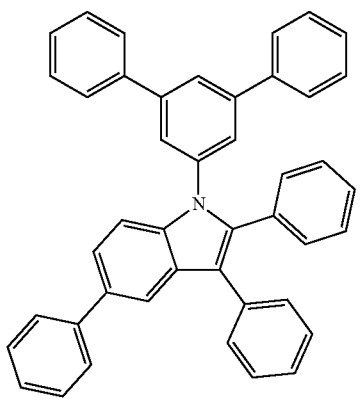
<d-35>
<d-36>
Further, in the above Chemical Formula 1 according to the present invention,
Ar$_4$ may be a dibenzofuranyl group or a dibenzothiophenyl group.
Specifically, the compound represented by Chemical Formula 1 may have a structure of any one of the chemical formula of e-1 to e-16 below.
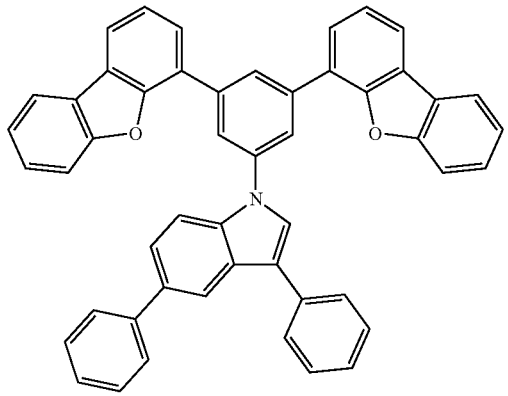
<e-1>
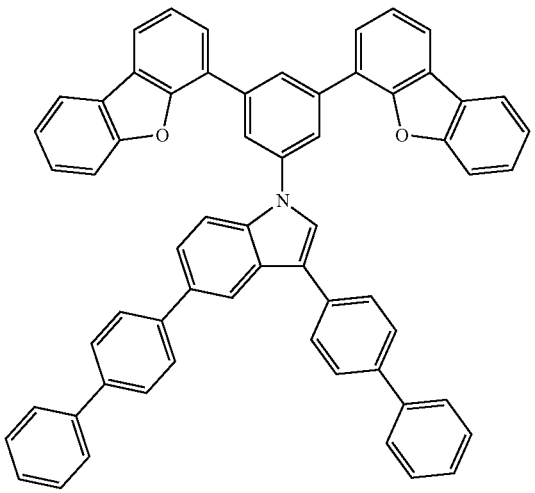
<e-2>

-continued
<e-3>
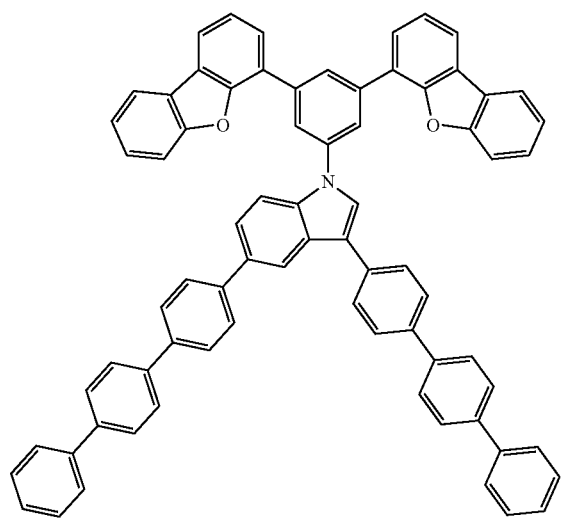
<e-6>
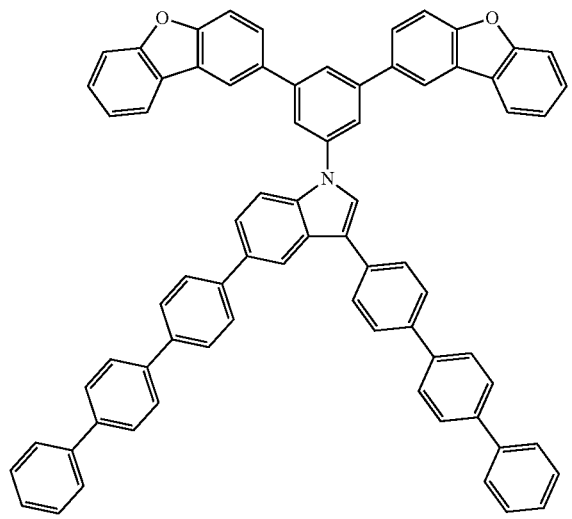
<e-4>
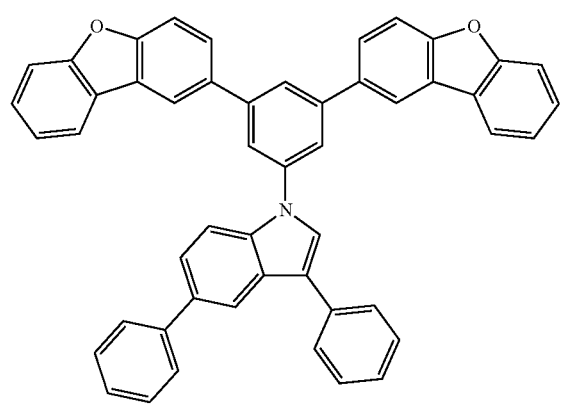
<e-7>
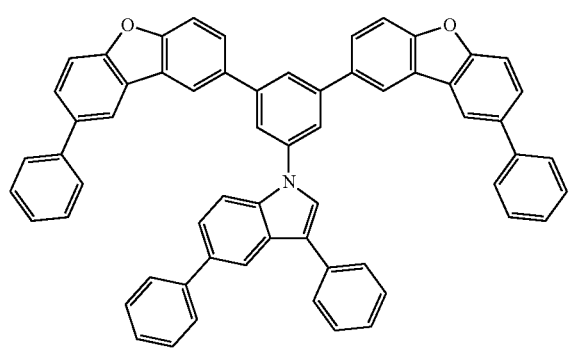
<e-5>
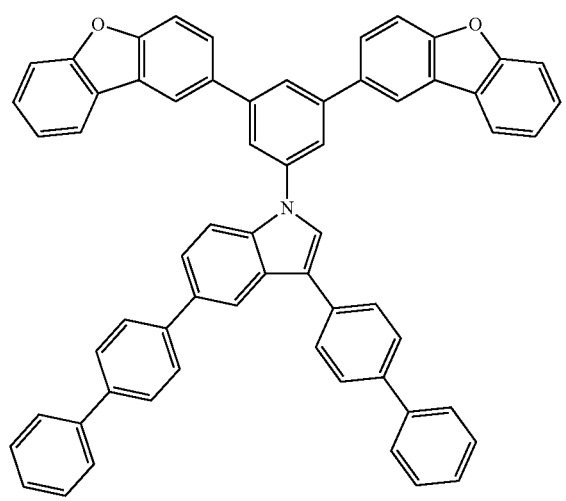
<e-8>
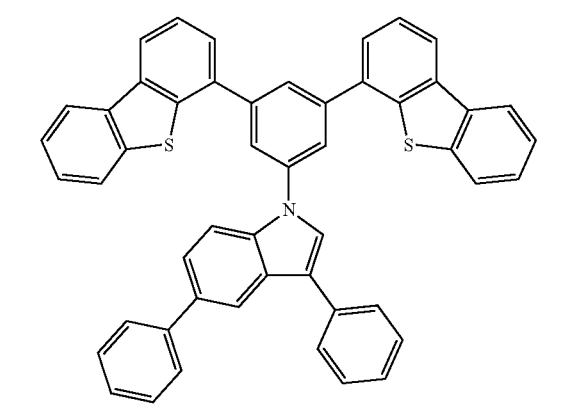

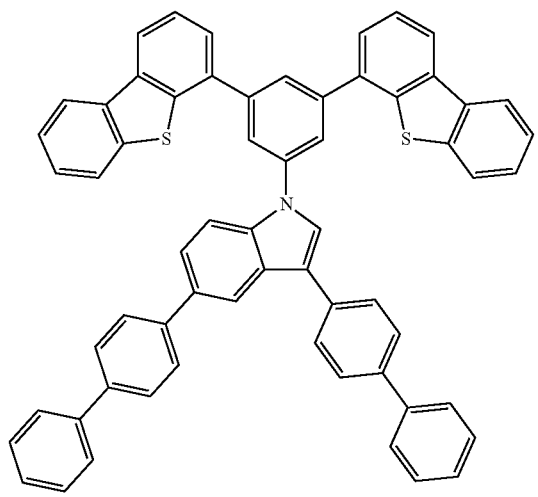
<e-9>
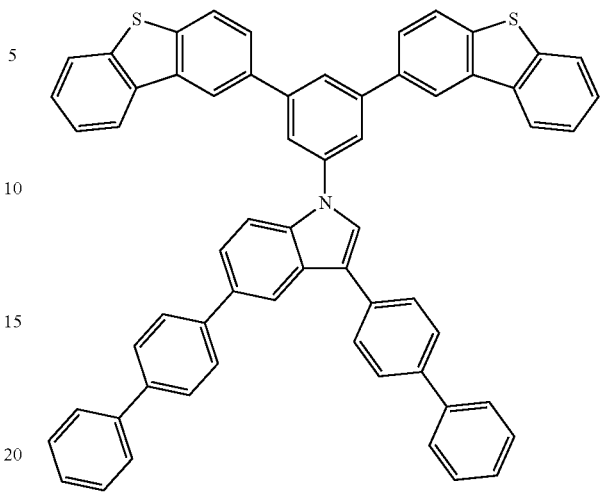
<e-12>
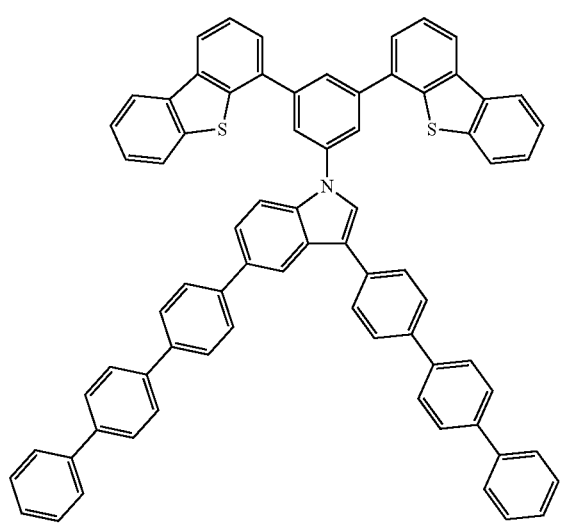
<e-10>
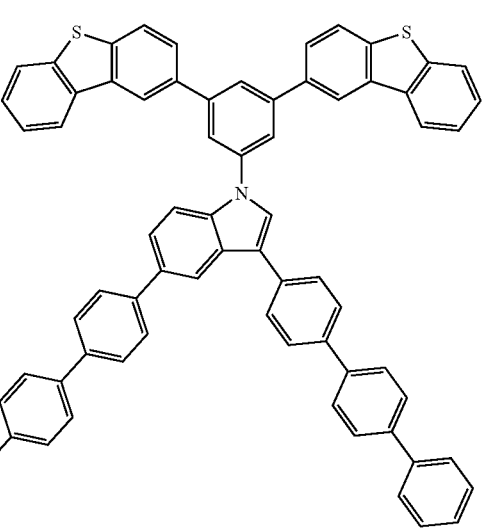
<e-13>
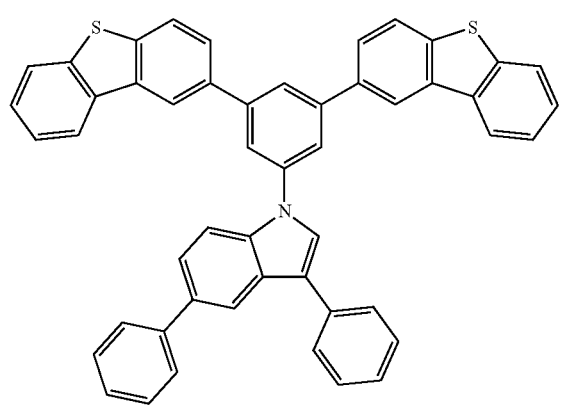
<e-11>
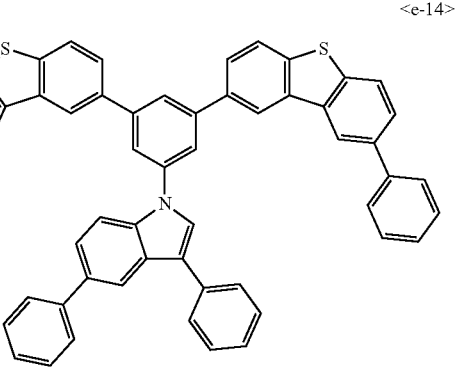
<e-14>

-continued

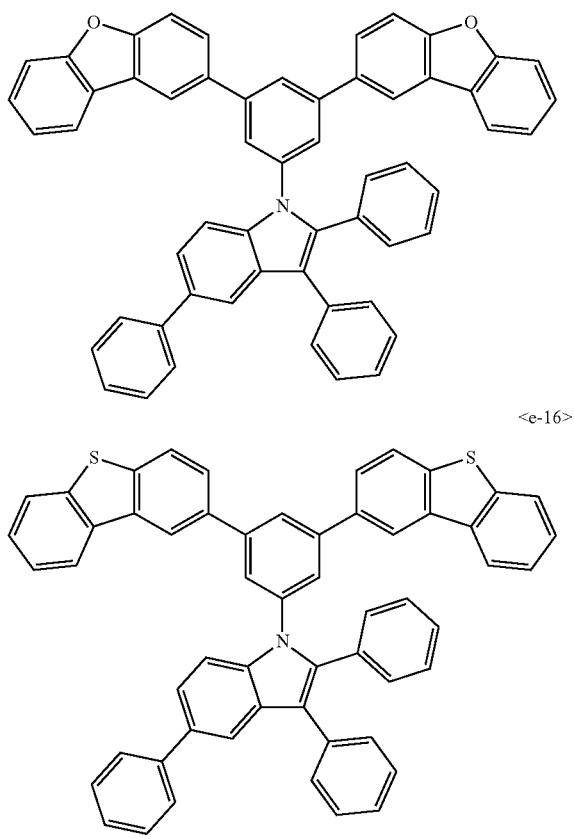

<e-15>

<e-16>

As another example, in the above Chemical Formula 1 according to the present invention,
Ar₁ may be a structure of Chemical Formula 3 below,
L₁ may be a single bond,
L₂ and L₃ may be each independently a single bond, or a phenylene group, which is unsubstituted or substituted with a phenyl group,
Ar₂ and Ar₃ may be each independently a phenyl group, a naphthyl group, or a phenanthryl group, and here, the phenyl group may be unsubstituted or substituted with a phenyl group, a biphenyl group, a naphthyl group, or a phenanthryl group, and
Y may be hydrogen, a phenyl group, or a biphenyl group.

[Chemical Formula 3]

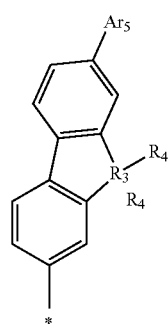

In the above Chemical Formula 3,
R₃ is a carbon atom or a silicon atom;
R₄ is hydrogen, an alkyl group having 1 to 4 carbon atoms, or an aryl group having 6 to 10 carbon atoms; and
Ar₅ is hydrogen or an aryl group having 6 to 30 carbon atoms.

In this case, in Chemical Formula 1 according to the present invention,
R₃ may be a carbon atom, and
Ar₅ may be hydrogen or a phenyl group.

Specifically, the compound represented by Chemical Formula 1 may have a structure of any one of the chemical formula of f-1 to f-31 below.

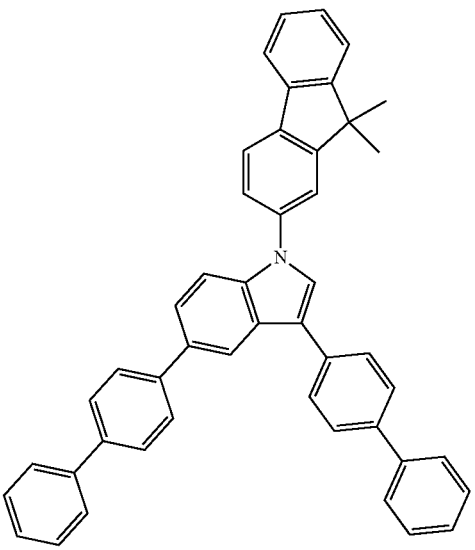

<f-1>

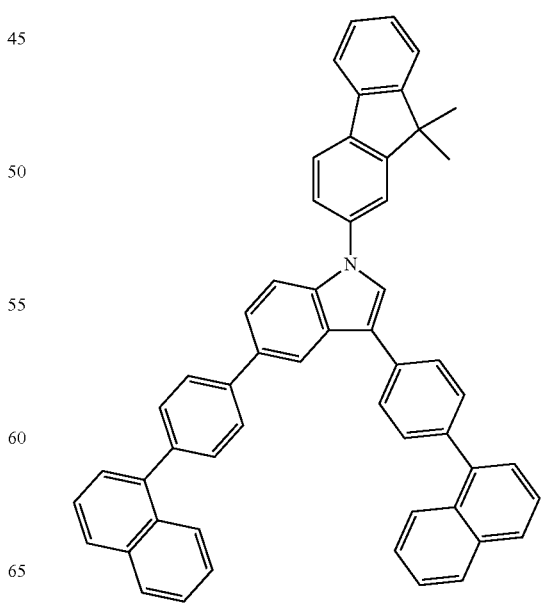

<f-2>

<f-3>
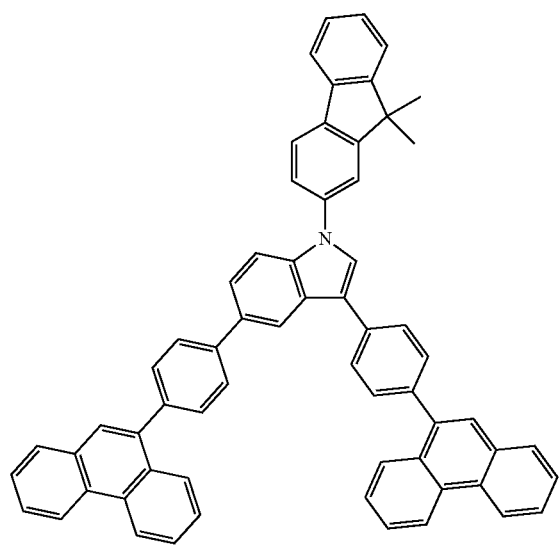
<f-4>
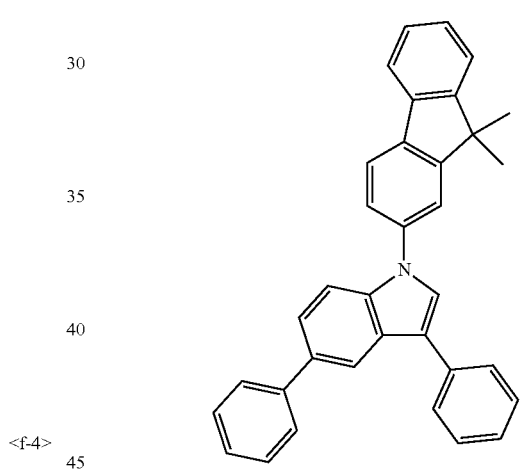
<f-5>
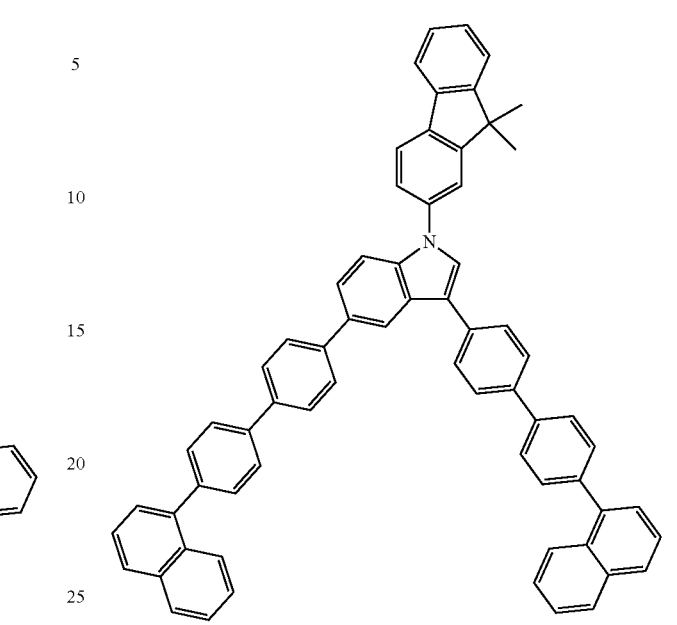
<f-6>
<f-7>
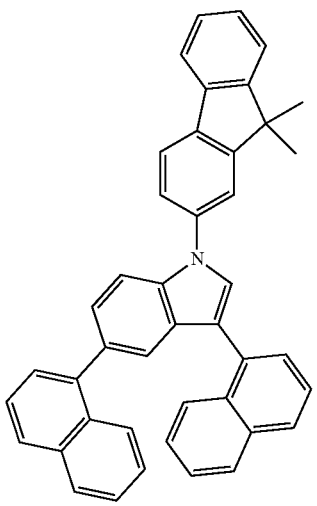

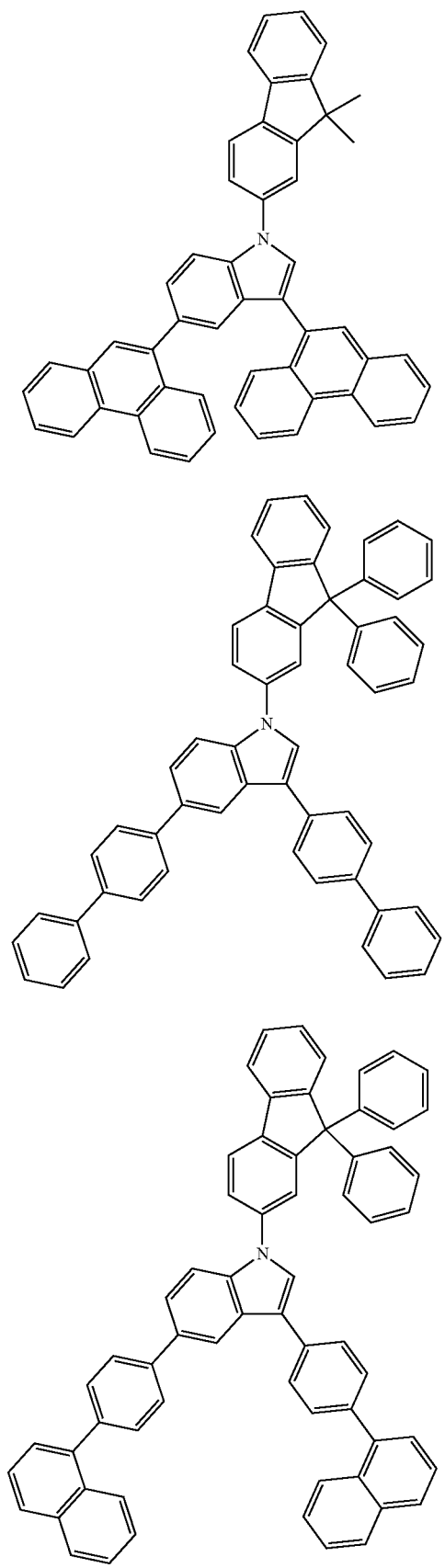
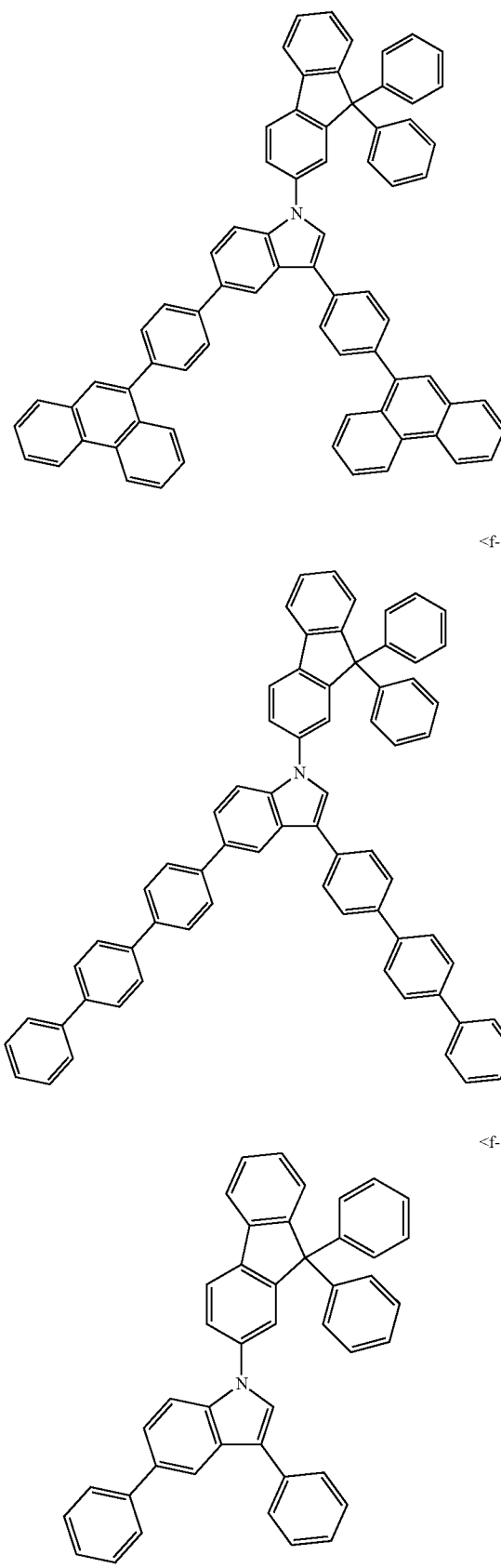

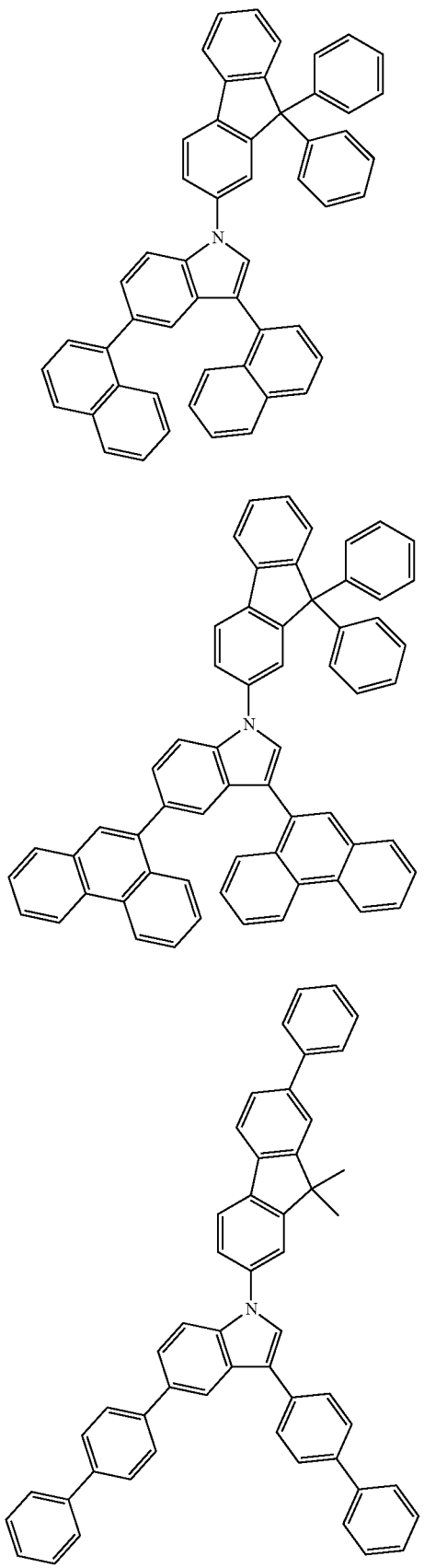
<f-14>
<f-15>
<f-16>
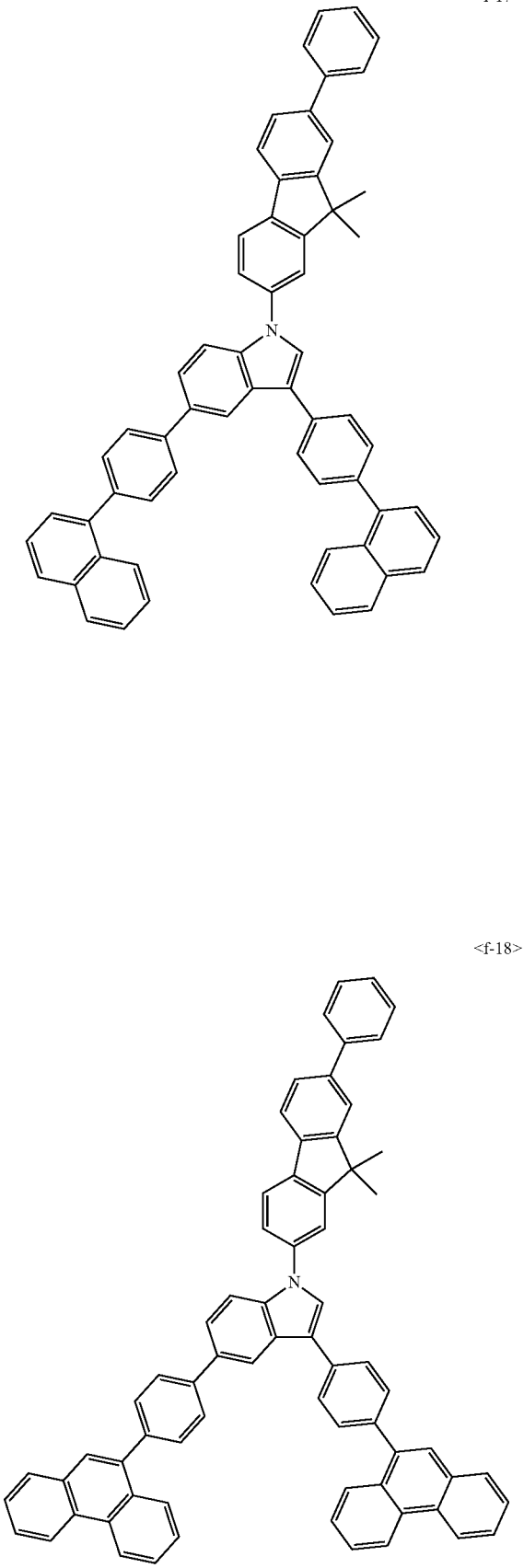
<f-17>
<f-18>

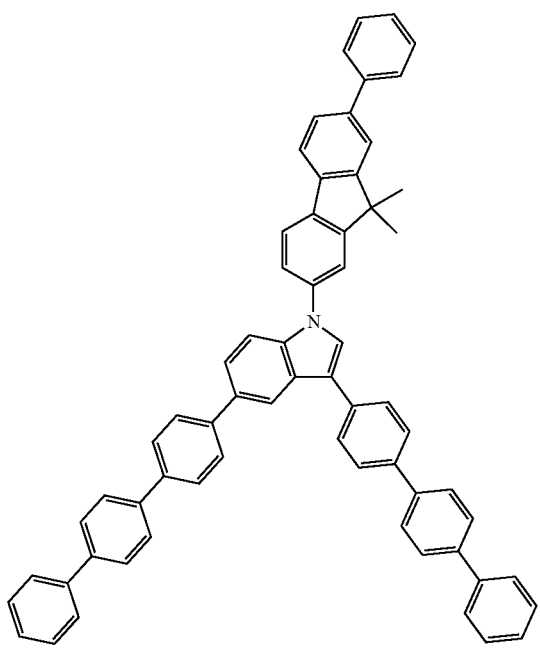
<f-19>
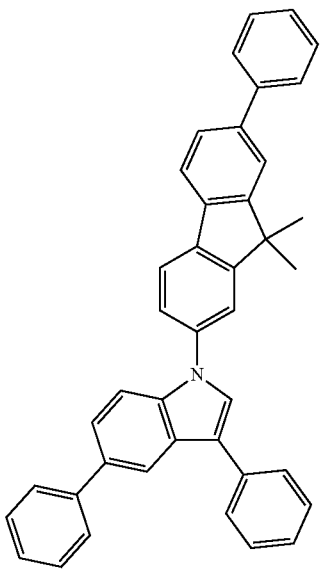
<f-21>
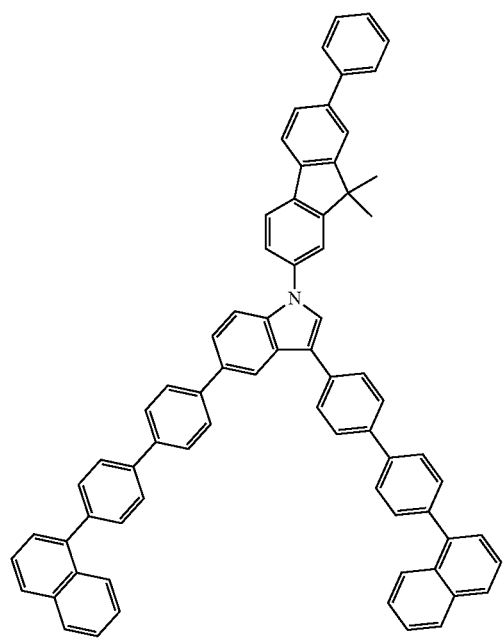
<f-20>
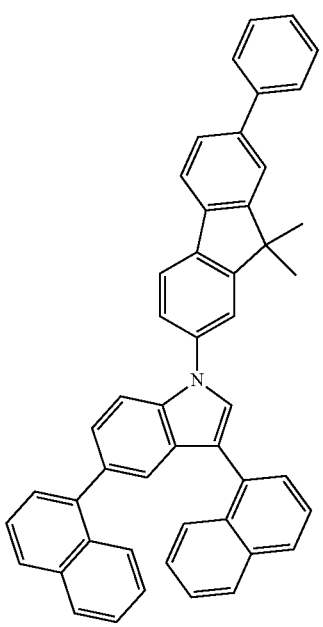
<f-22>

<f-23>
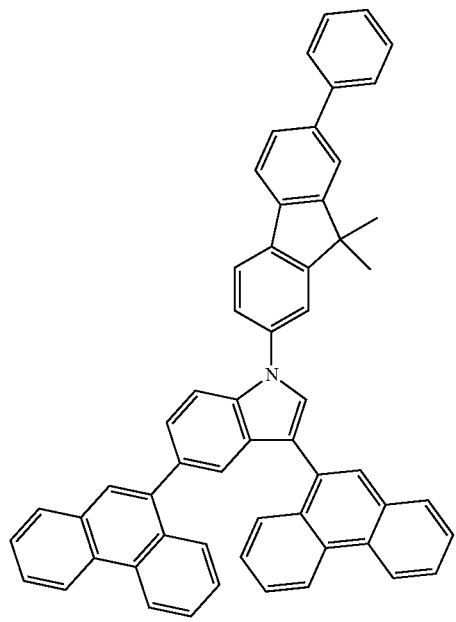
<f-24>
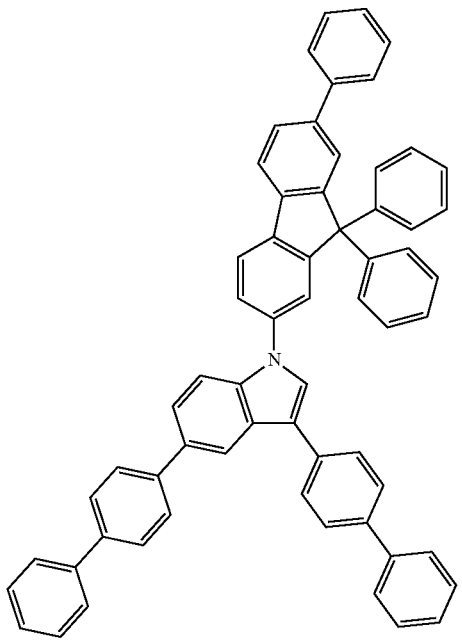
<f-25>
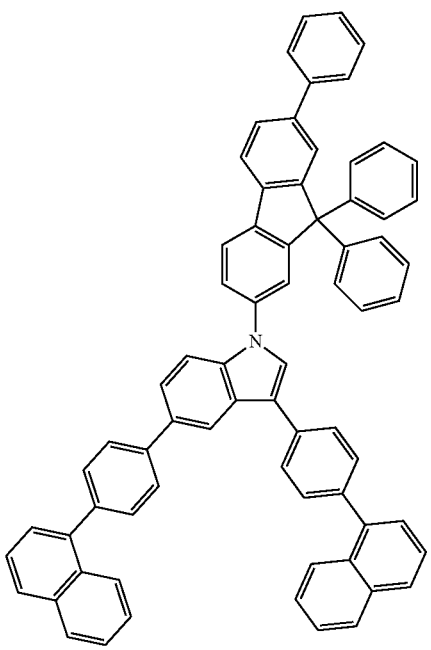
<f-26>
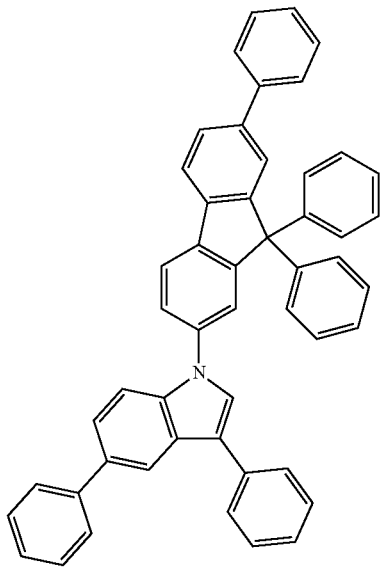

<f-27>
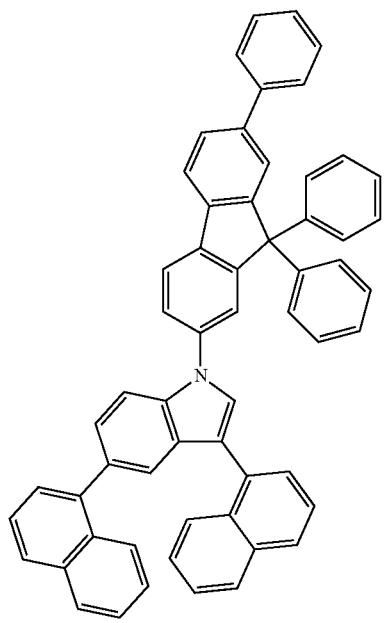
<f-28>
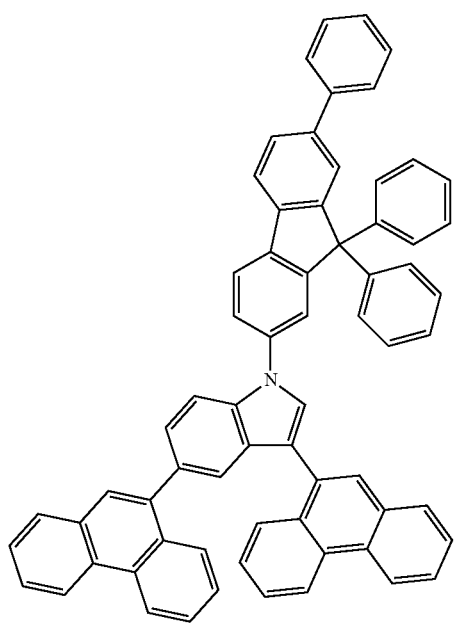
<f-29>
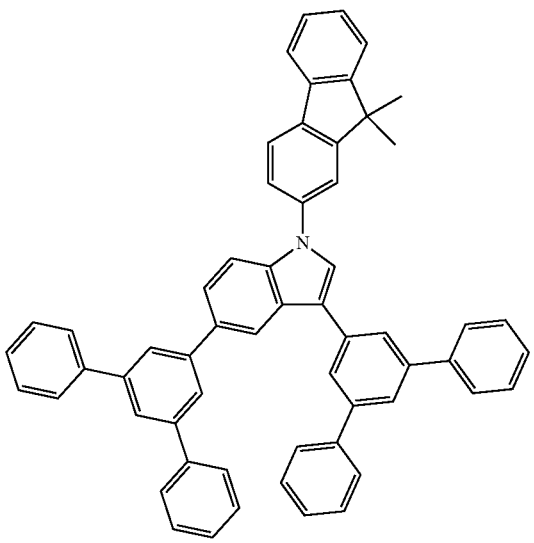
<f-30>
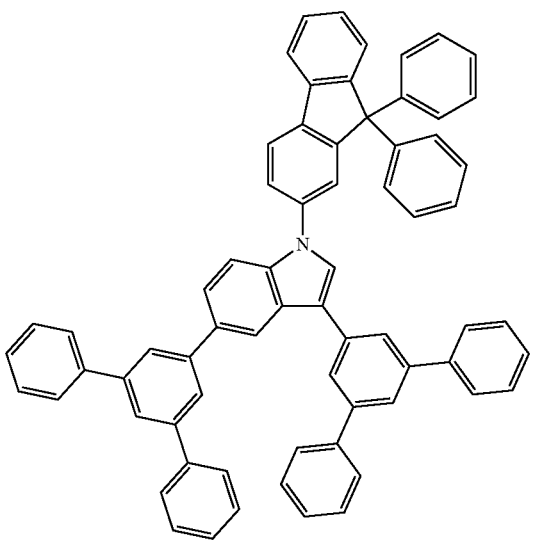

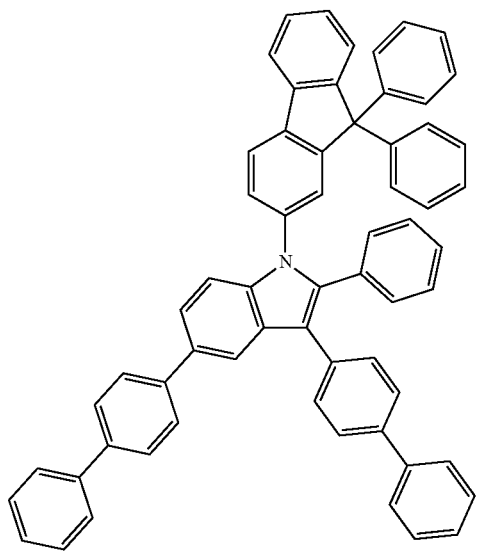
<f-31>
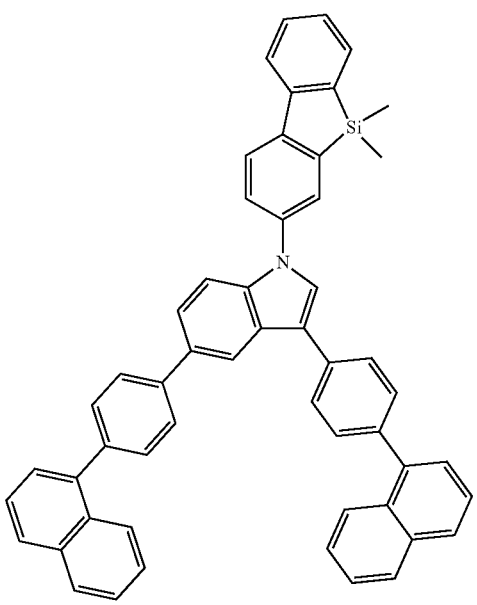
<g-2>
Further, in Chemical Formula 1 according to the present invention,
$R_3$ may be a silicon atom, and
$Ar_5$ may be hydrogen, a phenyl group, or a biphenyl group.
Specifically, the compound represented by Chemical Formula 1 may have a structure of any one of the chemical formula of g-1 to g-31 below.
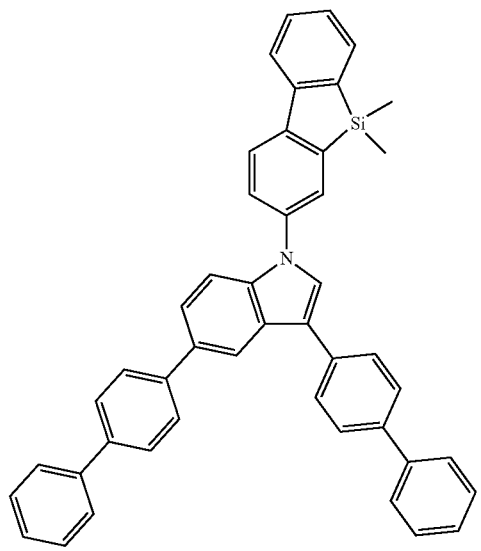
<g-1>
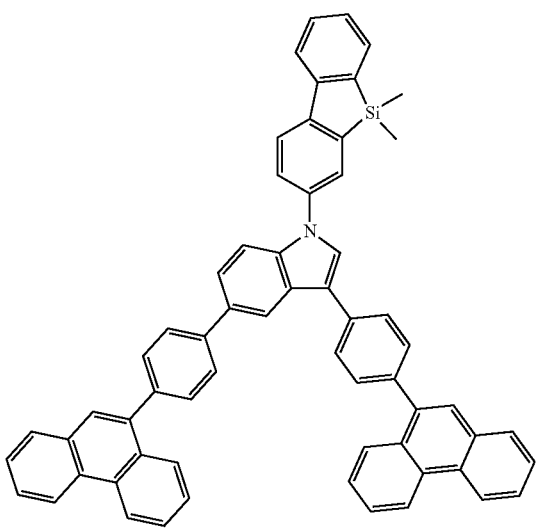
<g-3>

<g-4>
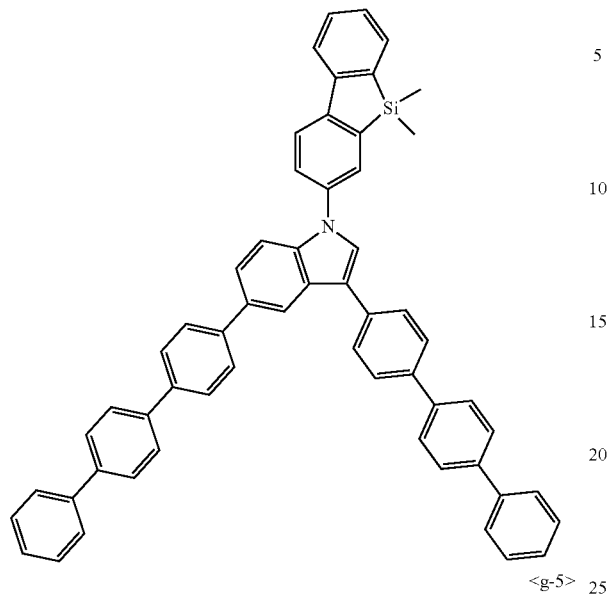
<g-5>
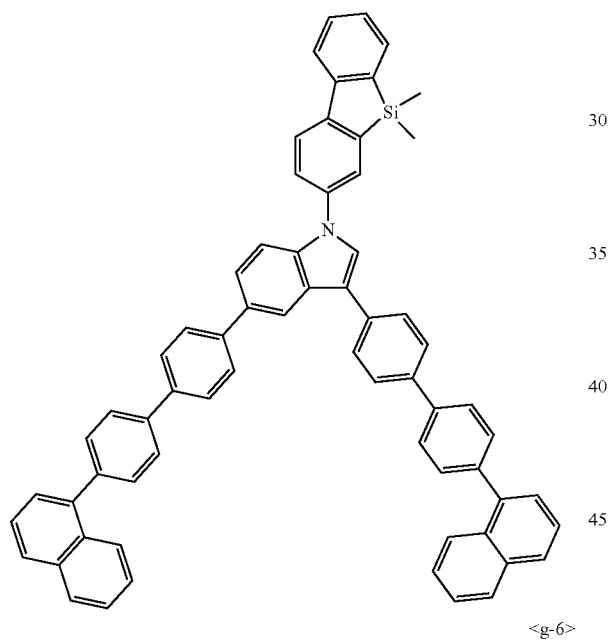
<g-6>
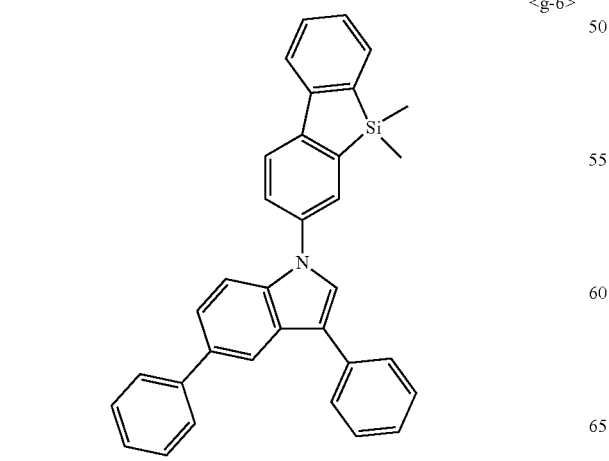
<g-7>
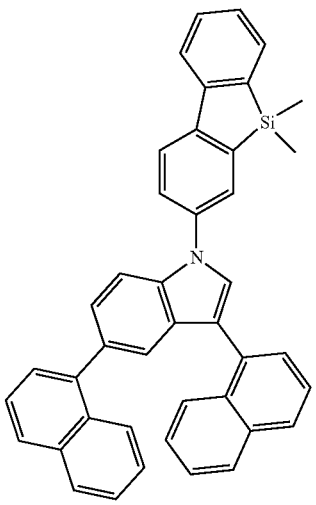
<g-8>
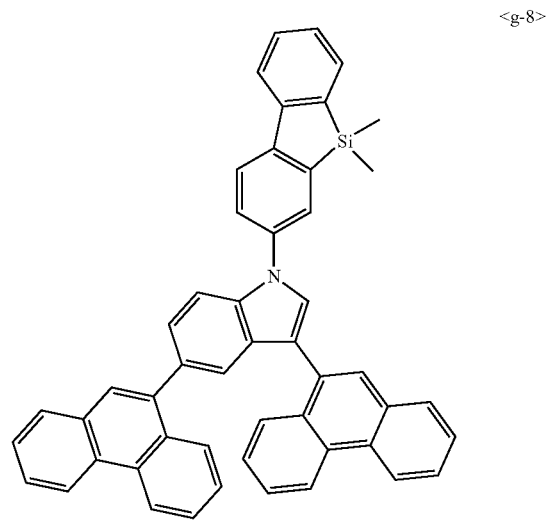
<g-9>
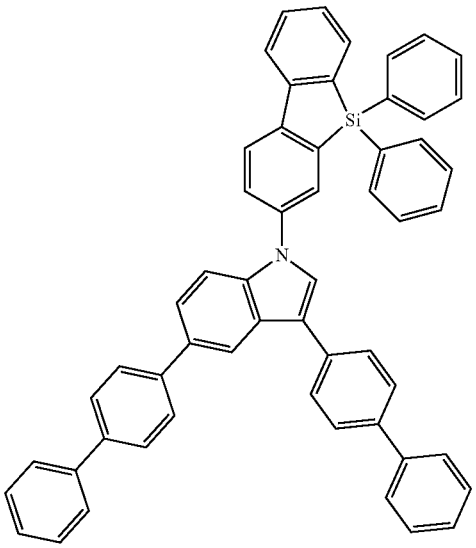

-continued
<g-10>
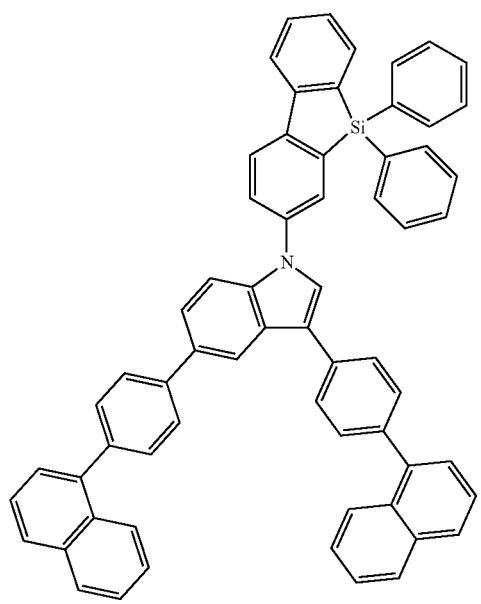
<g-11>
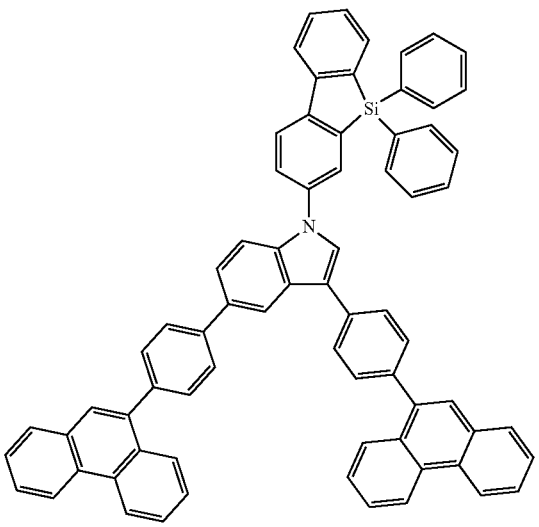
<g-12>
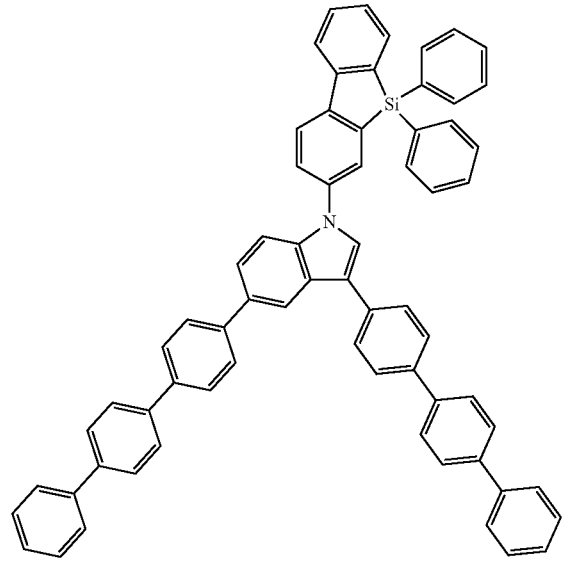
<g-13>
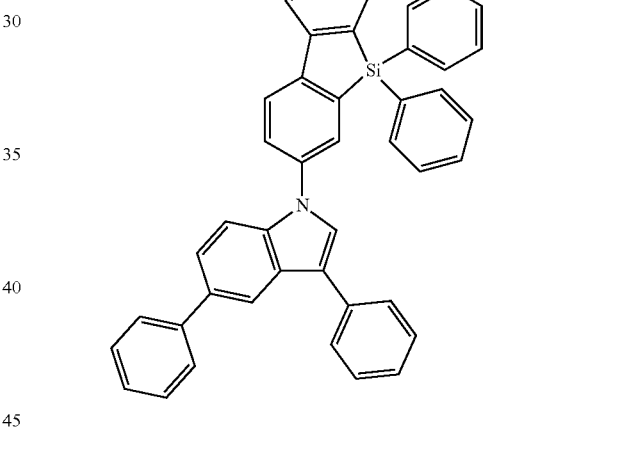
<g-14>
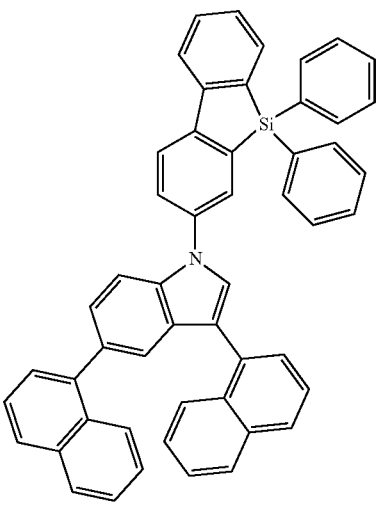

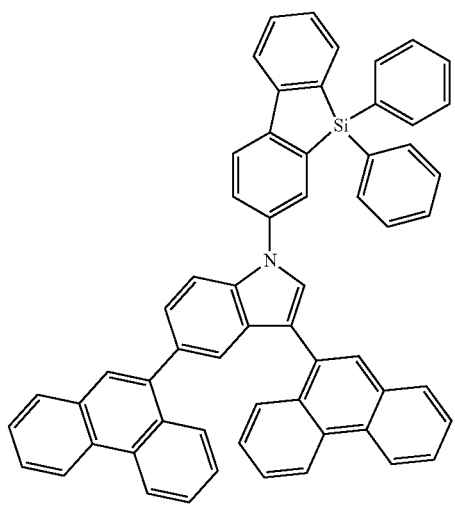
<g-15>
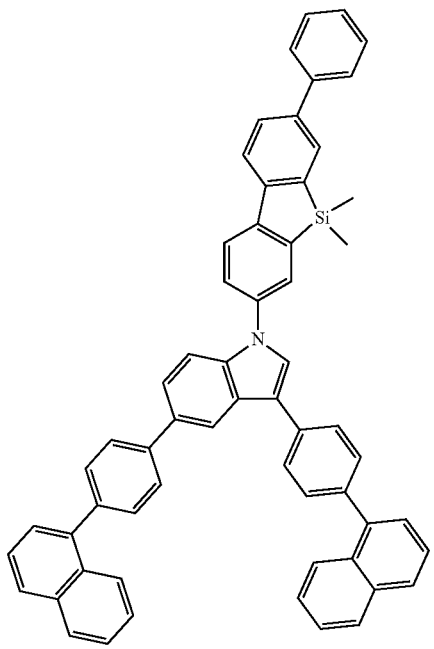
<g-17>
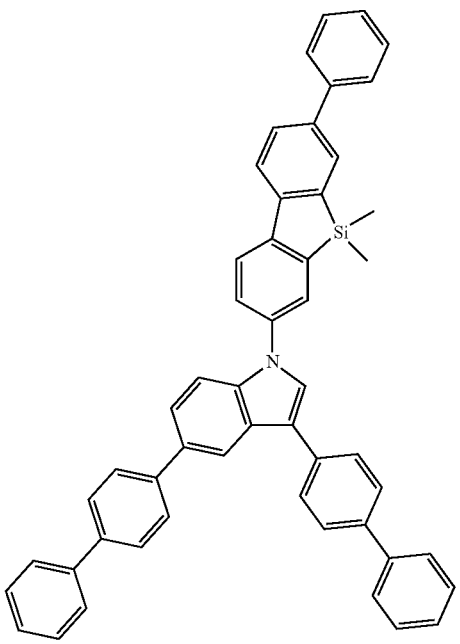
<g-16>
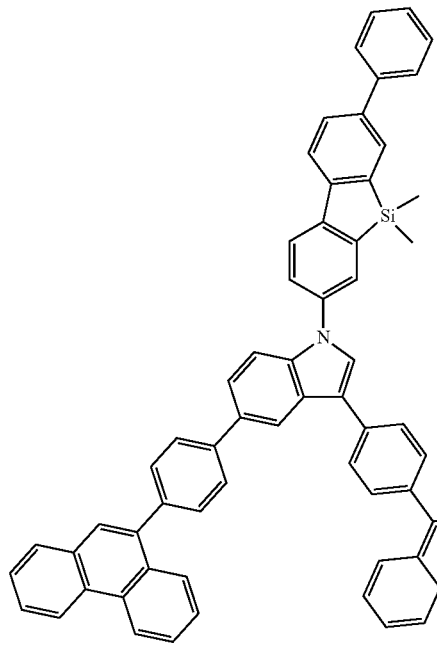
<g-18>

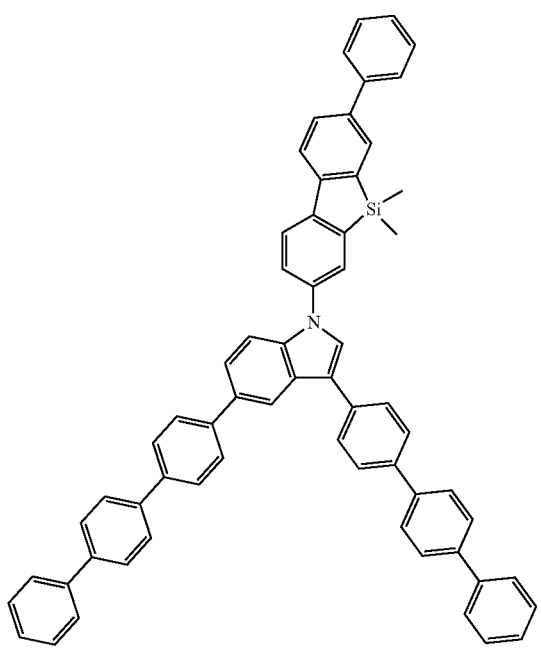
<g-19>
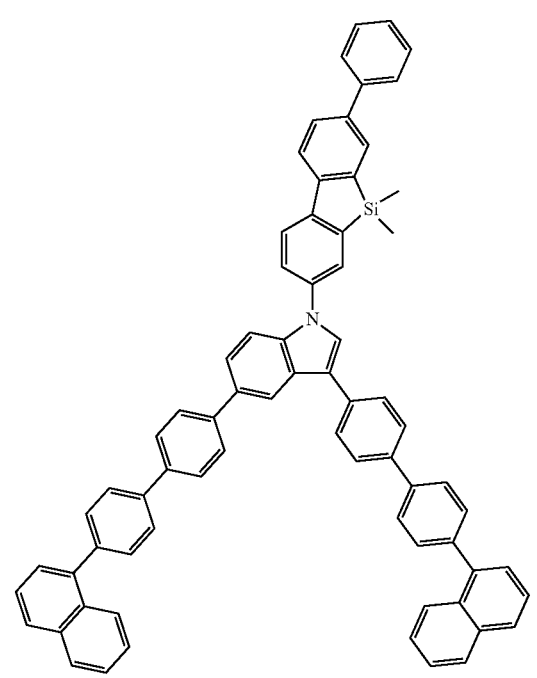
<g-20>
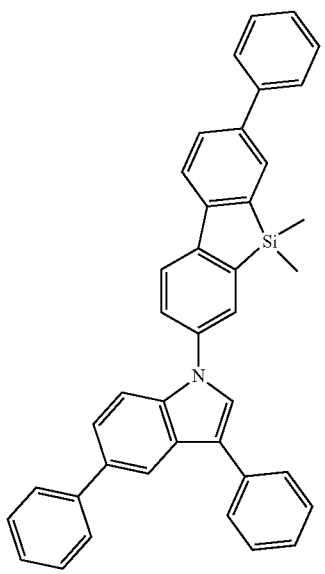
<g-21>
<g-22>

-continued
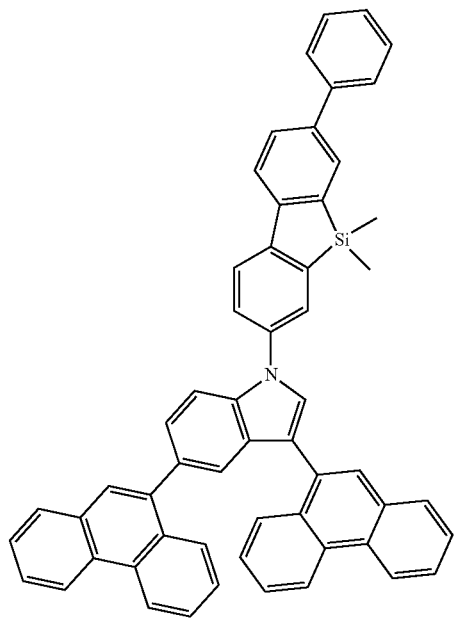
<g-23>
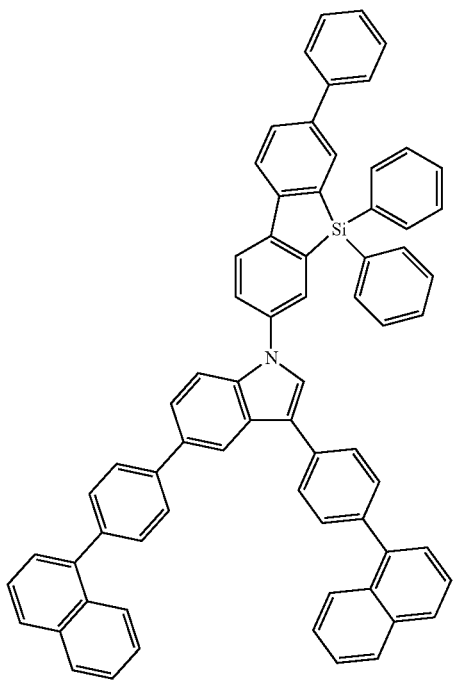
<g-25>
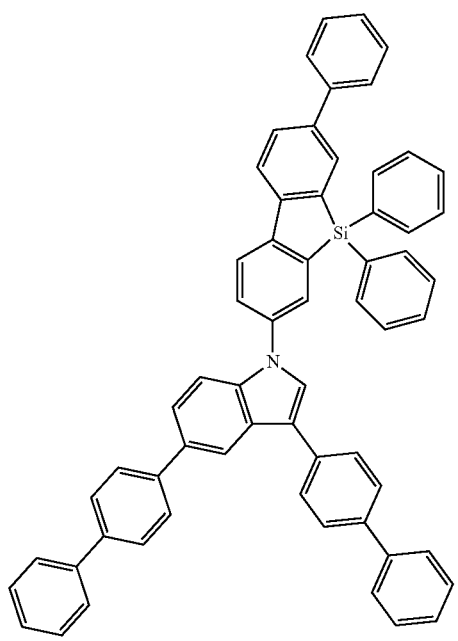
<g-24>
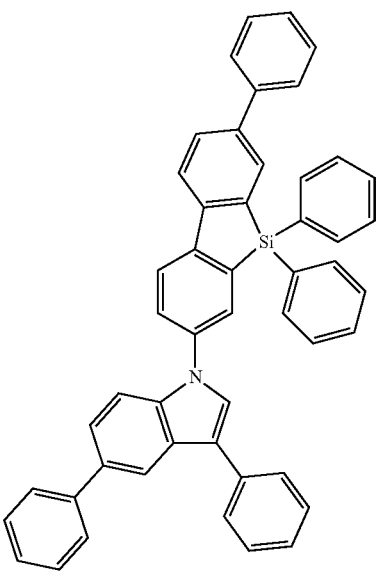
<g-26>

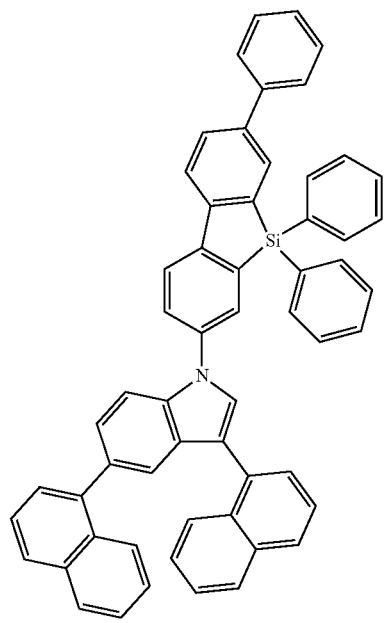
<g-27>
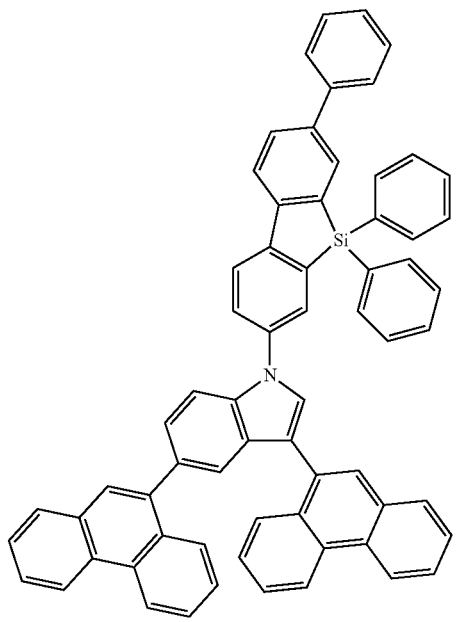
<g-28>
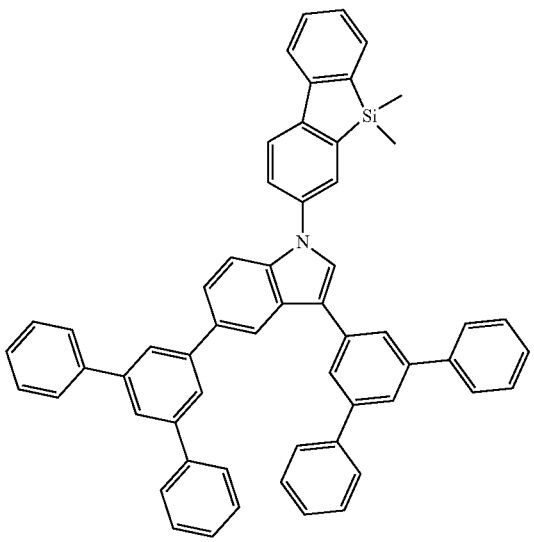
<g-29>
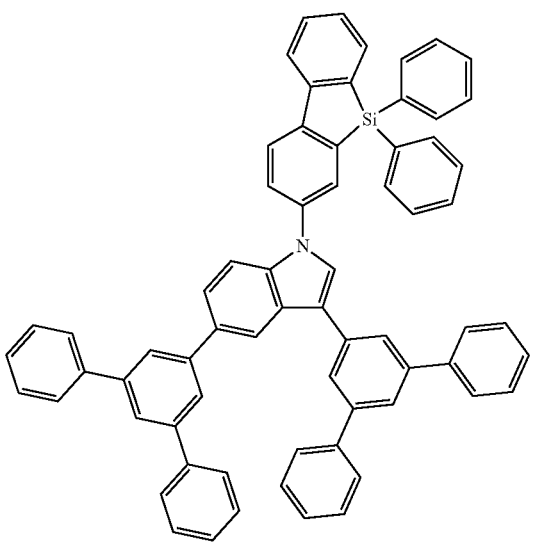
<g-30>

-continued

<g-31>

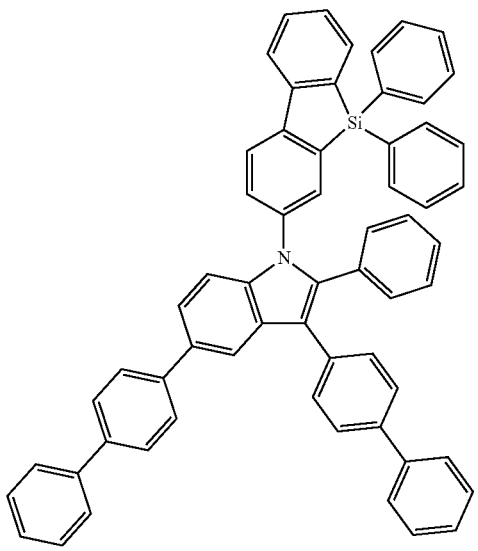

Further, the present invention, in an exemplary embodiment, provides a light emitting diode comprising:
a first electrode;
an organic layer provided on the first electrode;
a light emitting layer provided on the organic layer;
an electron transport layer provided on the light emitting layer; and
a second electrode provided on the electron transport layer, wherein the organic layer includes a compound represented by Chemical Formula 1 below:

<Chemical Formula 1>

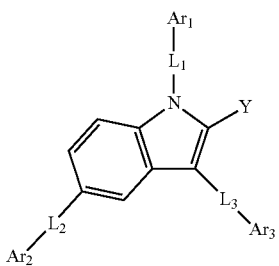

In the above Chemical Formula 1, $Ar_1$, $Ar_2$, $Ar_3$, $L_1$, $L_2$, $L_3$ and Y are defined as above.

Recently, as the application range of a light emitting diode has been extended to a high current/high output field, there is a need for increasing the light emitting efficiency and improving the light emitting lifetime of the light emitting diode. In this case, the light emitting efficiency and the light emitting lifetime may be improved only when holes and electrons in the light emitting layer are smoothly combined. However, electrons injected from a second electrode may pass through a light emitting layer, and overflow into a hole transport layer, and the combination efficiency of holes and electrons in the light emitting layer may be decreased. Accordingly, for holes and electrons in the light emitting layer to be efficiently combined, it must be possible to prevent excitons formed in the light emitting layer from being diffused and dissociated while blocking electrons injected from the second electrode from escaping from the light emitting layer.

In order to overcome the problem, the light emitting diode according to the present invention may have a structure including an organic layer including a compound represented by Chemical Formula 1 between a first electrode and a light emitting layer. The organic layer according to the present invention may prevent electrons injected from a second electrode from flowing into a hole transport layer through a light emitting layer, or excitons formed in the light emitting layer from being diffused toward the first electrode and non-radiatively decayed.

Further, the organic layer may prevent excitons formed in a light emitting layer from being non-radiatively decayed through the process of "exciton dissociation" at the interface between the light emitting layer and the hole transport layer. That is, the organic layer may maximize the production efficiency and radiative decay of excitons in a light emitting layer by blocking electrons and excitons from escaping from the light emitting layer to meet the charge balance in the light emitting layer, and accordingly, the light emitting efficiency of the light emitting diode may be increased, and the driving voltage may be lowered to improve the light emitting lifetime.

Figure 2:
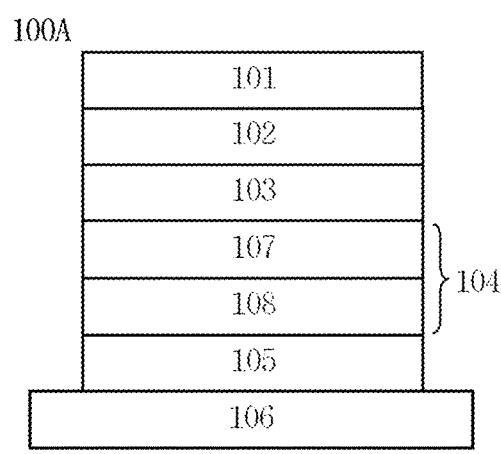
FIG. 2 is an image illustrating a structure of a light emitting diode manufactured in another exemplary embodiment according to the present invention.
Figure 3:
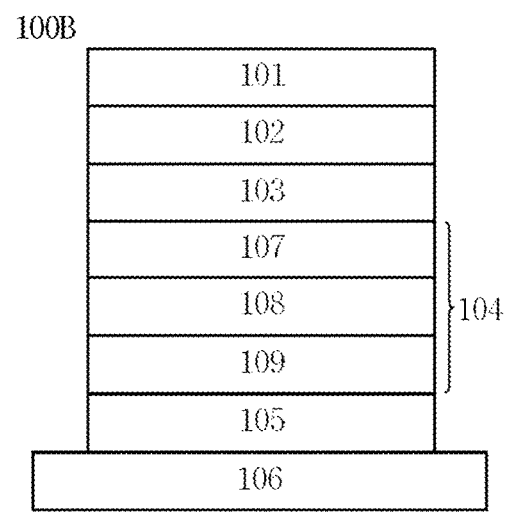
FIG. 3 is an image illustrating a structure of a light emitting diode manufactured in yet another exemplary embodiment according to the present invention.

FIGS. 1 to 3 are images illustrating a schematic structural cross-sectional view of a light emitting diode according to the present invention.

The light emitting diode 100 to 100B according to the present invention may have a structure in which a first electrode 105, an organic layer 104, a light emitting layer 103, an electron transport layer 102, and a second electrode 101 are sequentially stacked on a base substrate 106.

Hereinafter, each constituent element of the light emitting diode according to the present invention will be described in detail with reference to FIGS. 1 to 3.

First, in light emitting diodes 100 to 100B according to the present invention, the first electrode 105 is formed as a conductive material on the base substrate 106, and thus, serves as an anode of the light emitting diodes 100 to 100B.

In this case, the first electrode 105 may be a transparent electrode or an opaque (reflective) electrode. When the first electrode 105 is a transparent electrode, the first electrode 105 may include indium tin oxide (ITO), tin oxide ($SnO_2$), and the like. Further, when the first electrode 105 is an opaque (reflective) electrode, the first electrode 105 may have an ITO/silver (Ag)/ITO structure.

Next, in the light emitting diodes 100 to 100B according to the present invention, the organic layer 104 is disposed between the first electrode 105 and the light emitting layer 103, and may have a single layer structure or a multilayer structure of two or more layers.

Specifically, the organic layer 104 according to the present invention may have a single layer structure, as illustrated in FIG. 1, or may have a multilayer structure of two or more layers including a first organic layer 107, a second organic layer 108, a third organic layer 109, and the like, as illustrated in FIGS. 2 and 3.

In the organic layer 104, an organic layer formed at a position which is brought into contact with the light emitting layer 103, that is, the organic layer 104 having a single layer structure illustrated in FIG. 1 or the first organic layer 107 included in the organic layer 104 having a multilayer structure illustrated in FIGS. 2 and 3 includes a compound represented by Chemical Formula 1 according to the present invention, is formed at a position which is brought into contact with the light emitting layer 103, and may serve as an electron blocking layer (EBL), an exciton blocking layer or an exciton dissociation blocking layer (EDBL).

Further, in an organic layer which is not brought into contact with the light emitting layer, that is, an organic layer 104 having a multilayer structure, an extra organic layer such as the second organic layer 108 and the third organic layer 109 except for the first organic layer 107 (hereinafter, referred to as "an extra organic layer") is disposed between the first organic layer 107 and the first electrode 105, and may serve as a hole transporting layer and/or a hole injecting layer.

Referring to FIG. 3, the second organic layer 108 which is not brought into contact with the light emitting layer 103 may serve as a hole transporting layer. In this case, the second organic layer 108 may include, for example, 4,4-bis [N-(1-naphthyl)-N-phenyl-amine]biphenyl (α-NPD), N,N-diphenyl-N,N-bis(3-methylphenyl)-1,1-biphenyl-4,4-diamine (TPD), poly-(N-vinylcarbazole) (PVCz), and the like either alone or in a mixture of two or more thereof.

Further, the third organic layer 109 which is not brought into contact with the light emitting layer may serve as a hole injecting layer. In this case, the third organic layer 109 is stacked between the first electrode 105 and the second organic layer 108, and may include, for example, copper phthalocyanine (CuPc), but the compound is not limited thereto.

In addition, the extra organic layer may include a compound represented by Chemical Formula 6 below as a hole transport compound. More specifically, for example, in the case of a light emitting diode 100B in which a third organic layer 109, a second organic layer 108, and a first organic layer 107 are sequentially stacked on a first electrode 105, the first organic layer 107 which is brought into contact with the light emitting layer 103 may include a compound represented by Chemical Formula 1 as described above, and one or more of the second organic layer 108 and the third organic layer 109 which are not brought into contact with the light emitting layer 103 may include a compound represented by Chemical Formula 6.

[Chemical Formula 6]

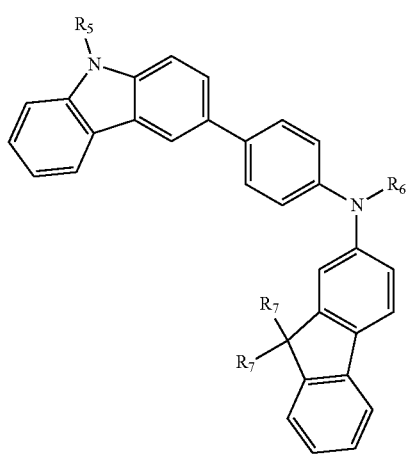

In the above Chemical Formula 6, $R_5$ and $R_7$ are each independently an alkyl group having 1 to 4 carbon atoms, or an aryl group having 6 to 30 carbon atoms, $R_6$ is an aryl group having 6 to 30 carbon atoms, or a heteroaryl group having 2 to 20 carbon atoms, and when $R_6$ is an aryl group having 6 to 30 carbon atoms or a heteroaryl group having 2 to 20 carbon atoms, the aryl group and the heteroaryl group are each independently unsubstituted or substituted with an alkyl group having 1 to 6 carbon atoms or an aryl group having 6 to 20 carbon atoms.

Specifically, in the above Chemical Formula 6 according to the present invention, $R_5$ may be a phenyl group which is unsubstituted or substituted with an alkyl group having 1 to 6 carbon atoms or an aryl group having 6 to 20 carbon atoms; a biphenyl group; a naphthyl group; or a phenanthryl group, and $R_7$ may be a methyl group, an ethyl group, or a phenyl group.

More specifically, the compound represented by Chemical Formula 6 may be a compound having a structure of Chemical Formula 6a below.

<Chemical Formula 6a>

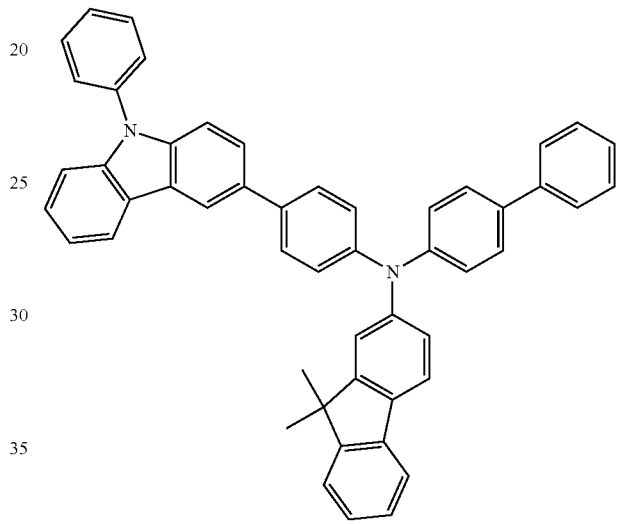

Furthermore, in the organic layer 104 according to the present invention, one of the extra organic layers which are not brought into contact with the light emitting layer 103 may further include one or more P-type dopants.

More specifically, for example, in a light emitting diode 100B including an organic layer 104 having a multilayer structure in which a third organic layer 109, a second organic layer 108, and a first organic layer 107 are sequentially stacked on a first electrode 105, the first organic layer 107 which is brought into contact with the light emitting layer 103 may include a compound of Chemical Formula 1 as described above, and one or more of the second organic layer 108 and the third organic layer 109 which are not brought into contact with the light emitting layer 103 may further include one or more P-type dopants.

In this case, the P-type dopant may include one or more P-type organic material dopants or P-type inorganic material dopants, and may also include both one or more P-type organic material dopants and one or more P-type inorganic material dopants.

The P-type organic material dopant may include, for example, hexadecafluorophthalocyanine (F16CuPc), 11,11,12,12-tetracyanonaphtho-2,6-quinodimethane (TNAP), 3,6-difluoro-2,5,7,7,8,8-hexacyano-quinodimethane (F2-HCNQ), tetracyanoquinodimethane (TCNQ), and the like, and may also include one or more of compounds represented by Chemical Formula 7 to 11 below.

[Chemical Formula 7]

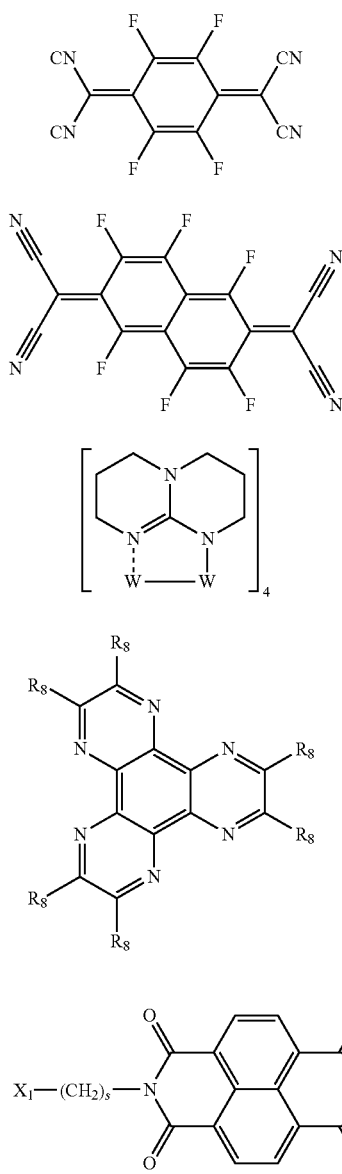

[Chemical Formula 8]

[Chemical Formula 9]

[Chemical Formula 10]

[Chemical Formula 11]

<Chemical Formula 11a>

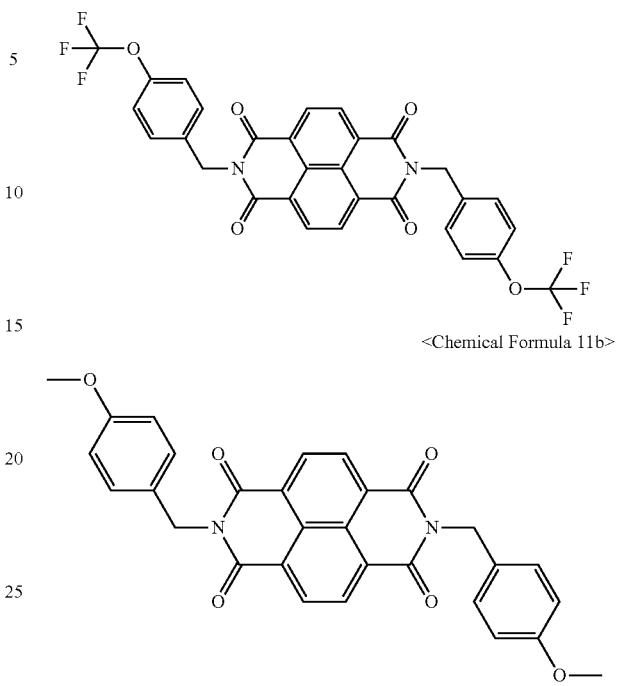

<Chemical Formula 11b>

In the above Chemical Formula 10 and 11, $R_8$ is a cyano group, a sulfone group, a sulfoxide group, a sulfonamide group, a sulfonate group, a nitro group, or a trifluoromethyl group;

s and t are each independently an integer of 1 to 5;

$X_1$ and $X_2$ are each independently an aryl group having 6 to 30 carbon atoms or a heteroaryl group having 2 to 20 carbon atoms, and the aryl group and the heteroaryl group are each independently unsubstituted or substituted with one or more substituents selected from the group consisting of an alkyl group having 1 to 5 carbon atoms, an alkoxy group having 1 to 5 carbon atoms, a haloalkoxy group having 1 to 5 carbon atoms, a hydroxy group, and a halogen group.

More specifically, the compound represented by Chemical Formula 1 may be a compound represented by Chemical Formula 11a or Chemical Formula 11b below:

Further, examples of the P-type inorganic material dopant include metal oxides, metal halides, and the like. Specifically, the P-type inorganic material dopant may include $MoO_3$, $V_2O_5$, $WO_3$, $SnO_2$, $ZnO$, $MnO_2$, $CoO_2$, $ReO_3$, $TiO_2$, $FeCl_3$, $SbCl_5$, $MgF_2$, and the like, and these may be used either alone or in a mixture of two or more thereof.

Furthermore, the content of the P-type dopant may be about 0.5 part by weight to about 20 parts by weight or about 0.5 part by weight to about 5 parts by weight based on 100 parts by weight of a hole transport compound. Also, the content of the P-type dopant may be about 1 part by weight to about 10 parts by weight, about 1 part by weight to about 5 parts by weight, about 1.5 parts by weight to about 6 parts by weight, or about 2 parts by weight to about 5 parts by weight based on 100 parts by weight of the hole transport compound.

When the content of the P-type dopant is about 0.5 part by weight to about 20 parts by weight based on 100 parts by weight of the hole transport compound, the P-type dopant may prevent an excessive leakage current from being generated without degrading physical properties of the hole transport compound. In addition, the energy barrier at the interface with each of the upper and lower layers which are brought into contact with the third organic layer 109 may be reduced by the P-type dopant.

Meanwhile, in the light emitting diodes 100 to 100B according to the present invention, the organic layer 104 can increase the light emitting efficiency by adjusting the thickness according to the resonant length of the light emitting diodes 100 to 100B, and since the thickness can be adjusted so that excitons are capable of being formed not at the interface between a light emitting layer 103 and another layer, but at the center of the light emitting layer 103, the thickness is not particularly limited.

Specifically, when the organic layer 104 has a single layer structure, the organic layer 104 may have an average thickness within a range of 5 Å to 2,000 Å, and when the organic layer 104 has a multilayer structure of two or more layers, each individual layer may have an average thickness within a range of 5 Å to 1,000 Å.

Next, in the light emitting diodes 100 to 100B according to the present invention, the light emitting layer 103 is disposed between the organic layer 104 and the second electrode 101, and the wavelength of light emitted from the light emitting layer 103 may be different according to the type of compound which forms the light emitting layer 103. In this case, the compound, which forms the light emitting layer 103, is not particularly limited as long as the compound is generally used in the art, and a commercially available compound or a prepared compound may be used.

Next, in the light emitting diodes 100 to 100B according to the present invention, the electron transport layer 102 is disposed between the light emitting layer 103 and the second electrode 101, and may include an electron transporting layer (ETL) and/or an electron injecting layer (EIL) (not illustrated). In this case, the electron transport layer may include a compound represented by Chemical Formula 5 below.

[Chemical Formula 5]

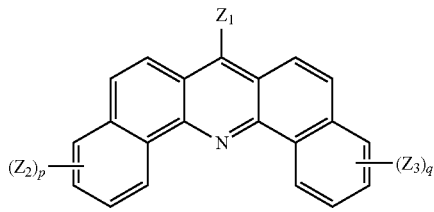

In the above Chemical Formula 5, $Z_1$ to $Z_3$ are each independently hydrogen, a halogen group, a cyano group, an alkyl group having 1 to 20 carbon atoms, an aryl group having 6 to 30 carbon atoms, a heteroaryl group having 2 to 20 carbon atoms, an alkoxy group having 1 to 20 carbon atoms or a diarylphosphine oxide group having 6 to 20 carbon atoms, when $Z_1$ to $Z_3$ are each independently an aryl group having 6 to 30 carbon atoms, a heteroaryl group having 2 to 20 carbon atoms, or a diarylphosphine oxide group having 6 to 20 carbon atoms, the aryl group, the heteroaryl group, and the diarylphosphine oxide group are unsubstituted or substituted with one or more substituents selected from the group consisting of an alkyl group having 1 to 6 carbon atoms, an aryl group having 6 to 20 carbon atoms, and a diarylphosphine oxide group having 6 to 20 carbon atoms, and p and q are each independently an integer of 1 to 3.

Specifically, the compound represented by Chemical Formula 5 may be a compound represented by Chemical Formula 5a below:

<Chemical Formula 5a>

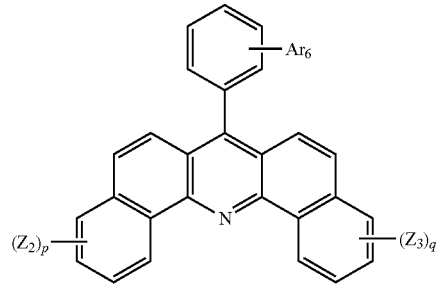

In the above Chemical Formula 5a, $Ar_6$ is hydrogen, an unsubstituted phenyl group, a biphenyl group, a naphthyl group, a phenanthryl group, a pyrenyl group, a pyridyl group, an imidazolyl group, a benzothienyl group, a benzoxazolyl group, or a diarylphosphine oxide group, $Z_2$ to $Z_3$ are each independently hydrogen, a phenyl group, a biphenyl group, a naphthyl group, or a phenanthryl group, and p and q are each independently 1 to 3.

Even more specifically, the compound represented by Chemical Formula 5a may be selected from the structures of Chemical Formula 5a-1 to 5a-7 below:

<Chemical Formula 5a-1>

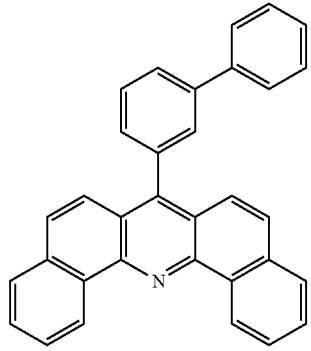

<Chemical Formula 5a-2>

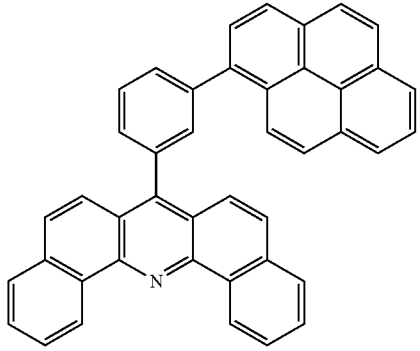

<Chemical Formula 5a-3>

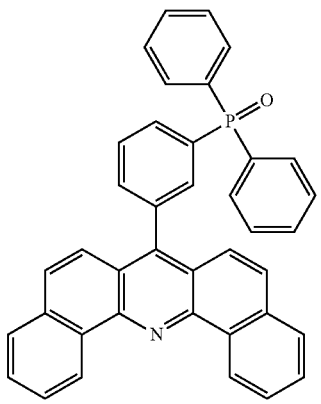

<Chemical Formula 5a-4>

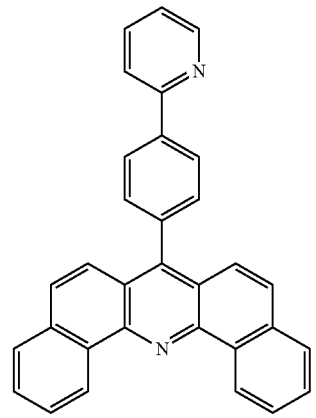

<Chemical Formula 5a-5>

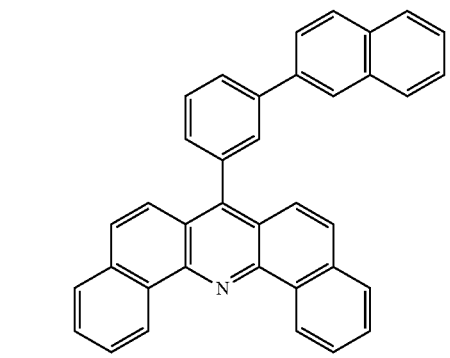

<Chemical Formula 5a-6>

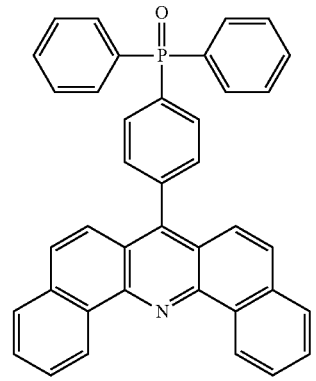

<Chemical Formula 5a-7>

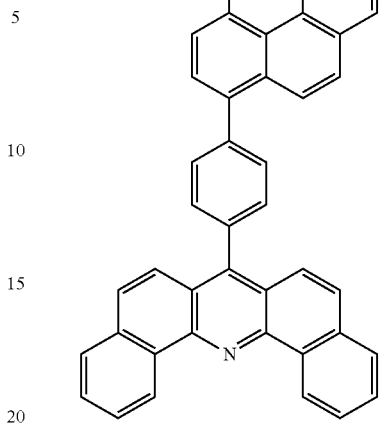

Further, the light emitting diodes 100 to 100B according to the present invention may further include an organic layer (not illustrated) disposed between the light emitting layer 103 and the second electrode 101.

The organic layer is disposed between the light emitting layer 103 and the second electrode 101, specifically, between the light emitting layer 103 and the electron transport layer 102, and may serve as a hole blocking layer (HBL) which prevents holes from passing through the light emitting layer 103 from the first electrode 105 and flowing into the electron transport layer 102.

Further, the organic layer may serve as an exciton blocking layer which prevents excitons formed in the light emitting layer 103 from being diffused toward the second electrode 101 and non-radiatively decayed.

In this case, the organic layer may increase the light emitting efficiency by adjusting the thickness according to the resonant length of the light emitting diodes 100 to 100B, and may allow excitons to be formed not at the interface between the light emitting layer 103 and another layer, but at the center of the light emitting layer 103.

Next, in the light emitting diodes 100 to 100B according to the present invention, the second electrode 101 is disposed as a conductive material on the light emitting layer 103, and thus, serves as a cathode of the light emitting diodes 100 to 100B.

In this case, the second electrode 101 may include a metal such as nickel, magnesium, calcium, silver, aluminum, and indium, or an alloy including two or more metals thereof, and more specifically, may include aluminum. Further, the second electrode 101 may include a single layer structure or a multilayer structure of two or more layers of the metal(s).

In addition, when the first electrode 105 is an opaque electrode, the second electrode 101 may be a transparent or semi-transparent electrode, and in this case, the second electrode 101 may include an alloy including magnesium and silver, and may have a thickness of 100 Å to 150 Å.

In addition, in the light emitting diodes 100 to 100B according to the present invention, the first electrode 105, the organic layer 104, the light emitting layer 103, the electron transport layer 102, the second electrode 101, and the like described above may be manufactured by using a typical evaporation method, but any method may be applied without limitation as long as it is a method which is typically used in the art other than the evaporation method.

Furthermore, the present invention, in an exemplary embodiment, provides an electronic device including the light emitting diode described above. In this case, the electronic device according to the present invention may be a display device or an illumination device, but is not limited thereto.

Since the electronic device according to the present invention includes a light emitting diode in which the light emitting efficiency is increased and the light emitting lifetime is improved by introducing a compound represented by Chemical Formula 1 between a first electrode and a light emitting layer, the electronic device can be used even in a high current/high output field which requires high luminance/high reliability.

EXAMPLES

Hereinafter, the present invention will be described in more detail with reference to Examples and Experimental Examples.

However, the following Examples and Experimental Examples are only for exemplifying the present invention, and the contents of the present invention are not limited by the following Examples and Experimental Examples.

Example 1

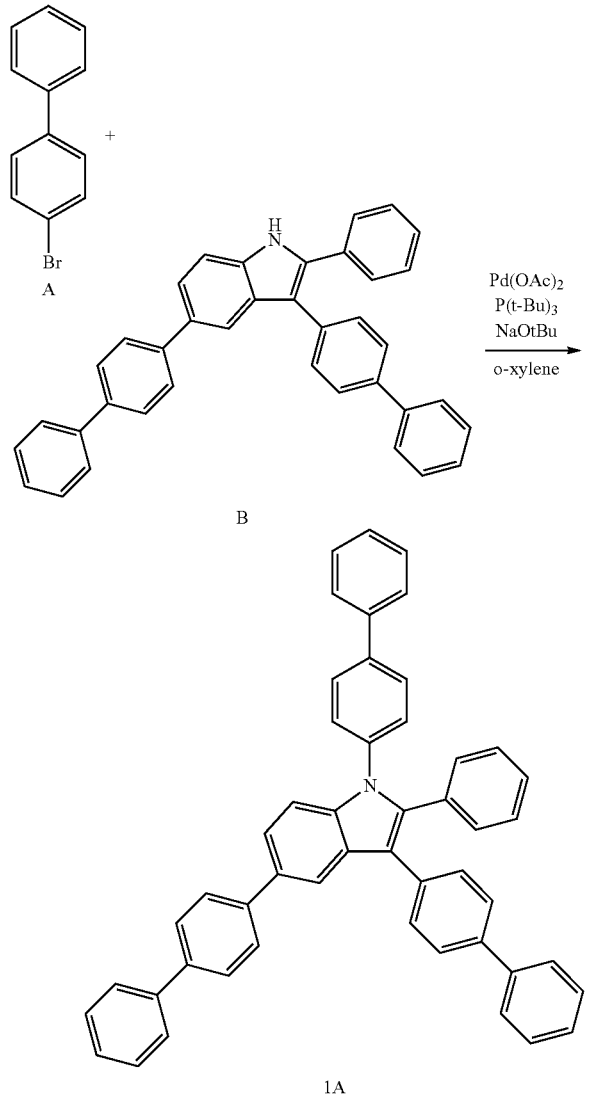

After a 500-mL three-neck round-bottom flask was filled with nitrogen gas, o-xylene (280 mL) was injected thereinto, Compound A (20.0 g, 85.8 mmol), Compound B (47.0 g, 94.4 mmol), palladium acetate (Pd(OAc)$_2$, 385 mg, 1.72 mmol), sodium tert-butoxide (NaO t-Bu, 9.9 g, 103.0 mmol), and tri tert-butylphosphine (P(t-Bu)$_3$, 1.7 ml) were introduced thereinto, and then the resulting mixture was stirred at 130° C. for 10 hours. Thereafter, a white target compound (Chemical Formula 1A, 39.0 g, 70%) was obtained by cooling the reactants to room temperature, introducing the reactants into methanol (2,800 mL), and then stirring the resulting mixture for 30 minutes and filtering the mixture.

MALDI-TOF: m/z=649.2813 (C$_{50}$H$_{35}$N=649.28).

Example 2

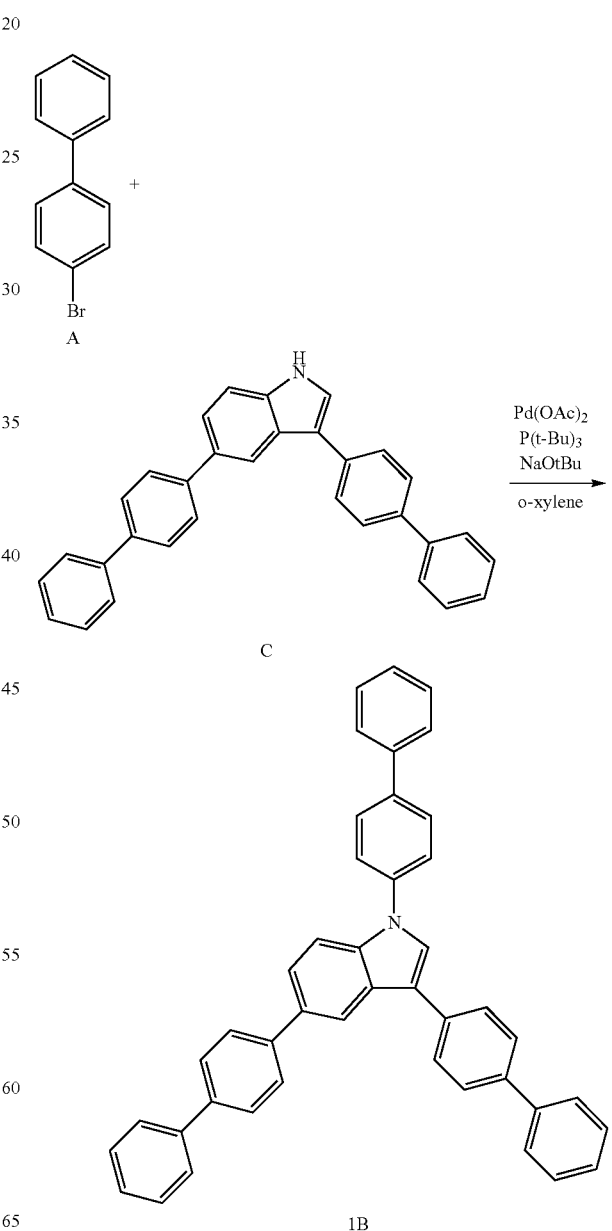

After a 500-mL three-neck round-bottom flask was filled with nitrogen gas, o-xylene (180 mL) was injected thereinto, Compound A (15.0 g, 64.4 mmol), Compound C (29.8 g, 70.8 mmol), palladium acetate (Pd(OAc)$_2$, 289 mg, 1.29 mmol), sodium tert-butoxide (NaO t-Bu, 5.6 g, 58.2 mmol), and tri tert-butylphosphine (P(t-Bu)$_3$, 1.7 ml) were introduced thereinto, and then the resulting mixture was stirred at 130° C. for 9 hours. Thereafter, a gray target compound (Chemical Formula 1B, 20.9 g, 75%) was obtained by cooling the reactants to room temperature, introducing the reactants into methanol (1,800 mL), and then stirring the resulting mixture for 20 minutes and filtering the mixture.

MALDI-TOF: m/z=573.2457 (C$_{44}$H$_{31}$N=573.25).

Example 3

After a 500-mL three-neck round-bottom flask was filled with nitrogen gas, o-xylene (120 mL) was injected thereinto, Compound D (10.0 g, 29.5 mmol), Compound E (18.6 g, 32.4 mmol), palladium acetate (Pd(OAc)$_2$, 132 mg, 0.59 mmol), sodium tert-butoxide (NaO t-Bu, 3.4 g, 35.4 mmol), and tri tert-butylphosphine (P(t-Bu)$_3$, 1.7 ml) were introduced thereinto, and then the resulting mixture was stirred at 130° C. for 11 hours. Thereafter, a white target compound (Chemical Formula 1C, 21.5 g, 80%) was obtained by cooling the reactants to room temperature, introducing the reactants into methanol (1,200 mL), and then stirring the resulting mixture for 20 minutes and filtering the mixture.

MALDI-TOF: m/z=831.3060 (C$_{62}$H$_{41}$NS=831.30).

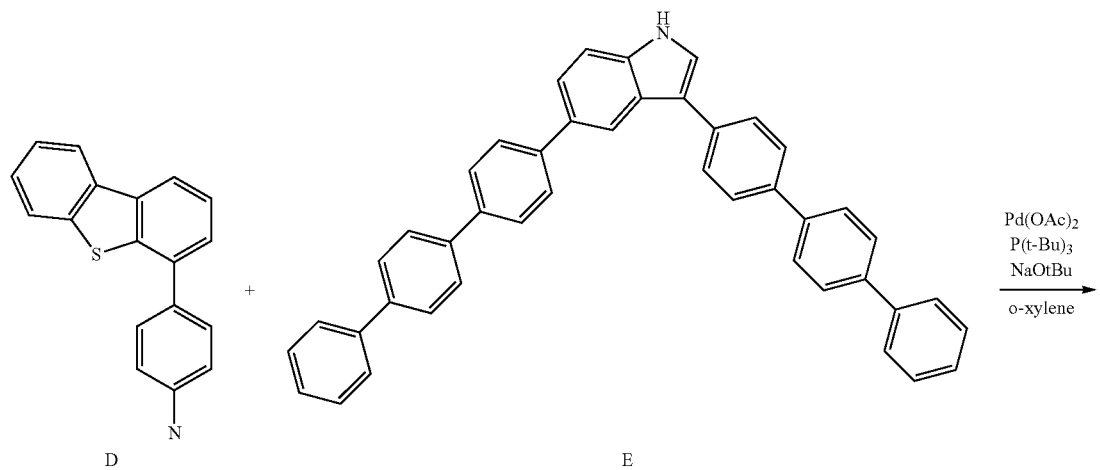

D                                    E

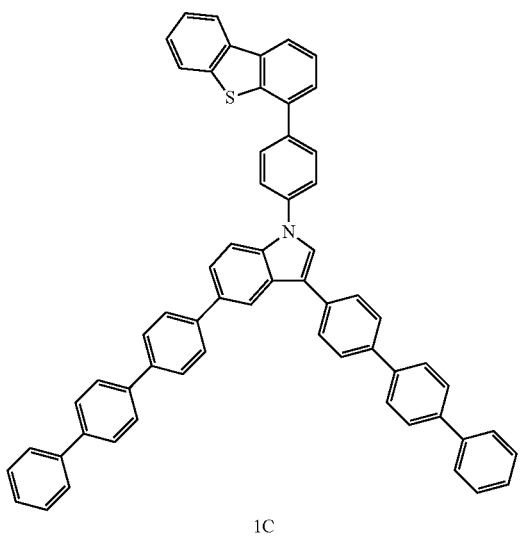

1C

Example 4

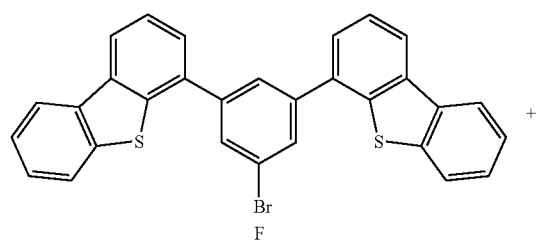

F

+

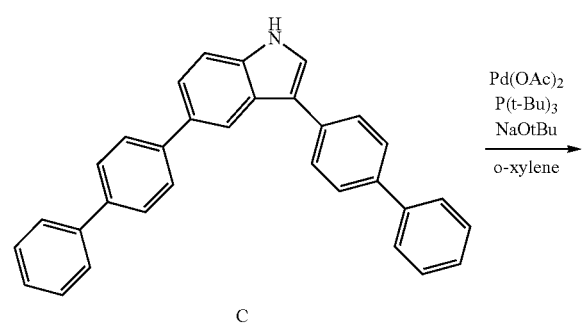

C

→ (Pd(OAc)$_2$, P(t-Bu)$_3$, NaOtBu, o-xylene)

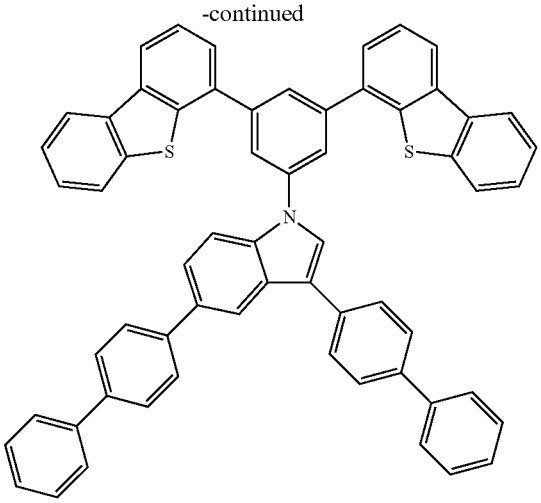

1D

After a 500-mL three-neck round-bottom flask was filled with nitrogen gas, o-xylene (120 mL) was injected thereinto, Compound F (15.0 g, 28.8 mmol), Compound C (13.3 g, 31.6 mmol), palladium acetate (Pd(OAc)$_2$, 129 mg, 0.58 mmol), sodium tert-butoxide (NaO t-Bu, 3.3 g, 34.5 mmol), and tri tert-butylphosphine (P(t-Bu)$_3$, 1.7 ml) were introduced thereinto, and then the resulting mixture was stirred at 130° C. for 10 hours. Thereafter, a white target compound (Chemical Formula 1D, 27.9 g, 83%) was obtained by cooling the reactants to room temperature, introducing the reactants into methanol (1,200 mL), and then stirring the resulting mixture for 30 minutes and filtering the mixture.

MALDI-TOF: m/z=861.2524 (C$_{62}$H$_{39}$NS$_2$=861.25).

Example 5

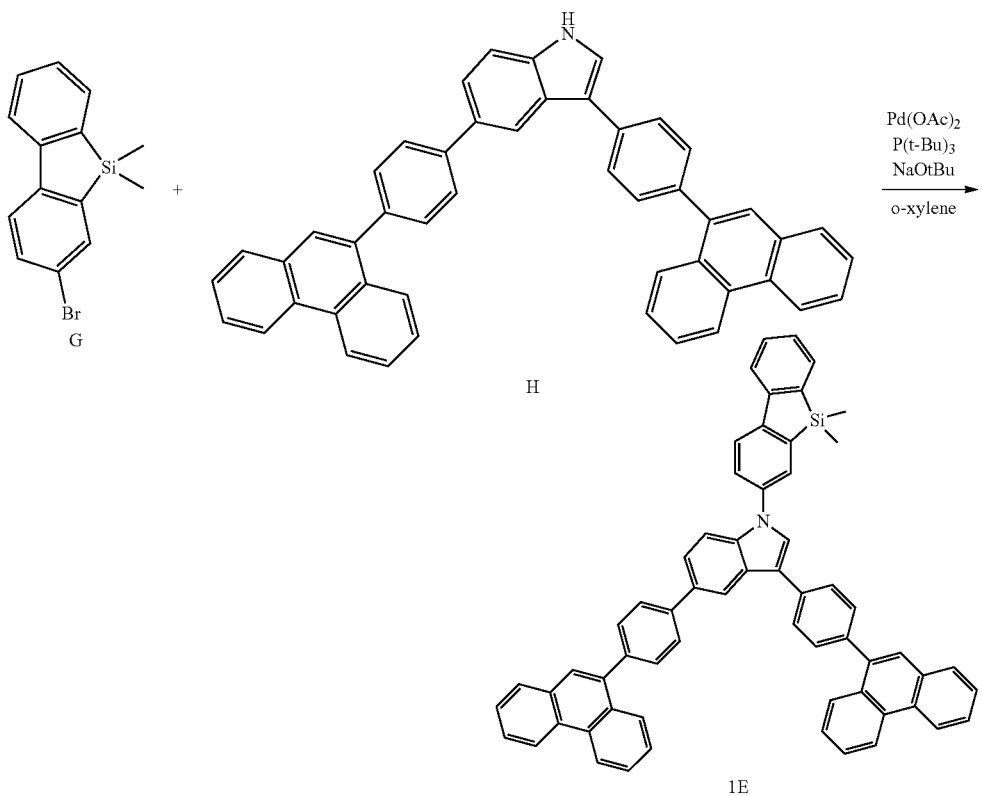

After a 500-mL three-neck round-bottom flask was filled with nitrogen gas, o-xylene (280 mL) was injected thereinto, Compound G (20.0 g, 69.1 mmol), Compound H (47.3 g, 76.1 mmol), palladium acetate (Pd(OAc)$_2$, 310 mg, 1.38 mmol), sodium tert-butoxide (NaO t-Bu, 8.0 g, 83.0 mmol), and tri tert-butylphosphine (P(t-Bu)$_3$, 1.7 ml) were introduced thereinto, and then the resulting mixture was stirred at 130° C. for 9 hours. Thereafter, a pale gray target compound (Chemical Formula 1E, 37.6 g, 70%) was obtained by cooling the reactants to room temperature, introducing the reactants into methanol (2,800 mL), and then stirring the resulting mixture for 30 minutes and filtering the mixture.

MALDI-TOF: m/z=829.3165 (C$_{62}$H$_{43}$NSi=830.10).

Example 6

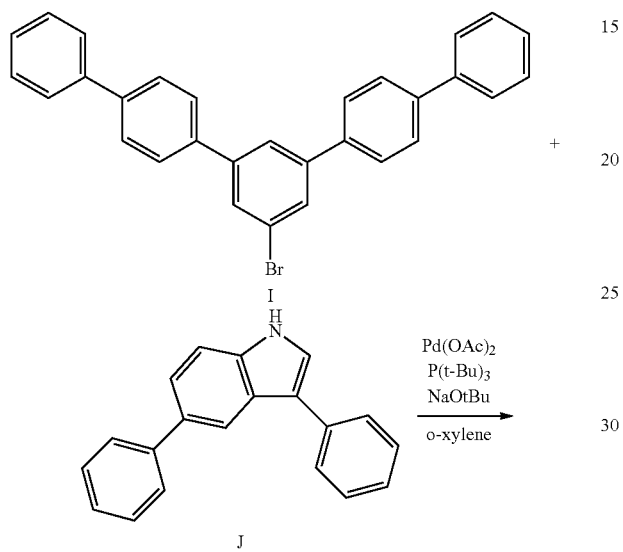

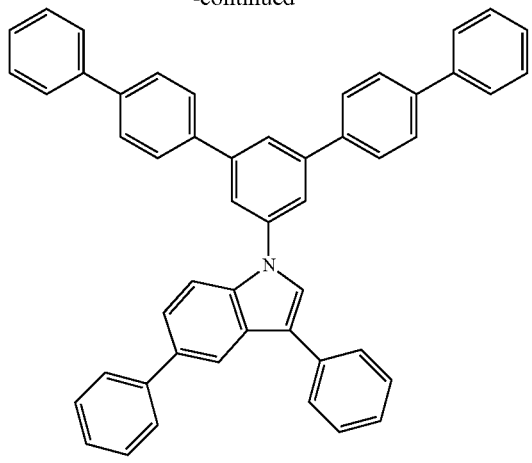

1F

After a 500-mL three-neck round-bottom flask was filled with nitrogen gas, o-xylene (100 mL) was injected thereinto, Compound I (15.0 g, 32.5 mmol), Compound H (9.6 g, 35.8 mmol), palladium acetate (Pd(OAc)$_2$, 146 mg, 0.65 mmol), sodium tert-butoxide (NaO t-Bu, 3.7 g, 39.0 mmol), and tri tert-butylphosphine (P(t-Bu)$_3$, 1.7 ml) were introduced thereinto, and then the resulting mixture was stirred at 130° C. for 10 hours. Thereafter, a pale gray target compound (Chemical Formula 1F, 27.1 g, 86%) was obtained by cooling the reactants to room temperature, introducing the reactants into methanol (1,000 mL), and then stirring the resulting mixture for 30 minutes and filtering the mixture.

MALDI-TOF: m/z=649.2770 (C$_{50}$H$_{35}$N=649.28).

Example 7

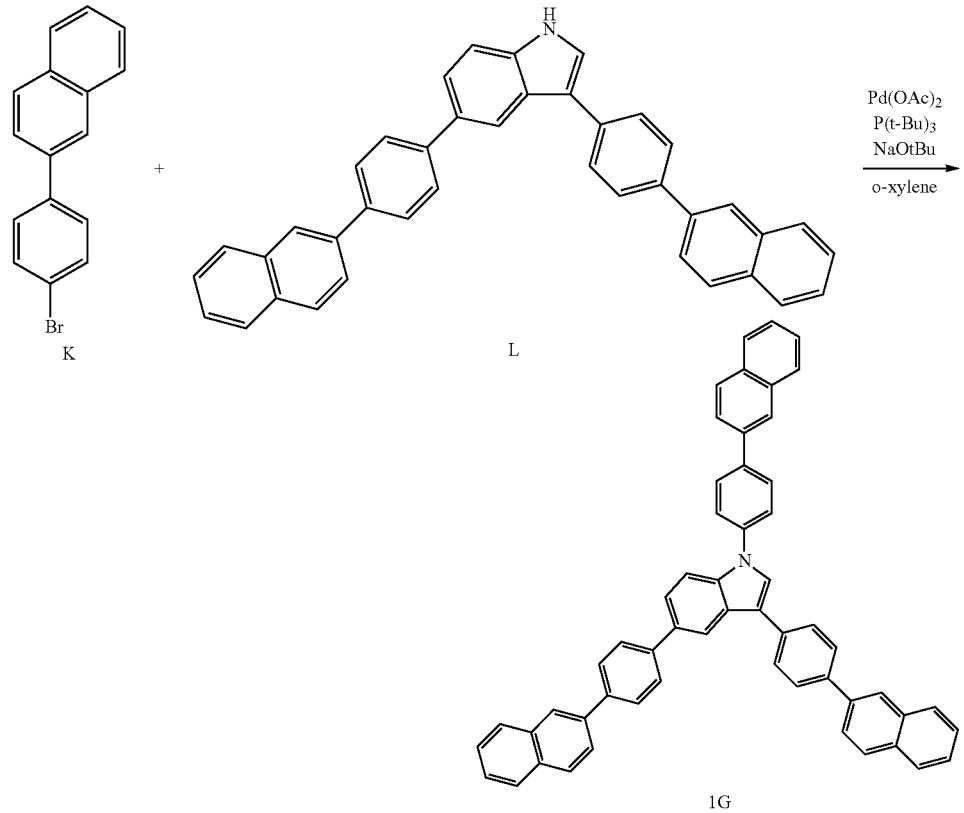

After a 500-mL three-neck round-bottom flask was filled with nitrogen gas, o-xylene (12 mL) was injected thereinto, Compound K (10.0 g, 35.3 mmol), Compound L (20.3 g, 38.8 mmol), palladium acetate (Pd(OAc)$_2$, 159 mg, 0.71 mmol), sodium tert-butoxide (NaO t-Bu, 4.1 g, 42.4 mmol), and tri tert-butylphosphine (P(t-Bu)$_3$, 1.7 ml) were introduced thereinto, and then the resulting mixture was stirred at 130° C. for 11 hours. Thereafter, a gray target compound (Chemical Formula 1G, 14.1 g, 75%) was obtained by cooling the reactants to room temperature, introducing the reactants into methanol (1,200 mL), and then stirring the resulting mixture for 20 minutes and filtering the mixture.

MALDI-TOF: m/z=723.2926 (C$_{56}$H$_{37}$N=723.29).

Example 8

After a 500-mL three-neck round-bottom flask was filled with nitrogen gas, o-xylene (200 mL) was injected thereinto, Compound M (15.0 g, 54.9 mmol), Compound H (37.6 g, 60.4 mmol), palladium acetate (Pd(OAc)$_2$, 247 mg, 1.10 mmol), sodium tert-butoxide (NaO t-Bu, 6.3 g, 65.9 mmol), and tri tert-butylphosphine (P(t-Bu)$_3$, 1.7 ml) were introduced thereinto, and then the resulting mixture was stirred at 130° C. for 10 hours. Thereafter, a gray target compound (Chemical Formula 1H, 24.7 g, 78%) was obtained by cooling the reactants to room temperature, introducing the reactants into methanol (2,000 mL), and then stirring the resulting mixture for 40 minutes and filtering the mixture.

MALDI-TOF: m/z=813.3396 (C$_{63}$H$_{43}$N=813.34).

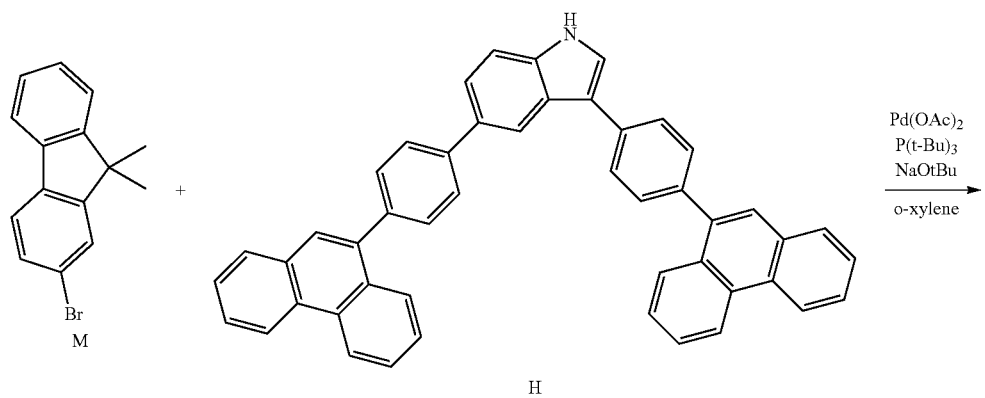

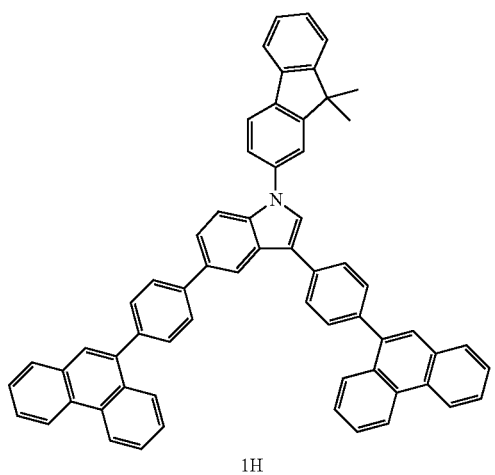

1H

Example 9

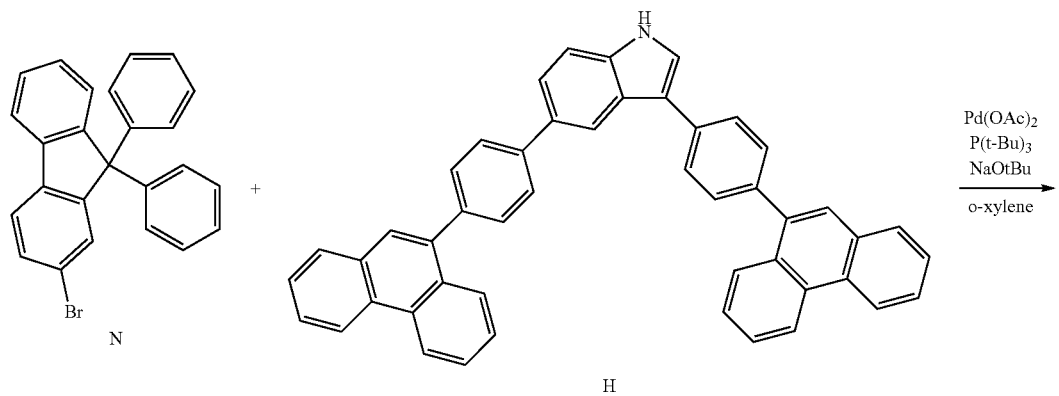

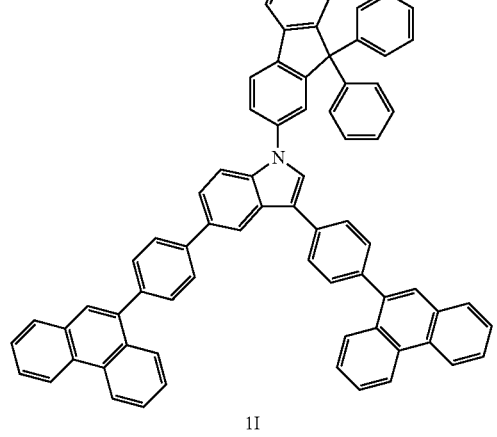

After a 500-mL three-neck round-bottom flask was filled with nitrogen gas, o-xylene (200 mL) was injected thereinto, Compound N (20.0 g, 50.3 mmol), Compound H (34.4 g, 55.4 mmol), palladium acetate (Pd(OAc)$_2$, 226 mg, 1.0 mmol), sodium tert-butoxide (NaO t-Bu, 5.8 g, 60.4 mmol), and tri tert-butylphosphine (P(t-Bu)$_3$, 1.7 ml) were introduced thereinto, and then the resulting mixture was stirred at 130° C. for 9 hours. Thereafter, a white target compound (Chemical Formula 1I, 36.5 g, 75%) was obtained by cooling the reactants to room temperature, introducing the reactants into methanol (2,000 mL), and then stirring the resulting mixture for 30 minutes and filtering the mixture.

MALDI-TOF: m/z=937.3709 (C$_{73}$H$_{47}$N=937.37).

Example 10

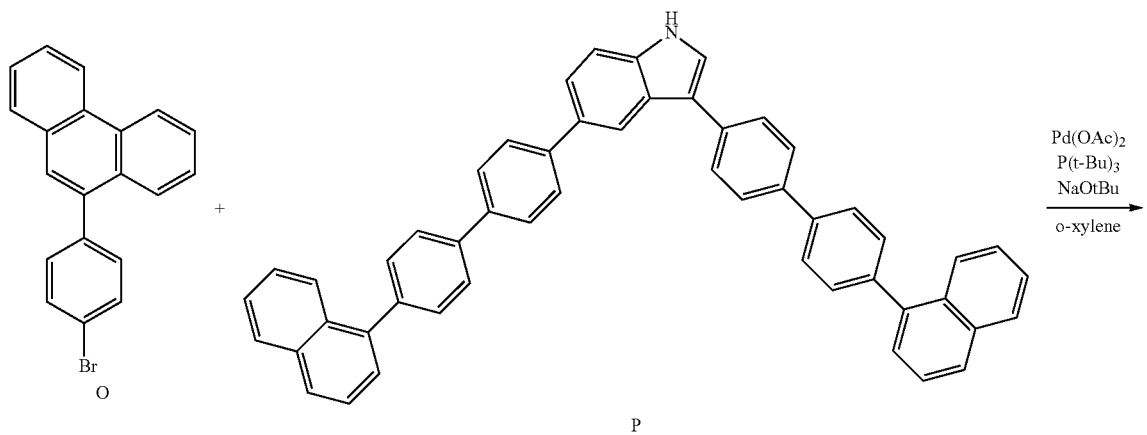

-continued

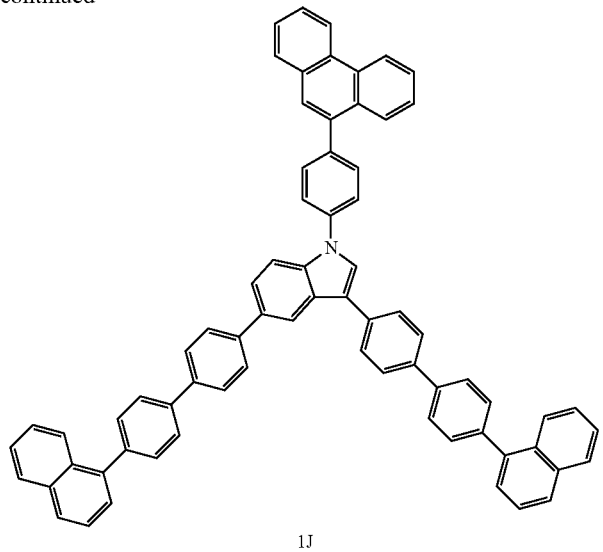

1J

After a 500-mL three-neck round-bottom flask was filled with nitrogen gas, o-xylene (200 mL) was injected thereinto, Compound O (15.0 g, 48.5 mmol), Compound P (33.4 g, 49.5 mmol), palladium acetate (Pd(OAc)$_2$, 202 mg, 0.90 mmol), sodium tert-butoxide (NaO t-Bu, 5.19 g, 54.0 mmol), and tri tert-butylphosphine (P(t-Bu)$_3$, 1.7 ml) were introduced thereinto, and then the resulting mixture was stirred at 130° C. for 12 hours. Thereafter, a pale gray target compound (Chemical Formula 1J, 34.1 g, 76%) was obtained by cooling the reactants to room temperature, introducing the reactants into methanol (2,000 mL), and then stirring the resulting mixture for 40 minutes and filtering the mixture.

MALDI-TOF: m/z=925.3709 (C$_{72}$H$_{47}$N=925.37).

Example 11

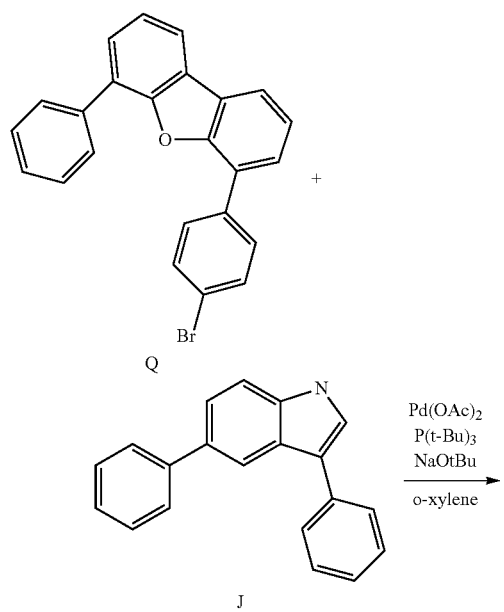

-continued

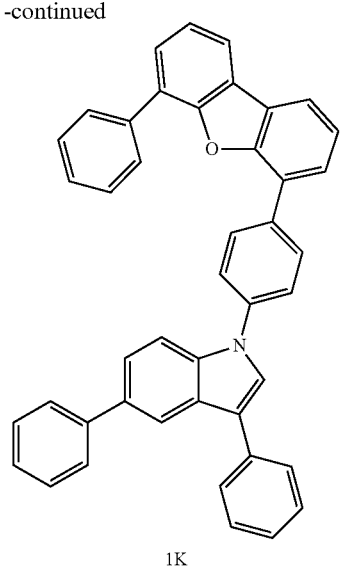

1K

After a 500-mL three-neck round-bottom flask was filled with nitrogen gas, o-xylene (200 mL) was injected thereinto, Compound Q (32.6 g, 81.7 mmol), Compound J (20.0 g, 74.3 mmol), palladium acetate (Pd(OAc)$_2$, 333 mg, 1.49 mmol), sodium tert-butoxide (NaO t-Bu, 8.6 g, 89.1 mmol), and tri tert-butylphosphine (P(t-Bu)$_3$, 1.7 ml) were introduced thereinto, and then the resulting mixture was stirred at 130° C. for 6 hours. Thereafter, a pale gray target compound (Chemical Formula 1K, 38.5 g, 70%) was obtained by cooling the reactants to room temperature, introducing the reactants into methanol (2,000 mL), and then stirring the resulting mixture for 30 minutes and filtering the mixture.

MALDI-TOF: m/z=587.2275 (C$_{44}$H$_{29}$NO=587.22).

Example 12

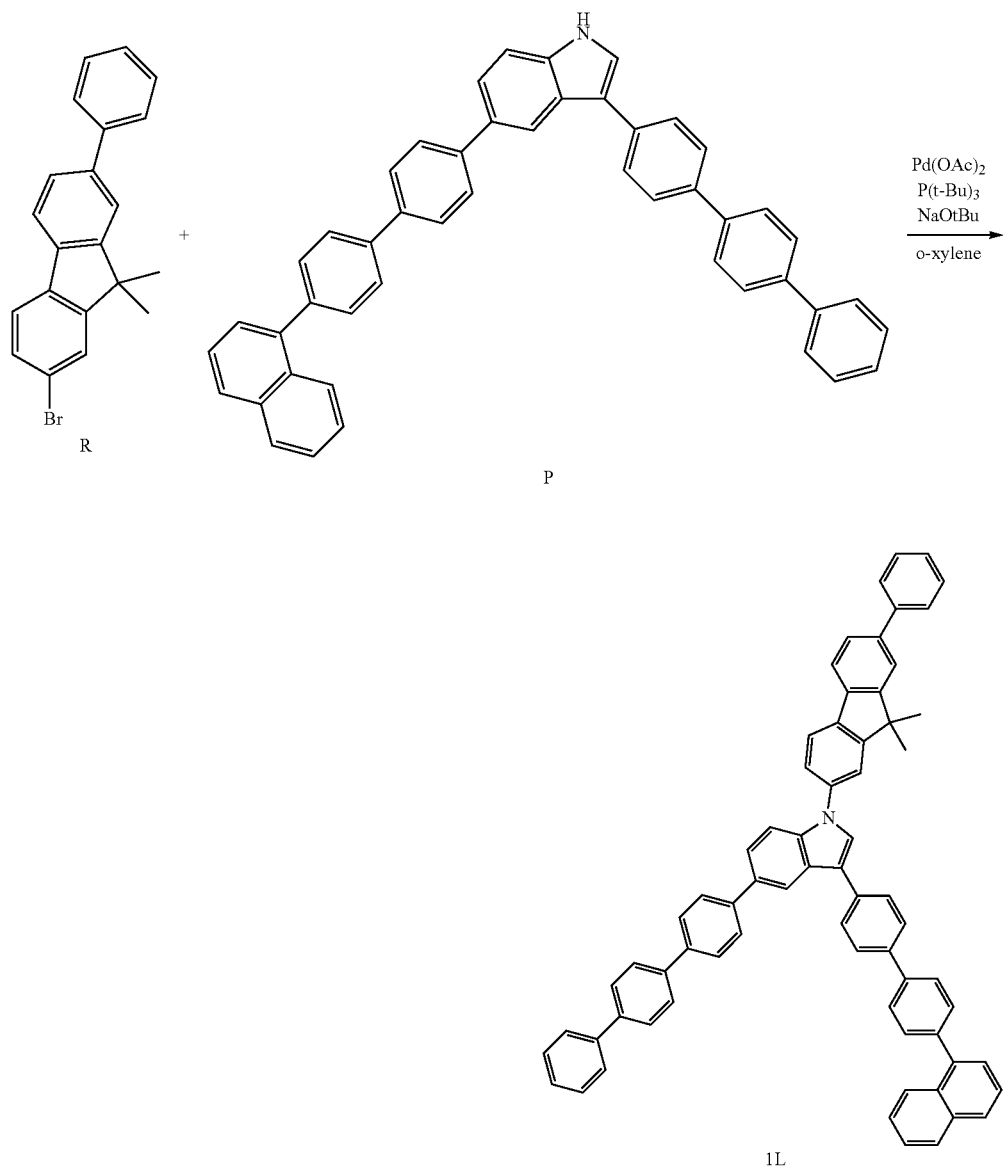

After a 500-mL three-neck round-bottom flask was filled with nitrogen gas, o-xylene (200 mL) was injected thereinto, Compound R (8.6 g, 24.5 mmol), Compound P (15.0 g, 22.3 mmol), palladium acetate (Pd(OAc)$_2$, 100 mg, 0.45 mmol), sodium tert-butoxide (NaO t-Bu, 2.6 g, 26.7 mmol), and tri tert-butylphosphine (P(t-Bu)$_3$, 1.7 ml) were introduced thereinto, and then the resulting mixture was stirred at 130° C. for 11 hours. Thereafter, a gray target compound (Chemical Formula 1L, 15.7 g, 75%) was obtained by cooling the reactants to room temperature, introducing the reactants into methanol (2,000 mL), and then stirring the resulting mixture for 20 minutes and filtering the mixture.

MALDI-TOF: m/z=941.4022 (C$_{73}$H$_{51}$N=941.40).

Example 13

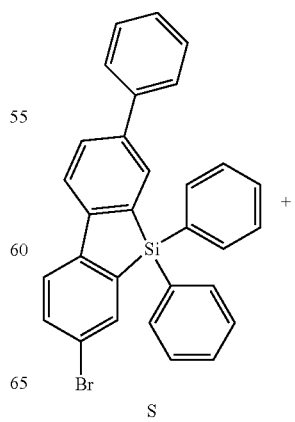

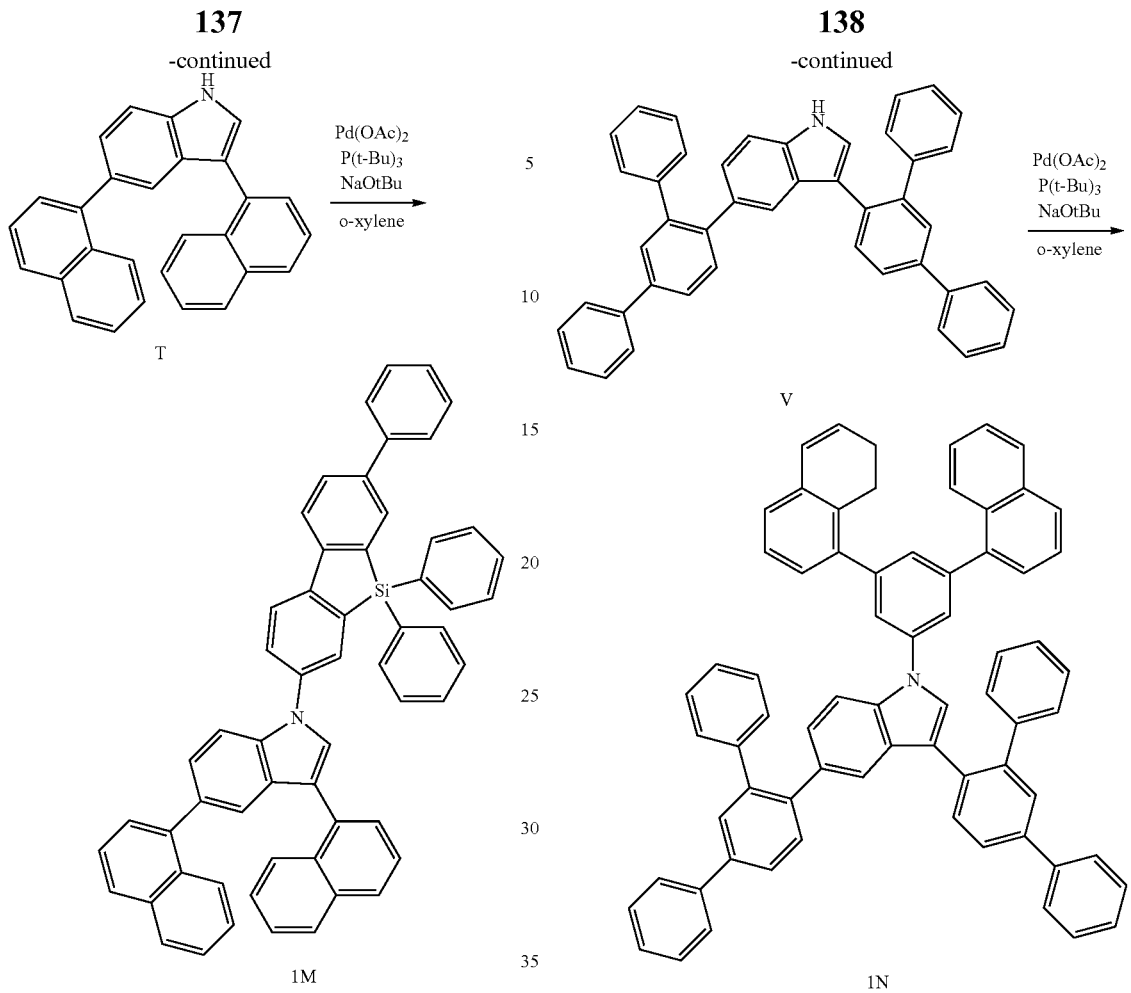

After a 500-mL three-neck round-bottom flask was filled with nitrogen gas, o-xylene (200 mL) was injected thereinto, Compound S (13.6 g, 27.7 mmol), Compound T (10.0 g, 25.2 mmol), palladium acetate (Pd(OAc)$_2$, 113 mg, 0.50 mmol), sodium tert-butoxide (NaO t-Bu, 2.9 g, 30.3 mmol), and tri tert-butylphosphine (P(t-Bu)$_3$, 1.7 ml) were introduced thereinto, and then the resulting mixture was stirred at 130° C. for 7 hours. Thereafter, a white target compound (Chemical Formula 1M, 15.7 g, 80%) was obtained by cooling the reactants to room temperature, introducing the reactants into methanol (2,000 mL), and then stirring the resulting mixture for 20 minutes and filtering the mixture.

MALDI-TOF: m/z=777.2892 (C$_{58}$H$_{39}$NSi=777.29).

Example 14

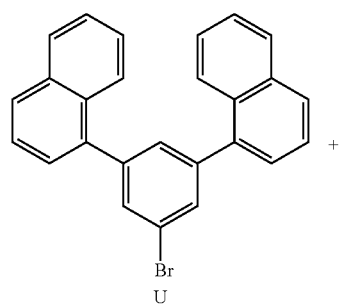

+

After a 500-mL three-neck round-bottom flask was filled with nitrogen gas, o-xylene (200 mL) was injected thereinto, Compound U (11.8 g, 28.8 mmol), Compound V (15 g, 26.1 mmol), palladium acetate (Pd(OAc)$_2$, 117 mg, 0.52 mmol), sodium tert-butoxide (NaO t-Bu, 3.0 g, 31.4 mmol), and tri tert-butylphosphine (P(t-Bu)$_3$, 1.7 ml) were introduced thereinto, and then the resulting mixture was stirred at 130° C. for 12 hours. Thereafter, a white target compound (Chemical Formula 1N, 17.2 g, 73%) was obtained by cooling the reactants to room temperature, introducing the reactants into methanol (2,000 mL), and then stirring the resulting mixture for 30 minutes and filtering the mixture.

MALDI-TOF: m/z=901.3709 (C$_{70}$H$_{47}$N=901.37).

Example 15

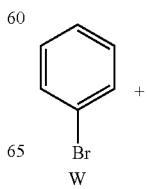

+

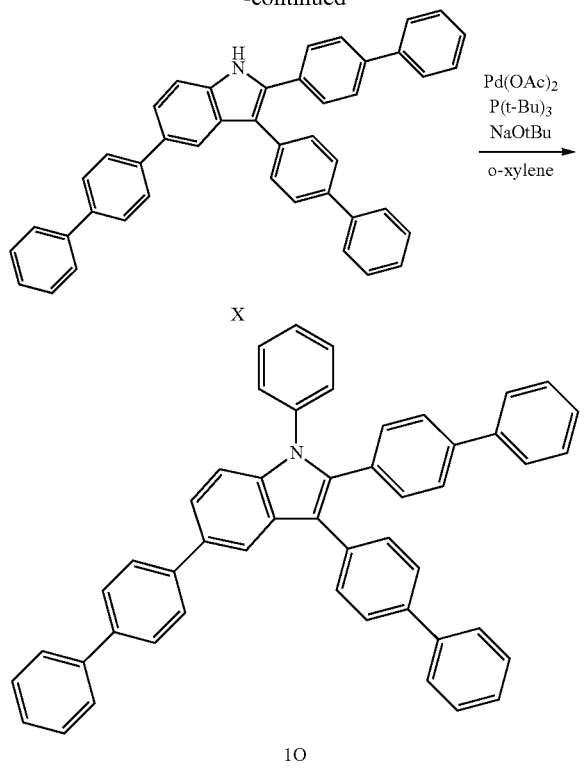

After a 500-mL three-neck round-bottom flask was filled with nitrogen gas, o-xylene (200 mL) was injected thereinto, Compound W (6.0 g, 38.3 mmol), Compound X (20.0 g, 34.9 mmol), palladium acetate (Pd(OAc)$_2$, 157 mg, 0.70 mmol), sodium tert-butoxide (NaO t-Bu, 4.0 g, 41.8 mmol), and tri tert-butylphosphine (P(t-Bu)$_3$, 1.7 ml) were introduced thereinto, and then the resulting mixture was stirred at 130° C. for 6 hours. Thereafter, a pale gray target compound (Chemical Formula 1O, 17.0 g, 75%) was obtained by cooling the reactants to room temperature, introducing the reactants into methanol (2,000 mL), and then stirring the resulting mixture for 30 minutes and filtering the mixture.

MALDI-TOF: m/z=649.8311 (C$_{50}$H$_{35}$N=649.82).

Examples 16 to 25. Manufacture of Light Emitting Diode

A third organic layer having a thickness of 100 Å was formed by evaporating a compound represented by Chemical Formula 12 below as a host material at a rate of 1 Å/sec, and simultaneously, co-evaporating a P-type dopant (HAT-CN) represented by Chemical Formula 13 below at a ratio of 3 parts by weight based on 100 parts by weight of the host material, on a first electrode formed of indium tin oxide (ITO). A second organic layer was formed by evaporating the compound represented by Chemical Formula 12 to a thickness of 300 Å on the third organic layer.

A first organic layer was formed by evaporating each of the compounds prepared in Examples 1 to 15 to a thickness of 100 Å on the second organic layer, as shown in Table 1 below.

A light emitting layer having a thickness of about 200 Å was formed by co-evaporating a compound represented by Chemical Formula 13 below and a compound represented by Chemical Formula 14 below at a weight ratio of 100:5 on the first organic layer.

And then, an electron transporting layer having a thickness of 360 Å was formed by co-evaporating a compound represented by Chemical Formula 15 below and a compound represented by Chemical Formula 16 below at a weight ratio of 50:50 on the light emitting layer. Subsequently, an electron injecting layer having a thickness of 5 Å was formed on the electron transporting layer by using a compound represented by Chemical Formula 17 below.

Finally, a light emitting diode was manufactured by forming a second electrode as an aluminum thin film having a thickness of 1,000 Å on the electron injecting layer.

TABLE 1

|  | First organic layer |
| --- | --- |
| Example 16 | Compound of Chemical Formula 1A prepared in Example 1 |
| Example 17 | Compound of Chemical Formula 1B prepared in Example 2 |
| Example 18 | Compound of Chemical Formula 1C prepared in Example 3 |
| Example 19 | Compound of Chemical Formula 1D prepared in Example 4 |
| Example 20 | Compound of Chemical Formula 1E prepared in Example 5 |
| Example 21 | Compound of Chemical Formula 1F prepared in Example 6 |
| Example 22 | Compound of Chemical Formula 1G prepared in Example 7 |
| Example 23 | Compound of Chemical Formula 1H prepared in Example 8 |
| Example 24 | Compound of Chemical Formula 1I prepared in Example 9 |
| Example 25 | Compound of Chemical Formula 1J prepared in Example 10 |
| Example 26 | Compound of Chemical Formula 1K prepared in Example 11 |
| Example 27 | Compound of Chemical Formula 1L prepared in Example 12 |
| Example 28 | Compound of Chemical Formula 1M prepared in Example 13 |
| Example 29 | Compound of Chemical Formula 1N prepared in Example 14 |
| Example 30 | Compound of Chemical Formula 1O prepared in Example 15 |

[Chemical Formula 12]

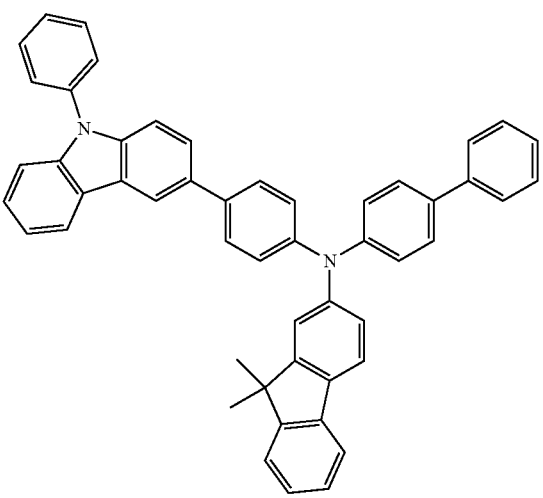

-continued

[Chemical Formula 13]

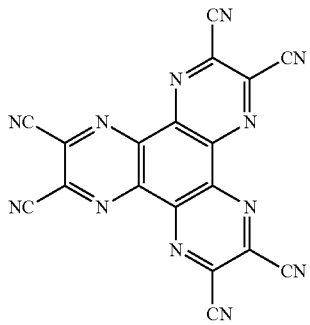

[Chemical Formula 14]

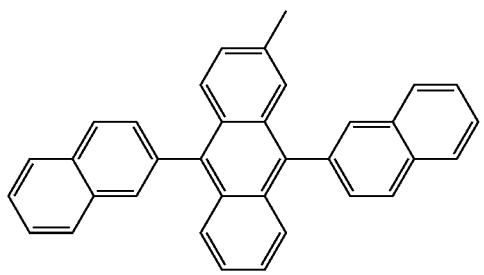

[Chemical Formula 15]

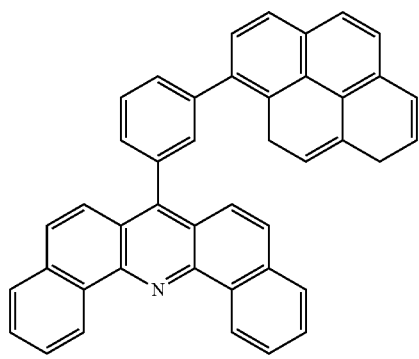

[Chemical Formula 16]

-continued

[Chemical Formula 17]

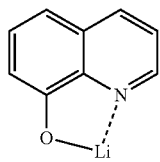

Comparative Example 1

A light emitting diode, which did not include a first organic layer, was manufactured in the same manner as in Example 16, except that in Example 16, the first organic layer was not formed and a light emitting layer was formed on a second organic layer.

Comparative Example 2

A light emitting diode including a first organic layer was manufactured in the same manner as in Example 16, except that in Example 16, the first organic layer was formed by using a compound represented by Chemical Formula 18 below instead of forming the first organic layer by using the compound (Chemical Formula 1A) prepared in Example 1.

[Chemical Formula 18]

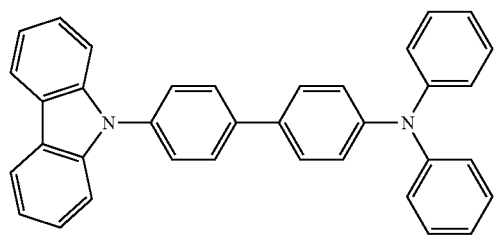

Comparative Example 3

A light emitting diode including a first organic layer was manufactured in the same manner as in Example 16, except that in Example 16, the first organic layer was formed by using a compound represented by Chemical Formula 19 below instead of forming the first organic layer by using the compound (Chemical Formula 1A) prepared in Example 1.

[Chemical Formula 19]

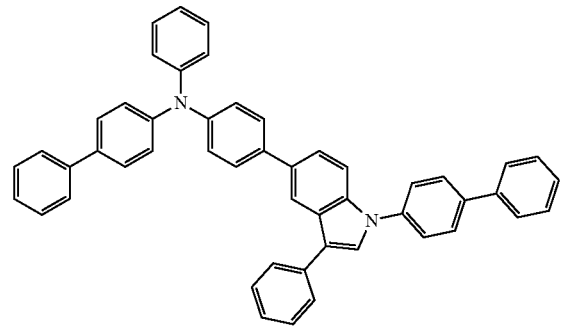

Comparative Example 4

A light emitting diode including a first organic layer was manufactured in the same manner as in Example 16, except that in Example 16, the first organic layer was formed by using the compound represented by Chemical Formula 20 instead of forming the first organic layer by using the compound (Chemical Formula 1A) prepared in Example 1.

[Chemical Formula 20]

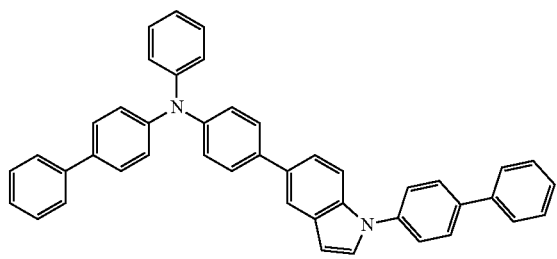

Experimental Example 1. Evaluation of Light Emitting Efficiency and Light Emitting Lifetime of Light Emitting Diode In order to evaluate the light emitting efficiency and light emitting lifetime of a light emitting diode including a compound represented by Chemical Formula 1 according to the present invention in a first organic layer, an experiment as described below was performed.

First, a UV curing sealant was dispensed at the edge of a cover glass to which a moisture absorbent was attached in a glove box under a nitrogen atmosphere, and then each of the light emitting diodes manufactured in Examples 16 to 30 and Comparative Examples 1 to 4 was laminated to the cover glass. Thereafter, the laminated light emitting diode was cured by being irradiated with UV rays, and the light emitting efficiency of the cured light emitting diode was measured. In this case, the light emitting efficiency was measured by establishing a value when the luminance was 1,000 cd/m² as a reference, and the unit of the measured value was lm/W.

Next, the light emitting lifetime of each of the light emitting diodes manufactured in Examples 16 to 30 and Comparative Examples 1 to 4 was measured by using a lifetime measuring apparatus installed in an oven for measurement, which was maintained constantly at a temperature of 25° C. In this case, $T_{50}$ means a time taken for the luminance of the light emitting diode to become 50% as compared to the initial luminance, when the initial luminance of the light-emitting diode is 5,000 cd/m². The value for the lifetime may be converted into a lifetime which is expected in the case where the measurement is made under other measurement conditions based on a conversion equation publicly known to a person skilled in the art. The measurement results are shown in Table 2 below.

TABLE 2

|  | Light emitting efficiency [lm/W] | Light emitting lifetime ($T_{50}$[hr]) |
| --- | --- | --- |
| Example 16 | 9.6 | 389 |
| Example 17 | 8.4 | 331 |
| Example 18 | 8.5 | 345 |
| Example 19 | 7.2 | 276 |
| Example 20 | 9.3 | 376 |
| Example 21 | 7.7 | 299 |
| Example 22 | 6.5 | 269 |
| Example 23 | 7.5 | 288 |
| Example 24 | 8.9 | 358 |
| Example 25 | 9.4 | 380 |
| Example 26 | 8.7 | 372 |
| Example 27 | 7.4 | 289 |
| Example 28 | 7.6 | 305 |
| Example 29 | 6.9 | 311 |
| Example 30 | 7.3 | 352 |
| Comparative Example 1 | 4.2 | 135 |
| Comparative Example 2 | 6.5 | 251 |
| Comparative Example 3 | 6.4 | 245 |
| Comparative Example 4 | 4.7 | 183 |

As shown in the above Table 2, it can be seen that the light emitting diode according to the present invention has excellent light emitting efficiency and an excellent light emitting lifetime.

More specifically, referring to Table 2, a light emitting diode including a compound represented by Chemical Formula 1 according to the present invention in a first organic layer was found to have a light emitting efficiency of 6.5 to 9.6 lm/W and a light emitting lifetime of 269 to 389 hours.

In contrast, in the case of a light emitting diode (Comparative Example 1) which did not include a first organic layer, it was confirmed that the light emitting efficiency was 4.2 lm/W, the light emitting lifetime was 135 hours, and the light emitting efficiency and lifetime were significantly low compared to those of the light emitting diode according to the present invention. Further, even in the case of a light emitting diode (Comparative Example 2) which did not include a compound represented by Chemical Formula 1 even though the light emitting diode included the first organic layer, it can be seen that the light emitting efficiency and the light emitting lifetime were 6.5 lm/W and 251 hours, respectively, which are low values.

In particular, in the case of light emitting diodes (Comparative Examples 3 and 4) including a compound having a structure, in which an aryl group such as a phenyl group at the No. 3 position of indole was not substituted or an amine group such as a triarylamine group was introduced at the No. 5 position of indole even though the aryl group was substituted, in a first organic layer, the light emitting efficiencies of Comparative Examples 3 and 4 were 6.4 lm/W and 4.7 lm/W, respectively, and the light emitting lifetime of Comparative Examples 3 and 4 were also 245 hours and 183 hours, respectively, which are low values even though the light emitting diodes included a compound having a structure similar to Chemical Formula 1 in the first organic layer.

That is, it can be seen that the light emitting diode including the compound represented by Chemical Formula 1 according to the present invention in the first organic layer had a light emitting efficiency increased by about 1.55 times to about 2.29 times and a light emitting lifetime improved by about 1.99 times to about 2.88 times compared to a light emitting diode (Comparative Example 1) which did not include the first organic layer. Further, it can be seen that even though the light emitting diode includes a first organic layer, the light emitting diode had a light emitting efficiency increased by up to about 1.48 times and a light emitting lifetime improved by about 1.07 times to about 1.55 times compared to a light emitting diode (Comparative Example 2) including a compound having a structure different from Chemical Formula 1 according to the present invention.

Furthermore, in the case of a light emitting diode (Example 16) including the compound of Chemical Formula 1 prepared in Example 1 in the first organic layer, the light emitting efficiency was improved by 1.50 times and 2.04 times, respectively, compared to the light emitting diodes (Comparative Examples 3 and 4) including the compound of Chemical Formula 19 or the compound of Chemical Formula 20, which have a structure similar to the compound of Chemical Formula 1, in the first organic layer. In addition, the light emitting lifetime was increased by 1.59 times and 2.13 times, respectively.

From these results, it can be seen that the light emitting diode according to the present invention has an effect of significantly improving the light emitting efficiency and the light emitting lifetime by forming a first organic layer which is disposed between a first electrode and a light emitting layer by using a compound represented by Chemical Formula 1 in which an aryl group is introduced at the Nos. 1, 2, 3, and 5 positions of an indolyl group, and simultaneously, an aryl group or a heteroaryl group is introduced at a nitrogen atom of an indolyl group through a linker, compared to a light emitting diode which does not include the first organic layer, or does not include a compound of Chemical Formula 1 even though the light emitting diode includes the first organic layer.

Therefore, since the light emitting diode according to the present invention has an excellent effect of improving the light emitting efficiency and lifetime of the light emitting diode, it can be usefully used in an electronic device in the high current/high output field which requires high luminance/high reliability.

What is claimed is:

1. A compound represented by Chemical Formula 1 below:

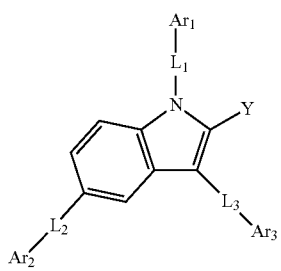

<Chemical Formula 1> in the above Chemical Formula 1,
Ar$_1$ is a structure of Chemical Formula 2 below,
L$_1$ is a single bond or an arylene group having 6 to 20 carbon atoms;
L$_2$ and L$_3$ are each independently a single bond, or an arylene group having 6 to 20 carbon atoms, which is unsubstituted or substituted with an aryl group having 6 to 30 carbon atoms;
Ar$_2$ and Ar$_3$ are each independently an aryl group having 6 to 30 carbon atoms, which is unsubstituted or substituted with an aryl group having 6 to 30 carbon atoms, and the aryl group having 6 to 30 carbon atoms, which is the substituent of the aryl group having 6 to 30 carbon atoms, is unsubstituted or substituted with an aryl group having 6 to 20 carbon atoms; and
Y is hydrogen, or an aryl group having 6 to 30 carbon atoms, which is unsubstituted or substituted with an aryl group having 6 to 30 carbon atoms,

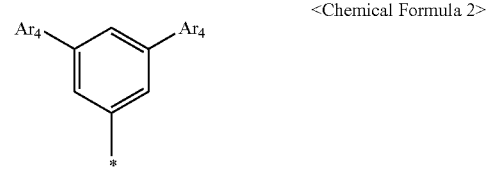

<Chemical Formula 2> in the above Chemical Formula 2,
wherein Ar$_4$ is each independently an aryl group having 6 to 30 carbon atoms or a heteroaryl group having 2 to 20 carbon atoms, which is unsubstituted or substituted with one or more substituents selected from a group consisting of an alkyl group having 1 to 4 carbon atoms, Si(R$_2$)$_3$, a cyano group, a halogen group, a haloalkyl group having 1 to 6 carbon atoms, an alkoxy group having 1 to 6 carbon atoms, and an aryl group having 6 to 30 carbon atoms,
wherein at least one Ar$_4$ is a dibenzofuranyl group or a dibenzothiophenyl group, which is unsubstituted or substituted with a phenyl group.

2. A compound represented by Chemical Formula 1 below:

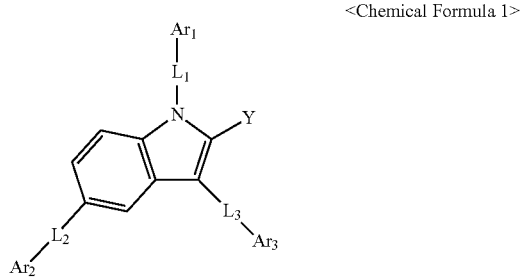

<Chemical Formula 1> in the above Chemical Formula 1,
Ar$_1$ is a phenyl group substituted with one of a trimethylsilyl group, or a trifluoromethyl group;
L$_1$ is a single bond or an arylene group having 6 to 20 carbon atoms;
L$_2$ and L$_3$ are each independently a single bond, or an arylene group having 6 to 20 carbon atoms, which is unsubstituted or substituted with an aryl group having 6 to 30 carbon atoms;
Ar$_2$ and Ar$_3$ are each independently an aryl group having 6 to 30 carbon atoms, which is unsubstituted or substituted with an aryl group having 6 to 30 carbon atoms, and the aryl group having 6 to 30 carbon atoms, which is the substituent of the aryl group having 6 to 30 carbon atoms, is unsubstituted or substituted with an aryl group having 6 to 20 carbon atoms; and
Y is hydrogen, or an aryl group having 6 to 30 carbon atoms, which is unsubstituted or substituted with an aryl group having 6 to 30 carbon atoms.

3. The compound of claim 2, wherein the compound has a structure of any one of the chemical formula of c-1, c-3, c-4, c-9, c-11, c-12, c-17 and c-18 below:

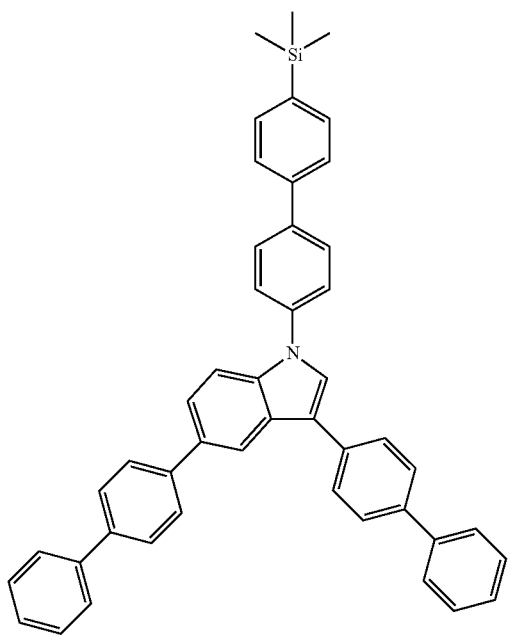
<c-1>
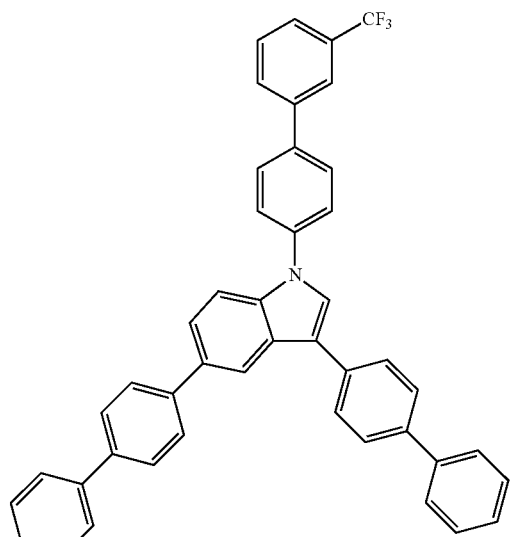
<c-4>
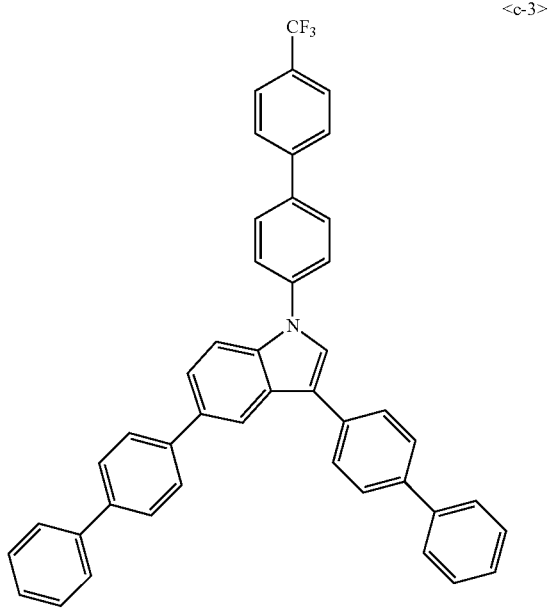
<c-3>
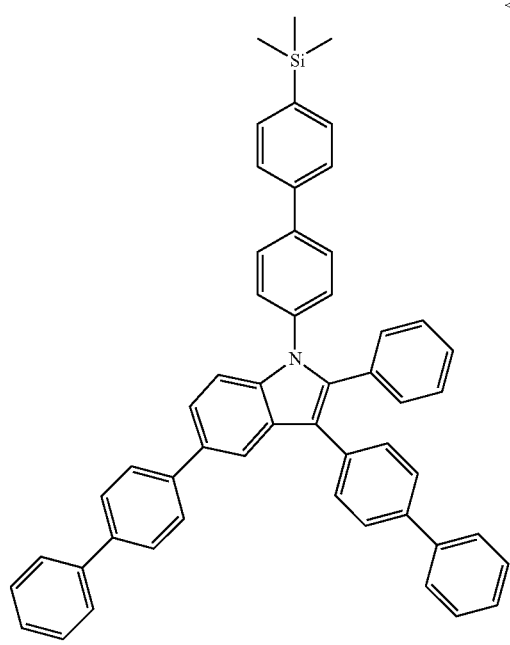
<c-9>

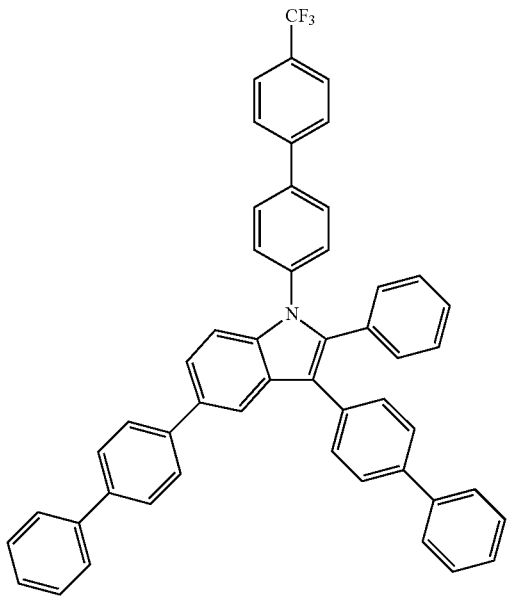

<c-11>

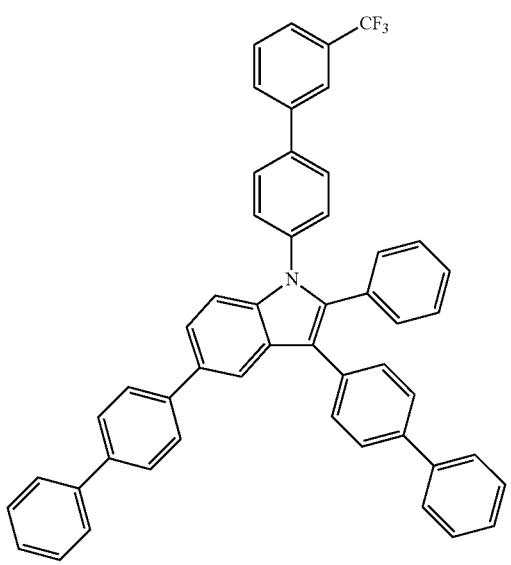

<c-12>

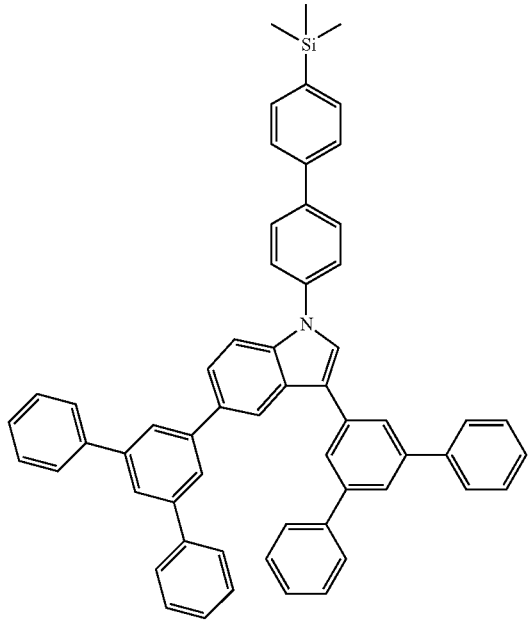

<c-17>

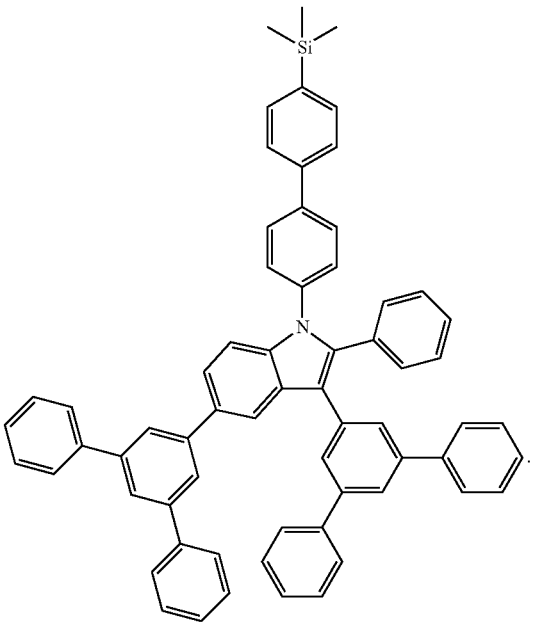

<c-18>

4. The compound of claim 1, wherein
$L_1$ is a single bond or a phenylene group,
$L_2$ and $L_3$ are each independently a single bond; or a phenylene group which is unsubstituted or substituted with a phenyl group,
$Ar_2$ and $Ar_3$ are each independently a phenyl group, a naphthyl group, or a phenanthryl group, wherein the phenyl group is unsubstituted or substituted with a phenyl group, a biphenyl group, a naphthyl group, or a phenanthryl group, and
Y is hydrogen, a phenyl group, or a biphenyl group.

5. The compound of claim 1, wherein one of $Ar_4$ is a phenyl group, a biphenyl group, a naphthyl group or a phenanthryl group, which is unsubstituted or substituted with one or more substituents selected from a group consisting of a trimethylsilyl group, a cyano group, a trifluoromethyl group, a fluoro group, and a methoxy group, and wherein the other Ar$_4$ is a dibenzofuranyl group or a dibenzothiophenyl group, which is unsubstituted or substituted with a phenyl group.

6. The compound of claim 1, wherein both Ar$_4$ is a dibenzofuranyl group or a dibenzothiophenyl group, which is unsubstituted or substituted with a phenyl group.

7. The compound of claim 1, wherein the compound has a structure of any one of the chemical formulas of e-1 to e-16 below:

<e-1>

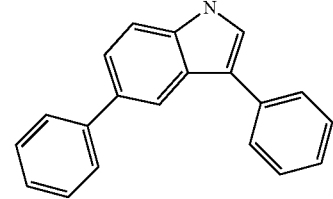

<e-2>

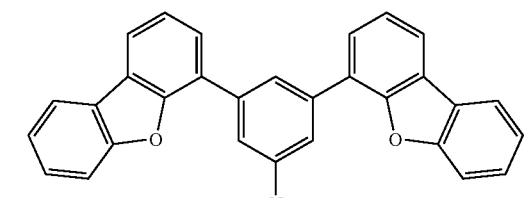

<e-3>

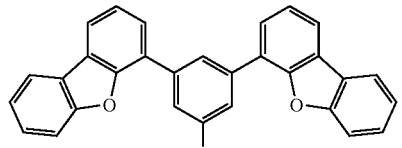
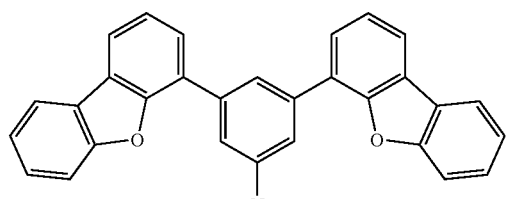

<e-4>

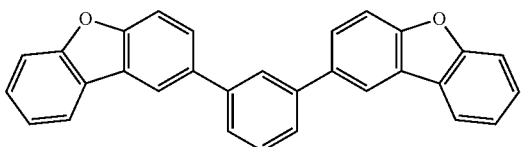
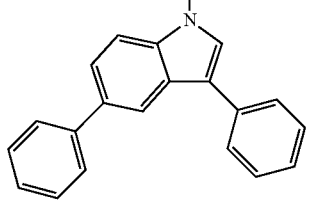

<e-5>

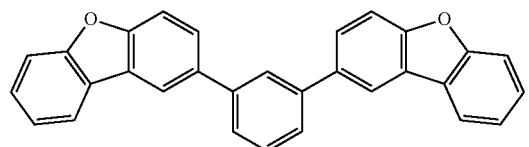
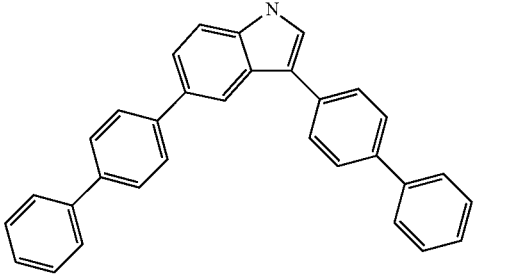

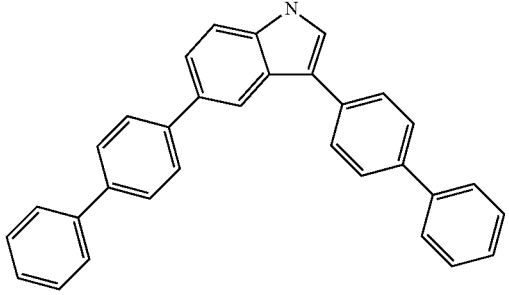

<e-6>
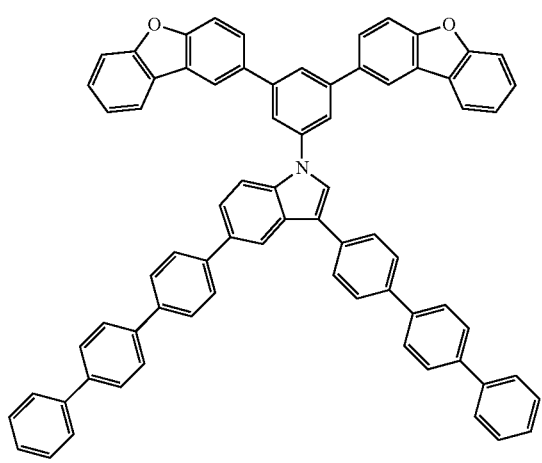
<e-7>
<e-8>
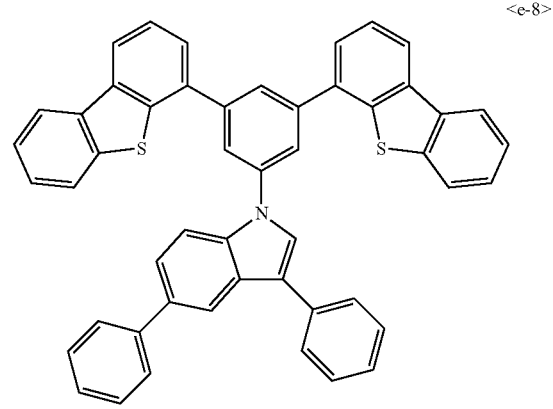
<e-9>
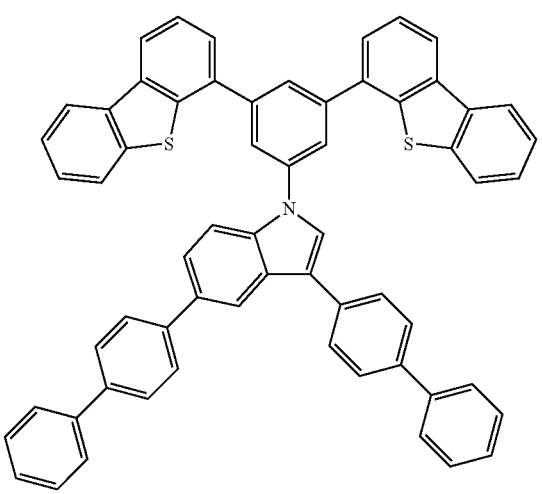
<e-10>
<e-11>
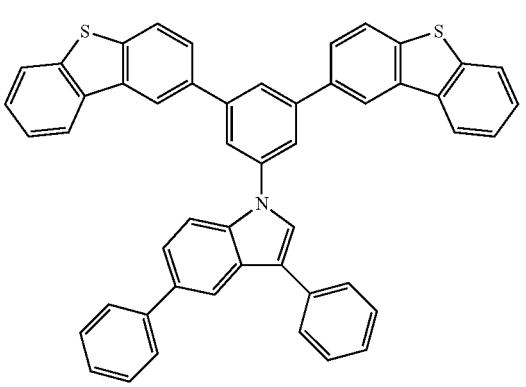

-continued

<e-12>
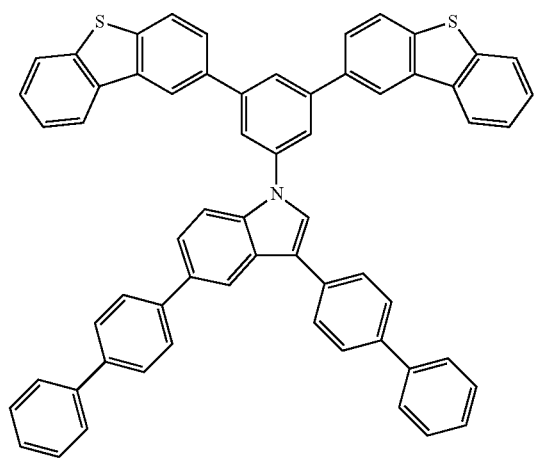

<e-13>
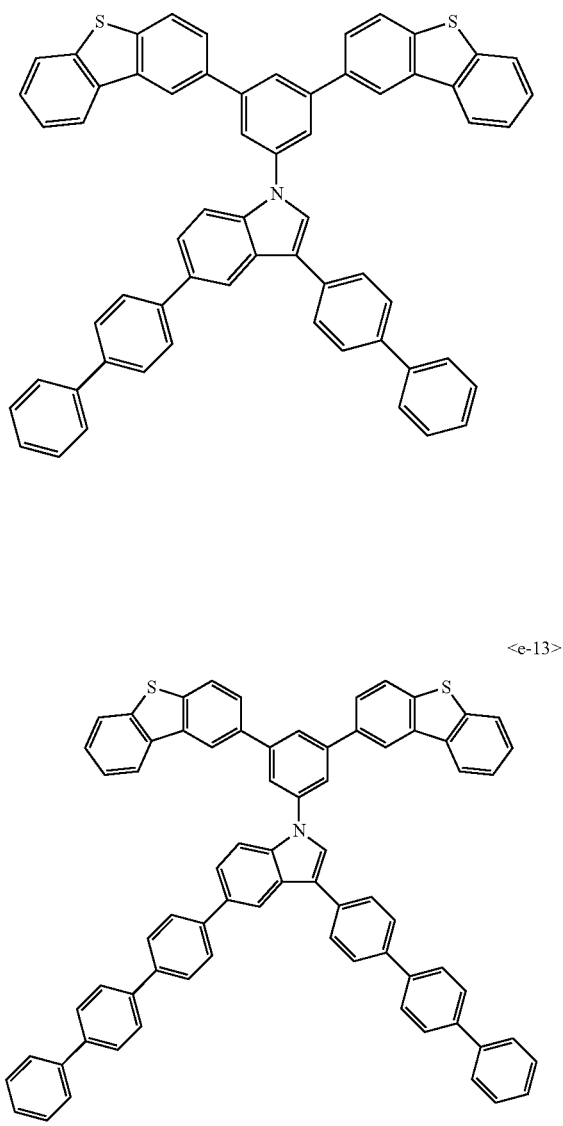

<e-14>
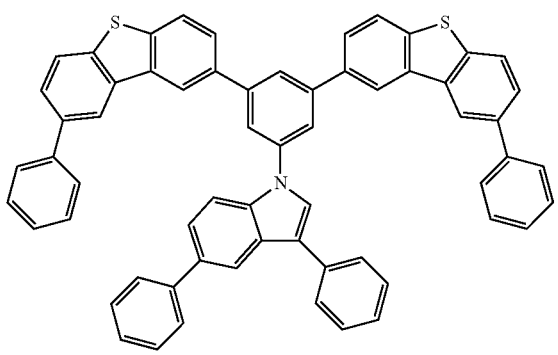

-continued

<e-15>
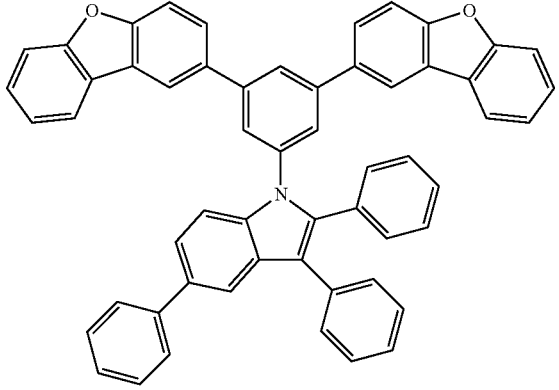

<e-16>
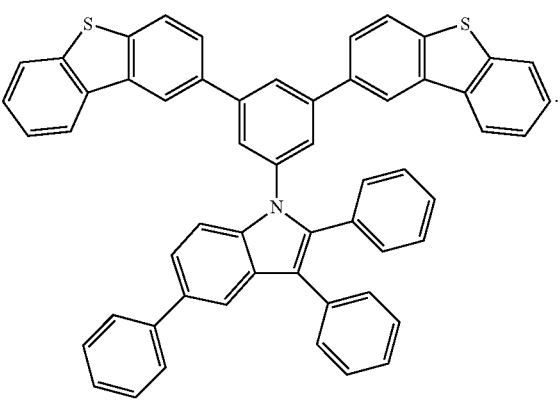

8. A light emitting diode comprising:
a first electrode;
an organic layer provided on the first electrode;
a light emitting layer provided on the organic layer;
an electron transport layer provided on the light emitting layer; and
a second electrode provided on the electron transport layer,
wherein the organic layer includes a compound represented by Chemical Formula 1 below,
wherein the electron transport layer includes a compound represented by Chemical Formula 5 below:

[Chemical Formula 1]
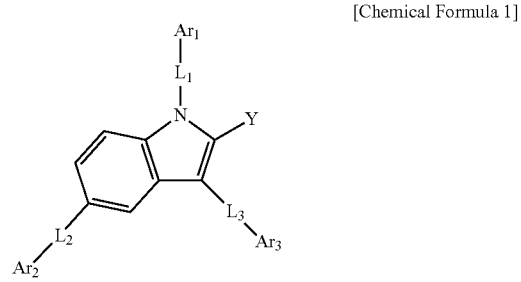

in the above Chemical Formula 1, $Ar_1$ is a fluorenyl group, a dibenzosilolyl group, or an aryl group having 6 to 30 carbon atoms or a heteroaryl group having 5 to 20 carbon atoms, which is unsubstituted or substituted with one or more substituents selected from a group consisting of an alkyl group having 1 to 4 carbon atoms, Si(R₁)₃, a cyano group, a halogen group, a haloalkyl group having 1 to 6 carbon atoms, an alkoxy group having 1 to 6 carbon atoms, an aryl group having 6 to 30 carbon atoms and a heteroaryl group having 2 to 20 carbon atoms;

the fluorenyl group or the dibenzosilolyl group is each independently unsubstituted or substituted with one or more substituents selected from a group consisting of an alkyl group having 1 to 4 carbon atoms and an aryl group having 6 to 10 carbon atoms;

$R_1$ is each independently hydrogen or an alkyl group having 1 to 4 carbon atoms; and $Ar_2$, $Ar_3$, $L_1$, $L_2$, $L_3$ and Y are as defined in claim 1,

[Chemical Formula 5]

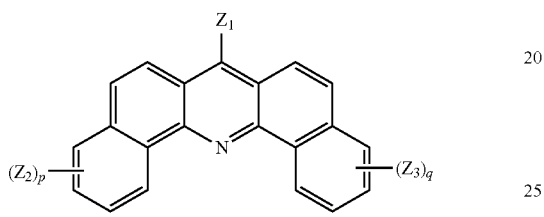

in the above Chemical Formula 5, $Z_1$ to $Z_3$ are each independently hydrogen, a halogen group, a cyano group, an alkyl group having 1 to 20 carbon atoms, an aryl group having 6 to 30 carbon atoms, a heteroaryl group having 2 to 20 carbon atoms, an alkoxy group having 1 to 20 carbon atoms or a diarylphosphine oxide group having 6 to 20 carbon atoms, when $Z_1$ to $Z_3$ are each independently an aryl group having 6 to 30 carbon atoms, a heteroaryl group having 2 to 20 carbon atoms, or a diarylphosphine oxide group having 6 to 20 carbon atoms, the aryl group, the heteroaryl group, and the diarylphosphine oxide group are unsubstituted or substituted with one or more substituents selected from a group consisting of an alkyl group having 1 to 6 carbon atoms, an aryl group having 6 to 20 carbon atoms, and a diarylphosphine oxide group having 6 to 20 carbon atoms, and p and q are each independently an integer of 1 to 3.

9. The light emitting diode of claim 8, wherein in the above Chemical Formula 1, $L_1$ is a phenylene group or a naphthylene group, $L_2$ and $L_3$ are each independently a single bond, or a phenylene group which is unsubstituted or substituted with a phenyl group, $Ar_2$ and $Ar_3$ are each independently a phenyl group, a naphthyl group, or a phenanthryl group, wherein the phenyl group is unsubstituted or substituted with a phenyl group, a biphenyl group, a naphthyl group, or a phenanthryl group, and Y is hydrogen, a phenyl group, or a biphenyl group.

10. The light emitting diode of claim 9, wherein in the above Chemical Formula 1, $Ar_1$ is a phenyl group, a naphthyl group, or a phenanthryl group.

11. The light emitting diode of claim 8, wherein the organic layer includes a compound that has a structure of any one of the chemical formula of a-1 to a-66 below:

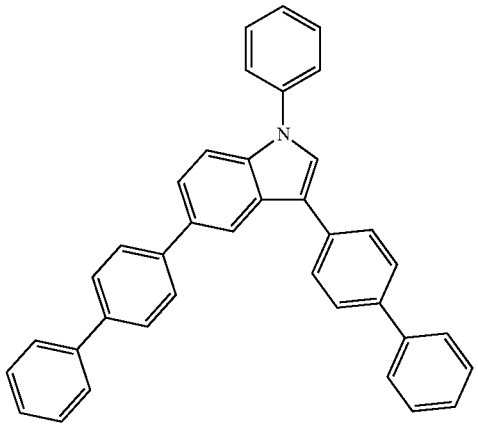

<a-1>

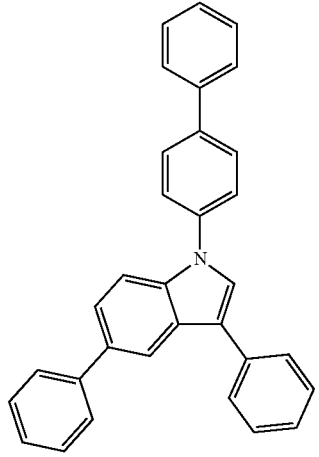

<a-2>

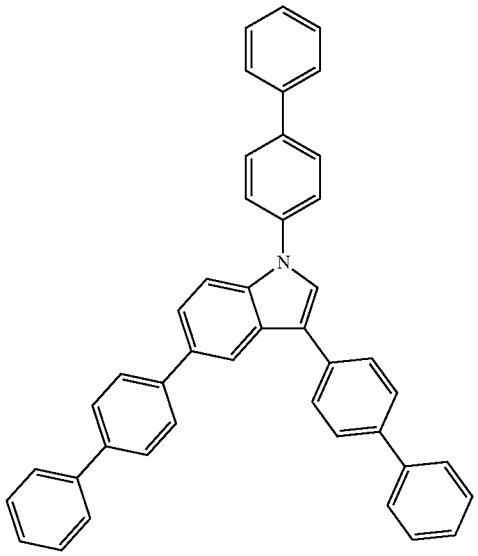

<a-3>

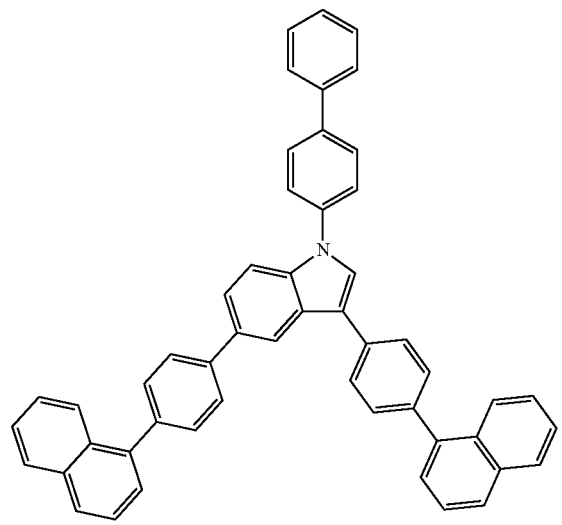
<a-4>
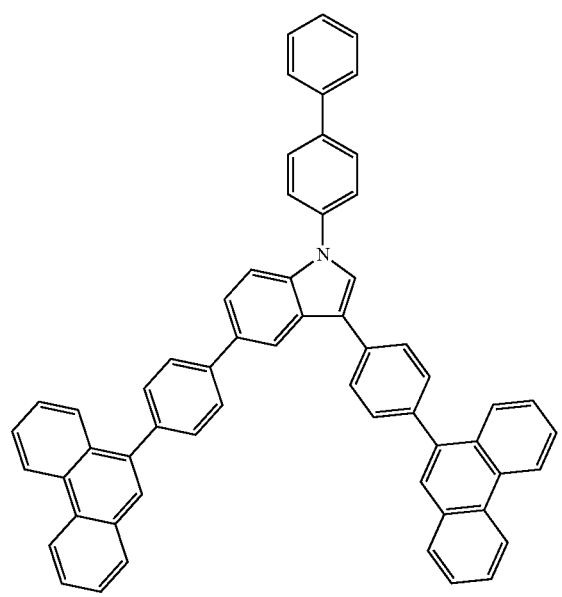
<a-5>
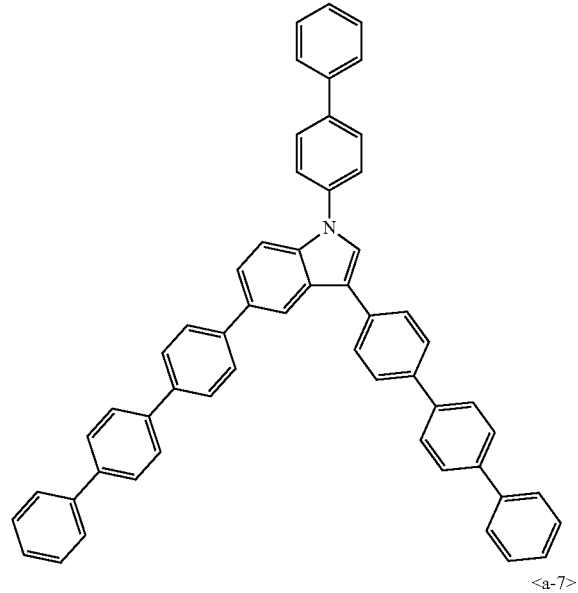
<a-6>
<a-7>
<a-8>

<a-9>
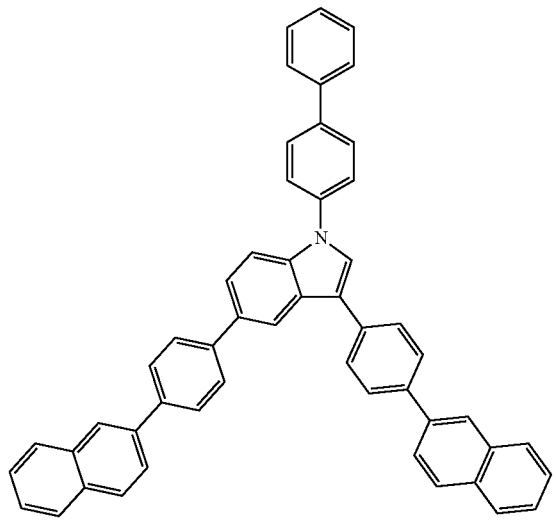
<a-10>
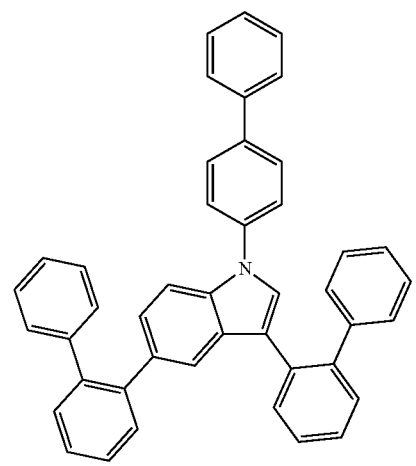
<a-11>
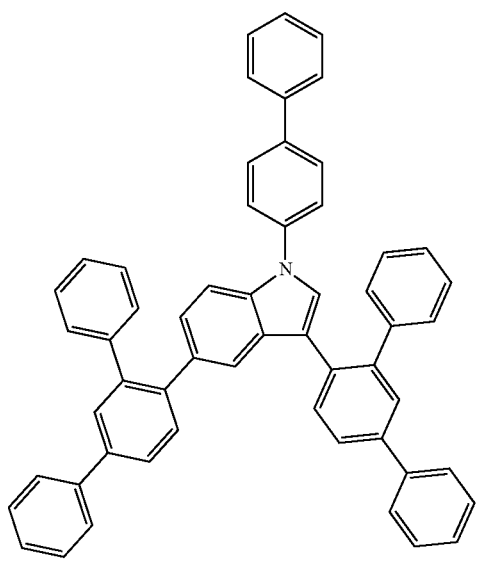
<a-12>
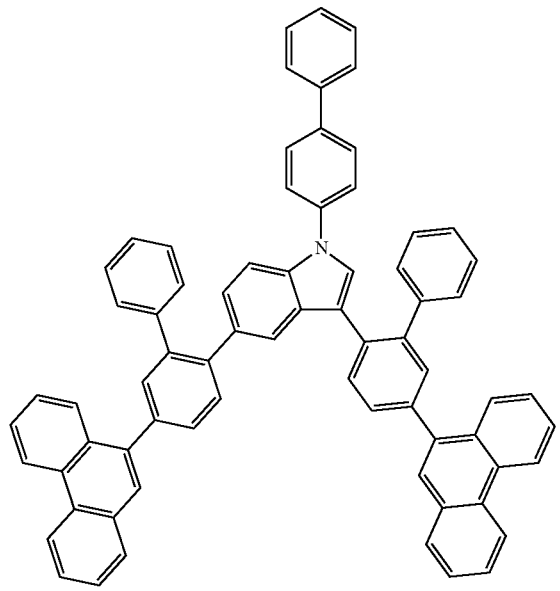
<a-13>
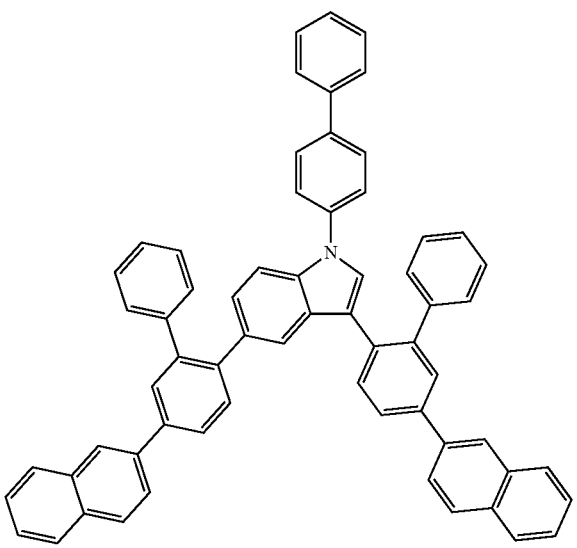
<a-14>
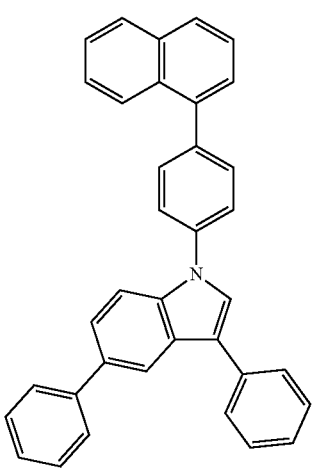

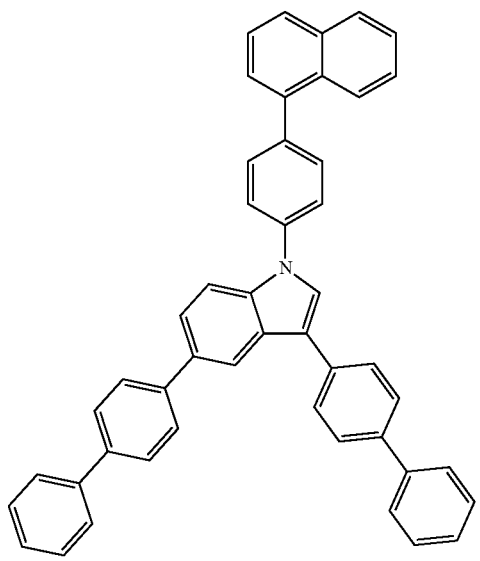
<a-15>
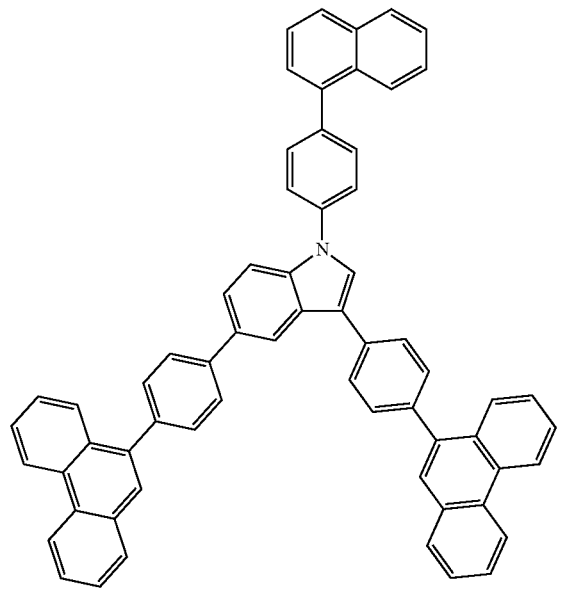
<a-17>
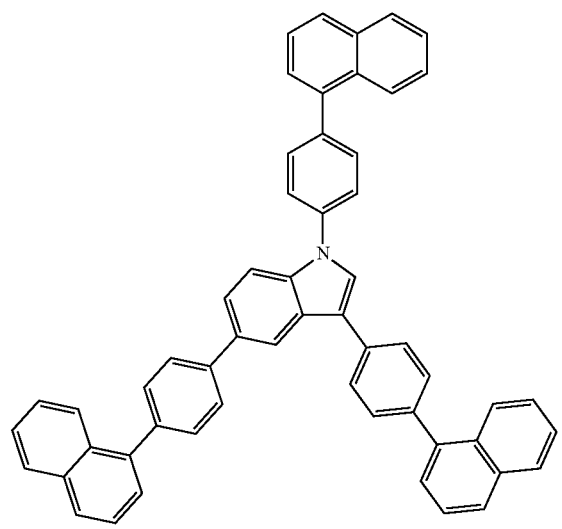
<a-16>
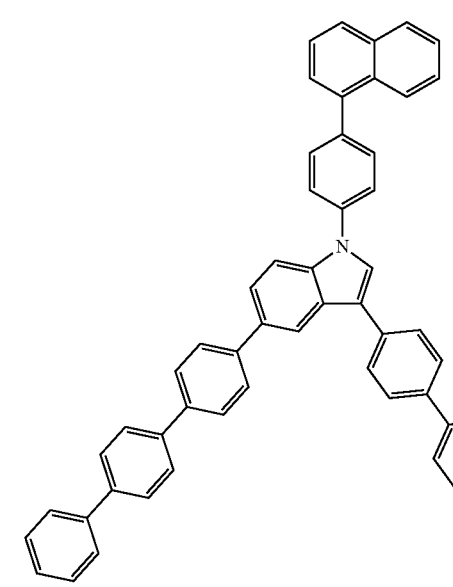
<a-18>

-continued
<a-19>
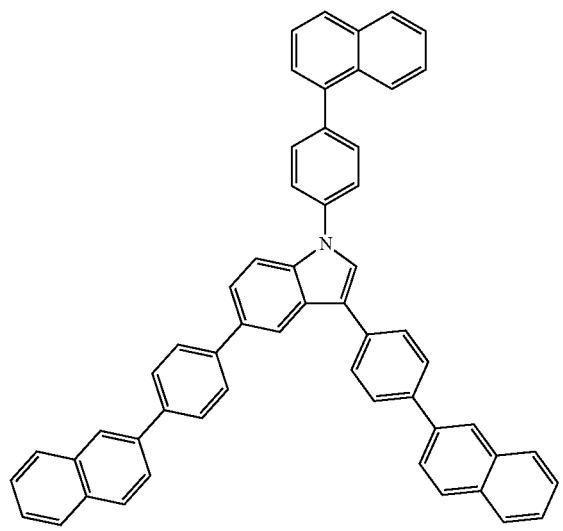
<a-20>
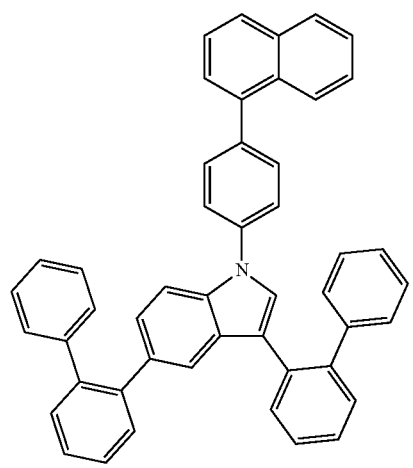
<a-21>
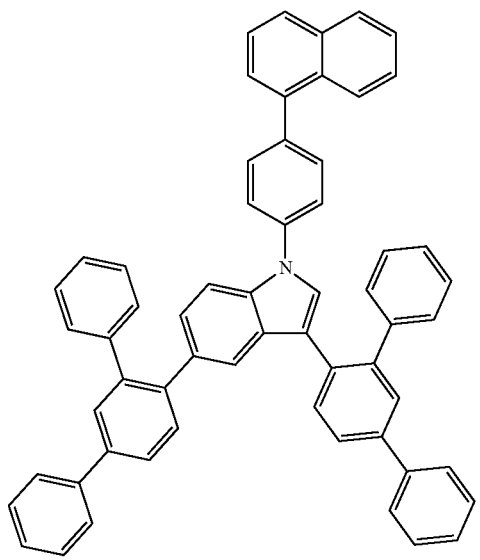
-continued
<a-22>
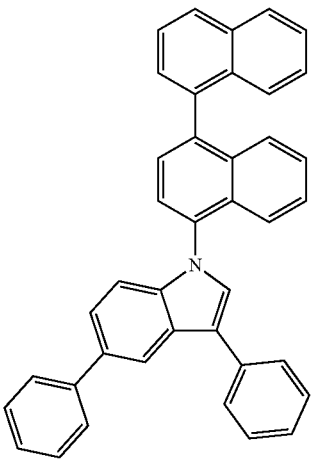
<a-23>
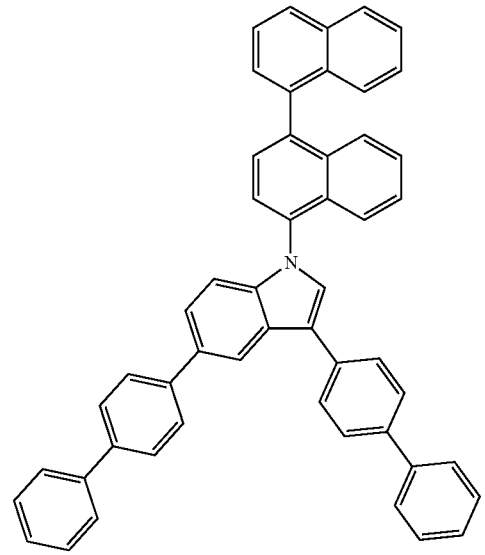
<a-24>
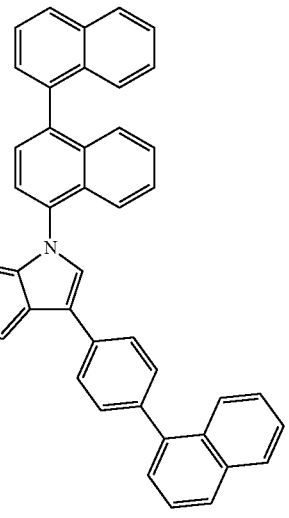

<a-25>
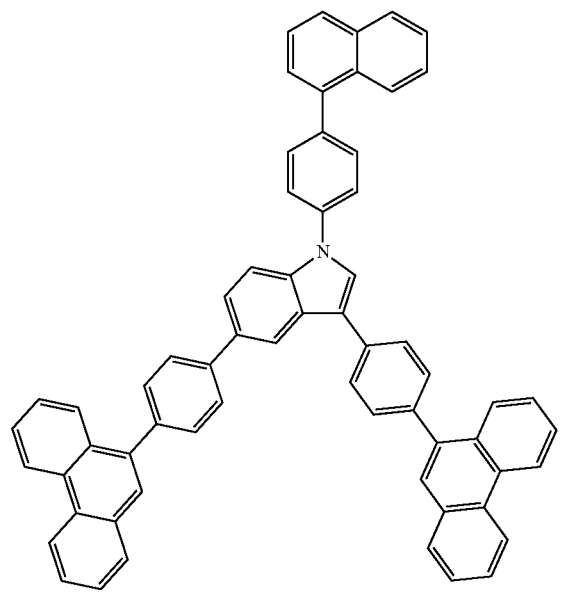
<a-26>
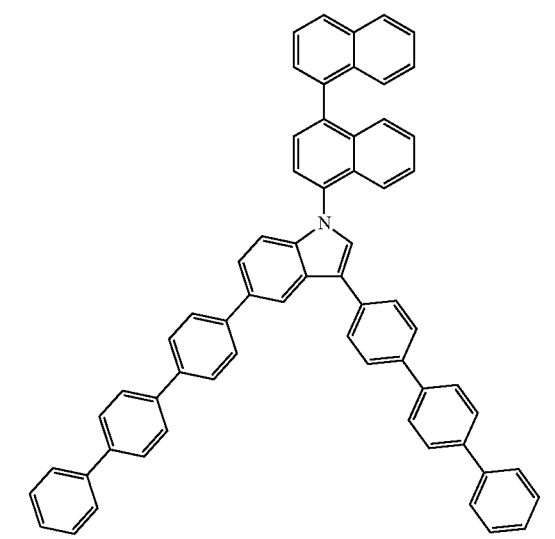
<a-27>
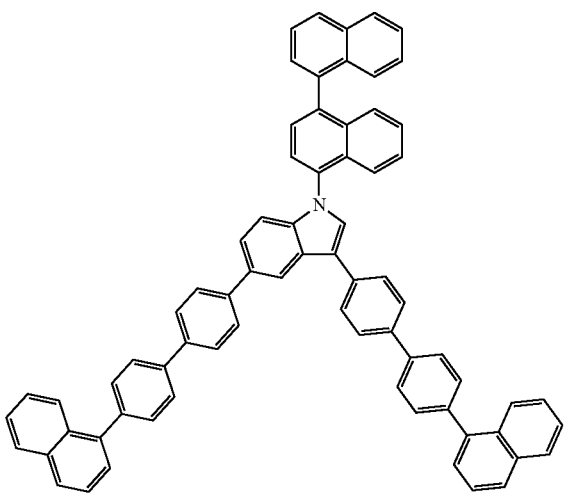
<a-28>
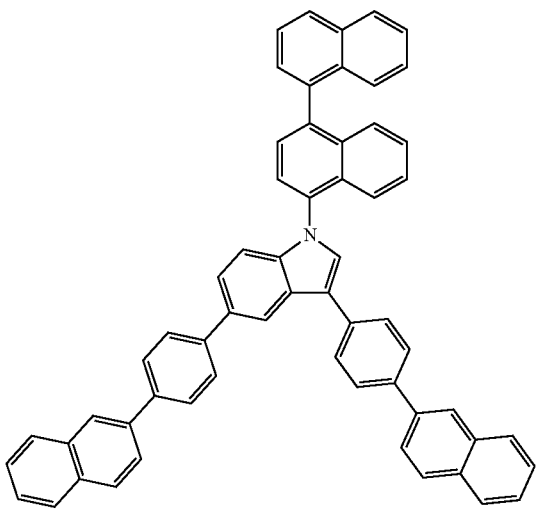
<a-29>
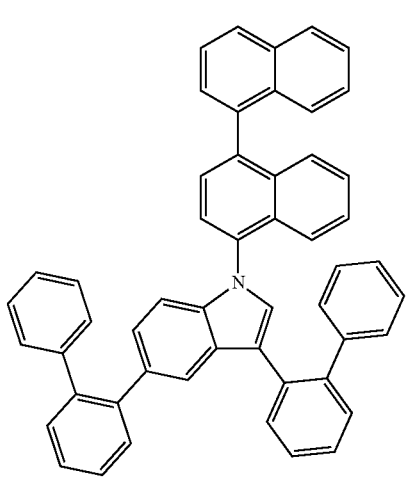
<a-30>
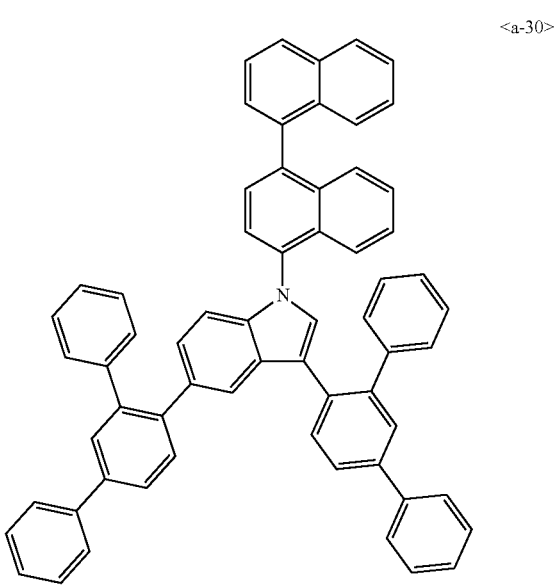

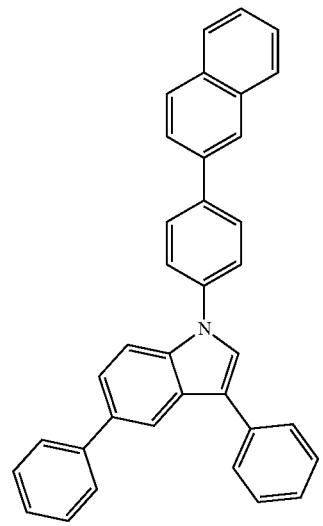 <a-31>
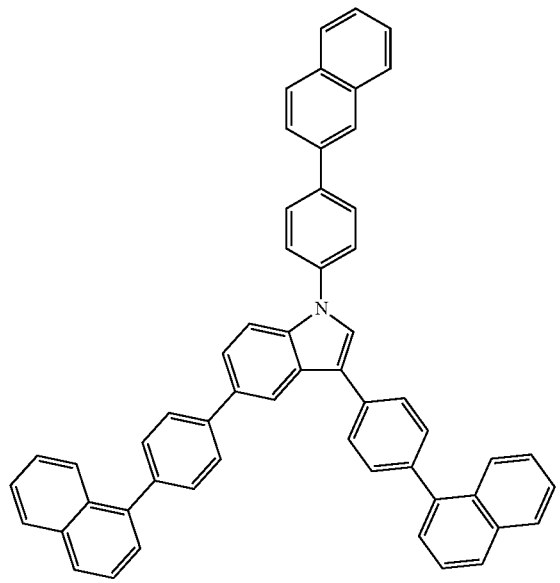 <a-33>
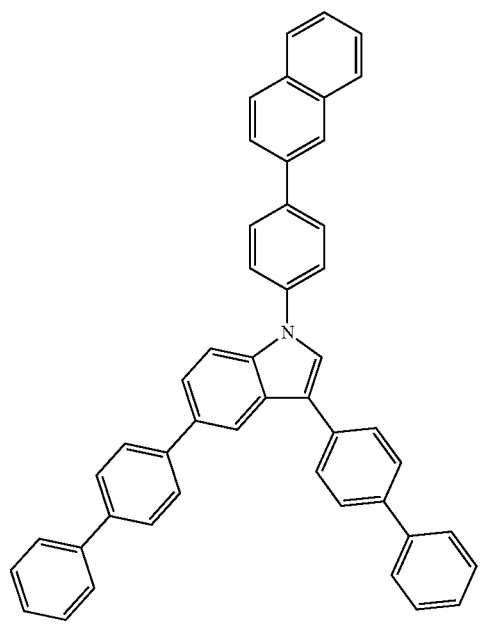 <a-32>
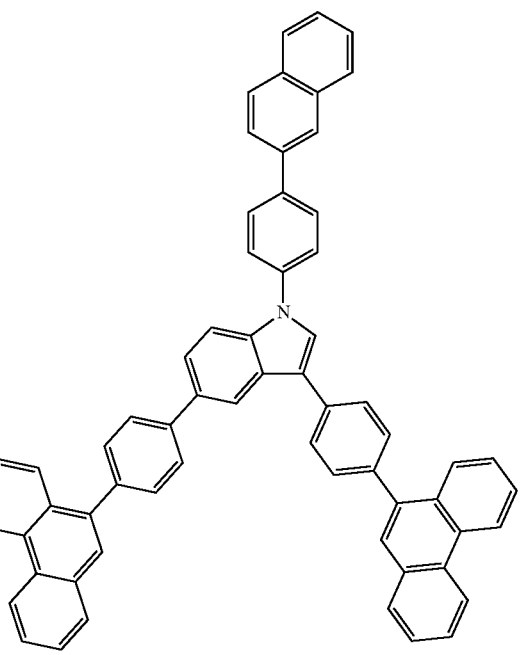 <a-34>

<a-35>
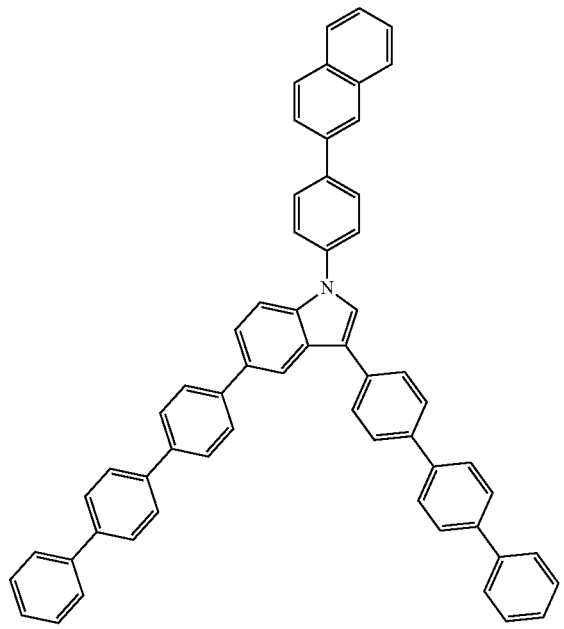
<a-37>
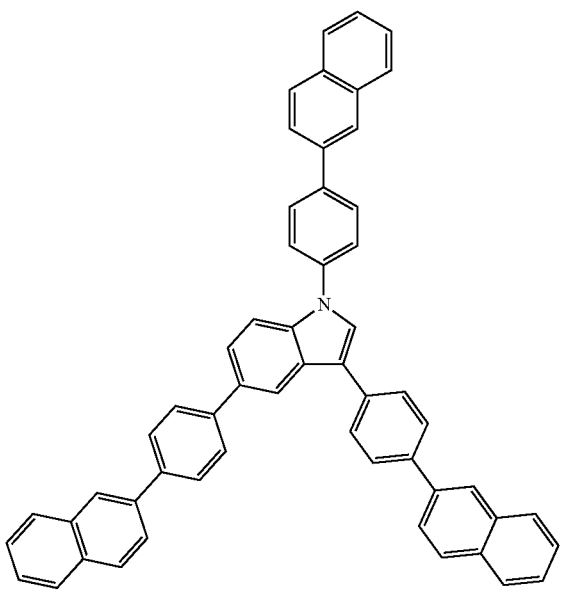
<a-36>
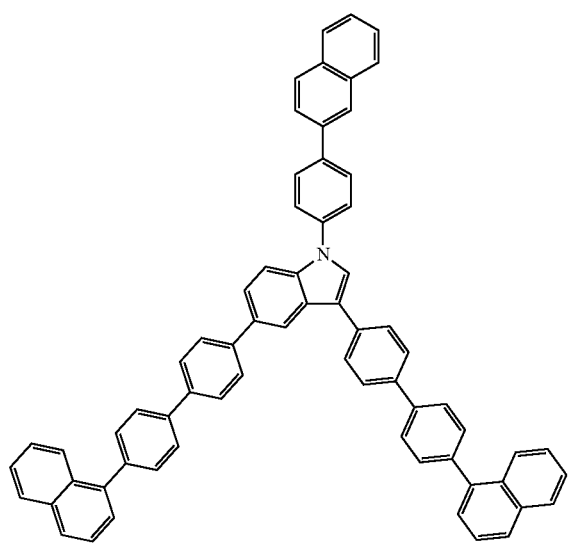
<a-38>
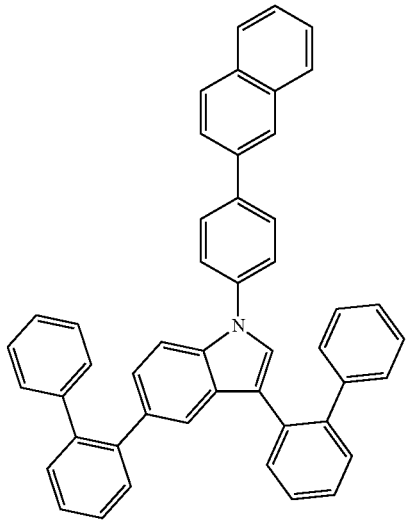

<a-39>
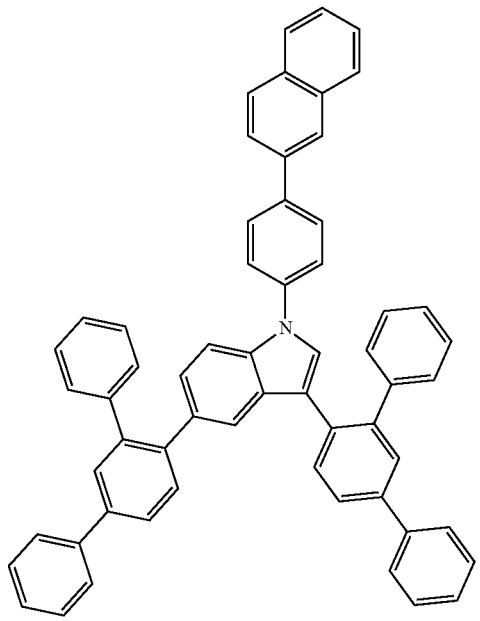
<a-40>
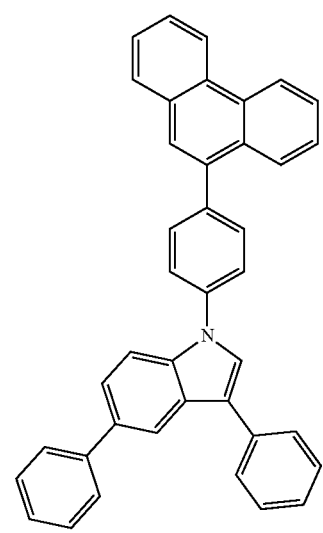
<a-41>
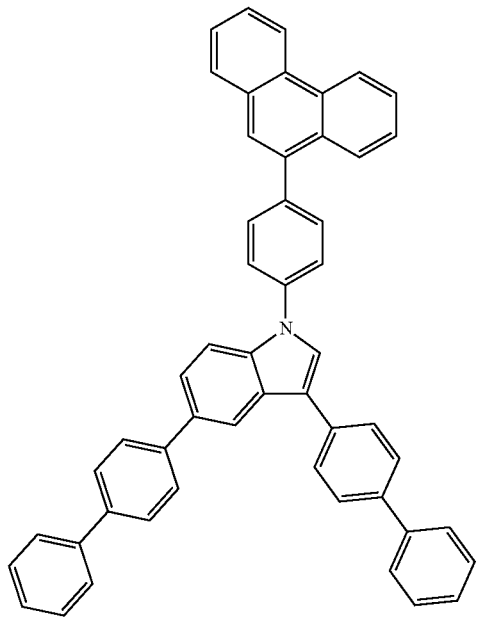
<a-42>
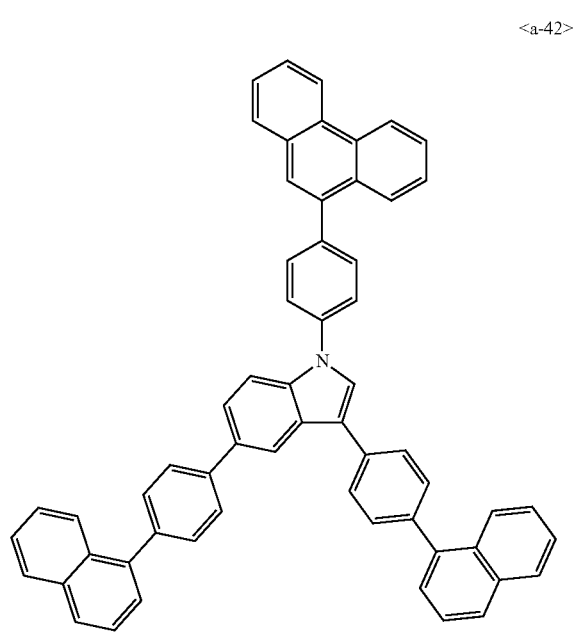

<a-43>
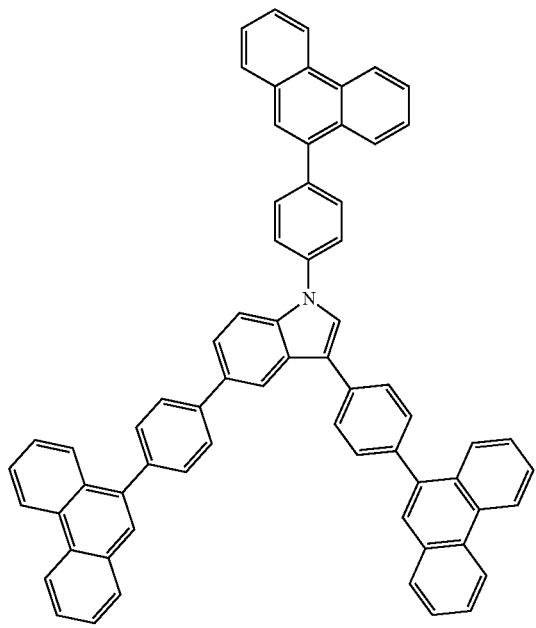
<a-45>
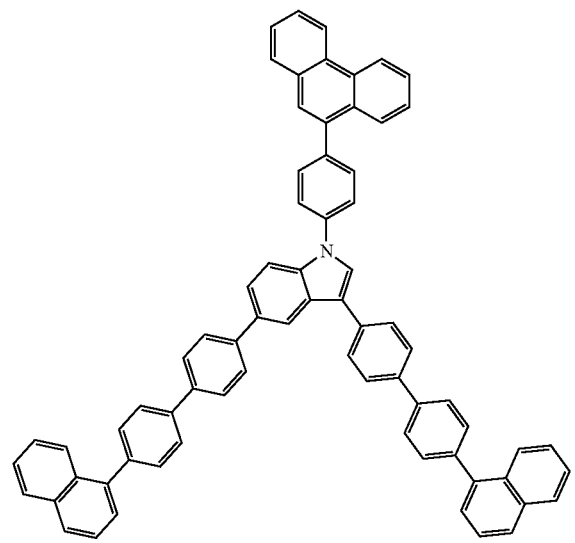
<a-44>
<a-46>
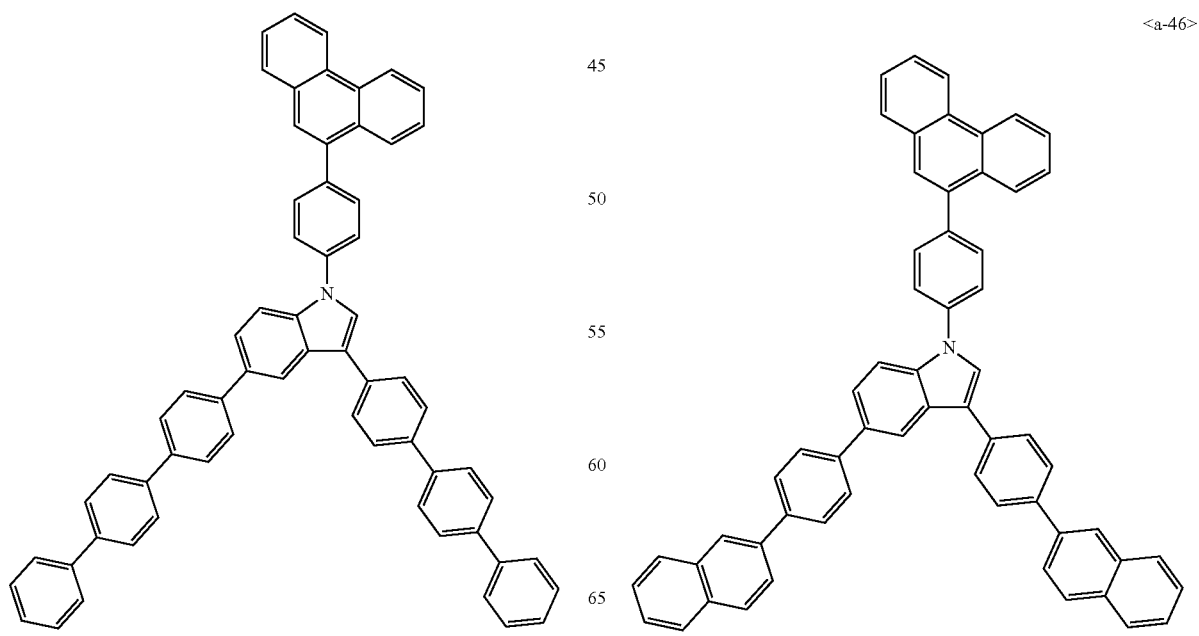

<a-47>
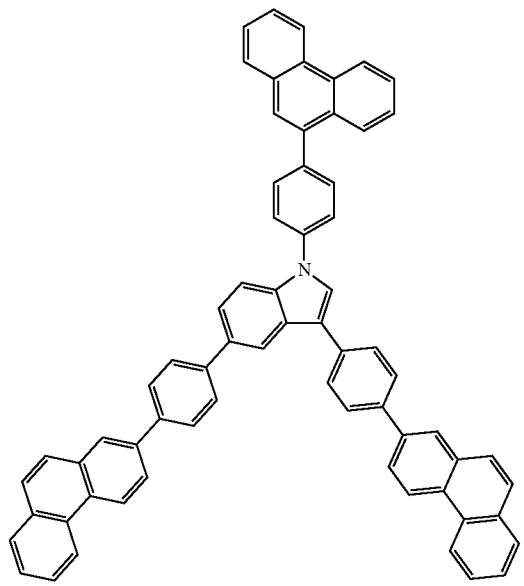
<a-49>
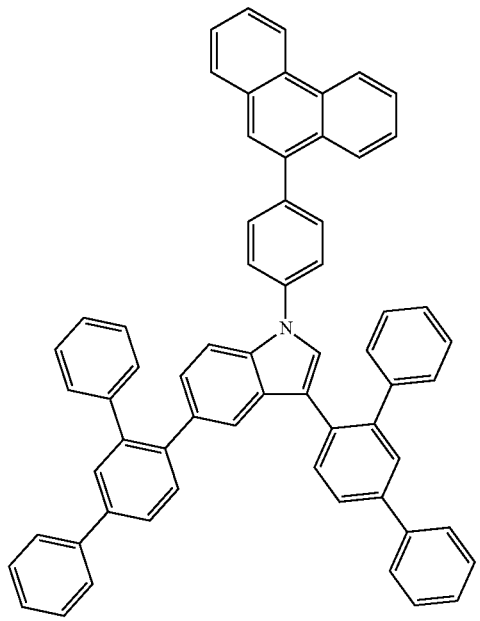
<a-48>
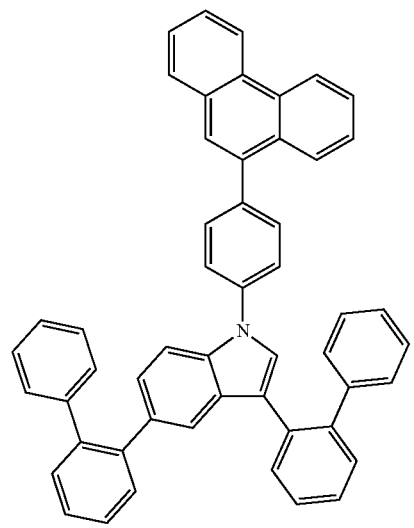
<a-50>
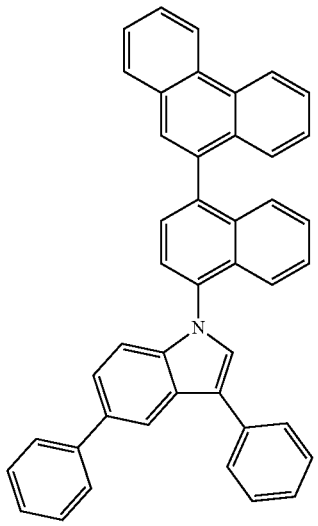

<a-51>
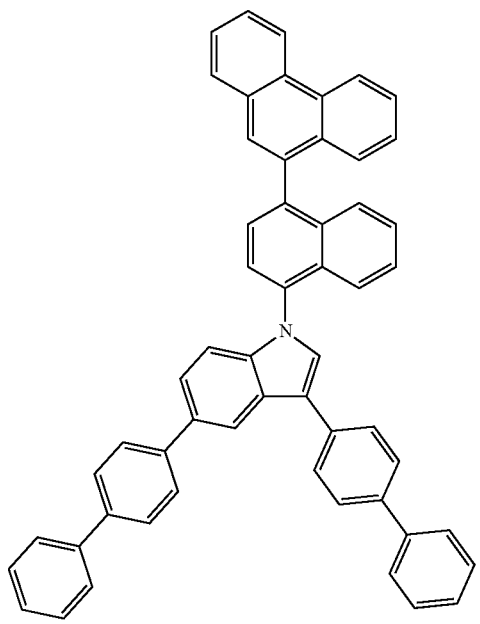
<a-53>
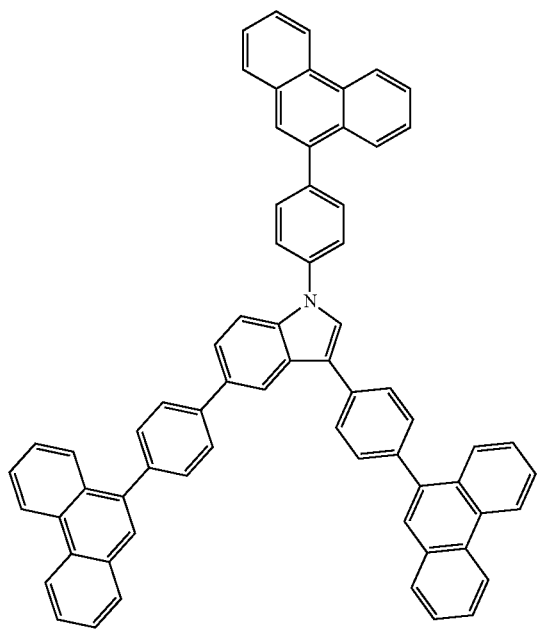
<a-52>
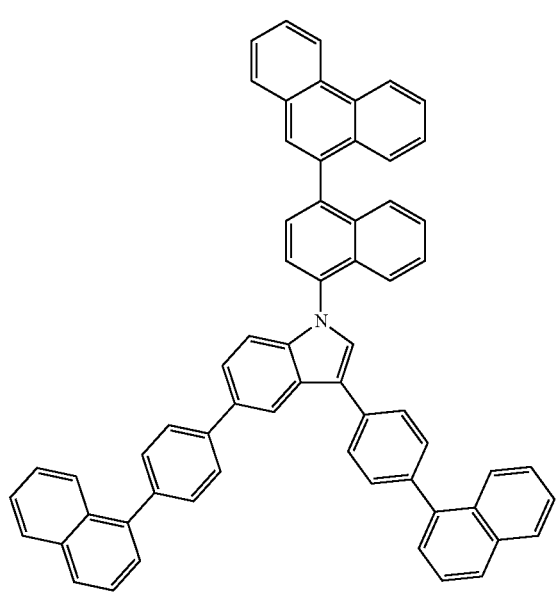
<a-54>
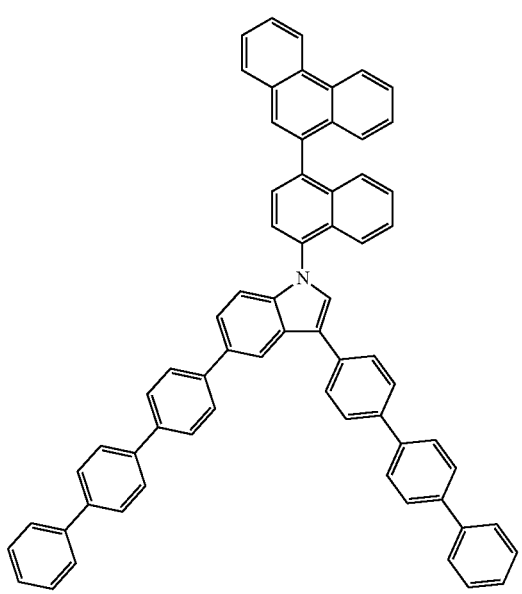

<a-55>
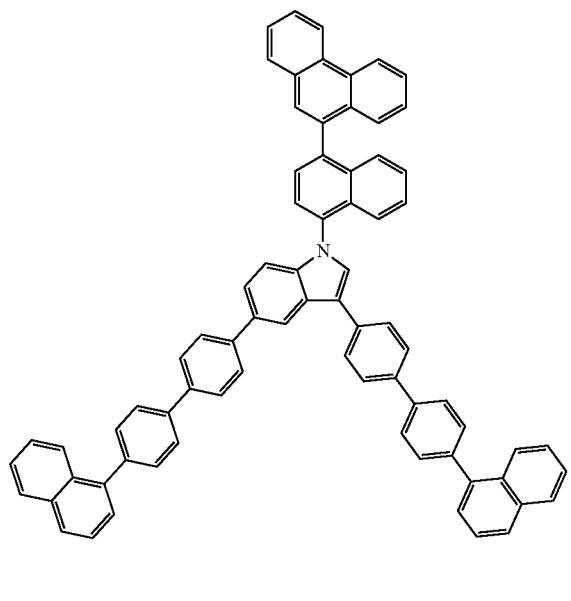
<a-56>
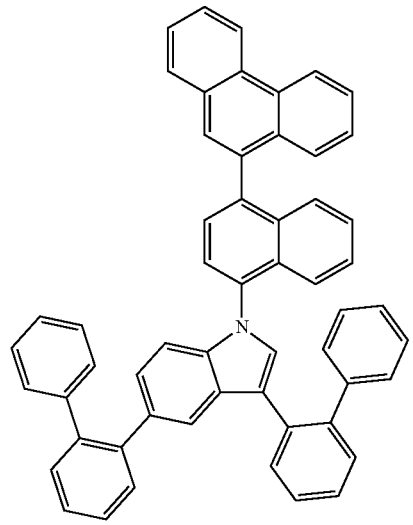
<a-57>
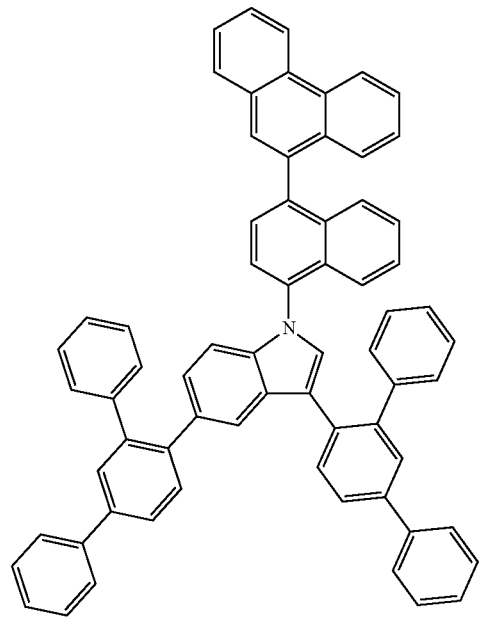
<a-58>
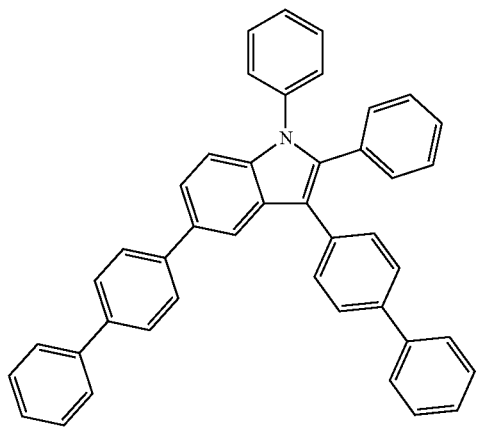
<a-59>
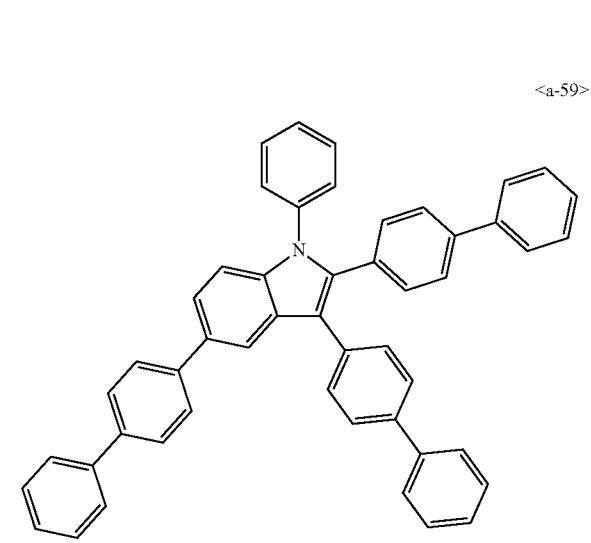

<a-60>
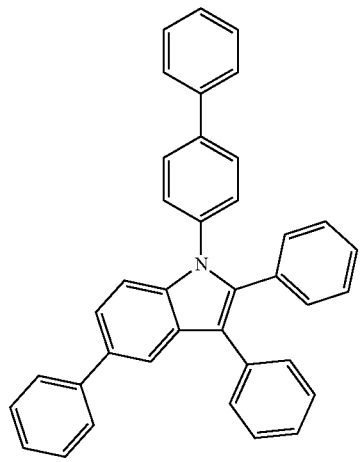
<a-61>
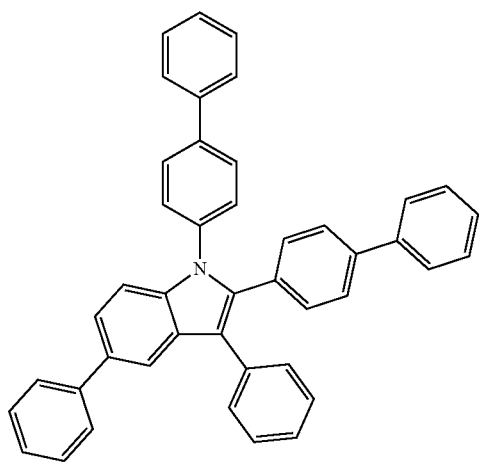
<a-62>
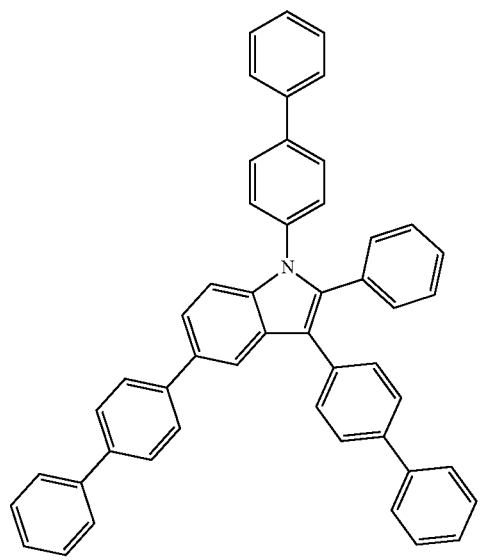
<a-63>
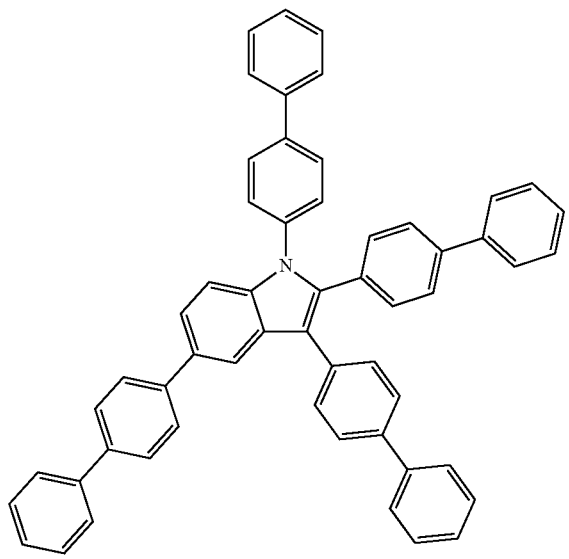
<a-64>
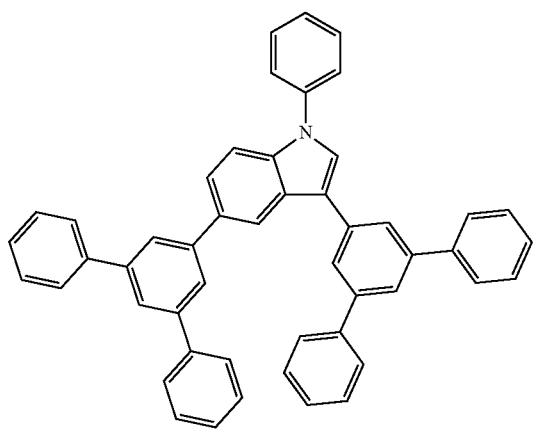
<a-65>
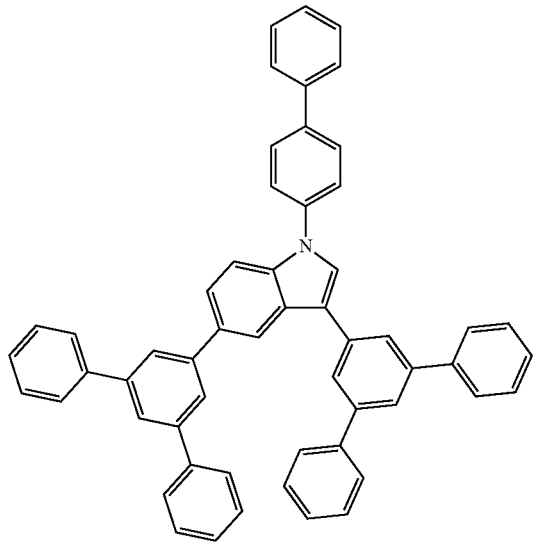

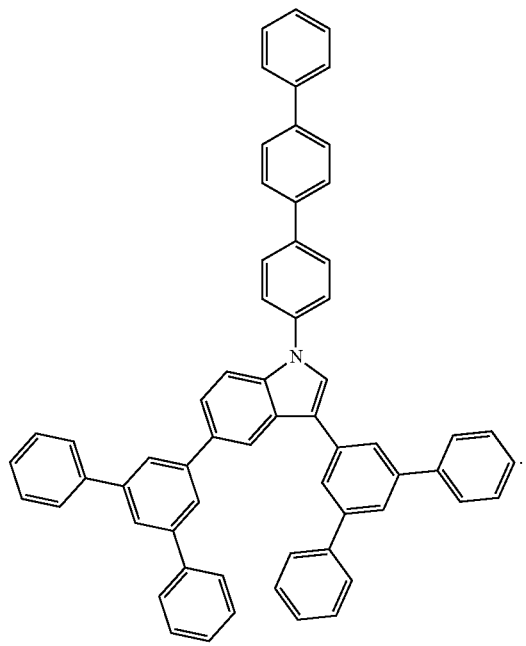
<a-66>
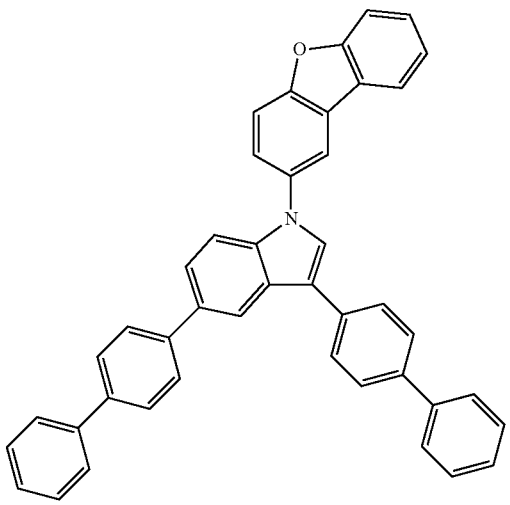
<b-2>
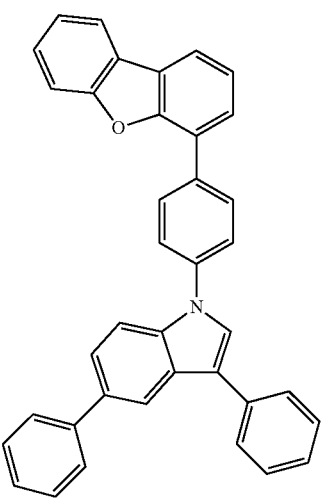
<b-3>
12. The light emitting diode of claim 9, wherein in the above Chemical Formula 1, Ar$_1$ is a dibenzofuranyl group or a dibenzothiophenyl group.
13. The light emitting diode of claim 8, wherein the organic layer includes a compound that has a structure of any one of the chemical formula of b-1 to b-48 below:
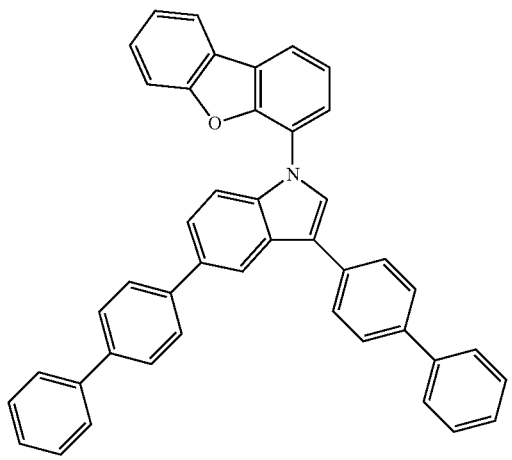
<b-1>
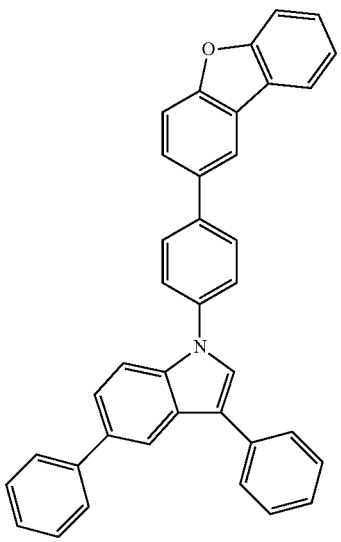
<b-4>

<b-5>
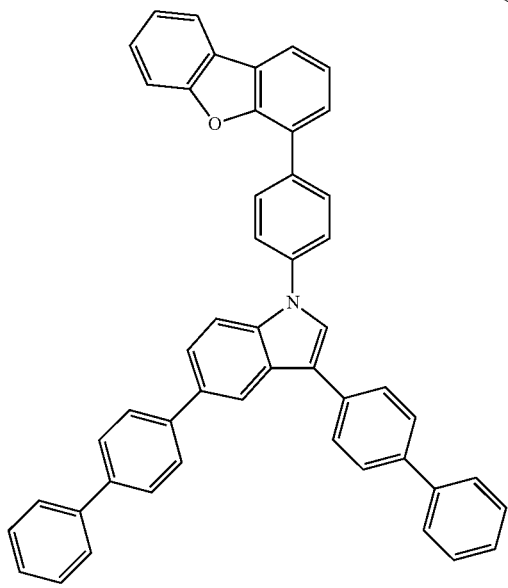
<b-6>
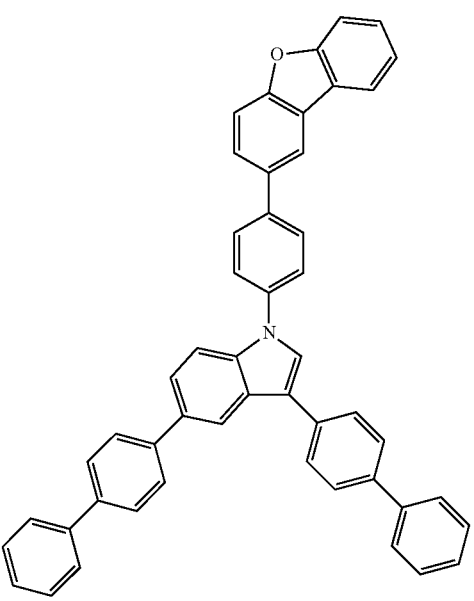
<b-7>
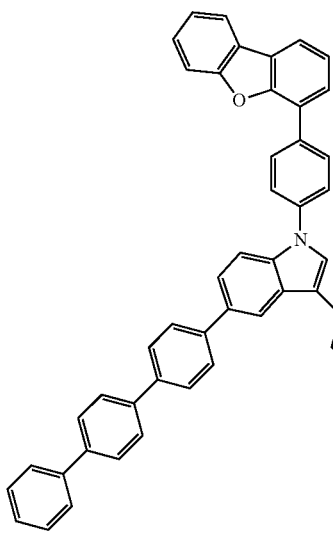
<b-8>
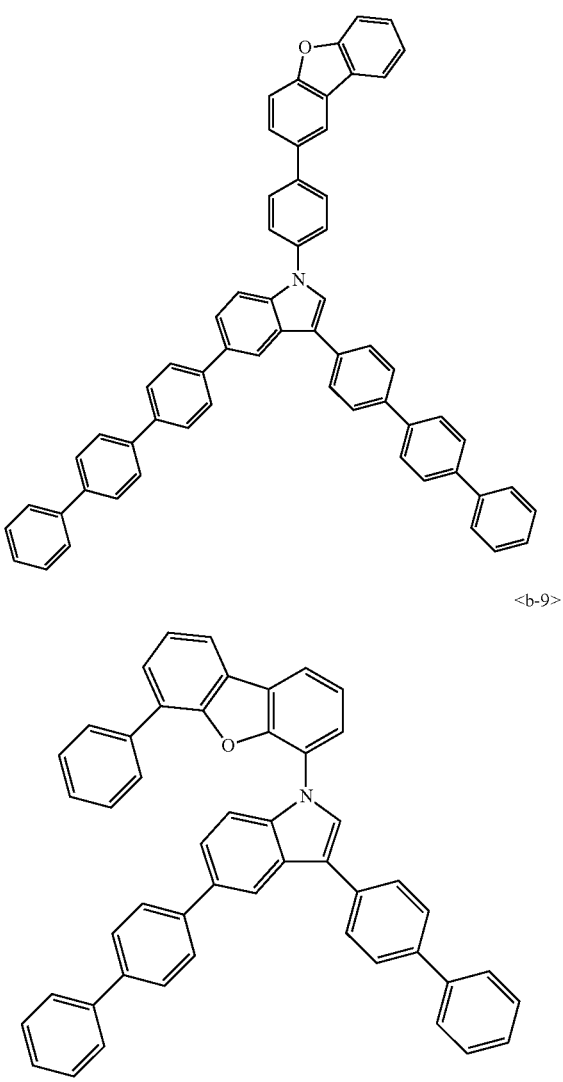
<b-9>

<b-10>
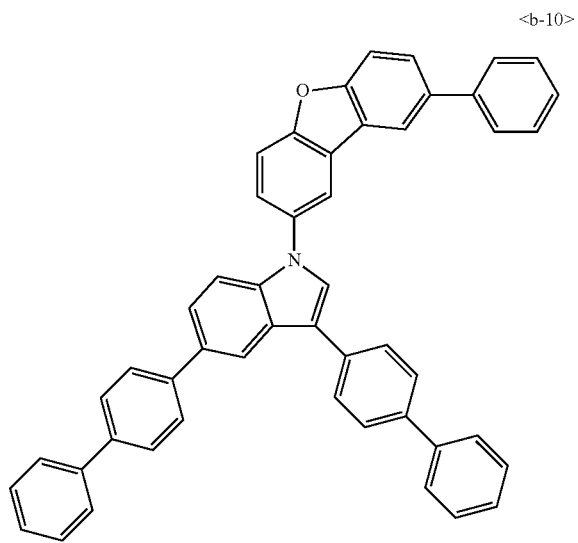
<b-11>
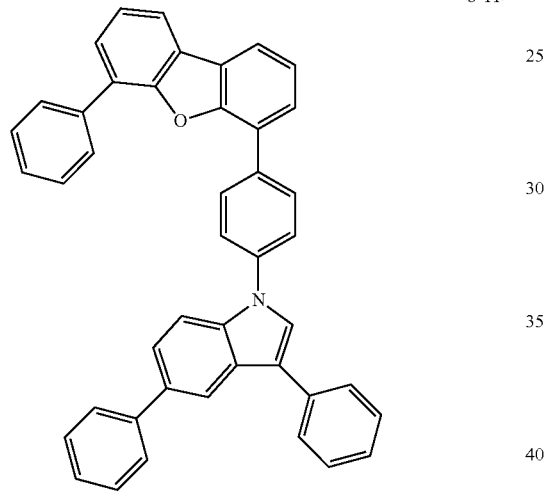
<b-12>
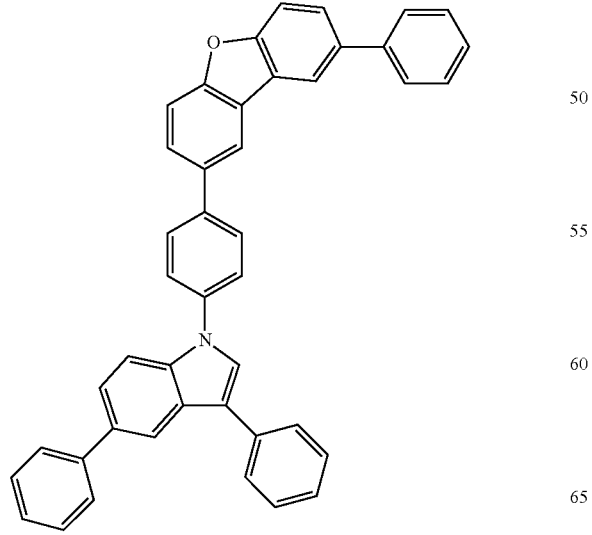
<b-13>
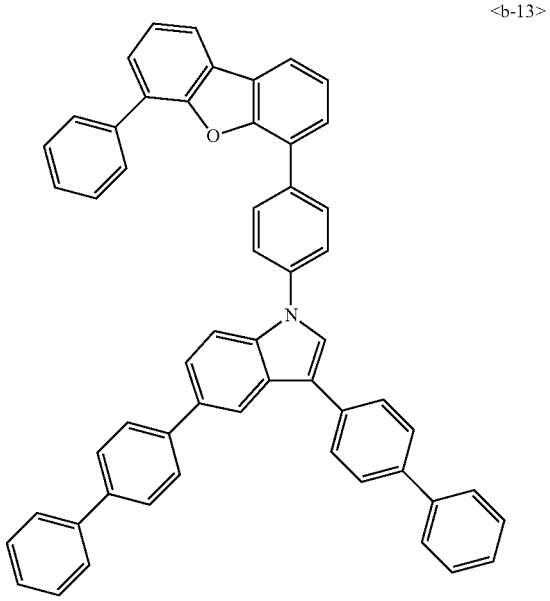
<b-14>

<b-15>
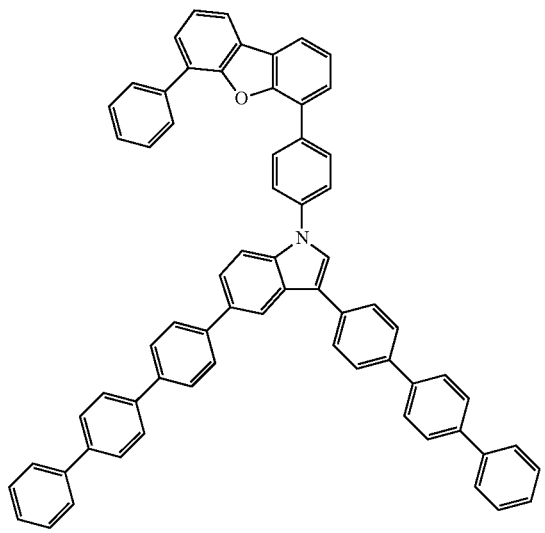
<b-16>
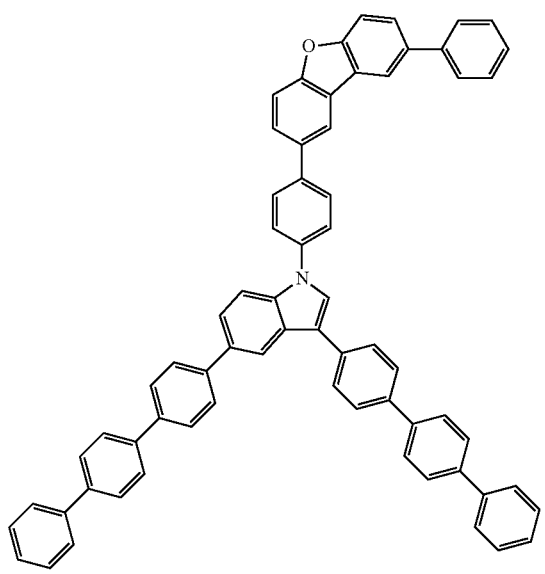
<b-17>
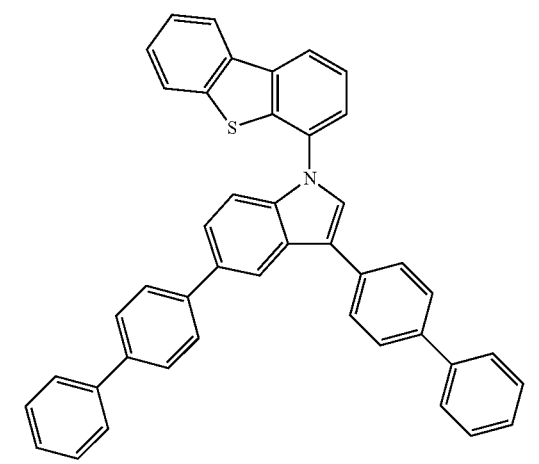
<b-18>
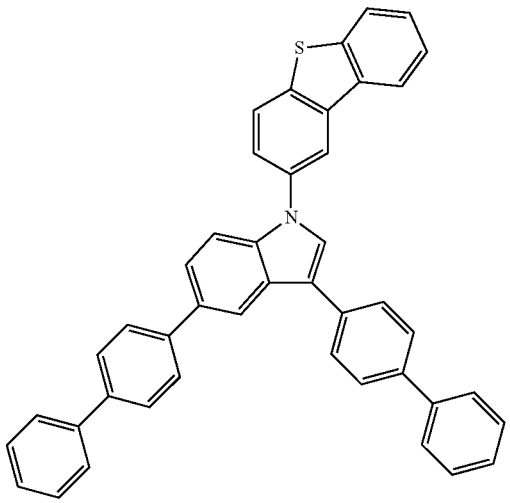
<b-19>
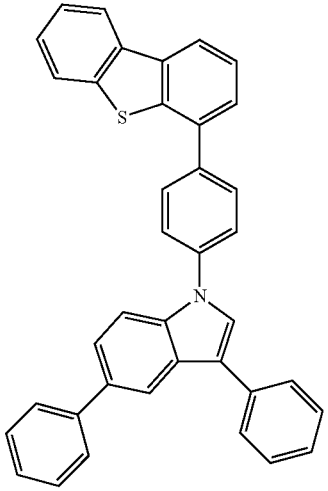
<b-20>
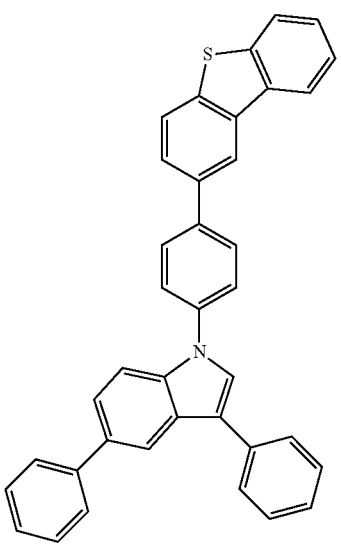

<b-21>
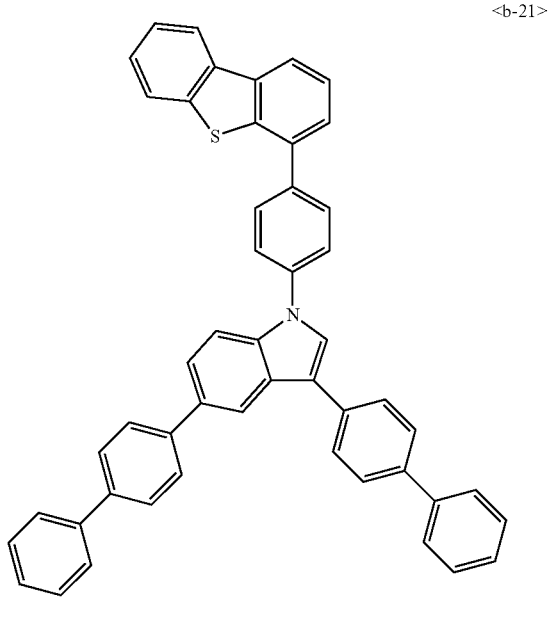
<b-22>
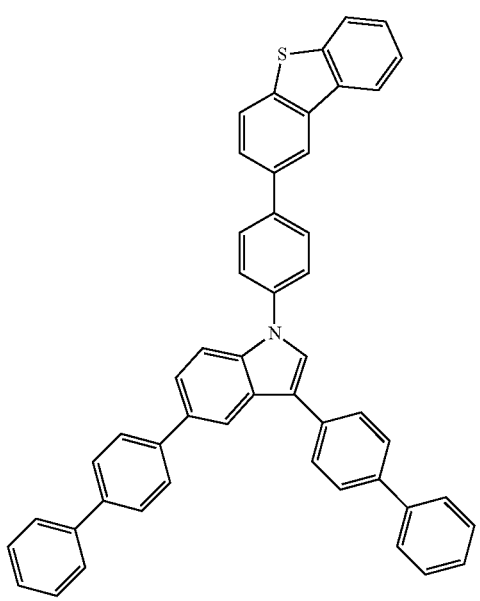
<b-23>
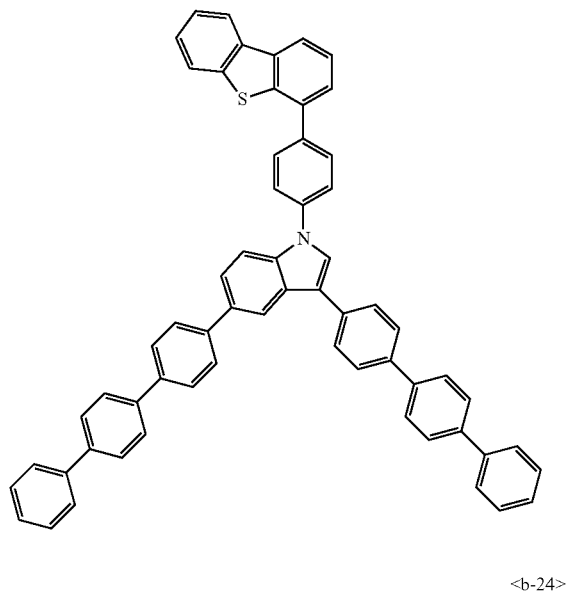
<b-24>
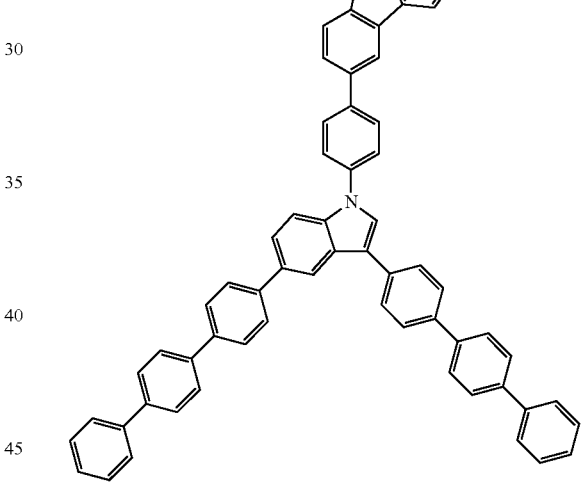
<b-25>
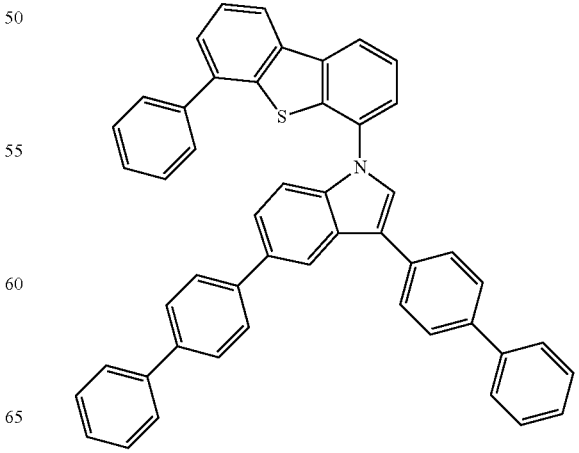

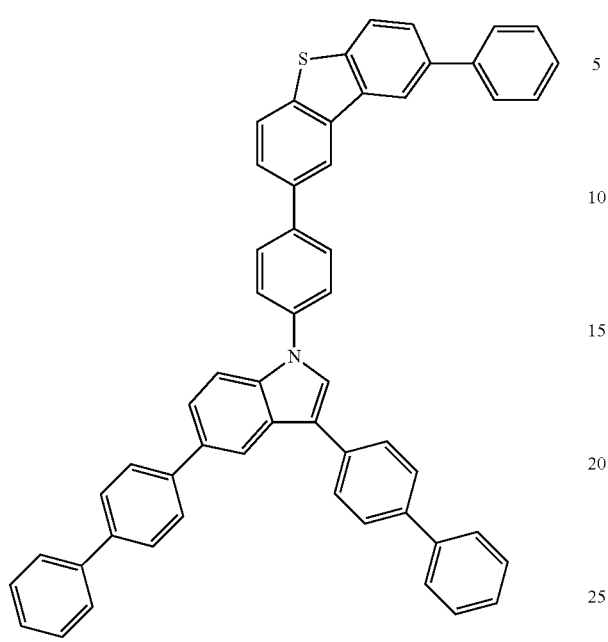
<b-26>
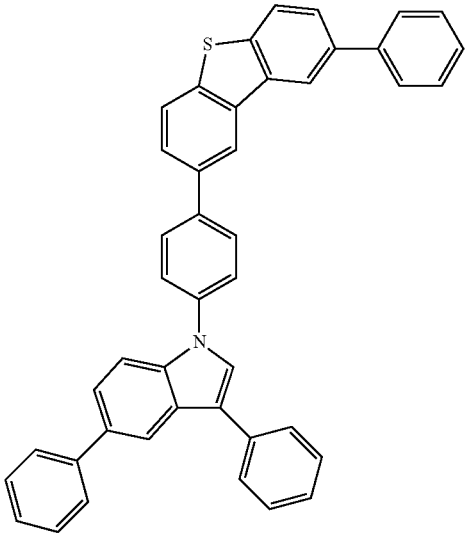
<b-28>
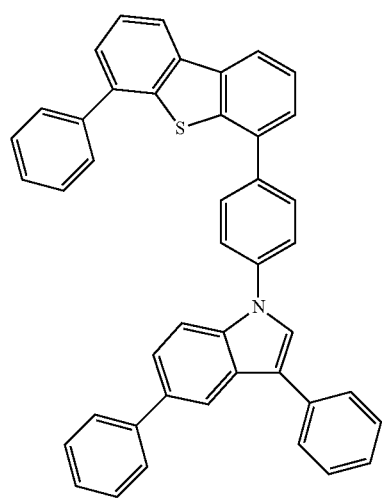
<b-27>
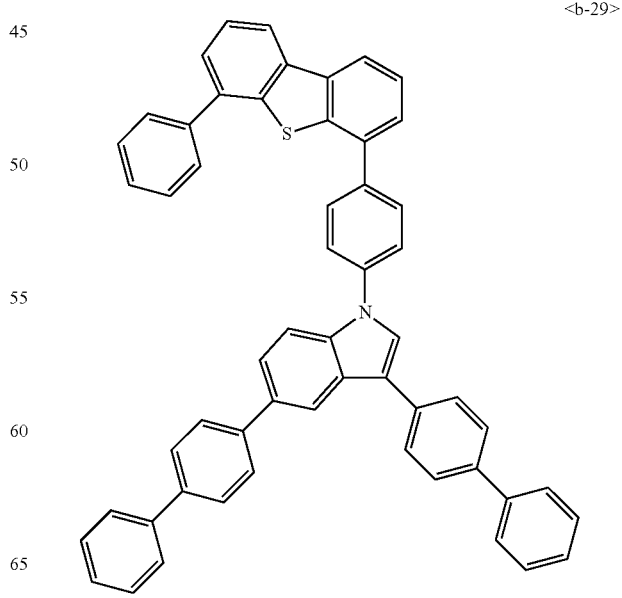
<b-29>

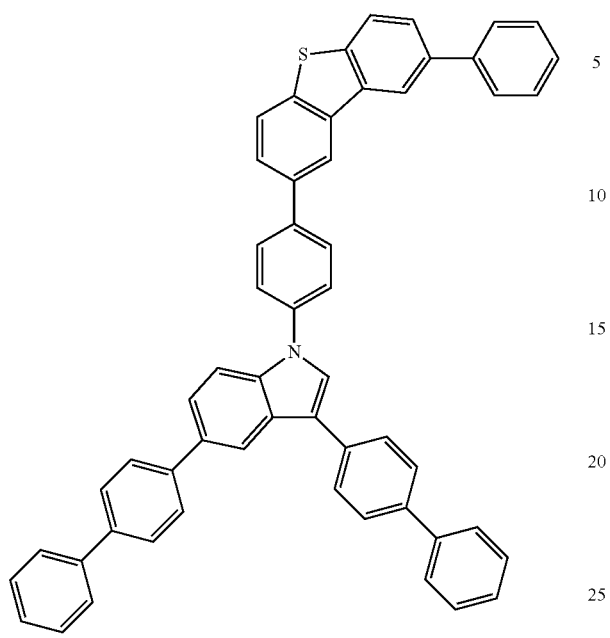
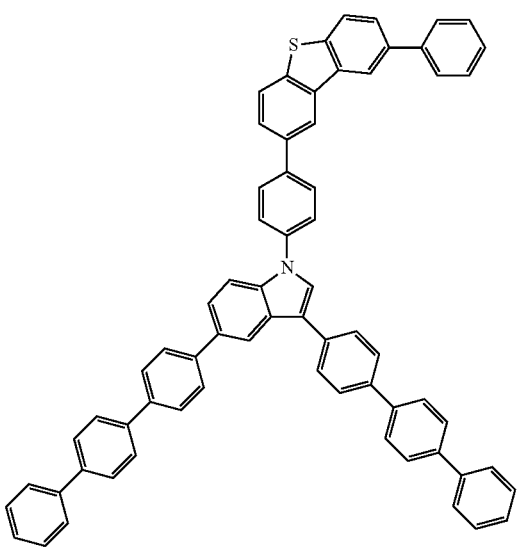

<b-35>
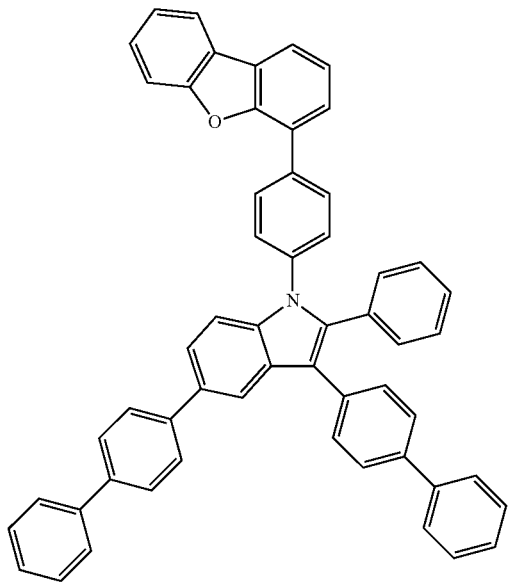
<b-36>
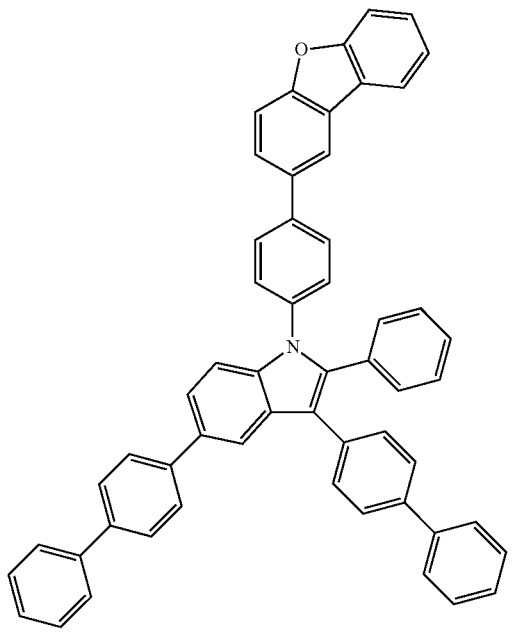
<b-37>
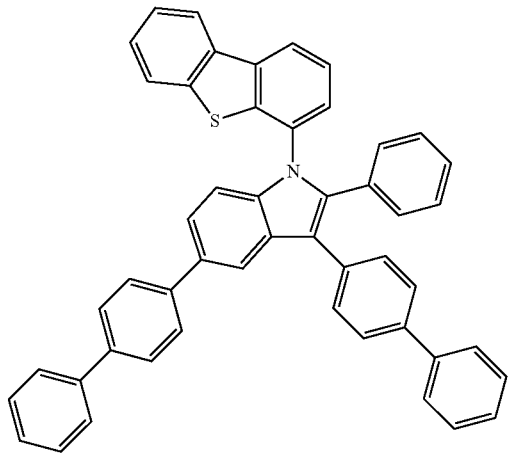
<b-38>
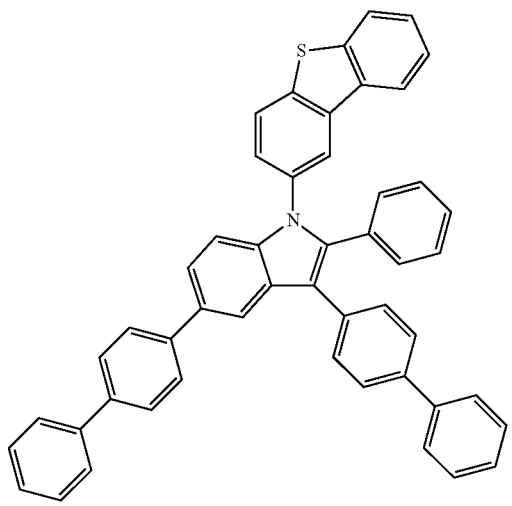
<b-39>
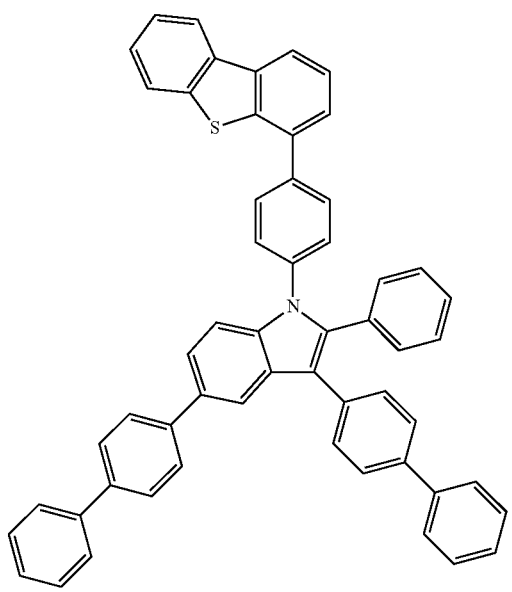

<b-40>
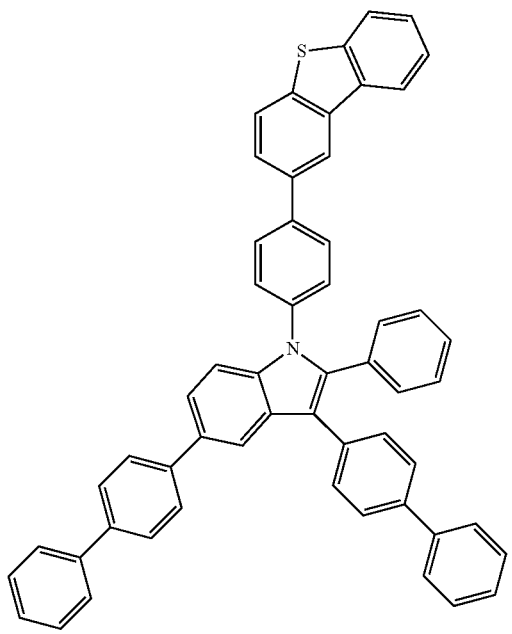
<b-42>
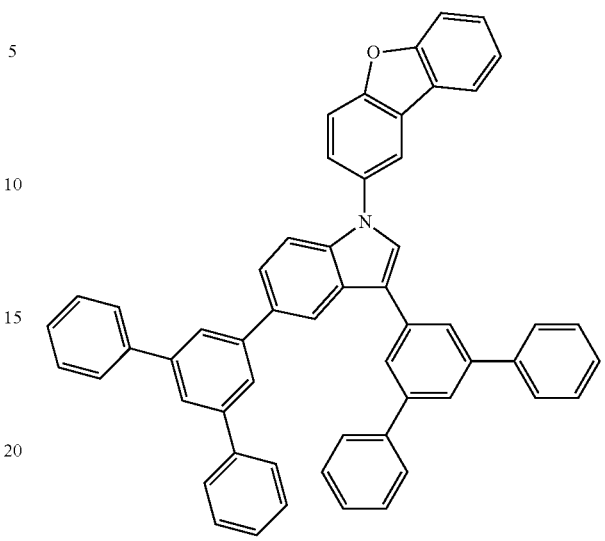
<b-41>
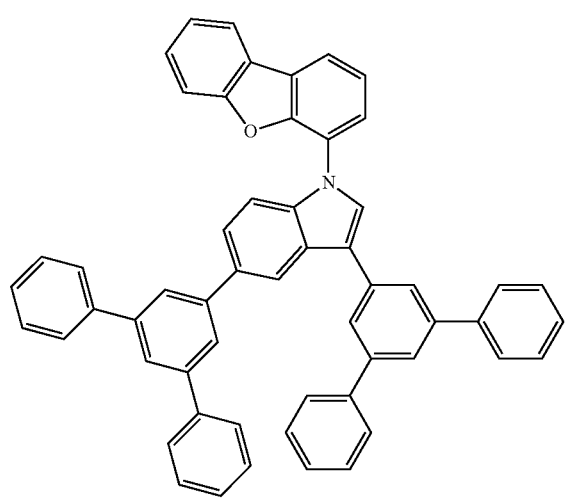
<b-43>
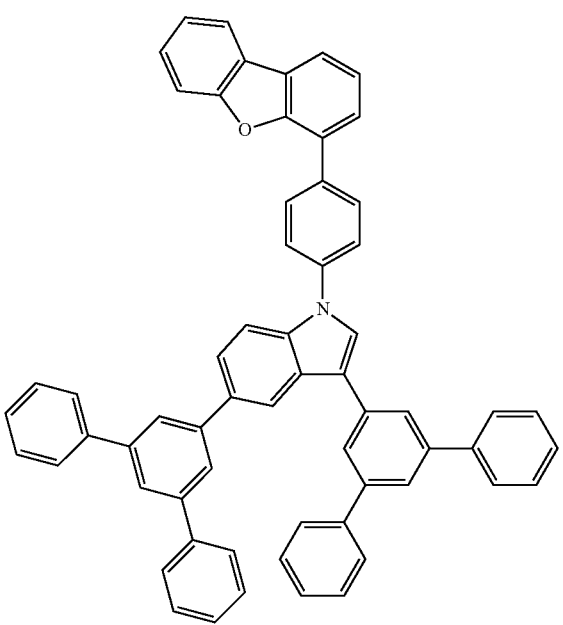

<b-44>
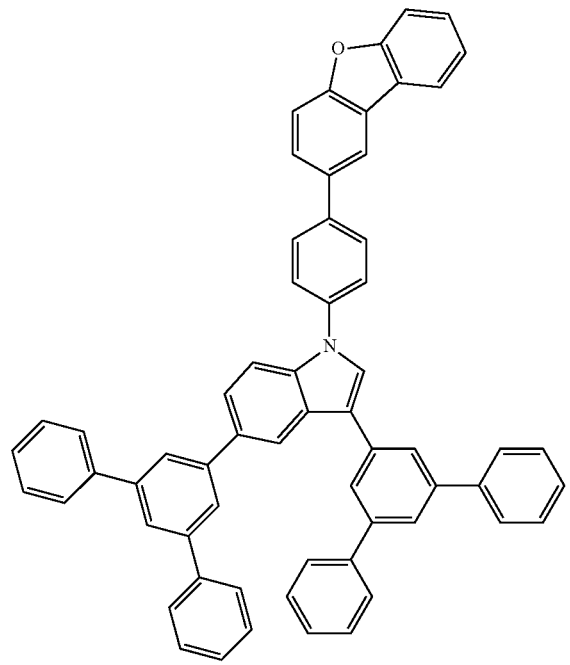
<b-45>
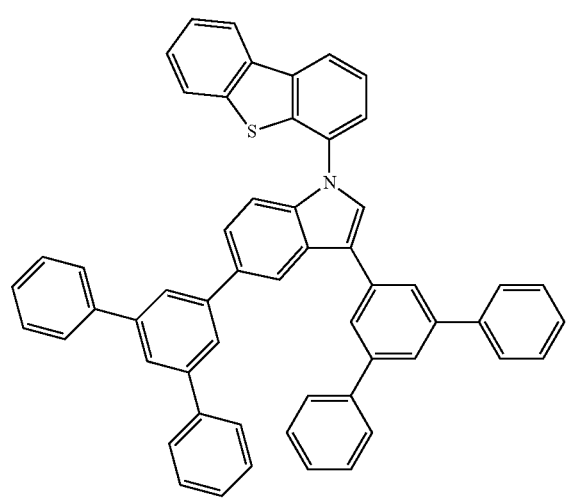
<b-46>
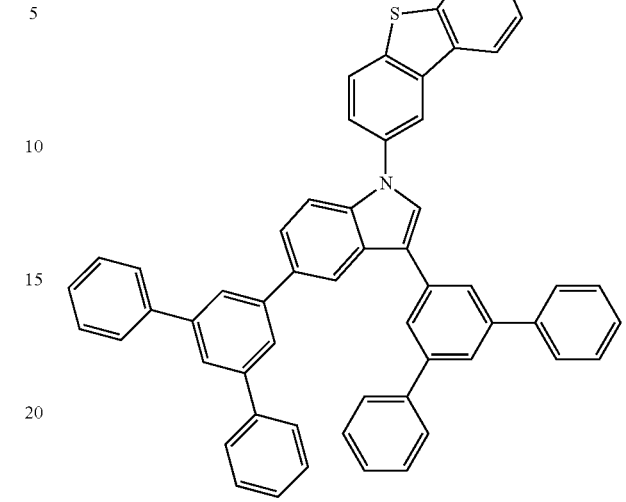
<b-47>
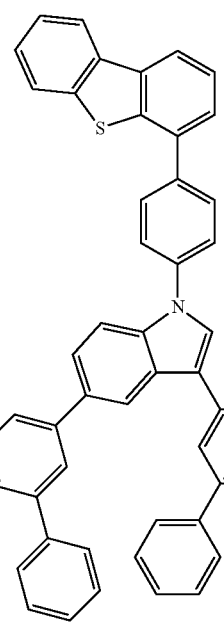

<b-48>

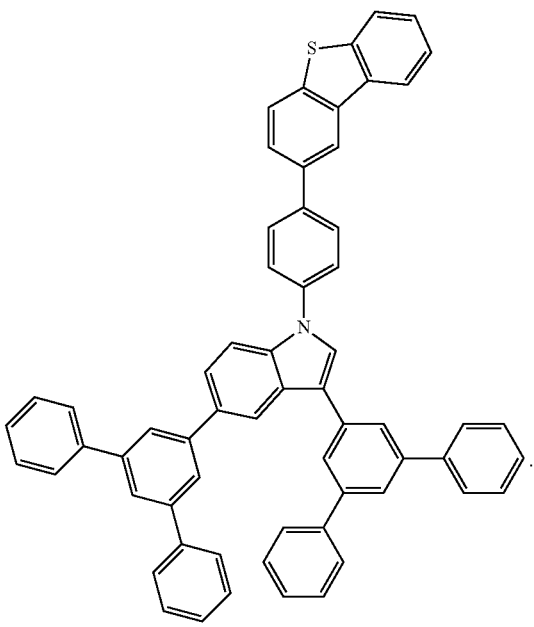

14. The light emitting diode of claim 8, wherein in the above Chemical Formula 1, $Ar_1$ is a phenyl group substituted with one of a trimethylsilyl group, a cyano group, a trifluoromethyl group, a fluoro group, or a methoxy group.

15. The light emitting diode of claim 8, in the above Chemical Formula 1, wherein $Ar_1$ is a structure of Chemical Formula 2 below,
  $L_1$ is a single bond or a phenylene group,
  $L_2$ and $L_3$ are each independently a single bond; or a phenylene group which is unsubstituted or substituted with a phenyl group,
  $Ar_2$ and $Ar_3$ are each independently a phenyl group, a naphthyl group, or a phenanthryl group, and here, the phenyl group is unsubstituted or substituted with a phenyl group, a biphenyl group, a naphthyl group, or a phenanthryl group, and
  Y is hydrogen, a phenyl group, or a biphenyl group:

[Chemical Formula 2]

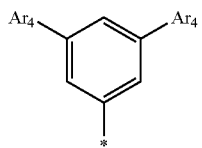

in the above Chemical Formula 2,
  $Ar_4$ is an aryl group having 6 to 30 carbon atoms or a heteroaryl group having 2 to 20 carbon atoms, which is unsubstituted or substituted with one or more substituents selected from a group consisting of an alkyl group having 1 to 4 carbon atoms, $Si(R_2)_3$, a cyano group, a halogen group, a haloalkyl group having 1 to 6 carbon atoms, an alkoxy group having 1 to 6 carbon atoms, and an aryl group having 6 to 30 carbon atoms, and
  here, $R_2$ is an alkyl group having 1 to 4 carbon atoms.

16. The light emitting diode of claim 15, wherein $Ar_4$ is a phenyl group, a biphenyl group, a naphthyl group or a phenanthryl group, which is unsubstituted or substituted with one or more substituents selected from a group consisting of a trimethylsilyl group, a cyano group, a trifluoromethyl group, a fluoro group, and a methoxy group.

17. The light emitting diode of claim 15, wherein both $Ar_4$ is a dibenzofuranyl group or a dibenzothiophenyl group, which is unsubstituted or substituted with a phenyl group.

18. The light emitting diode of claim 8, wherein in the above Chemical Formula 1, $Ar_1$ is a structure of Chemical Formula 3 below,
  $L_1$ is a single bond,
  $L_2$ and $L_3$ are each independently a single bond, or a phenylene group which is unsubstituted or substituted with a phenyl group,
  $Ar_2$ and $Ar_3$ are each independently a phenyl group, a naphthyl group, or a phenanthryl group, and here, the phenyl group is unsubstituted or substituted with a phenyl group, a biphenyl group, a naphthyl group, or a phenanthryl group, and
  Y is hydrogen, a phenyl group, or a biphenyl group:

[Chemical Formula 3]

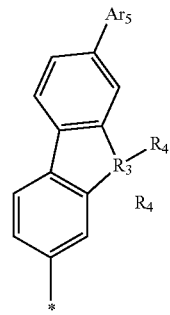

in the above Chemical Formula 3,
  $R_3$ is a carbon atom or a silicon atom;
  $R_4$ is hydrogen, an alkyl group having 1 to 4 carbon atoms, or an aryl group having 6 to 10 carbon atoms; and
  $Ar_5$ is hydrogen or an aryl group having 6 to 30 carbon atoms.

19. The light emitting diode of claim 18, wherein in the above Chemical Formula 3, $R_3$ is a carbon atom, and $Ar_5$ is hydrogen or a phenyl group.

20. The light emitting diode of claim 18, wherein in the above Chemical Formula 3, $R_3$ is a silicon atom, and $Ar_5$ is hydrogen, a phenyl group, or a biphenyl group.

* * * * *